(12) United States Patent
Hu et al.

(10) Patent No.: US 10,633,434 B2
(45) Date of Patent: Apr. 28, 2020

(54) ANTI-C5 ANTIBODIES

(71) Applicant: Regeneron Pharmaceuticals, Inc., Tarrytown, NY (US)

(72) Inventors: Ying Hu, Scarsdale, NY (US); Adrianna Latuszek, Sleepy Hollow, NY (US); Carmelo Romano, Tarrytown, NY (US); William Olson, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 255 days.

(21) Appl. No.: 15/621,689

(22) Filed: Jun. 13, 2017

(65) Prior Publication Data

US 2017/0355757 A1 Dec. 14, 2017

Related U.S. Application Data

(60) Provisional application No. 62/349,705, filed on Jun. 14, 2016, provisional application No. 62/405,561, filed on Oct. 7, 2016, provisional application No. 62/422,107, filed on Nov. 15, 2016.

(51) Int. Cl.
| | | |
|---|---|---|
| *A61K 39/395* | (2006.01) | |
| *C07K 16/28* | (2006.01) | |
| *C07K 16/18* | (2006.01) | |
| *A61K 45/06* | (2006.01) | |
| *A61K 39/00* | (2006.01) | |

(52) U.S. Cl.
CPC .......... *C07K 16/18* (2013.01); *A61K 39/3955* (2013.01); *A61K 45/06* (2013.01); *A61K 2039/505* (2013.01); *A61K 2039/54* (2013.01); *C07K 2317/21* (2013.01); *C07K 2317/33* (2013.01); *C07K 2317/34* (2013.01); *C07K 2317/51* (2013.01); *C07K 2317/515* (2013.01); *C07K 2317/565* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 4,686,100 A | 8/1987 | Raffin et al. | |
| 5,562,904 A | 10/1996 | Bother et al. | |
| 5,853,722 A | 12/1998 | Rollins et al. | |
| 6,074,642 A | 6/2000 | Wang et al. | |
| 6,355,245 B1 | 3/2002 | Evans et al. | |
| 6,534,058 B2 | 3/2003 | Fung et al. | |
| 6,866,845 B1 | 3/2005 | Ward et al. | |
| 7,279,158 B2 | 10/2007 | Wang et al. | |
| 7,361,339 B2 | 4/2008 | Bell | |
| 7,432,356 B2 | 10/2008 | Fung et al. | |
| 7,582,298 B2 | 9/2009 | Stevens et al. | |
| 7,745,608 B2 | 6/2010 | Manoharan et al. | |
| 7,763,708 B2 | 7/2010 | Okada et al. | |
| 7,999,081 B2 | 8/2011 | Tedesco et al. | |
| 8,206,716 B2 | 6/2012 | Fung et al. | |
| 8,241,628 B2 | 8/2012 | Diefenbach-Streiber et al. | |
| 8,246,995 B2 | 8/2012 | Dai et al. | |
| 8,257,740 B1 | 9/2012 | Sung et al. | |
| 8,282,929 B2 | 10/2012 | Tedesco et al. | |
| 8,372,404 B2 | 2/2013 | Fung et al. | |
| 8,445,190 B2 | 5/2013 | Lambris et al. | |
| 8,703,136 B2 | 4/2014 | Baas et al. | |
| 8,802,096 B2 | 8/2014 | Guo et al. | |
| 8,883,158 B2 | 11/2014 | Diefenbach-Streiber et al. | |
| 8,907,072 B2 | 12/2014 | Fung et al. | |
| 8,962,819 B2 | 2/2015 | Tedesco et al. | |
| 8,999,340 B2 | 4/2015 | Magro | |
| 9,011,852 B2 | 4/2015 | Rother et al. | |
| 9,051,365 B2 | 6/2015 | Johnson et al. | |
| 9,073,983 B2 | 7/2015 | Guo et al. | |
| 9,079,949 B1 | 7/2015 | Andrien, Jr. et al. | |
| 9,107,861 B1 | 8/2015 | Andrien, Jr. et al. | |
| 9,133,269 B2 | 9/2015 | McConnell et al. | |
| 9,206,251 B2 | 12/2015 | Andrien, Jr. et al. | |
| 9,388,235 B2 | 7/2016 | Halstead et al. | |
| 9,415,102 B2 | 8/2016 | Zhou et al. | |

(Continued)

FOREIGN PATENT DOCUMENTS

| | | |
|---|---|---|
| AU | 2013200223 B2 | 8/2015 |
| AU | 2014201433 B2 | 5/2016 |

(Continued)

OTHER PUBLICATIONS

Kussie et al., J. Immunol. 152: 146-152 (1994). (Year: 1994).*
Chen et al., EMBO J., 14: 2784-2794 (1995). (Year: 1995).*
Colman, Research in Immunology 145: 33-36 (1994). (Year: 1994).*
Rudikoff et al., Proc Natl Acad Sci USA 79: 1979-1983 (1982). (Year: 1982).*
D'Angelo et al,, Many Routes to an Antibody Heavy-Chain CDR3: Necessary, Yet Insufficient, for Specific Binding (Frontiers in Immunology vol. 9, Article 395 Mar. 2018; doi: 10.3389/fimmu.2018.00395. (Year: 2018).*
Piche-Nicholas et al., Changes in complemetarity-determining regions significantly alter IgG binding to the neonatal Fc receptor (FcRN) and pharmacokinetics (MABS 2018, vol. 10, No. 1, 81-94, doi.org/10.1080/19420862.2017.1389355. (Year: 2018).*

(Continued)

*Primary Examiner* — Phillip Gambel
(74) *Attorney, Agent, or Firm* — Fox Rothschild LLP

(57) ABSTRACT

The present invention provides monoclonal antibodies that bind to the complement factor 5 (C5) protein, and methods of use thereof. In various embodiments of the invention, the antibodies are fully human antibodies that bind to C5 protein. In some embodiments, the antibodies of the invention are useful for inhibiting or neutralizing C5 activity, thus providing a means of treating or preventing a C5-related disease or disorder in humans. In some embodiments, the invention provides for an anti-C5 antibody that has improved pharmacokinetic and pharmacodynamic properties, e.g., a half-life of more than 10 days.

18 Claims, 18 Drawing Sheets

Specification includes a Sequence Listing.

(56) References Cited

U.S. PATENT DOCUMENTS

| | | | |
|---|---|---|---|
| 9,447,176 | B2 | 9/2016 | Rother et al. |
| 9,458,233 | B2 | 10/2016 | Guo et al. |
| 9,494,601 | B2 | 11/2016 | McKnight et al. |
| 9,663,574 | B2 | 5/2017 | Andrien, Jr. et al. |
| 9,718,880 | B2 | 8/2017 | Bell et al. |
| 9,725,504 | B2 | 8/2017 | Bell et al. |
| 9,732,149 | B2 | 8/2017 | Bell et al. |
| 9,765,135 | B2 | 9/2017 | Ruike et al. |
| 9,890,377 | B2 | 2/2018 | Igawa et al. |
| 9,891,219 | B2 | 2/2018 | Lennon et al. |
| 10,472,623 | B2 | 11/2019 | Igawa et al. |
| 2004/0101920 | A1 | 5/2004 | Radziejewski et al. |
| 2004/0115194 | A1 | 6/2004 | Wang |
| 2009/0175875 | A1 | 7/2009 | Etemad-Gilbertson et al. |
| 2010/0331527 | A1 | 12/2010 | Davis et al. |
| 2011/0195454 | A1 | 8/2011 | Mcwhirter et al. |
| 2012/0308559 | A1 | 12/2012 | Bell et al. |
| 2013/0022615 | A1 | 1/2013 | Diefenbach-Streiber et al. |
| 2013/0064836 | A1* | 3/2013 | Diefenbach-Streiber ............ C07K 16/18 424/172.1 |
| 2014/0056888 | A1 | 2/2014 | Zhou et al. |
| 2014/0170140 | A1 | 6/2014 | Bennett et al. |
| 2014/0243504 | A1 | 8/2014 | Davis et al. |
| 2015/0158936 | A1 | 6/2015 | Johnson et al. |
| 2016/0031975 | A1 | 2/2016 | Diefenbach-Streiber et al. |
| 2016/0051673 | A1 | 2/2016 | Hunter et al. |
| 2016/0068592 | A1 | 3/2016 | Chung et al. |
| 2016/0168237 | A1 | 6/2016 | Fontenot et al. |
| 2016/0200805 | A1 | 7/2016 | Fung et al. |
| 2016/0237146 | A1 | 8/2016 | Connor |
| 2016/0299305 | A1 | 10/2016 | Fabian et al. |
| 2016/0362482 | A1 | 12/2016 | Medof |
| 2016/0369010 | A1 | 12/2016 | Celeste et al. |
| 2018/0016327 | A1 | 1/2018 | Murata et al. |
| 2018/0022824 | A1 | 1/2018 | Baas et al. |
| 2018/0333488 | A1 | 11/2018 | Francois et al. |
| 2019/0177436 | A1 | 6/2019 | Devalaraja-Narashimha |

FOREIGN PATENT DOCUMENTS

| | | |
|---|---|---|
| AU | 2015201676 B2 | 10/2016 |
| EP | 0219524 B1 | 1/1992 |
| EP | 1425042 B1 | 4/2007 |
| EP | 0758904 B1 | 11/2009 |
| EP | 1325033 B1 | 11/2009 |
| EP | 1529063 B1 | 4/2011 |
| EP | 1720571 B1 | 6/2012 |
| EP | 2113516 B1 | 5/2014 |
| EP | 1755674 B1 | 11/2014 |
| EP | 2061810 B1 | 11/2014 |
| EP | 1988882 B1 | 12/2014 |
| EP | 2328616 B1 | 4/2015 |
| EP | 2894165 A1 | 7/2015 |
| EP | 2563813 B1 | 8/2015 |
| EP | 2698166 B1 | 9/2015 |
| EP | 1545611 B1 | 11/2016 |
| EP | 2359834 B1 | 11/2016 |
| EP | 2380907 B1 | 11/2016 |
| EP | 2504362 B1 | 11/2016 |
| EP | 2542255 B1 | 11/2016 |
| EP | 3124029 A1 | 2/2017 |
| EP | 2552955 B1 | 5/2017 |
| EP | 3167888 A1 | 5/2017 |
| EP | 2815766 B1 | 7/2017 |
| EP | 1878441 B1 | 1/2018 |
| EP | 2978451 B1 | 11/2019 |
| WO | 9302188 A1 | 2/1993 |
| WO | 9400560 A1 | 1/1994 |
| WO | 9529697 A1 | 11/1995 |
| WO | 9609043 A1 | 3/1996 |
| WO | 200230985 A2 | 4/2002 |
| WO | 2004007553 A1 | 1/2004 |
| WO | 200422096 A1 | 3/2004 |
| WO | 04106369 A2 | 12/2004 |
| WO | 2005074607 A2 | 8/2005 |
| WO | 2005/103081 A1 | 11/2005 |
| WO | 2006122257 A2 | 11/2006 |
| WO | 200756227 A2 | 5/2007 |
| WO | 2007106585 A1 | 9/2007 |
| WO | 0829169 A2 | 3/2008 |
| WO | 200829167 A1 | 3/2008 |
| WO | 200830505 A2 | 3/2008 |
| WO | 2008069889 A2 | 6/2008 |
| WO | 2009125825 | 10/2009 |
| WO | 2010015608 A1 | 2/2010 |
| WO | 2010151526 A1 | 12/2010 |
| WO | 2011137395 A1 | 11/2011 |
| WO | 2013174936 A1 | 11/2013 |
| WO | 2014/047500 A1 | 3/2014 |
| WO | 2014119969 A1 | 8/2014 |
| WO | 2014160958 A1 | 10/2014 |
| WO | 201539126 A1 | 3/2015 |
| WO | 2015103438 A2 | 7/2015 |
| WO | 2015/120130 A1 | 8/2015 |
| WO | 2015/127134 A2 | 8/2015 |
| WO | 2015/134894 A1 | 9/2015 |
| WO | 2015140304 A1 | 9/2015 |
| WO | 15171523 A1 | 11/2015 |
| WO | 2015/198243 A2 | 12/2015 |
| WO | 1609956 A1 | 1/2016 |
| WO | 201694834 A2 | 6/2016 |
| WO | 2016098356 A1 | 6/2016 |
| WO | 2016/117346 A1 | 7/2016 |
| WO | 2016/160756 A2 | 10/2016 |
| WO | 2016/178980 A1 | 11/2016 |
| WO | 16201301 A1 | 12/2016 |
| WO | 2016200627 A1 | 12/2016 |
| WO | 201735362 A1 | 3/2017 |
| WO | 201744811 A1 | 3/2017 |
| WO | 2017/062649 A1 | 4/2017 |
| WO | 2017/064615 A1 | 4/2017 |
| WO | 201755908 A1 | 4/2017 |
| WO | 2017/075325 A1 | 5/2017 |
| WO | 2017/104779 A1 | 6/2017 |
| WO | 2017/123636 A1 | 7/2017 |
| WO | 2017/132259 A1 | 8/2017 |
| WO | 2017140903 A1 | 8/2017 |
| WO | 17205101 A1 | 11/2017 |
| WO | 17214518 A1 | 12/2017 |
| WO | 2017212375 A1 | 12/2017 |
| WO | 2017212391 A1 | 12/2017 |
| WO | 2017217524 A1 | 12/2017 |
| WO | 1809588 A1 | 1/2018 |
| WO | 2018053039 A1 | 3/2018 |
| WO | 1871624 A1 | 4/2018 |
| WO | 18106589 A1 | 6/2018 |
| WO | 18109588 A2 | 6/2018 |
| WO | 2018143266 A1 | 8/2018 |
| WO | 18165062 A1 | 9/2018 |
| WO | 18175833 A1 | 9/2018 |
| WO | 18195034 A1 | 10/2018 |
| WO | 18234118 A1 | 12/2018 |

OTHER PUBLICATIONS

Kabat et al., "Sequences of Proteins of Immunological Interest", vol. 1, NIH Publication No. 913242 (1991), pp. xiii-44, 103-130.

Kabat et al., "Sequences of Proteins of Immunological Interest", vol. 1, NIH Publication No. 913242 (1991), pp. 131-286.

Kabat et al., "Sequences of Proteins of Immunological Interest", vol. 1, NIH Publication No. 913242 (1991), pp. 287-431.

Kabat et al., "Sequences of Proteins of Immunological Interest", vol. 1, NIH Publication No. 913242 (1991), pp. 432-539, 647-698.

Kabat et al., "Sequences of Proteins of Immunological Interest", vol. 1, NIH Publication No. 913242 (1991), pp. 699-723, 1138-1174, 1229-1341.

Kabat et al., "Sequences of Proteins of Immunological Interest", vol. 1, NIH Publication No. 913242 (1991), pp. 1342-1476, 1571-1599.

(56) References Cited

OTHER PUBLICATIONS

Kabat et al., "Sequences of Proteins of Immunological Interest", vol. 1, NIH Publication No. 913242 (1991), pp. 1600-1610, 2130-2163.

Sahelijo et al., "First in Human Single-Ascending Dose Study: Safety, Biomarker, Pharmacokinetics and Exposure-Response Relationships of ALXN1210, a Humanized Monoclonal Antibody to C5, with Marked Half-Life Extension and Potential for Significantly Longer Dosing Intervals", Blood, 126(23):4777 (2015).

Hillmen et al., "Effect of eculizumab on hemolysis and transfusion requirements in patients with paroxysmal nocturnal hemoglobinuria," The New England Journal of Medicine, 350(6):552-559 (Feb. 2004).

Hillmen et al., "The complement inhibitor eculizumab in paroxysmal nocturnal hemoglobinuria," The New England Journal of Medicine, 355(12):1233-43 (Sep. 2006).

Kurolap et al., "Loss of CD55 in Eculizumab-Responsive Protein-Losing Enteropathy," The New England Journal of Medicine, 377(1):87-89 (Jul. 2017).

Marzari et al., "The cleavage site of C5 from man and animals as a common target for neutralizing human monoclonal antibodies: in vitro and in vivo studies," Eur J Immunol, 32(10):2773-82 (Oct. 2002).

Nishimura et al., "Genetic variants in C5 and poor response to eculizumab," The New England Journal of Medicine, 370(7):632-639 (Feb. 2014).

SOLIRIS® (eculizumab) Label (Oct. 2017).

Xu et al., "Targeting the complement system for the management of retinal inflammatory and degenerative diseases", European Journal of Pharmacology 787:94-104 (2016).

Zuber et al., "Use of eculizumab for atypical haemolytic uraemic syndrome and C3 glomerulopathies", Nature Reviews, Nephrology, 8:643-657(2012).

Nozaki et al., "Drusen complement components C3a and C5a promote choroidal neovascularization", PNAS, 103 (7):2328-2333 (2006).

Noris et al., "Dynamics of complement activation in aHUS and how to monitor eculizumab therapy", Blood, 124(11):1715-1726 (2014).

Nishimura et al., "Genetic Variants in C5 and Poor Response to Eculizumab", The New Engliand Journal of Medicine, 370(7):632-639 (2014).

Bennett et al., "Intrathecal Pathogenic Anti-Aquaprin-4 Antibodies in Early Neuromyeliltics Optica", NIH Public Access, Author Manuscript, Ann Neurol., 66(5):617-629 (2009).

Chen et al., "Inhibition of the Alternative pathway of complement activation reduces inflammation in experimental autoimmune uveoretinitis", Eur. J. Immunol, 40:2870-2881 (2010).

De Vries et al., "Inhibition of complement factor C5 protects against renal ischemia-reperfusion injury: inhibition of late apoptosis and inflammation", Transplantation, 75(3):375-382 (2003).

Copland et al., "Systemic and local anti-C5 therapy reduces the disease severity in experimental autoimmne uveoretinitis", Clinical & Experimental Immunology, 159:303-314 (2009).

Montalvo et al., "Complement Deposits on Ocular Tissues Adjacent to Sites of Inflammation", Current Eye Research, 32:917-922 (2007).

Xu et al., "Complement C5 Gene Confers Risk for Acute Anterior", Genetics, Invest Ophtharmol Vis. Sci, 56:4954-4690 (2015).

International Search Report for PCT/US2017/037226 (dated Aug. 23, 2017).

Wong et al., "Anticomplement C5 therapy with eculizumab for the treatment of paroxysmal nocturnal hemoglobinuria and atypical hemolytic uremic syndrome", Translational Research, 165 (2): 306-320 (2015).

NPL_Q1 2017 Regeneron Pharmaceuticals Inc Earnings Call Transcript (May 4, 2017).

\* cited by examiner

SEQUENCE LISTING

```
<160> NUMBER OF SEQ ID NOS: 366

<210> SEQ ID NO 1
<211> LENGTH: 357
<212> TYPE: DNA
<213> ORGANISM: Artificial Sequence
<220> FEATURE:
<223> OTHER INFORMATION: synthetic

<400> SEQUENCE: 1
caggtgcagc tggtggagtc tgggggaggc gtggtccagc ctggaaggtc cctgagactc      60
tcctgtgtag cgtctggatt caccttcagt agttatggca ttcactgggt ccgccaggct     120
ccaggcaagg ggctggagtg ggtggcagtt atatgggatg atggaaataa tataaactat     180
tcagactccg tgaagggccg attcatcatc tccagagaca attccaggaa gacagtgtat     240
ctgcaaatga acagcctgag aggcgaggac acggctgttt attactgtgc gagagatgcc     300
cccatagcac cagtccctga ctattgggc cagggaaccc tggtcaccgt ctcctca        357

<210> SEQ ID NO 2
<211> LENGTH: 119
<212> TYPE: PRT
<213> ORGANISM: Artificial Sequence
<220> FEATURE:
<223> OTHER INFORMATION: synthetic

<400> SEQUENCE: 2

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Ile His Trp Val Arg Gln Ala Pro Gly Lys Gly Leu Glu Trp Val
        35                  40                  45

Ala Val Ile Trp Asp Asp Gly Asn Asn Ile Asn Tyr Ser Asp Ser Val
    50                  55                  60

Lys Gly Arg Phe Ile Ile Ser Arg Asp Asn Ser Arg Lys Thr Val Tyr
65                  70                  75                  80

Leu Gln Met Asn Ser Leu Arg Gly Glu Asp Thr Ala Val Tyr Tyr Cys
                85                  90                  95

Ala Arg Asp Ala Pro Ile Ala Pro Val Pro Asp Tyr Trp Gly Gln Gly
            100                 105                 110

Thr Leu Val Thr Val Ser Ser
        115

<210> SEQ ID NO 3
<211> LENGTH: 24
<212> TYPE: DNA
<213> ORGANISM: Artificial Sequence
<220> FEATURE:
```

<223> OTHER INFORMATION: synthetic

<400> SEQUENCE: 3
ggattcacct tcagtagtta tggc                                    24

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

Gly Phe Thr Phe Ser Ser Tyr Gly
1               5

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
atatgggatg atggaaataa tata                                    24

<210> SEQ ID NO 6
<211> LENGTH: 8
<212> TYPE: PRT
<213> ORGANISM: Artificial Sequence
<220> FEATURE:
<223> OTHER INFORMATION: synthetic

<400> SEQUENCE: 6

Ile Trp Asp Asp Gly Asn Asn Ile
1               5

<210> SEQ ID NO 7
<211> LENGTH: 36
<212> TYPE: DNA
<213> ORGANISM: Artificial Sequence
<220> FEATURE:
<223> OTHER INFORMATION: synthetic

<400> SEQUENCE: 7
gcgagagatg cccccatagc accagtccct gactat                       36

<210> SEQ ID NO 8
<211> LENGTH: 12
<212> TYPE: PRT
<213> ORGANISM: Artificial Sequence
<220> FEATURE:
<223> OTHER INFORMATION: synthetic

<400> SEQUENCE: 8

Ala Arg Asp Ala Pro Ile Ala Pro Val Pro Asp Tyr
1               5                   10

<210> SEQ ID NO 9
<211> LENGTH: 321
<212> TYPE: DNA
<213> ORGANISM: Artificial Sequence
<220> FEATURE:
<223> OTHER INFORMATION: synthetic

<400> SEQUENCE: 9

```
gacatccaga tgacccagtc tccttccacc ctgtctgcat ctgtaggaga cagagtcacc    60
atcacttgcc gggccagtca gagtattagt agttggttgg cctggtatca gcagaaacca   120
gggaaagccc ctaagctcct gatctataag gcgtctagtt tagacactgg ggtcccatca   180
aggttcagcg gcagtggatc tgggacagag ttcactctca ccatcagcag cctgcagcct   240
gatgattttg caacttatta ctgccaacag tataatactt attcgtacac ttttggcctg   300
gggaccaaac tggagatcaa a                                             321
```

```
<210> SEQ ID NO 10
<211> LENGTH: 107
<212> TYPE: PRT
<213> ORGANISM: Artificial Sequence
<220> FEATURE:
<223> OTHER INFORMATION: synthetic

<400> SEQUENCE: 10
```

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Asp Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Tyr Ser Tyr
                85                  90                  95

Thr Phe Gly Leu Gly Thr Lys Leu Glu Ile Lys
            100                 105

```
<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11
cagagtatta gtagttgg                                                  18

<210> SEQ ID NO 12
<211> LENGTH: 6
<212> TYPE: PRT
<213> ORGANISM: Artificial Sequence
<220> FEATURE:
<223> OTHER INFORMATION: synthetic

<400> SEQUENCE: 12
```

Gln Ser Ile Ser Ser Trp
1               5

```
<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13 aaggcgtct                                                            9
```

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Lys Ala Ser
1

<210> SEQ ID NO 15
<211> LENGTH: 27
<212> TYPE: DNA
<213> ORGANISM: Artificial Sequence
<220> FEATURE:
<223> OTHER INFORMATION: synthetic

<400> SEQUENCE: 15
caacagtata atacttattc gtacact         27

<210> SEQ ID NO 16
<211> LENGTH: 9
<212> TYPE: PRT
<213> ORGANISM: Artificial Sequence
<220> FEATURE:
<223> OTHER INFORMATION: synthetic

<400> SEQUENCE: 16

Gln Gln Tyr Asn Thr Tyr Ser Tyr Thr
1               5

<210> SEQ ID NO 17
<211> LENGTH: 357
<212> TYPE: DNA
<213> ORGANISM: Artificial Sequence
<220> FEATURE:
<223> OTHER INFORMATION: synthetic

<400> SEQUENCE: 17
caggtgcaac tggtggagtc tgggggaggc ttggtcaagc ctggagggtc cctgagactc      60
tcctgtgcag cttctggatt caccttcagt gactactaca tgagctggat ccgccaggct     120
ccagggaagg ggctggagtg ggtttcatat attagcagta gtggtaatac cataaaatat     180
gcagactcta tgaagggccg attcaccatc tccagggaca acgccaagaa atcactgttt     240
gtggaaatga acagcctgag agccgaggac acggccgtgt attactgtgc gaggtataaa     300
agttcgtccg actactttga ccactggggc cagggaaccc tggtcaccgt ctcctca        357

<210> SEQ ID NO 18
<211> LENGTH: 119
<212> TYPE: PRT
<213> ORGANISM: Artificial Sequence
<220> FEATURE:
<223> OTHER INFORMATION: synthetic

<400> SEQUENCE: 18

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

```
Ser Tyr Ile Ser Ser Gly Asn Thr Ile Lys Tyr Ala Asp Ser Met
 50                  55                  60

Lys Gly Arg Phe Thr Ile Ser Arg Asp Asn Ala Lys Lys Ser Leu Phe
 65                  70                  75                  80

Val Glu Met Asn Ser Leu Arg Ala Glu Asp Thr Ala Val Tyr Tyr Cys
                 85                  90                  95

Ala Arg Tyr Lys Ser Ser Asp Tyr Phe Asp His Trp Gly Gln Gly
            100                 105                 110

Thr Leu Val Thr Val Ser Ser
        115
```

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
ggattcacct tcagtgacta ctac                                      24

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

```
Gly Phe Thr Phe Ser Asp Tyr Tyr
 1               5
```

<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21
attagcagta gtggtaatac cata                                      24

<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

```
Ile Ser Ser Ser Gly Asn Thr Ile
 1               5
```

<210> SEQ ID NO 23
<211> LENGTH: 36
<212> TYPE: DNA
<213> ORGANISM: Artificial Sequence
<220> FEATURE:
<223> OTHER INFORMATION: synthetic

<400> SEQUENCE: 23
gcgaggtata aaagttcgtc cgactacttt gaccac                         36

```
<210> SEQ ID NO 24
<211> LENGTH: 12
<212> TYPE: PRT
<213> ORGANISM: Artificial Sequence
<220> FEATURE:
<223> OTHER INFORMATION: synthetic

<400> SEQUENCE: 24

Ala Arg Tyr Lys Ser Ser Ser Asp Tyr Phe Asp His
1               5                   10

<210> SEQ ID NO 25
<211> LENGTH: 321
<212> TYPE: DNA
<213> ORGANISM: Artificial Sequence
<220> FEATURE:
<223> OTHER INFORMATION: synthetic

<400> SEQUENCE: 25
gaaattgtgt tgacacagtc tccagccacc ctgtctttgt ctccagggga aagagccacc      60
ctctcctgca gggccagtca gagtgttagg agttacttag cctggtacca acagaaacct    120
ggccaggctc ccaggctcct catctatgat gcatccaaca gggccactgc catcccagcc    180
aggttcagtg gcagtgggtc tgggacagac ttcactctca ccatcagcag cctagagcct    240
gaagatttag cagtttatta ctgtcagcag tctggcaact ggccgctcac tttcggcgga    300
gggaccaagg tggagatcaa a                                              321

<210> SEQ ID NO 26
<211> LENGTH: 107
<212> TYPE: PRT
<213> ORGANISM: Artificial Sequence
<220> FEATURE:
<223> OTHER INFORMATION: synthetic

<400> SEQUENCE: 26

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Ala Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Leu Ala Val Tyr Tyr Cys Gln Gln Ser Gly Asn Trp Pro Leu
                85                  90                  95

Thr Phe Gly Gly Gly Thr Lys Val Glu Ile Lys
            100                 105

<210> SEQ ID NO 27
<211> LENGTH: 18
<212> TYPE: DNA
<213> ORGANISM: Artificial Sequence
<220> FEATURE:
<223> OTHER INFORMATION: synthetic

<400> SEQUENCE: 27
cagagtgtta ggagttac                                                   18

<210> SEQ ID NO 28
```

```
<211> LENGTH: 6
<212> TYPE: PRT
<213> ORGANISM: Artificial Sequence
<220> FEATURE:
<223> OTHER INFORMATION: synthetic

<400> SEQUENCE: 28

Gln Ser Val Arg Ser Tyr
1               5

<210> SEQ ID NO 29
<211> LENGTH: 9
<212> TYPE: DNA
<213> ORGANISM: Artificial Sequence
<220> FEATURE:
<223> OTHER INFORMATION: synthetic

<400> SEQUENCE: 29 gatgcatcc                                                                  9

<210> SEQ ID NO 30
<211> LENGTH: 3
<212> TYPE: PRT
<213> ORGANISM: Artificial Sequence
<220> FEATURE:
<223> OTHER INFORMATION: synthetic

<400> SEQUENCE: 30

Asp Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: synthetic

<400> SEQUENCE: 31
cagcagtctg gcaactggcc gctcact                                             27

<210> SEQ ID NO 32
<211> LENGTH: 9
<212> TYPE: PRT
<213> ORGANISM: Artificial Sequence
<220> FEATURE:
<223> OTHER INFORMATION: synthetic

<400> SEQUENCE: 32

Gln Gln Ser Gly Asn Trp Pro Leu Thr
1               5

<210> SEQ ID NO 33
<211> LENGTH: 357
<212> TYPE: DNA
<213> ORGANISM: Artificial Sequence
<220> FEATURE:
<223> OTHER INFORMATION: synthetic

<400> SEQUENCE: 33
caggtgcagc tggtggagtc tgggggaggc gtggtccagc ctggagggtc cttgagactc          60
tcctgtggag cgtctggatt caccttcagt acttatggca tgcactgggt ccgccaggct         120
ccaggcaagg ggctggagtg ggtggcagtt atctgggatg atggaaataa taaatattat         180
gcagactccg tgaagggccg attcaccatc tccagagaca attcgaagaa cacgctgtat         240
```

```
ctgcagatga acagcctgag agccgaggac acggctgttt attactgtgc gagagattca    300
gaggtcgccc cagttgggga ctactggggc cagggcaccc tggtcaccgt ctcctca       357
```

<210> SEQ ID NO 34
<211> LENGTH: 119
<212> TYPE: PRT
<213> ORGANISM: Artificial Sequence
<220> FEATURE:
<223> OTHER INFORMATION: synthetic
<400> SEQUENCE: 34

```
Gln Val Gln Leu Val Glu Ser Gly Gly Gly Val Val Gln Pro Gly Arg
1               5                   10                  15

Ser Leu Arg Leu Ser Cys Gly Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Asp Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Glu Val Ala Pro Val Gly Asp Tyr Trp Gly Gln Gly
            100                 105                 110

Thr Leu Val Thr Val Ser Ser
        115
```

<210> SEQ ID NO 35
<211> LENGTH: 24
<212> TYPE: DNA
<213> ORGANISM: Artificial Sequence
<220> FEATURE:
<223> OTHER INFORMATION: synthetic
<400> SEQUENCE: 35

```
ggattcacct tcagtactta tggc                                           24
```

<210> SEQ ID NO 36
<211> LENGTH: 8
<212> TYPE: PRT
<213> ORGANISM: Artificial Sequence
<220> FEATURE:
<223> OTHER INFORMATION: synthetic
<400> SEQUENCE: 36

```
Gly Phe Thr Phe Ser Thr Tyr Gly
1               5
```

<210> SEQ ID NO 37
<211> LENGTH: 24
<212> TYPE: DNA
<213> ORGANISM: Artificial Sequence
<220> FEATURE:
<223> OTHER INFORMATION: synthetic
<400> SEQUENCE: 37

```
atctgggatg atggaaataa taaa                                           24
```

<210> SEQ ID NO 38
<211> LENGTH: 8
<212> TYPE: PRT

```
<213> ORGANISM: Artificial Sequence
<220> FEATURE:
<223> OTHER INFORMATION: synthetic

<400> SEQUENCE: 38

Ile Trp Asp Asp Gly Asn Asn Lys
1               5

<210> SEQ ID NO 39
<211> LENGTH: 36
<212> TYPE: DNA
<213> ORGANISM: Artificial Sequence
<220> FEATURE:
<223> OTHER INFORMATION: synthetic

<400> SEQUENCE: 39
gcgagagatt cagaggtcgc cccagttggg gactac                        36

<210> SEQ ID NO 40
<211> LENGTH: 12
<212> TYPE: PRT
<213> ORGANISM: Artificial Sequence
<220> FEATURE:
<223> OTHER INFORMATION: synthetic

<400> SEQUENCE: 40

Ala Arg Asp Ser Glu Val Ala Pro Val Gly Asp Tyr
1               5                   10

<210> SEQ ID NO 41
<211> LENGTH: 321
<212> TYPE: DNA
<213> ORGANISM: Artificial Sequence
<220> FEATURE:
<223> OTHER INFORMATION: synthetic

<400> SEQUENCE: 41
gacatccaga tgacccagtc tccttccacc ctgtctgcat ctgtaggaga cagagtcact     60
atcatttgcc gggccagtca gagtattaac aggtggttgg cctggtatca gcagaaacca    120
gggaaggccc ctaaactcct gatctataag gcgtctagtt tagaaagtgg ggtcccatca    180
aggttcagcg gcagtggatc tgggacagaa ttcactctca ccatcagcag cctgcagcct    240
gatgattttg cagcttatta ctgccaacag tataatgatt attcgtacac ttttggccag    300
gggaccaagc tggagatcaa a                                              321

<210> SEQ ID NO 42
<211> LENGTH: 107
<212> TYPE: PRT
<213> ORGANISM: Artificial Sequence
<220> FEATURE:
<223> OTHER INFORMATION: synthetic

<400> SEQUENCE: 42

Asp Ile Gln Met Thr Gln Ser Pro Ser Thr Leu Ser Ala Ser Val Gly
1               5                   10                  15

Asp Arg Val Thr Ile Ile Cys Arg Ala Ser Gln Ser Ile Asn Arg Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
```

```
                65                  70                  75                  80
Asp Asp Phe Ala Ala Tyr Tyr Cys Gln Gln Tyr Asn Asp Tyr Ser Tyr
                    85                  90                  95

Thr Phe Gly Gln Gly Thr Lys Leu Glu Ile Lys
            100                 105
```

<210> SEQ ID NO 43
<211> LENGTH: 18
<212> TYPE: DNA
<213> ORGANISM: Artificial Sequence
<220> FEATURE:
<223> OTHER INFORMATION: synthetic

<400> SEQUENCE: 43
cagagtatta acaggtgg                                          18

<210> SEQ ID NO 44
<211> LENGTH: 6
<212> TYPE: PRT
<213> ORGANISM: Artificial Sequence
<220> FEATURE:
<223> OTHER INFORMATION: synthetic

<400> SEQUENCE: 44

```
Gln Ser Ile Asn Arg Trp
1               5
```

<210> SEQ ID NO 45
<211> LENGTH: 9
<212> TYPE: DNA
<213> ORGANISM: Artificial Sequence
<220> FEATURE:
<223> OTHER INFORMATION: synthetic

<400> SEQUENCE: 45 aaggcgtct                                                     9

<210> SEQ ID NO 46
<211> LENGTH: 3
<212> TYPE: PRT
<213> ORGANISM: Artificial Sequence
<220> FEATURE:
<223> OTHER INFORMATION: synthetic

<400> SEQUENCE: 46

```
Lys Ala Ser
1
```

<210> SEQ ID NO 47
<211> LENGTH: 27
<212> TYPE: DNA
<213> ORGANISM: Artificial Sequence
<220> FEATURE:
<223> OTHER INFORMATION: synthetic

<400> SEQUENCE: 47
caacagtata atgattattc gtacact                                27

<210> SEQ ID NO 48
<211> LENGTH: 9
<212> TYPE: PRT
<213> ORGANISM: Artificial Sequence
<220> FEATURE:
<223> OTHER INFORMATION: synthetic

<400> SEQUENCE: 48

Gln Gln Tyr Asn Asp Tyr Ser Tyr Thr
1               5

<210> SEQ ID NO 49
<211> LENGTH: 366
<212> TYPE: DNA
<213> ORGANISM: Artificial Sequence
<220> FEATURE:
<223> OTHER INFORMATION: synthetic

<400> SEQUENCE: 49

```
gaggtgcagc tggtggagtc tgggggagac ttggtccagc ctggagggtc cctgagactc      60
tcctgtgcag cctctggatt caccttcagt gaccactata tggactgggt ccgccaggct     120
ccagggaagg ggctggactg gattggccgt attagaaaca agctaacgc ttataacaca      180
gaatacgccg cgtctgtgag aggcagattc accatctcaa gagatgattc acagaattta     240
ctgtatctgc aaatgaacag cctgaaaacc gatgacacgg ccgtatatta ttgtgttaga     300
gtctggaact acgcctactt cgctatggac gtctggggcc aagggaccac ggtcaccgtc     360
tcctca                                                                366
```

<210> SEQ ID NO 50
<211> LENGTH: 122
<212> TYPE: PRT
<213> ORGANISM: Artificial Sequence
<220> FEATURE:
<223> OTHER INFORMATION: synthetic

<400> SEQUENCE: 50

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Asp Trp Ile
        35                  40                  45

Gly Arg Ile Arg Asn Lys Ala Asn Ala Tyr Asn Thr Glu Tyr Ala Ala
    50                  55                  60

Ser Val Arg Gly Arg Phe Thr Ile Ser Arg Asp Asp Ser Gln Asn Leu
65                  70                  75                  80

Leu Tyr Leu Gln Met Asn Ser Leu Lys Thr Asp Asp Thr Ala Val Tyr
                85                  90                  95

Tyr Cys Val Arg Val Trp Asn Tyr Ala Tyr Phe Ala Met Asp Val Trp
            100                 105                 110

Gly Gln Gly Thr Thr Val Thr Val Ser Ser
        115                 120

<210> SEQ ID NO 51
<211> LENGTH: 24
<212> TYPE: DNA
<213> ORGANISM: Artificial Sequence
<220> FEATURE:
<223> OTHER INFORMATION: synthetic

<400> SEQUENCE: 51

```
ggattcacct tcagtgacca ctat                                             24
```

<210> SEQ ID NO 52
<211> LENGTH: 8
<212> TYPE: PRT
<213> ORGANISM: Artificial Sequence
<220> FEATURE:
<223> OTHER INFORMATION: synthetic

<400> SEQUENCE: 52

Gly Phe Thr Phe Ser Asp His Tyr
1               5

<210> SEQ ID NO 53
<211> LENGTH: 30
<212> TYPE: DNA
<213> ORGANISM: Artificial Sequence
<220> FEATURE:
<223> OTHER INFORMATION: synthetic

<400> SEQUENCE: 53
attagaaaca aagctaacgc ttataacaca                                    30

<210> SEQ ID NO 54
<211> LENGTH: 10
<212> TYPE: PRT
<213> ORGANISM: Artificial Sequence
<220> FEATURE:
<223> OTHER INFORMATION: synthetic

<400> SEQUENCE: 54

Ile Arg Asn Lys Ala Asn Ala Tyr Asn Thr
1               5                   10

<210> SEQ ID NO 55
<211> LENGTH: 39
<212> TYPE: DNA
<213> ORGANISM: Artificial Sequence
<220> FEATURE:
<223> OTHER INFORMATION: synthetic

<400> SEQUENCE: 55
gttagagtct ggaactacgc ctacttcgct atggacgtc                          39

<210> SEQ ID NO 56
<211> LENGTH: 13
<212> TYPE: PRT
<213> ORGANISM: Artificial Sequence
<220> FEATURE:
<223> OTHER INFORMATION: synthetic

<400> SEQUENCE: 56

Val Arg Val Trp Asn Tyr Ala Tyr Phe Ala Met Asp Val
1               5                   10

<210> SEQ ID NO 57
<211> LENGTH: 321
<212> TYPE: DNA
<213> ORGANISM: Artificial Sequence
<220> FEATURE:
<223> OTHER INFORMATION: synthetic

<400> SEQUENCE: 57
gacatccaga tgacccagtc tccatcctcc ctatctgcat ctgtgggaga cagagtcacc    60
atcacttgcc ggtcaagtca gaacattgga atcttttta  actggtatca acaaaaacca   120
ggggaagccc ctaacctcct gatctccgct gcatccagtt tacacagtgg ggtcccttca   180
aggttcagtg gcagtgggtc tgggacagat tcactctca  ccatcggcag tctgcagcct   240
gaagattttg cgacttacta ctgtcaacag acgtacaata ccatattcac tttcggccct   300
gggaccaaag tggatatcaa a                                            321

<210> SEQ ID NO 58
<211> LENGTH: 107
<212> TYPE: PRT
<213> ORGANISM: Artificial Sequence
<220> FEATURE:
<223> OTHER INFORMATION: synthetic

<400> SEQUENCE: 58

```
Asp Ile Gln Met Thr Gln Ser Pro Ser Ser Leu Ser Ala Ser Val Gly
1               5                   10                  15

Asp Arg Val Thr Ile Thr Cys Arg Ser Gln Asn Ile Gly Ile Phe
            20                  25                  30

Leu Asn Trp Tyr Gln Gln Lys Pro Gly Glu Ala Pro Asn Leu Leu Ile
                35                  40                  45

Ser Ala Ala Ser Ser Leu His Ser Gly Val Pro Ser Arg Phe Ser Gly
        50                  55                  60

Ser Gly Ser Gly Thr Asp Phe Thr Leu Thr Ile Gly Ser Leu Gln Pro
65                  70                  75                  80

Glu Asp Phe Ala Thr Tyr Tyr Cys Gln Gln Thr Tyr Asn Thr Ile Phe
                85                  90                  95

Thr Phe Gly Pro Gly Thr Lys Val Asp Ile Lys
            100                 105
```

<210> SEQ ID NO 59
<211> LENGTH: 18
<212> TYPE: DNA
<213> ORGANISM: Artificial Sequence
<220> FEATURE:
<223> OTHER INFORMATION: synthetic

<400> SEQUENCE: 59
cagaacattg gaatcttt                                                    18

<210> SEQ ID NO 60
<211> LENGTH: 6
<212> TYPE: PRT
<213> ORGANISM: Artificial Sequence
<220> FEATURE:
<223> OTHER INFORMATION: synthetic

<400> SEQUENCE: 60

```
Gln Asn Ile Gly Ile Phe
1               5
```

<210> SEQ ID NO 61
<211> LENGTH: 9
<212> TYPE: DNA
<213> ORGANISM: Artificial Sequence
<220> FEATURE:
<223> OTHER INFORMATION: synthetic

<400> SEQUENCE: 61 gctgcatcc                                                               9

<210> SEQ ID NO 62
<211> LENGTH: 3
<212> TYPE: PRT
<213> ORGANISM: Artificial Sequence
<220> FEATURE:
<223> OTHER INFORMATION: synthetic

<400> SEQUENCE: 62

Ala Ala Ser
1

<210> SEQ ID NO 63
<211> LENGTH: 27
<212> TYPE: DNA
<213> ORGANISM: Artificial Sequence
<220> FEATURE:
<223> OTHER INFORMATION: synthetic

<400> SEQUENCE: 63
caacagacgt acaataccat attcact                                              27

<210> SEQ ID NO 64
<211> LENGTH: 9
<212> TYPE: PRT
<213> ORGANISM: Artificial Sequence
<220> FEATURE:
<223> OTHER INFORMATION: synthetic

<400> SEQUENCE: 64

Gln Gln Thr Tyr Asn Thr Ile Phe Thr
1               5

<210> SEQ ID NO 65
<211> LENGTH: 363
<212> TYPE: DNA
<213> ORGANISM: Artificial Sequence
<220> FEATURE:
<223> OTHER INFORMATION: synthetic

<400> SEQUENCE: 65
gaggtgcagc tggtggagtc tgggggagac ttggtacagc ctgggggtc cctgagactc            60 tcctgtgcag cctctggatt cacctttagc agctatgcca tgaactgggt ccgccagggt          120
ccagggaagg gactggagtg ggtctcagct attagtggtc gtggtgatag tacatactac          180
gcagactccg tgaagggccg gctcaccatc tccagagaca attccaagaa cacgctgtat          240
ctgcaaatga acagcctgag agccgaggac acggccgtat attactgtgt gaaagagggg          300
gagcaactcg tctactggta cttcgatctc tggggccgtg gcaccctggt caccgtctcc          360
tca                                                                       363

<210> SEQ ID NO 66
<211> LENGTH: 121
<212> TYPE: PRT
<213> ORGANISM: Artificial Sequence
<220> FEATURE:
<223> OTHER INFORMATION: synthetic

<400> SEQUENCE: 66

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Gly Pro Gly Lys Gly Leu Glu Trp Val
        35                  40                  45

Ser Ala Ile Ser Gly Arg Gly Asp Ser Thr Tyr Tyr Ala Asp Ser Val
    50                  55                  60

Lys Gly Arg Leu Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Val Lys Glu Gly Glu Gln Leu Val Tyr Trp Tyr Phe Asp Leu Trp Gly
            100                 105                 110

Arg Gly Thr Leu Val Thr Val Ser Ser
        115                 120
```

<210> SEQ ID NO 67
<211> LENGTH: 24
<212> TYPE: DNA
<213> ORGANISM: Artificial Sequence
<220> FEATURE:
<223> OTHER INFORMATION: synthetic

<400> SEQUENCE: 67
ggattcacct ttagcagcta tgcc                                          24

<210> SEQ ID NO 68
<211> LENGTH: 8
<212> TYPE: PRT
<213> ORGANISM: Artificial Sequence
<220> FEATURE:
<223> OTHER INFORMATION: synthetic

<400> SEQUENCE: 68

```
Gly Phe Thr Phe Ser Ser Tyr Ala
1               5
```

<210> SEQ ID NO 69
<211> LENGTH: 24
<212> TYPE: DNA
<213> ORGANISM: Artificial Sequence
<220> FEATURE:
<223> OTHER INFORMATION: synthetic

<400> SEQUENCE: 69
attagtggtc gtggtgatag taca                                          24

<210> SEQ ID NO 70
<211> LENGTH: 8
<212> TYPE: PRT
<213> ORGANISM: Artificial Sequence
<220> FEATURE:
<223> OTHER INFORMATION: synthetic

<400> SEQUENCE: 70

```
Ile Ser Gly Arg Gly Asp Ser Thr
1               5
```

<210> SEQ ID NO 71
<211> LENGTH: 42
<212> TYPE: DNA
<213> ORGANISM: Artificial Sequence
<220> FEATURE:
<223> OTHER INFORMATION: synthetic

<400> SEQUENCE: 71
gtgaaagagg gggagcaact cgtctactgg tacttcgatc tc                      42

<210> SEQ ID NO 72
<211> LENGTH: 14
<212> TYPE: PRT
<213> ORGANISM: Artificial Sequence
<220> FEATURE:
<223> OTHER INFORMATION: synthetic

<400> SEQUENCE: 72

```
Val Lys Glu Gly Glu Gln Leu Val Tyr Trp Tyr Phe Asp Leu
1               5                   10
```

<210> SEQ ID NO 73
<211> LENGTH: 321
<212> TYPE: DNA
<213> ORGANISM: Artificial Sequence
<220> FEATURE:
<223> OTHER INFORMATION: synthetic

<400> SEQUENCE: 73

```
gacatccaga tgacccagtc tccatcctcc ctgtctgcat ctgtaggaga cagagtcacc      60
atcacttgcc gggcaagtca gaccattagc aacttttac attggtatca gcagaaacca     120
gggaaagccc ctaagctcct gatctatgct gcatccagtt tgcaaagtgg ggtcccatca    180
aggttcagtg gcagtggatc tgggacagat ttcactctca ccatcagcag tctgcaacct   240
gaagattttt caacttactt ctgtcaacag agttacacta ccccgctcac tttcggcgga  300
gggaccaagg tggagatcaa a                                            321
```

<210> SEQ ID NO 74
<211> LENGTH: 107
<212> TYPE: PRT
<213> ORGANISM: Artificial Sequence
<220> FEATURE:
<223> OTHER INFORMATION: synthetic

<400> SEQUENCE: 74

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Asn Phe
            20                  25                  30

Leu His Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ser Thr Tyr Phe Cys Gln Gln Ser Tyr Thr Thr Pro Leu
                85                  90                  95

Thr Phe Gly Gly Gly Thr Lys Val Glu Ile Lys
            100                 105
```

<210> SEQ ID NO 75
<211> LENGTH: 18
<212> TYPE: DNA
<213> ORGANISM: Artificial Sequence
<220> FEATURE:
<223> OTHER INFORMATION: synthetic

<400> SEQUENCE: 75

```
cagaccatta gcaacttt                                                   18
```

<210> SEQ ID NO 76
<211> LENGTH: 6
<212> TYPE: PRT
<213> ORGANISM: Artificial Sequence
<220> FEATURE:
<223> OTHER INFORMATION: synthetic

<400> SEQUENCE: 76

Gln Thr Ile Ser Asn Phe

<210> SEQ ID NO 77
<211> LENGTH: 9
<212> TYPE: DNA
<213> ORGANISM: Artificial Sequence
<220> FEATURE:
<223> OTHER INFORMATION: synthetic

<400> SEQUENCE: 77 gctgcatcc                                                                                      9

<210> SEQ ID NO 78
<211> LENGTH: 3
<212> TYPE: PRT
<213> ORGANISM: Artificial Sequence
<220> FEATURE:
<223> OTHER INFORMATION: synthetic

<400> SEQUENCE: 78

Ala Ala Ser
1

<210> SEQ ID NO 79
<211> LENGTH: 27
<212> TYPE: DNA
<213> ORGANISM: Artificial Sequence
<220> FEATURE:
<223> OTHER INFORMATION: synthetic

<400> SEQUENCE: 79
caacagagtt acactacccc gctcact                                                                 27

<210> SEQ ID NO 80
<211> LENGTH: 9
<212> TYPE: PRT
<213> ORGANISM: Artificial Sequence
<220> FEATURE:
<223> OTHER INFORMATION: synthetic

<400> SEQUENCE: 80

Gln Gln Ser Tyr Thr Thr Pro Leu Thr
1               5

<210> SEQ ID NO 81
<211> LENGTH: 363
<212> TYPE: DNA
<213> ORGANISM: Artificial Sequence
<220> FEATURE:
<223> OTHER INFORMATION: synthetic

<400> SEQUENCE: 81
gaggtgcagc tggtggagtc tgggggaggc ttggtgaggt cggggggtc cctgagactc        60 tcctgtgcag cctctggatt cacctttaac agatatgcca tgacctgggt ccgccaggct      120
ccagggaagg ggctggagtg ggtctcagct ataagtggta gtggtagcag cacatactac      180
acagactccg tgaaaggccg gttcaccatc tccagagaca attccaagaa ttcggtggat      240
ctgcaaatgc acagcctgag agtcgaagac acggccatat attattgtgc gagagggact      300
acagtcacta cggggtacgg tatggacgtc tggggccaag ggaccacggt caccgtctcc      360
tca                                                                    363

<210> SEQ ID NO 82
<211> LENGTH: 121

```
<212> TYPE: PRT
<213> ORGANISM: Artificial Sequence
<220> FEATURE:
<223> OTHER INFORMATION: synthetic

<400> SEQUENCE: 82

Glu Val Gln Leu Val Glu Ser Gly Gly Gly Leu Val Arg Ser Gly Gly
1               5                   10                  15

Ser Leu Arg Leu Ser Cys Ala Ala Ser Gly Phe Thr Phe Asn Arg Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Ser Thr Tyr Tyr Thr Asp Ser Val
    50                  55                  60

Lys Gly Arg Phe Thr Ile Ser Arg Asp Asn Ser Lys Asn Ser Val Asp
65                  70                  75                  80

Leu Gln Met His Ser Leu Arg Val Glu Asp Thr Ala Ile Tyr Tyr Cys
                85                  90                  95

Ala Arg Gly Thr Thr Val Thr Gly Tyr Gly Met Asp Val Trp Gly
            100                 105                 110

Gln Gly Thr Thr Val Thr Val Ser Ser
        115                 120

<210> SEQ ID NO 83
<211> LENGTH: 24
<212> TYPE: DNA
<213> ORGANISM: Artificial Sequence
<220> FEATURE:
<223> OTHER INFORMATION: synthetic

<400> SEQUENCE: 83
ggattcacct ttaacagata tgcc                                          24

<210> SEQ ID NO 84
<211> LENGTH: 8
<212> TYPE: PRT
<213> ORGANISM: Artificial Sequence
<220> FEATURE:
<223> OTHER INFORMATION: synthetic

<400> SEQUENCE: 84

Gly Phe Thr Phe Asn Arg Tyr Ala
1               5

<210> SEQ ID NO 85
<211> LENGTH: 24
<212> TYPE: DNA
<213> ORGANISM: Artificial Sequence
<220> FEATURE:
<223> OTHER INFORMATION: synthetic

<400> SEQUENCE: 85
ataagtggta gtggtagcag caca                                          24

<210> SEQ ID NO 86
<211> LENGTH: 8
<212> TYPE: PRT
<213> ORGANISM: Artificial Sequence
<220> FEATURE:
<223> OTHER INFORMATION: synthetic

<400> SEQUENCE: 86

Ile Ser Gly Ser Gly Ser Ser Thr
```

<210> SEQ ID NO 87
<211> LENGTH: 42
<212> TYPE: DNA
<213> ORGANISM: Artificial Sequence
<220> FEATURE:
<223> OTHER INFORMATION: synthetic

<400> SEQUENCE: 87

```
gcgagaggga ctacagtcac tacggggtac ggtatggacg tc                              42
```

<210> SEQ ID NO 88
<211> LENGTH: 14
<212> TYPE: PRT
<213> ORGANISM: Artificial Sequence
<220> FEATURE:
<223> OTHER INFORMATION: synthetic

<400> SEQUENCE: 88

Ala Arg Gly Thr Thr Val Thr Thr Gly Tyr Gly Met Asp Val
1               5                   10

<210> SEQ ID NO 89
<211> LENGTH: 321
<212> TYPE: DNA
<213> ORGANISM: Artificial Sequence
<220> FEATURE:
<223> OTHER INFORMATION: synthetic

<400> SEQUENCE: 89

```
gacatccaga tgacccagtc tccatcctcc ctgtctgcat ctgtaggaga cagagtcacc          60
ttcacttgcc aggcgagtca ggacattacc aattctttaa attggtatca acagaaacct        120
gggagagccc ctaagctcct gatctacgat gcatcgtatt tgaaggcagg ggtcccatca        180
agattcagtg gaagtggatc tgggacagat tttactttca ccatcagcag cctgcagcct        240
gaagatattg caacatatta ctgtcaacaa tatgatgatc tcccatacac ttttggccag        300
gggaccaagc tggagatcaa a                                                   321
```

<210> SEQ ID NO 90
<211> LENGTH: 107
<212> TYPE: PRT
<213> ORGANISM: Artificial Sequence
<220> FEATURE:
<223> OTHER INFORMATION: synthetic

<400> SEQUENCE: 90

Asp Ile Gln Met Thr Gln Ser Pro Ser Ser Leu Ser Ala Ser Val Gly
1               5                   10                  15

Asp Arg Val Thr Phe Thr Cys Gln Ala Ser Gln Asp Ile Thr Asn Ser
            20                  25                  30

Leu Asn Trp Tyr Gln Gln Lys Pro Gly Arg Ala Pro Lys Leu Leu Ile
        35                  40                  45

Tyr Asp Ala Ser Tyr Leu Lys Ala Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asp Leu Pro Tyr
                85                  90                  95

Thr Phe Gly Gln Gly Thr Lys Leu Glu Ile Lys
            100                 105

<210> SEQ ID NO 91
<211> LENGTH: 18
<212> TYPE: DNA
<213> ORGANISM: Artificial Sequence
<220> FEATURE:
<223> OTHER INFORMATION: synthetic

<400> SEQUENCE: 91
caggacatta ccaattct                                                 18

<210> SEQ ID NO 92
<211> LENGTH: 6
<212> TYPE: PRT
<213> ORGANISM: Artificial Sequence
<220> FEATURE:
<223> OTHER INFORMATION: synthetic

<400> SEQUENCE: 92

Gln Asp Ile Thr Asn Ser
1               5

<210> SEQ ID NO 93
<211> LENGTH: 9
<212> TYPE: DNA
<213> ORGANISM: Artificial Sequence
<220> FEATURE:
<223> OTHER INFORMATION: synthetic

<400> SEQUENCE: 93 gatgcatcg                                                            9

<210> SEQ ID NO 94
<211> LENGTH: 3
<212> TYPE: PRT
<213> ORGANISM: Artificial Sequence
<220> FEATURE:
<223> OTHER INFORMATION: synthetic

<400> SEQUENCE: 94

Asp Ala Ser
1

<210> SEQ ID NO 95
<211> LENGTH: 27
<212> TYPE: DNA
<213> ORGANISM: Artificial Sequence
<220> FEATURE:
<223> OTHER INFORMATION: synthetic

<400> SEQUENCE: 95
caacaatatg atgatctccc atacact                                        27

<210> SEQ ID NO 96
<211> LENGTH: 9
<212> TYPE: PRT
<213> ORGANISM: Artificial Sequence
<220> FEATURE:
<223> OTHER INFORMATION: synthetic

<400> SEQUENCE: 96

Gln Gln Tyr Asp Asp Leu Pro Tyr Thr
1               5

<210> SEQ ID NO 97
<211> LENGTH: 360

<212> TYPE: DNA
<213> ORGANISM: Artificial Sequence
<220> FEATURE:
<223> OTHER INFORMATION: synthetic

<400> SEQUENCE: 97

```
caggtgcagc tgcaggagtc gggcccagga ctggtgaagc cttcggagac cctgtccctc      60
acctgcactg tctctggtga ctccgtcagt agttcctact ggacctggat ccggcagccc     120
ccagggaagg gactggagtg gattggctat atctattaca gtgggagttc caactacaac     180
ccctccctca agagtcgagc caccatttca gtagacacgt ccaagaacca gttctccctg     240
aagctgagtt ctgtgaccgc tgcggacacg gccgtatatt actgtgcgag agaagggaac     300
gtggatacaa ctatgatatt tgactactgg ggccagggaa ccctggtcac cgtctcctca     360
```

<210> SEQ ID NO 98
<211> LENGTH: 120
<212> TYPE: PRT
<213> ORGANISM: Artificial Sequence
<220> FEATURE:
<223> OTHER INFORMATION: synthetic

<400> SEQUENCE: 98

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Asp Ser Val Ser Ser
            20                  25                  30
Tyr Trp Thr Trp Ile Arg Gln Pro Pro Gly Lys Gly Leu Glu Trp Ile
        35                  40                  45
Gly Tyr Ile Tyr Tyr Ser Gly Ser Ser Asn Tyr Asn Pro Ser Leu Lys
    50                  55                  60
Ser Arg Ala Thr Ile Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Arg Glu Gly Asn Val Asp Thr Thr Met Ile Phe Asp Tyr Trp Gly Gln
            100                 105                 110
Gly Thr Leu Val Thr Val Ser Ser
        115                 120
```

<210> SEQ ID NO 99
<211> LENGTH: 24
<212> TYPE: DNA
<213> ORGANISM: Artificial Sequence
<220> FEATURE:
<223> OTHER INFORMATION: synthetic

<400> SEQUENCE: 99

```
ggtgactccg tcagtagttc ctac                                             24
```

<210> SEQ ID NO 100
<211> LENGTH: 8
<212> TYPE: PRT
<213> ORGANISM: Artificial Sequence
<220> FEATURE:
<223> OTHER INFORMATION: synthetic

<400> SEQUENCE: 100

```
Gly Asp Ser Val Ser Ser Ser Tyr
1               5
```

```
<210> SEQ ID NO 101
<211> LENGTH: 21
<212> TYPE: DNA
<213> ORGANISM: Artificial Sequence
<220> FEATURE:
<223> OTHER INFORMATION: synthetic

<400> SEQUENCE: 101
atctattaca gtgggagttc c                                              21

<210> SEQ ID NO 102
<211> LENGTH: 7
<212> TYPE: PRT
<213> ORGANISM: Artificial Sequence
<220> FEATURE:
<223> OTHER INFORMATION: synthetic

<400> SEQUENCE: 102

Ile Tyr Tyr Ser Gly Ser Ser
1               5

<210> SEQ ID NO 103
<211> LENGTH: 42
<212> TYPE: DNA
<213> ORGANISM: Artificial Sequence
<220> FEATURE:
<223> OTHER INFORMATION: synthetic

<400> SEQUENCE: 103
gcgagagaag ggaacgtgga tacaactatg atatttgact ac                       42

<210> SEQ ID NO 104
<211> LENGTH: 14
<212> TYPE: PRT
<213> ORGANISM: Artificial Sequence
<220> FEATURE:
<223> OTHER INFORMATION: synthetic

<400> SEQUENCE: 104

Ala Arg Glu Gly Asn Val Asp Thr Thr Met Ile Phe Asp Tyr
1               5                   10

<210> SEQ ID NO 105
<211> LENGTH: 321
<212> TYPE: DNA
<213> ORGANISM: Artificial Sequence
<220> FEATURE:
<223> OTHER INFORMATION: synthetic

<400> SEQUENCE: 105
gccatccaga tgacccagtc tccatcctcc ctgtctgcat ctgtaggaga cagagtcacc    60
atcacttgcc gggcaagtca gggcattaga aatgatttag ctggtatca acagaaacca    120 gggaaagccc ctaaactcct gatctatgct gcatccagtt tacaaagtgg ggtcccatcg   180
aggttcgccg gccgtggatc tggcacagat ttcactctca ccatcagcag cctgcagcct   240
gaagattttg caactt atta ctgtctacaa gatttcaatt acccgtggac gttcggccaa   300
gggaccaagg tggaaatcaa a                                             321

<210> SEQ ID NO 106
<211> LENGTH: 107
<212> TYPE: PRT
<213> ORGANISM: Artificial Sequence
<220> FEATURE:
<223> OTHER INFORMATION: synthetic
```

```
<400> SEQUENCE: 106

Ala Ile Gln Met Thr Gln Ser Pro Ser Ser Leu Ser Ala Ser Val Gly
1               5                  10                 15

Asp Arg Val Thr Ile Thr Cys Arg Ala Ser Gln Gly Ile Arg Asn Asp
            20                  25                 30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ala Gly
50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Phe Asn Tyr Pro Trp
                85                  90                  95

Thr Phe Gly Gln Gly Thr Lys Val Glu Ile Lys
            100                 105

<210> SEQ ID NO 107
<211> LENGTH: 18
<212> TYPE: DNA
<213> ORGANISM: Artificial Sequence
<220> FEATURE:
<223> OTHER INFORMATION: synthetic

<400> SEQUENCE: 107
cagggcatta gaaatgat                                              18

<210> SEQ ID NO 108
<211> LENGTH: 6
<212> TYPE: PRT
<213> ORGANISM: Artificial Sequence
<220> FEATURE:
<223> OTHER INFORMATION: synthetic

<400> SEQUENCE: 108

Gln Gly Ile Arg Asn Asp
1               5

<210> SEQ ID NO 109
<211> LENGTH: 9
<212> TYPE: DNA
<213> ORGANISM: Artificial Sequence
<220> FEATURE:
<223> OTHER INFORMATION: synthetic

<400> SEQUENCE: 109 gctgcatcc                                                         9

<210> SEQ ID NO 110
<211> LENGTH: 3
<212> TYPE: PRT
<213> ORGANISM: Artificial Sequence
<220> FEATURE:
<223> OTHER INFORMATION: synthetic

<400> SEQUENCE: 110

Ala Ala Ser
1

<210> SEQ ID NO 111
<211> LENGTH: 27
<212> TYPE: DNA
<213> ORGANISM: Artificial Sequence
<220> FEATURE:
```

<223> OTHER INFORMATION: synthetic

<400> SEQUENCE: 111
ctacaagatt tcaattaccc gtggacg    27

<210> SEQ ID NO 112
<211> LENGTH: 9
<212> TYPE: PRT
<213> ORGANISM: Artificial Sequence
<220> FEATURE:
<223> OTHER INFORMATION: synthetic

<400> SEQUENCE: 112

Leu Gln Asp Phe Asn Tyr Pro Trp Thr
1               5

<210> SEQ ID NO 113
<211> LENGTH: 321
<212> TYPE: DNA
<213> ORGANISM: Artificial Sequence
<220> FEATURE:
<223> OTHER INFORMATION: synthetic

<400> SEQUENCE: 113
gccatccaga tgacccagtc tccatcctcc ctgtctgcat ctgtaggaga cagagtcacc    60
atcacttgcc gggcaagtca gggcattaga aatgatttag ctggtatca acagaaacca   120 gggaaagccc ctaaactcct gatctatgct gcatccagtt tacaaagtgg ggtcccatcg   180
aggttcgccg gccgtggatc tggcacagat tcactctca ccatcagcag cctgcagcct    240
gaagattttg caacttatta ctgtcatcaa gatttcaatt acccgtggac gttcggccaa   300
gggaccaagg tggaaatcaa a                                              321

<210> SEQ ID NO 114
<211> LENGTH: 107
<212> TYPE: PRT
<213> ORGANISM: Artificial Sequence
<220> FEATURE:
<223> OTHER INFORMATION: synthetic

<400> SEQUENCE: 114

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ala Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys His Gln Asp Phe Asn Tyr Pro Trp
                85                  90                  95

Thr Phe Gly Gln Gly Thr Lys Val Glu Ile Lys
            100                 105

<210> SEQ ID NO 115
<211> LENGTH: 18
<212> TYPE: DNA
<213> ORGANISM: Artificial Sequence
<220> FEATURE:
<223> OTHER INFORMATION: synthetic

```
<400> SEQUENCE: 115
cagggcatta gaaatgat                                              18

<210> SEQ ID NO 116
<211> LENGTH: 6
<212> TYPE: PRT
<213> ORGANISM: Artificial Sequence
<220> FEATURE:
<223> OTHER INFORMATION: synthetic

<400> SEQUENCE: 116

Gln Gly Ile Arg Asn Asp
1               5

<210> SEQ ID NO 117
<211> LENGTH: 9
<212> TYPE: DNA
<213> ORGANISM: Artificial Sequence
<220> FEATURE:
<223> OTHER INFORMATION: synthetic

<400> SEQUENCE: 117 gctgcatcc                                                         9

<210> SEQ ID NO 118
<211> LENGTH: 3
<212> TYPE: PRT
<213> ORGANISM: Artificial Sequence
<220> FEATURE:
<223> OTHER INFORMATION: synthetic

<400> SEQUENCE: 118

Ala Ala Ser
1

<210> SEQ ID NO 119
<211> LENGTH: 27
<212> TYPE: DNA
<213> ORGANISM: Artificial Sequence
<220> FEATURE:
<223> OTHER INFORMATION: synthetic

<400> SEQUENCE: 119
catcaagatt tcaattaccc gtggacg                                    27

<210> SEQ ID NO 120
<211> LENGTH: 9
<212> TYPE: PRT
<213> ORGANISM: Artificial Sequence
<220> FEATURE:
<223> OTHER INFORMATION: synthetic

<400> SEQUENCE: 120

His Gln Asp Phe Asn Tyr Pro Trp Thr
1               5

<210> SEQ ID NO 121
<211> LENGTH: 360
<212> TYPE: DNA
<213> ORGANISM: Artificial Sequence
<220> FEATURE:
<223> OTHER INFORMATION: synthetic

<400> SEQUENCE: 121
caggtgcagc tgcaggagtc gggcccagga ctggtgaagc cttcggagac cctgtccctc    60
```

```
acctgcactg tctctggtga ctccgtcagt agttcctact ggacctggat ccggcagccc    120
ccagggaagg gactggagtg gattggctat atctattaca gtgggagttc caactacaac    180
ccctccctca agagtcgagc caccatttca gtagacacgt ccaagaacca gttctccctg    240
aagctgagtt ctgtgaccgc tgcggacacg gccgtatatt actgtgcgag agaacataac    300
gtggatacaa ctatgatatt tgactactgg ggccagggaa ccctggtcac cgtctcctca    360
```

<210> SEQ ID NO 122
<211> LENGTH: 120
<212> TYPE: PRT
<213> ORGANISM: Artificial Sequence
<220> FEATURE:
<223> OTHER INFORMATION: synthetic

<400> SEQUENCE: 122

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Val Ser Ser Ser
            20                  25                  30

Tyr Trp Thr Trp Ile Arg Gln Pro Pro Gly Lys Gly Leu Glu Trp Ile
        35                  40                  45

Gly Tyr Ile Tyr Tyr Ser Gly Ser Ser Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu His Asn Val Asp Thr Thr Met Ile Phe Asp Tyr Trp Gly Gln
            100                 105                 110

Gly Thr Leu Val Thr Val Ser Ser
        115                 120

<210> SEQ ID NO 123
<211> LENGTH: 24
<212> TYPE: DNA
<213> ORGANISM: Artificial Sequence
<220> FEATURE:
<223> OTHER INFORMATION: synthetic

<400> SEQUENCE: 123
ggtgactccg tcagtagttc ctac                                            24

<210> SEQ ID NO 124
<211> LENGTH: 8
<212> TYPE: PRT
<213> ORGANISM: Artificial Sequence
<220> FEATURE:
<223> OTHER INFORMATION: synthetic

<400> SEQUENCE: 124

Gly Asp Ser Val Ser Ser Ser Tyr
1               5

<210> SEQ ID NO 125
<211> LENGTH: 21
<212> TYPE: DNA
<213> ORGANISM: Artificial Sequence
<220> FEATURE:
<223> OTHER INFORMATION: synthetic

<400> SEQUENCE: 125

```
atctattaca gtgggagttc c                                              21
```

<210> SEQ ID NO 126
<211> LENGTH: 7
<212> TYPE: PRT
<213> ORGANISM: Artificial Sequence
<220> FEATURE:
<223> OTHER INFORMATION: synthetic

<400> SEQUENCE: 126

Ile Tyr Tyr Ser Gly Ser Ser
1               5

<210> SEQ ID NO 127
<211> LENGTH: 42
<212> TYPE: DNA
<213> ORGANISM: Artificial Sequence
<220> FEATURE:
<223> OTHER INFORMATION: synthetic

<400> SEQUENCE: 127

```
gcgagagaac ataacgtgga tacaactatg atatttgact ac                       42
```

<210> SEQ ID NO 128
<211> LENGTH: 14
<212> TYPE: PRT
<213> ORGANISM: Artificial Sequence
<220> FEATURE:
<223> OTHER INFORMATION: synthetic

<400> SEQUENCE: 128

Ala Arg Glu His Asn Val Asp Thr Thr Met Ile Phe Asp Tyr
1               5                   10

<210> SEQ ID NO 129
<211> LENGTH: 321
<212> TYPE: DNA
<213> ORGANISM: Artificial Sequence
<220> FEATURE:
<223> OTHER INFORMATION: synthetic

<400> SEQUENCE: 129

```
gccatccaga tgacccagtc tccatcctcc ctgtctgcat ctgtaggaga cagagtcacc    60
atcacttgcc gggcaagtca gggcattaga aatgatttag ctggtatca acagaaacca   120
gggaaagccc ctaaactcct gatctatgct gcatccagtt tacaaagtgg ggtcccatcg   180
aggttcgccg gccgtggatc tggcacagat ttcactctca ccatcagcag cctgcagcct   240
gaagattttg caacttatta ctgtctacaa gatttcaatt acccgtggca cttcggccaa   300
gggaccaagg tggaaatcaa a                                             321
```

<210> SEQ ID NO 130
<211> LENGTH: 107
<212> TYPE: PRT
<213> ORGANISM: Artificial Sequence
<220> FEATURE:
<223> OTHER INFORMATION: synthetic

<400> SEQUENCE: 130

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ala Gly
 50                  55                  60

Arg Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Phe Asn Tyr Pro Trp
                 85                  90                  95

His Phe Gly Gln Gly Thr Lys Val Glu Ile Lys
            100                 105

<210> SEQ ID NO 131
<211> LENGTH: 18
<212> TYPE: DNA
<213> ORGANISM: Artificial Sequence
<220> FEATURE:
<223> OTHER INFORMATION: synthetic

<400> SEQUENCE: 131
cagggcatta gaaatgat                                                 18

<210> SEQ ID NO 132
<211> LENGTH: 6
<212> TYPE: PRT
<213> ORGANISM: Artificial Sequence
<220> FEATURE:
<223> OTHER INFORMATION: synthetic

<400> SEQUENCE: 132

Gln Gly Ile Arg Asn Asp
 1               5

<210> SEQ ID NO 133
<211> LENGTH: 9
<212> TYPE: DNA
<213> ORGANISM: Artificial Sequence
<220> FEATURE:
<223> OTHER INFORMATION: synthetic

<400> SEQUENCE: 133 gctgcatcc                                                            9

<210> SEQ ID NO 134
<211> LENGTH: 3
<212> TYPE: PRT
<213> ORGANISM: Artificial Sequence
<220> FEATURE:
<223> OTHER INFORMATION: synthetic

<400> SEQUENCE: 134

Ala Ala Ser
 1

<210> SEQ ID NO 135
<211> LENGTH: 27
<212> TYPE: DNA
<213> ORGANISM: Artificial Sequence
<220> FEATURE:
<223> OTHER INFORMATION: synthetic

<400> SEQUENCE: 135
ctacaagatt tcaattaccc gtggcac                                       27

<210> SEQ ID NO 136

<211> LENGTH: 9
<212> TYPE: PRT
<213> ORGANISM: Artificial Sequence
<220> FEATURE:
<223> OTHER INFORMATION: synthetic

<400> SEQUENCE: 136

Leu Gln Asp Phe Asn Tyr Pro Trp His
1               5

<210> SEQ ID NO 137
<211> LENGTH: 360
<212> TYPE: DNA
<213> ORGANISM: Artificial Sequence
<220> FEATURE:
<223> OTHER INFORMATION: synthetic

<400> SEQUENCE: 137

```
caggtgcagc tgcaggagtc gggcccagga ctggtgaagc cttcggagac cctgtccctc      60
acctgcactg tctctggtga ctccgtcagt agttcctact ggacctggat ccggcagccc     120
ccagggaagg gactggagtg gattggctat atctattaca gtgggagttc aactacaac      180
ccctccctca gagtcgagc caccatttca gtagacacgt ccaagaacca gttctccctg     240
aagctgagtt ctgtgaccgc tgcggacacg gccgtatatt actgtgcgag agaagggaac     300
gtggatacaa ctatgataca tgactactgg ggccagggaa ccctggtcac cgtctcctca     360
```

<210> SEQ ID NO 138
<211> LENGTH: 120
<212> TYPE: PRT
<213> ORGANISM: Artificial Sequence
<220> FEATURE:
<223> OTHER INFORMATION: synthetic

<400> SEQUENCE: 138

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Val Ser Ser Ser
            20                  25                  30

Tyr Trp Thr Trp Ile Arg Gln Pro Pro Gly Lys Gly Leu Glu Trp Ile
        35                  40                  45

Gly Tyr Ile Tyr Tyr Ser Gly Ser Ser Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Asn Val Asp Thr Thr Met Ile His Asp Tyr Trp Gly Gln
            100                 105                 110

Gly Thr Leu Val Thr Val Ser Ser
        115                 120

<210> SEQ ID NO 139
<211> LENGTH: 24
<212> TYPE: DNA
<213> ORGANISM: Artificial Sequence
<220> FEATURE:
<223> OTHER INFORMATION: synthetic

<400> SEQUENCE: 139

```
ggtgactccg tcagtagttc ctac                                              24
```

<210> SEQ ID NO 140
<211> LENGTH: 8
<212> TYPE: PRT
<213> ORGANISM: Artificial Sequence
<220> FEATURE:
<223> OTHER INFORMATION: synthetic

<400> SEQUENCE: 140

Gly Asp Ser Val Ser Ser Ser Tyr
1               5

<210> SEQ ID NO 141
<211> LENGTH: 21
<212> TYPE: DNA
<213> ORGANISM: Artificial Sequence
<220> FEATURE:
<223> OTHER INFORMATION: synthetic

<400> SEQUENCE: 141
atctattaca gtgggagttc c                                           21

<210> SEQ ID NO 142
<211> LENGTH: 7
<212> TYPE: PRT
<213> ORGANISM: Artificial Sequence
<220> FEATURE:
<223> OTHER INFORMATION: synthetic

<400> SEQUENCE: 142

Ile Tyr Tyr Ser Gly Ser Ser
1               5

<210> SEQ ID NO 143
<211> LENGTH: 42
<212> TYPE: DNA
<213> ORGANISM: Artificial Sequence
<220> FEATURE:
<223> OTHER INFORMATION: synthetic

<400> SEQUENCE: 143
gcgagagaag ggaacgtgga tacaactatg atacatgact ac                    42

<210> SEQ ID NO 144
<211> LENGTH: 14
<212> TYPE: PRT
<213> ORGANISM: Artificial Sequence
<220> FEATURE:
<223> OTHER INFORMATION: synthetic

<400> SEQUENCE: 144

Ala Arg Glu Gly Asn Val Asp Thr Thr Met Ile His Asp Tyr
1               5                   10

<210> SEQ ID NO 145
<211> LENGTH: 360
<212> TYPE: DNA
<213> ORGANISM: Artificial Sequence
<220> FEATURE:
<223> OTHER INFORMATION: synthetic

<400> SEQUENCE: 145
caggtgcagc tgcaggagtc gggcccagga ctggtgaagc cttcggagac cctgtccctc    60
acctgcactg tctctggtga ctccgtcagt agttcctact ggacctggat ccggcagccc   120
ccagggaagg gactggagtg gattggctat atctattaca gtgggagttc caactacaac   180

```
ccctccctca agagtcgagc caccatttca gtagacacgt ccaagaacca gttctccctg    240
aagctgagtt ctgtgaccgc tgcggacacg gccgtatatt actgtgcgag agaagggaac    300
gtggatcaca ctatgatatt tgactactgg ggccaggaa ccctggtcac cgtctcctca     360
```

<210> SEQ ID NO 146
<211> LENGTH: 120
<212> TYPE: PRT
<213> ORGANISM: Artificial Sequence
<220> FEATURE:
<223> OTHER INFORMATION: synthetic

<400> SEQUENCE: 146

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Val Ser Ser Ser
            20                  25                  30

Tyr Trp Thr Trp Ile Arg Gln Pro Pro Gly Lys Gly Leu Glu Trp Ile
        35                  40                  45

Gly Tyr Ile Tyr Tyr Ser Gly Ser Ser Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Asn Val Asp His Thr Met Ile Phe Asp Tyr Trp Gly Gln
            100                 105                 110

Gly Thr Leu Val Thr Val Ser Ser
        115                 120

<210> SEQ ID NO 147
<211> LENGTH: 24
<212> TYPE: DNA
<213> ORGANISM: Artificial Sequence
<220> FEATURE:
<223> OTHER INFORMATION: synthetic

<400> SEQUENCE: 147
ggtgactccg tcagtagttc ctac                                            24

<210> SEQ ID NO 148
<211> LENGTH: 8
<212> TYPE: PRT
<213> ORGANISM: Artificial Sequence
<220> FEATURE:
<223> OTHER INFORMATION: synthetic

<400> SEQUENCE: 148

Gly Asp Ser Val Ser Ser Ser Tyr
1               5

<210> SEQ ID NO 149
<211> LENGTH: 21
<212> TYPE: DNA
<213> ORGANISM: Artificial Sequence
<220> FEATURE:
<223> OTHER INFORMATION: synthetic

<400> SEQUENCE: 149
atctattaca gtgggagttc c                                               21

<210> SEQ ID NO 150

```
<211> LENGTH: 7
<212> TYPE: PRT
<213> ORGANISM: Artificial Sequence
<220> FEATURE:
<223> OTHER INFORMATION: synthetic

<400> SEQUENCE: 150

Ile Tyr Tyr Ser Gly Ser Ser
1               5

<210> SEQ ID NO 151
<211> LENGTH: 42
<212> TYPE: DNA
<213> ORGANISM: Artificial Sequence
<220> FEATURE:
<223> OTHER INFORMATION: synthetic

<400> SEQUENCE: 151
gcgagagaag ggaacgtgga tcacactatg atatttgact ac                      42

<210> SEQ ID NO 152
<211> LENGTH: 14
<212> TYPE: PRT
<213> ORGANISM: Artificial Sequence
<220> FEATURE:
<223> OTHER INFORMATION: synthetic

<400> SEQUENCE: 152

Ala Arg Glu Gly Asn Val Asp His Thr Met Ile Phe Asp Tyr
1               5                   10

<210> SEQ ID NO 153
<211> LENGTH: 360
<212> TYPE: DNA
<213> ORGANISM: Artificial Sequence
<220> FEATURE:
<223> OTHER INFORMATION: synthetic

<400> SEQUENCE: 153
caggtgcagc tggtggagtc tgggggaggc ttggtcaagc ctggagggtc cctgagactc    60
tcctgtgcag cctctggatt caccttcagt gactcctaca tgtcctggat ccgtcaggct   120
ccagggaagg gactagagtg gatttcatac attggtagta gtggtaatac cttttactac   180
gcagactctg tgaagggccg gttcaccatt tccagagaca cgccaacaa tttactgtat    240 ctgcaaatga ccagcctgag agccgaggac acggccgtgt attactgtgc gagagaagaa   300
ggcgattttt ggagtgccgt tgactcctgg ggccagggaa ccctggtcac cgtctcctca   360

<210> SEQ ID NO 154
<211> LENGTH: 120
<212> TYPE: PRT
<213> ORGANISM: Artificial Sequence
<220> FEATURE:
<223> OTHER INFORMATION: synthetic

<400> SEQUENCE: 154

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Tyr Met Ser Trp Ile Arg Gln Ala Pro Gly Lys Gly Leu Glu Trp Ile
        35                  40                  45

Ser Tyr Ile Gly Ser Ser Gly Asn Thr Phe Tyr Tyr Ala Asp Ser Val
    50                  55                  60
```

```
Lys Gly Arg Phe Thr Ile Ser Arg Asp Asn Ala Asn Leu Leu Tyr
 65                  70                  75                  80

Leu Gln Met Thr Ser Leu Arg Ala Glu Asp Thr Ala Val Tyr Tyr Cys
                 85                  90                  95

Ala Arg Glu Glu Gly Asp Phe Trp Ser Ala Val Asp Trp Gly Gln
            100                 105                 110

Gly Thr Leu Val Thr Val Ser Ser
        115                 120

<210> SEQ ID NO 155
<211> LENGTH: 24
<212> TYPE: DNA
<213> ORGANISM: Artificial Sequence
<220> FEATURE:
<223> OTHER INFORMATION: synthetic

<400> SEQUENCE: 155
ggattcacct tcagtgactc ctac                                            24

<210> SEQ ID NO 156
<211> LENGTH: 8
<212> TYPE: PRT
<213> ORGANISM: Artificial Sequence
<220> FEATURE:
<223> OTHER INFORMATION: synthetic

<400> SEQUENCE: 156

Gly Phe Thr Phe Ser Asp Ser Tyr
 1               5

<210> SEQ ID NO 157
<211> LENGTH: 24
<212> TYPE: DNA
<213> ORGANISM: Artificial Sequence
<220> FEATURE:
<223> OTHER INFORMATION: synthetic

<400> SEQUENCE: 157
attggtagta gtggtaatac cttt                                            24

<210> SEQ ID NO 158
<211> LENGTH: 8
<212> TYPE: PRT
<213> ORGANISM: Artificial Sequence
<220> FEATURE:
<223> OTHER INFORMATION: synthetic

<400> SEQUENCE: 158

Ile Gly Ser Ser Gly Asn Thr Phe
 1               5

<210> SEQ ID NO 159
<211> LENGTH: 39
<212> TYPE: DNA
<213> ORGANISM: Artificial Sequence
<220> FEATURE:
<223> OTHER INFORMATION: synthetic

<400> SEQUENCE: 159
gcgagagaag aaggcgattt ttggagtgcc gttgactcc                            39

<210> SEQ ID NO 160
<211> LENGTH: 13
<212> TYPE: PRT
```

<213> ORGANISM: Artificial Sequence
<220> FEATURE:
<223> OTHER INFORMATION: synthetic

<400> SEQUENCE: 160

Ala Arg Glu Glu Gly Asp Phe Trp Ser Ala Val Asp Ser
1               5                   10

<210> SEQ ID NO 161
<211> LENGTH: 321
<212> TYPE: DNA
<213> ORGANISM: Artificial Sequence
<220> FEATURE:
<223> OTHER INFORMATION: synthetic

<400> SEQUENCE: 161

```
gacatccagt tgacccagtc tccatccttc ctgtctgcat ctgtaggaga cagagtcacc      60
atcacttgct gggccagtca gggcattagc agttatttag cctggtatca gcaaaaacca     120
ggtaaagccc ctaaactcct gatccatact gcatccactt tgcaaagtgg ggtcccatca     180
aggttcagcg gcagtggatc tgggacagaa ttcactctca caatcagcaa cctgcagcct     240
gaagattttg caacttatta ctgtcaacag cttaatagtt acccattcac tttcggccct     300
gggaccaaag tggatatcaa a                                               321
```

<210> SEQ ID NO 162
<211> LENGTH: 107
<212> TYPE: PRT
<213> ORGANISM: Artificial Sequence
<220> FEATURE:
<223> OTHER INFORMATION: synthetic

<400> SEQUENCE: 162

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

His Thr Ala Ser Thr Leu Gln Ser Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Gln Gln Leu Asn Ser Tyr Pro Phe
                85                  90                  95

Thr Phe Gly Pro Gly Thr Lys Val Asp Ile Lys
            100                 105

<210> SEQ ID NO 163
<211> LENGTH: 18
<212> TYPE: DNA
<213> ORGANISM: Artificial Sequence
<220> FEATURE:
<223> OTHER INFORMATION: synthetic

<400> SEQUENCE: 163
cagggcatta gcagttat                                                    18

<210> SEQ ID NO 164
<211> LENGTH: 6
<212> TYPE: PRT
<213> ORGANISM: Artificial Sequence
<220> FEATURE:
<223> OTHER INFORMATION: synthetic

<400> SEQUENCE: 164

Gln Gly Ile Ser Ser Tyr
1               5

<210> SEQ ID NO 165
<211> LENGTH: 9
<212> TYPE: DNA
<213> ORGANISM: Artificial Sequence
<220> FEATURE:
<223> OTHER INFORMATION: synthetic

<400> SEQUENCE: 165 actgcatcc                                                              9

<210> SEQ ID NO 166
<211> LENGTH: 3
<212> TYPE: PRT
<213> ORGANISM: Artificial Sequence
<220> FEATURE:
<223> OTHER INFORMATION: synthetic

<400> SEQUENCE: 166

Thr Ala Ser
1

<210> SEQ ID NO 167
<211> LENGTH: 27
<212> TYPE: DNA
<213> ORGANISM: Artificial Sequence
<220> FEATURE:
<223> OTHER INFORMATION: synthetic

<400> SEQUENCE: 167
caacagctta atagttaccc attcact                                         27

<210> SEQ ID NO 168
<211> LENGTH: 9
<212> TYPE: PRT
<213> ORGANISM: Artificial Sequence
<220> FEATURE:
<223> OTHER INFORMATION: synthetic

<400> SEQUENCE: 168

Gln Gln Leu Asn Ser Tyr Pro Phe Thr
1               5

<210> SEQ ID NO 169
<211> LENGTH: 366
<212> TYPE: DNA
<213> ORGANISM: Artificial Sequence
<220> FEATURE:
<223> OTHER INFORMATION: synthetic

<400> SEQUENCE: 169
caggtgcagc tggtggagtc tgggggaggc gtggtccagc ctgggggtc cctgagactc        60 tcctgtgcag cctctggatt caccttcggt ggccatgcca tgcactgggt ccgccaggct      120
ccaggcaagg ggctggagtg gctggcagtt atatcatctg atggcagtaa taaacagtat      180
gcagattctg tgaagggccg attcaccatc tccagggaca atcccaagaa cacgctgtat      240
ctgcaaatga acagtctgag agttggggac acggctattt attactgtgc gaaagaggtg      300
gcacctcgtt attattatta cggtctggac gtctggggcc aagggaccac ggtcaccgtc      360
tcctca 366

```
<210> SEQ ID NO 170
<211> LENGTH: 122
<212> TYPE: PRT
<213> ORGANISM: Artificial Sequence
<220> FEATURE:
<223> OTHER INFORMATION: synthetic

<400> SEQUENCE: 170
```

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Gly Gly His
            20                  25                  30

Ala Met His Trp Val Arg Gln Ala Pro Gly Lys Gly Leu Glu Trp Leu
        35                  40                  45

Ala Val Ile Ser Ser Asp Gly Ser Asn Lys Gln Tyr Ala Asp Ser Val
    50                  55                  60

Lys Gly Arg Phe Thr Ile Ser Arg Asp Asn Pro Lys Asn Thr Leu Tyr
65                  70                  75                  80

Leu Gln Met Asn Ser Leu Arg Val Gly Asp Thr Ala Ile Tyr Tyr Cys
                85                  90                  95

Ala Lys Glu Val Ala Pro Arg Tyr Tyr Tyr Gly Leu Asp Val Trp
            100                 105                 110

Gly Gln Gly Thr Thr Val Thr Val Ser Ser
        115                 120

```
<210> SEQ ID NO 171
<211> LENGTH: 24
<212> TYPE: DNA
<213> ORGANISM: Artificial Sequence
<220> FEATURE:
<223> OTHER INFORMATION: synthetic

<400> SEQUENCE: 171
```
ggattcacct tcggtggcca tgcc                                          24

```
<210> SEQ ID NO 172
<211> LENGTH: 8
<212> TYPE: PRT
<213> ORGANISM: Artificial Sequence
<220> FEATURE:
<223> OTHER INFORMATION: synthetic

<400> SEQUENCE: 172
```

Gly Phe Thr Phe Gly Gly His Ala
1               5

```
<210> SEQ ID NO 173
<211> LENGTH: 24
<212> TYPE: DNA
<213> ORGANISM: Artificial Sequence
<220> FEATURE:
<223> OTHER INFORMATION: synthetic

<400> SEQUENCE: 173
```
atatcatctg atggcagtaa taaa                                          24

```
<210> SEQ ID NO 174
<211> LENGTH: 8
<212> TYPE: PRT
<213> ORGANISM: Artificial Sequence
```

<220> FEATURE:
<223> OTHER INFORMATION: synthetic

<400> SEQUENCE: 174

Ile Ser Ser Asp Gly Ser Asn Lys
1               5

<210> SEQ ID NO 175
<211> LENGTH: 45
<212> TYPE: DNA
<213> ORGANISM: Artificial Sequence
<220> FEATURE:
<223> OTHER INFORMATION: synthetic

<400> SEQUENCE: 175
gcgaaagagg tggcacctcg ttattattat tacggtctgg acgtc          45

<210> SEQ ID NO 176
<211> LENGTH: 15
<212> TYPE: PRT
<213> ORGANISM: Artificial Sequence
<220> FEATURE:
<223> OTHER INFORMATION: synthetic

<400> SEQUENCE: 176

Ala Lys Glu Val Ala Pro Arg Tyr Tyr Tyr Tyr Gly Leu Asp Val
1               5                   10                  15

<210> SEQ ID NO 177
<211> LENGTH: 318
<212> TYPE: DNA
<213> ORGANISM: Artificial Sequence
<220> FEATURE:
<223> OTHER INFORMATION: synthetic

<400> SEQUENCE: 177
gacatccaga tgacccagtc tccatcctcc ctgtctgcat ctgtgggaga cagagtcacc     60
atcacttgcc gggcgagtca ggacattagc aatttttag cctggtatca gcagaaacca    120
gggaaggttc ctaaactcct gatctatact gcatccactt tacaatcagg ggtcccatct   180
cggttcagtg gcagtggatc tgggacagat ttcactctca ccgtcagcag cctacagcct   240
gaagatgttg caacttatta ctgtcaaaag tatgccggcg ccctcacttt cggccctggg   300
accaaagtgg atatcaaa                                                 318

<210> SEQ ID NO 178
<211> LENGTH: 106
<212> TYPE: PRT
<213> ORGANISM: Artificial Sequence
<220> FEATURE:
<223> OTHER INFORMATION: synthetic

<400> SEQUENCE: 178

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Phe
                20                  25                  30

Leu Ala Trp Tyr Gln Gln Lys Pro Gly Lys Val Pro Lys Leu Leu Ile
            35                  40                  45

Tyr Thr Ala Ser Thr Leu Gln Ser Gly Val Pro Ser Arg Phe Ser Gly
        50                  55                  60

Ser Gly Ser Gly Thr Asp Phe Thr Leu Thr Val Ser Ser Leu Gln Pro
65                  70                  75                  80

Glu Asp Val Ala Thr Tyr Tyr Cys Gln Lys Tyr Ala Gly Ala Leu Thr
            85                  90                  95

Phe Gly Pro Gly Thr Lys Val Asp Ile Lys
        100                 105

<210> SEQ ID NO 179
<211> LENGTH: 18
<212> TYPE: DNA
<213> ORGANISM: Artificial Sequence
<220> FEATURE:
<223> OTHER INFORMATION: synthetic

<400> SEQUENCE: 179
caggacatta gcaatttt                                           18

<210> SEQ ID NO 180
<211> LENGTH: 6
<212> TYPE: PRT
<213> ORGANISM: Artificial Sequence
<220> FEATURE:
<223> OTHER INFORMATION: synthetic

<400> SEQUENCE: 180

Gln Asp Ile Ser Asn Phe
1               5

<210> SEQ ID NO 181
<211> LENGTH: 9
<212> TYPE: DNA
<213> ORGANISM: Artificial Sequence
<220> FEATURE:
<223> OTHER INFORMATION: synthetic

<400> SEQUENCE: 181 actgcatcc                                                      9

<210> SEQ ID NO 182
<211> LENGTH: 3
<212> TYPE: PRT
<213> ORGANISM: Artificial Sequence
<220> FEATURE:
<223> OTHER INFORMATION: synthetic

<400> SEQUENCE: 182

Thr Ala Ser
1

<210> SEQ ID NO 183
<211> LENGTH: 24
<212> TYPE: DNA
<213> ORGANISM: Artificial Sequence
<220> FEATURE:
<223> OTHER INFORMATION: synthetic

<400> SEQUENCE: 183
caaaagtatg ccggcgccct cact                                    24

<210> SEQ ID NO 184
<211> LENGTH: 8
<212> TYPE: PRT
<213> ORGANISM: Artificial Sequence
<220> FEATURE:
<223> OTHER INFORMATION: synthetic

<400> SEQUENCE: 184

Gln Lys Tyr Ala Gly Ala Leu Thr
1               5

<210> SEQ ID NO 185
<211> LENGTH: 357
<212> TYPE: DNA
<213> ORGANISM: Artificial Sequence
<220> FEATURE:
<223> OTHER INFORMATION: synthetic

<400> SEQUENCE: 185
gaggtgcagc tggtggagtc tgggggaggc ttggcacagc ctgggggtc cctgagactc      60 tcctgtgcag cctctggatt cacgtttaga agctatgcca tgagctgggt ccgccaggct    120
ccagggaagg ggccggagtg ggtctcaggt ataggtggta atggtgttac cacatactac    180
gcagactccg tgaagggccg gttcaccatc tccagagaca attccaagaa cacgctgttt    240
ctgcaaatga atagcctgag agccgaggac acggccgtat attattgtgt gcagggggt     300 ttaggtggtt attttacagg ctactgggc cagggaaccc tggtcaccgt ctcctca        357

<210> SEQ ID NO 186
<211> LENGTH: 119
<212> TYPE: PRT
<213> ORGANISM: Artificial Sequence
<220> FEATURE:
<223> OTHER INFORMATION: synthetic

<400> SEQUENCE: 186

Glu Val Gln Leu Val Glu Ser Gly Gly Gly Leu Ala Gln Pro Gly Gly
1               5                   10                  15

Ser Leu Arg Leu Ser Cys Ala Ala Ser Gly Phe Thr Phe Arg Ser Tyr
            20                  25                  30

Ala Met Ser Trp Val Arg Gln Ala Pro Gly Lys Gly Pro Glu Trp Val
        35                  40                  45

Ser Gly Ile Gly Gly Asn Gly Val Thr Thr Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Val Gln Gly Gly Leu Gly Gly Tyr Phe Thr Gly Tyr Trp Gly Gln Gly
            100                 105                 110

Thr Leu Val Thr Val Ser Ser
        115

<210> SEQ ID NO 187
<211> LENGTH: 24
<212> TYPE: DNA
<213> ORGANISM: Artificial Sequence
<220> FEATURE:
<223> OTHER INFORMATION: synthetic

<400> SEQUENCE: 187
ggattcacgt ttagaagcta tgcc      24

<210> SEQ ID NO 188
<211> LENGTH: 8
<212> TYPE: PRT
<213> ORGANISM: Artificial Sequence
<220> FEATURE:
<223> OTHER INFORMATION: synthetic

<400> SEQUENCE: 188

Gly Phe Thr Phe Arg Ser Tyr Ala
1               5

<210> SEQ ID NO 189
<211> LENGTH: 24
<212> TYPE: DNA
<213> ORGANISM: Artificial Sequence
<220> FEATURE:
<223> OTHER INFORMATION: synthetic

<400> SEQUENCE: 189
ataggtggta atggtgttac caca                                          24

<210> SEQ ID NO 190
<211> LENGTH: 8
<212> TYPE: PRT
<213> ORGANISM: Artificial Sequence
<220> FEATURE:
<223> OTHER INFORMATION: synthetic

<400> SEQUENCE: 190

Ile Gly Gly Asn Gly Val Thr Thr
1               5

<210> SEQ ID NO 191
<211> LENGTH: 36
<212> TYPE: DNA
<213> ORGANISM: Artificial Sequence
<220> FEATURE:
<223> OTHER INFORMATION: synthetic

<400> SEQUENCE: 191
gtgcaggggg gtttaggtgg ttattttaca ggctac                             36

<210> SEQ ID NO 192
<211> LENGTH: 12
<212> TYPE: PRT
<213> ORGANISM: Artificial Sequence
<220> FEATURE:
<223> OTHER INFORMATION: synthetic

<400> SEQUENCE: 192

Val Gln Gly Gly Leu Gly Gly Tyr Phe Thr Gly Tyr
1               5                   10

<210> SEQ ID NO 193
<211> LENGTH: 321
<212> TYPE: DNA
<213> ORGANISM: Artificial Sequence
<220> FEATURE:
<223> OTHER INFORMATION: synthetic

<400> SEQUENCE: 193
gacatccaga tgacccagtc tccatcctcc ctgtctgcat ctgtaggaga cagagtcacc    60
atcacttgcc gggcaagtca gagtattagt acctatttaa attggtatca gcagaatcca   120
gggaaagccc ctaaactcct gatctttgat gcatccagtt tgcaaagtgg ggtcccatca   180
aggttcagtg gcagtggatc tgggacagat ttcactctca ccatcagagg tctgcaacct   240
gaagattttg caacttacta ctgtcaacag agttacagtg ccccgctcac tttcggcgga   300
gggaccaagg tggagatcaa a                                            321

<210> SEQ ID NO 194

```
<211> LENGTH: 107
<212> TYPE: PRT
<213> ORGANISM: Artificial Sequence
<220> FEATURE:
<223> OTHER INFORMATION: synthetic

<400> SEQUENCE: 194

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Asn Pro Gly Lys Ala Pro Lys Leu Leu Ile
        35                  40                  45

Phe Asp Ala Ser Ser Leu Gln Ser Gly Val Pro Ser Arg Phe Ser Gly
    50                  55                  60

Ser Gly Ser Gly Thr Asp Phe Thr Leu Thr Ile Arg Gly Leu Gln Pro
65                  70                  75                  80

Glu Asp Phe Ala Thr Tyr Tyr Cys Gln Gln Ser Tyr Ser Ala Pro Leu
                85                  90                  95

Thr Phe Gly Gly Gly Thr Lys Val Glu Ile Lys
            100                 105

<210> SEQ ID NO 195
<211> LENGTH: 18
<212> TYPE: DNA
<213> ORGANISM: Artificial Sequence
<220> FEATURE:
<223> OTHER INFORMATION: synthetic

<400> SEQUENCE: 195
cagagtatta gtacctat                                                      18

<210> SEQ ID NO 196
<211> LENGTH: 6
<212> TYPE: PRT
<213> ORGANISM: Artificial Sequence
<220> FEATURE:
<223> OTHER INFORMATION: synthetic

<400> SEQUENCE: 196

Gln Ser Ile Ser Thr Tyr
1               5

<210> SEQ ID NO 197
<211> LENGTH: 9
<212> TYPE: DNA
<213> ORGANISM: Artificial Sequence
<220> FEATURE:
<223> OTHER INFORMATION: synthetic

<400> SEQUENCE: 197 gatgcatcc                                                                 9

<210> SEQ ID NO 198
<211> LENGTH: 3
<212> TYPE: PRT
<213> ORGANISM: Artificial Sequence
<220> FEATURE:
<223> OTHER INFORMATION: synthetic

<400> SEQUENCE: 198

Asp Ala Ser
1
```

<210> SEQ ID NO 199
<211> LENGTH: 27
<212> TYPE: DNA
<213> ORGANISM: Artificial Sequence
<220> FEATURE:
<223> OTHER INFORMATION: synthetic

<400> SEQUENCE: 199
caacagagtt acagtgcccc gctcact                                         27

<210> SEQ ID NO 200
<211> LENGTH: 9
<212> TYPE: PRT
<213> ORGANISM: Artificial Sequence
<220> FEATURE:
<223> OTHER INFORMATION: synthetic

<400> SEQUENCE: 200

Gln Gln Ser Tyr Ser Ala Pro Leu Thr
1               5

<210> SEQ ID NO 201
<211> LENGTH: 357
<212> TYPE: DNA
<213> ORGANISM: Artificial Sequence
<220> FEATURE:
<223> OTHER INFORMATION: synthetic

<400> SEQUENCE: 201
caggtgcagc tggtggagtc tgggggaggc gtggtccagc ctggggaggtc cctgagactc     60 tcctgtgcag cgtctggatt caccttcagt ggttatggca tgcactgggt ccgccaggct    120
ccaggcaagg gctggagtg gtggcactt atatggcttg atggaagtaa tgactactat    180
gcagactccg tgaagggccg attcaccatc tccagagaca attccaagaa cacgttatat    240
ctgcaaatga acagactgag agccgaggac acggctgtgt attactgtgc gagagatggc    300
ccggttgctg ctatacccga ctactggggc cagggaaccc tggtcaccgt ctcctca      357

<210> SEQ ID NO 202
<211> LENGTH: 119
<212> TYPE: PRT
<213> ORGANISM: Artificial Sequence
<220> FEATURE:
<223> OTHER INFORMATION: synthetic

<400> SEQUENCE: 202

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Gly Met His Trp Val Arg Gln Ala Pro Gly Lys Gly Leu Glu Trp Val
        35                  40                  45

Ala Leu Ile Trp Leu Asp Gly Ser Asn Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Arg Leu Arg Ala Glu Asp Thr Ala Val Tyr Tyr Cys
                85                  90                  95

Ala Arg Asp Gly Pro Val Ala Ala Ile Pro Asp Tyr Trp Gly Gln Gly
            100                 105                 110

Thr Leu Val Thr Val Ser Ser

<210> SEQ ID NO 203
<211> LENGTH: 24
<212> TYPE: DNA
<213> ORGANISM: Artificial Sequence
<220> FEATURE:
<223> OTHER INFORMATION: synthetic

<400> SEQUENCE: 203
ggattcacct tcagtggtta tggc                                         24

<210> SEQ ID NO 204
<211> LENGTH: 8
<212> TYPE: PRT
<213> ORGANISM: Artificial Sequence
<220> FEATURE:
<223> OTHER INFORMATION: synthetic

<400> SEQUENCE: 204

Gly Phe Thr Phe Ser Gly Tyr Gly
1               5

<210> SEQ ID NO 205
<211> LENGTH: 24
<212> TYPE: DNA
<213> ORGANISM: Artificial Sequence
<220> FEATURE:
<223> OTHER INFORMATION: synthetic

<400> SEQUENCE: 205
atatggcttg atggaagtaa tgac                                         24

<210> SEQ ID NO 206
<211> LENGTH: 8
<212> TYPE: PRT
<213> ORGANISM: Artificial Sequence
<220> FEATURE:
<223> OTHER INFORMATION: synthetic

<400> SEQUENCE: 206

Ile Trp Leu Asp Gly Ser Asn Asp
1               5

<210> SEQ ID NO 207
<211> LENGTH: 36
<212> TYPE: DNA
<213> ORGANISM: Artificial Sequence
<220> FEATURE:
<223> OTHER INFORMATION: synthetic

<400> SEQUENCE: 207
gcgagagatg gcccggttgc tgctataccc gactac                            36

<210> SEQ ID NO 208
<211> LENGTH: 12
<212> TYPE: PRT
<213> ORGANISM: Artificial Sequence
<220> FEATURE:
<223> OTHER INFORMATION: synthetic

<400> SEQUENCE: 208

Ala Arg Asp Gly Pro Val Ala Ala Ile Pro Asp Tyr
1               5                   10

<210> SEQ ID NO 209

```
<211> LENGTH: 321
<212> TYPE: DNA
<213> ORGANISM: Artificial Sequence
<220> FEATURE:
<223> OTHER INFORMATION: synthetic

<400> SEQUENCE: 209
gacatccaga tgacccagtc tccttccacc ctgtctgcat ctgtaggaga cagagtcacc    60
atcacttgcc gggccagtca gagtattagt aggtggttgg cctggtatca gctgaaacca   120
gggaaagccc ctaagctcct gatctataag gcgtctagtt tagaaagtgg ggtcccatca   180
aggttcagcg gcagtggatc tgggacagac ttcactctca ccatcagcag cctgcaacct   240
gatgattttg caacttatta ctgccaacag tataatactt attcgtacac ttttggccag   300
gggaccaagc tggagatcaa a                                             321

<210> SEQ ID NO 210
<211> LENGTH: 107
<212> TYPE: PRT
<213> ORGANISM: Artificial Sequence
<220> FEATURE:
<223> OTHER INFORMATION: synthetic

<400> SEQUENCE: 210

Asp Ile Gln Met Thr Gln Ser Pro Ser Thr Leu Ser Ala Ser Val Gly
 1               5                  10                  15
Asp Arg Val Thr Ile Thr Cys Arg Ala Ser Gln Ser Ile Ser Arg Trp
            20                  25                  30
Leu Ala Trp Tyr Gln Leu Lys Pro Gly Lys Ala Pro Lys Leu Leu Ile
        35                  40                  45
Tyr Lys Ala Ser Ser Leu Glu Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Asp Asp Phe Ala Thr Tyr Tyr Cys Gln Gln Tyr Asn Thr Tyr Ser Tyr
                85                  90                  95
Thr Phe Gly Gln Gly Thr Lys Leu Glu Ile Lys
            100                 105

<210> SEQ ID NO 211
<211> LENGTH: 18
<212> TYPE: DNA
<213> ORGANISM: Artificial Sequence
<220> FEATURE:
<223> OTHER INFORMATION: synthetic

<400> SEQUENCE: 211
cagagtatta gtaggtgg                                                  18

<210> SEQ ID NO 212
<211> LENGTH: 6
<212> TYPE: PRT
<213> ORGANISM: Artificial Sequence
<220> FEATURE:
<223> OTHER INFORMATION: synthetic

<400> SEQUENCE: 212

Gln Ser Ile Ser Arg Trp
 1               5

<210> SEQ ID NO 213
<211> LENGTH: 9
```

<212> TYPE: DNA
<213> ORGANISM: Artificial Sequence
<220> FEATURE:
<223> OTHER INFORMATION: synthetic

<400> SEQUENCE: 213 aaggcgtct                                                                  9

<210> SEQ ID NO 214
<211> LENGTH: 3
<212> TYPE: PRT
<213> ORGANISM: Artificial Sequence
<220> FEATURE:
<223> OTHER INFORMATION: synthetic

<400> SEQUENCE: 214

Lys Ala Ser
1

<210> SEQ ID NO 215
<211> LENGTH: 27
<212> TYPE: DNA
<213> ORGANISM: Artificial Sequence
<220> FEATURE:
<223> OTHER INFORMATION: synthetic

<400> SEQUENCE: 215
caacagtata atacttattc gtacact                                             27

<210> SEQ ID NO 216
<211> LENGTH: 9
<212> TYPE: PRT
<213> ORGANISM: Artificial Sequence
<220> FEATURE:
<223> OTHER INFORMATION: synthetic

<400> SEQUENCE: 216

Gln Gln Tyr Asn Thr Tyr Ser Tyr Thr
1               5

<210> SEQ ID NO 217
<211> LENGTH: 363
<212> TYPE: DNA
<213> ORGANISM: Artificial Sequence
<220> FEATURE:
<223> OTHER INFORMATION: synthetic

<400> SEQUENCE: 217
gaggtgcagc tggtggagtc tgggggaggt gtggtacggc ctgggggtc cctgagactc          60 tcctgtgcag cctctggatt caccttttgat gaatatggca tgacttgggt ccgccaagtt       120
ccagggaagg gctggagtg gtctctggt attacttgga atggtggttt cacagattat         180
acagactctg tgaagggccg attcaccagc tccagagaca acgccaagaa ctccctgtat        240
ctgcaaatga acagtctgag agccgaggac acggccttgt attactgtgc gagagatgga        300
tatagcagct cgtgggggc ttatgatata tgggccaag gacaatggt caccgtctct          360 tca                                                                     363

<210> SEQ ID NO 218
<211> LENGTH: 121
<212> TYPE: PRT
<213> ORGANISM: Artificial Sequence
<220> FEATURE:
<223> OTHER INFORMATION: synthetic

<400> SEQUENCE: 218

Glu Val Gln Leu Val Glu Ser Gly Gly Val Val Arg Pro Gly Gly
1               5                   10                  15

Ser Leu Arg Leu Ser Cys Ala Ala Ser Gly Phe Thr Phe Asp Glu Tyr
            20                  25                  30

Gly Met Thr Trp Val Arg Gln Val Pro Gly Lys Gly Leu Glu Trp Val
        35                  40                  45

Ser Gly Ile Thr Trp Asn Gly Gly Phe Thr Tyr Thr Asp Ser Val
    50                  55                  60

Lys Gly Arg Phe Thr Ser Ser Arg Asp Asn Ala Lys Asn Ser Leu Tyr
65              70                  75                  80

Leu Gln Met Asn Ser Leu Arg Ala Glu Asp Thr Ala Leu Tyr Tyr Cys
            85                  90                  95

Ala Arg Asp Gly Tyr Ser Ser Ser Trp Gly Ala Tyr Asp Ile Trp Gly
        100                 105                 110

Gln Gly Thr Met Val Thr Val Ser Ser
        115                 120

<210> SEQ ID NO 219
<211> LENGTH: 24
<212> TYPE: DNA
<213> ORGANISM: Artificial Sequence
<220> FEATURE:
<223> OTHER INFORMATION: synthetic

<400> SEQUENCE: 219
ggattcacct ttgatgaata tggc                                          24

<210> SEQ ID NO 220
<211> LENGTH: 8
<212> TYPE: PRT
<213> ORGANISM: Artificial Sequence
<220> FEATURE:
<223> OTHER INFORMATION: synthetic

<400> SEQUENCE: 220

Gly Phe Thr Phe Asp Glu Tyr Gly
1               5

<210> SEQ ID NO 221
<211> LENGTH: 24
<212> TYPE: DNA
<213> ORGANISM: Artificial Sequence
<220> FEATURE:
<223> OTHER INFORMATION: synthetic

<400> SEQUENCE: 221
attacttgga atggtggttt caca                                          24

<210> SEQ ID NO 222
<211> LENGTH: 8
<212> TYPE: PRT
<213> ORGANISM: Artificial Sequence
<220> FEATURE:
<223> OTHER INFORMATION: synthetic

<400> SEQUENCE: 222

Ile Thr Trp Asn Gly Gly Phe Thr
1               5

<210> SEQ ID NO 223
<211> LENGTH: 42

```
<212> TYPE: DNA
<213> ORGANISM: Artificial Sequence
<220> FEATURE:
<223> OTHER INFORMATION: synthetic

<400> SEQUENCE: 223
gcgagagatg gatatagcag ctcgtgggggg gcttatgata ta                    42

<210> SEQ ID NO 224
<211> LENGTH: 14
<212> TYPE: PRT
<213> ORGANISM: Artificial Sequence
<220> FEATURE:
<223> OTHER INFORMATION: synthetic

<400> SEQUENCE: 224

Ala Arg Asp Gly Tyr Ser Ser Ser Trp Gly Ala Tyr Asp Ile
 1               5                  10

<210> SEQ ID NO 225
<211> LENGTH: 321
<212> TYPE: DNA
<213> ORGANISM: Artificial Sequence
<220> FEATURE:
<223> OTHER INFORMATION: synthetic

<400> SEQUENCE: 225
gacatccaga tgacccagtc tccatcatcc ctgtctgcat ctgtgggaga cagagtcacc    60
atcacttgcc gggcaagtca gagcattagc acctatttaa attggtatca gcagaaacca   120
gggaaagccc ctaagctcct gatctatgct gcatccagtt tgcaaagtgg ggtcccatta   180
aggttcagtg gcagtggatc tgggactgat ttcactctca ccatcagcag tctgcaacct   240
gaagattttg caagttattt ctgtcaacag agttacagta ccccgtacac ttttggccag   300
gggaccaagc tggagatcaa a                                             321

<210> SEQ ID NO 226
<211> LENGTH: 107
<212> TYPE: PRT
<213> ORGANISM: Artificial Sequence
<220> FEATURE:
<223> OTHER INFORMATION: synthetic

<400> SEQUENCE: 226

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Thr Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Leu Arg Phe Ser Gly
        50                  55                  60

Ser Gly Ser Gly Thr Asp Phe Thr Leu Thr Ile Ser Ser Leu Gln Pro
 65                 70                  75                  80

Glu Asp Phe Ala Ser Tyr Phe Cys Gln Gln Ser Tyr Ser Thr Pro Tyr
                85                  90                  95

Thr Phe Gly Gln Gly Thr Lys Leu Glu Ile Lys
                100                 105

<210> SEQ ID NO 227
<211> LENGTH: 18
<212> TYPE: DNA
```

```
<213> ORGANISM: Artificial Sequence
<220> FEATURE:
<223> OTHER INFORMATION: synthetic

<400> SEQUENCE: 227
cagagcatta gcacctat                                                18

<210> SEQ ID NO 228
<211> LENGTH: 6
<212> TYPE: PRT
<213> ORGANISM: Artificial Sequence
<220> FEATURE:
<223> OTHER INFORMATION: synthetic

<400> SEQUENCE: 228

Gln Ser Ile Ser Thr Tyr
1               5

<210> SEQ ID NO 229
<211> LENGTH: 9
<212> TYPE: DNA
<213> ORGANISM: Artificial Sequence
<220> FEATURE:
<223> OTHER INFORMATION: synthetic

<400> SEQUENCE: 229 gctgcatcc                                                           9

<210> SEQ ID NO 230
<211> LENGTH: 3
<212> TYPE: PRT
<213> ORGANISM: Artificial Sequence
<220> FEATURE:
<223> OTHER INFORMATION: synthetic

<400> SEQUENCE: 230

Ala Ala Ser
1

<210> SEQ ID NO 231
<211> LENGTH: 27
<212> TYPE: DNA
<213> ORGANISM: Artificial Sequence
<220> FEATURE:
<223> OTHER INFORMATION: synthetic

<400> SEQUENCE: 231
caacagagtt acagtacccc gtacact                                       27

<210> SEQ ID NO 232
<211> LENGTH: 9
<212> TYPE: PRT
<213> ORGANISM: Artificial Sequence
<220> FEATURE:
<223> OTHER INFORMATION: synthetic

<400> SEQUENCE: 232

Gln Gln Ser Tyr Ser Thr Pro Tyr Thr
1               5

<210> SEQ ID NO 233
<211> LENGTH: 360
<212> TYPE: DNA
<213> ORGANISM: Artificial Sequence
<220> FEATURE:
<223> OTHER INFORMATION: synthetic
```

<400> SEQUENCE: 233

```
gaagtgcagc tggtggagtc tgggggaggc gtggtacagc ctgggggtc cctgagactc      60
tcctgtgcag cctctggatt caccttaat gattatgcca tgcactgggt ccgtcaagct     120
ccagggaagg gtctggagtg ggtctctctt attagtggag atggtggtaa cacatactat    180
gcagactctg tgaagggccg actcaccatc tccagagaca cagcaaaaa ctccctgtat     240
ctgcaaatga acagtctgag aacagaggac accgccttat attactgtgc aaaagataag    300
ggctggaact tcggttactt cgatctctgg ggccgtggca ccctggtcac tgtctcctca    360
```

<210> SEQ ID NO 234
<211> LENGTH: 120
<212> TYPE: PRT
<213> ORGANISM: Artificial Sequence
<220> FEATURE:
<223> OTHER INFORMATION: synthetic

<400> SEQUENCE: 234

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Leu Ile Ser Gly Asp Gly Gly Asn Thr Tyr Tyr Ala Asp Ser Val
    50                  55                  60

Lys Gly Arg Leu Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys Asp Lys Gly Trp Asn Phe Gly Tyr Phe Asp Leu Trp Gly Arg
            100                 105                 110

Gly Thr Leu Val Thr Val Ser Ser
        115                 120
```

<210> SEQ ID NO 235
<211> LENGTH: 24
<212> TYPE: DNA
<213> ORGANISM: Artificial Sequence
<220> FEATURE:
<223> OTHER INFORMATION: synthetic

<400> SEQUENCE: 235

```
ggattcacct ttaatgatta tgcc                                            24
```

<210> SEQ ID NO 236
<211> LENGTH: 8
<212> TYPE: PRT
<213> ORGANISM: Artificial Sequence
<220> FEATURE:
<223> OTHER INFORMATION: synthetic

<400> SEQUENCE: 236

```
Gly Phe Thr Phe Asn Asp Tyr Ala
1               5
```

<210> SEQ ID NO 237
<211> LENGTH: 24
<212> TYPE: DNA
<213> ORGANISM: Artificial Sequence
<220> FEATURE:

<223> OTHER INFORMATION: synthetic

<400> SEQUENCE: 237
attagtggag atggtggtaa caca                                              24

<210> SEQ ID NO 238
<211> LENGTH: 8
<212> TYPE: PRT
<213> ORGANISM: Artificial Sequence
<220> FEATURE:
<223> OTHER INFORMATION: synthetic

<400> SEQUENCE: 238

Ile Ser Gly Asp Gly Gly Asn Thr
1               5

<210> SEQ ID NO 239
<211> LENGTH: 39
<212> TYPE: DNA
<213> ORGANISM: Artificial Sequence
<220> FEATURE:
<223> OTHER INFORMATION: synthetic

<400> SEQUENCE: 239
gcaaaagata agggctggaa cttcggttac ttcgatctc                              39

<210> SEQ ID NO 240
<211> LENGTH: 13
<212> TYPE: PRT
<213> ORGANISM: Artificial Sequence
<220> FEATURE:
<223> OTHER INFORMATION: synthetic

<400> SEQUENCE: 240

Ala Lys Asp Lys Gly Trp Asn Phe Gly Tyr Phe Asp Leu
1               5                   10

<210> SEQ ID NO 241
<211> LENGTH: 327
<212> TYPE: DNA
<213> ORGANISM: Artificial Sequence
<220> FEATURE:
<223> OTHER INFORMATION: synthetic

<400> SEQUENCE: 241
gacatccaga tgacccagtc tccatcctcc ctgtctacat ctgtgggaga cagagtcacc        60
atcacttgcc gggcaagtca gaacattgac acctatttaa attggtatca gcagaaacca       120
gggaaagccc ctaaactcct gatctatgat gcatccagtt tacaaagtgg ggtcccatca       180
cggttcagtg gcagcggatc tgggacagat ttcactctca ccatcaccag tctgcaacct       240
gaagattttg ccacttacta ctgtcaacag aatgacaata ttcttcaccc tctcactttc       300
ggcggaggga ccaaggtgga gatcaaa                                           327

<210> SEQ ID NO 242
<211> LENGTH: 109
<212> TYPE: PRT
<213> ORGANISM: Artificial Sequence
<220> FEATURE:
<223> OTHER INFORMATION: synthetic

<400> SEQUENCE: 242

Asp Ile Gln Met Thr Gln Ser Pro Ser Ser Leu Ser Thr Ser Val Gly
1               5                   10                  15

```
Asp Arg Val Thr Ile Thr Cys Arg Ala Ser Gln Asn Ile Asp Thr Tyr
            20                  25                  30

Leu Asn Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Phe Ala Thr Tyr Tyr Cys Gln Gln Asn Asp Asn Ile Leu His
                85                  90                  95

Pro Leu Thr Phe Gly Gly Gly Thr Lys Val Glu Ile Lys
            100                 105
```

<210> SEQ ID NO 243
<211> LENGTH: 18
<212> TYPE: DNA
<213> ORGANISM: Artificial Sequence
<220> FEATURE:
<223> OTHER INFORMATION: synthetic

<400> SEQUENCE: 243
cagaacattg acacctat                                                 18

<210> SEQ ID NO 244
<211> LENGTH: 6
<212> TYPE: PRT
<213> ORGANISM: Artificial Sequence
<220> FEATURE:
<223> OTHER INFORMATION: synthetic

<400> SEQUENCE: 244

Gln Asn Ile Asp Thr Tyr
1               5

<210> SEQ ID NO 245
<211> LENGTH: 9
<212> TYPE: DNA
<213> ORGANISM: Artificial Sequence
<220> FEATURE:
<223> OTHER INFORMATION: synthetic

<400> SEQUENCE: 245 gatgcatcc                                                            9

<210> SEQ ID NO 246
<211> LENGTH: 3
<212> TYPE: PRT
<213> ORGANISM: Artificial Sequence
<220> FEATURE:
<223> OTHER INFORMATION: synthetic

<400> SEQUENCE: 246

Asp Ala Ser
1

<210> SEQ ID NO 247
<211> LENGTH: 33
<212> TYPE: DNA
<213> ORGANISM: Artificial Sequence
<220> FEATURE:
<223> OTHER INFORMATION: synthetic

<400> SEQUENCE: 247
caacagaatg acaatattct tcaccctctc act                                33

<210> SEQ ID NO 248
<211> LENGTH: 11
<212> TYPE: PRT
<213> ORGANISM: Artificial Sequence
<220> FEATURE:
<223> OTHER INFORMATION: synthetic

<400> SEQUENCE: 248

Gln Gln Asn Asp Asn Ile Leu His Pro Leu Thr
1               5                   10

<210> SEQ ID NO 249
<211> LENGTH: 369
<212> TYPE: DNA
<213> ORGANISM: Artificial Sequence
<220> FEATURE:
<223> OTHER INFORMATION: synthetic

<400> SEQUENCE: 249
gaggtgcagc tggtggagtc tgggggaggc ttggtccaac cggggggtc cctgagactc      60 tcctgtgcag cctctggatt ccactctaat agatattgga tggactgggt ccgccaggct    120
ccagggaagg ggctggagtg ggtggccaac ataaagcaag atggaagtga ggaaaactat    180
gtggactctg tgaagggccg attcaccatc tccagagaca acgccaagaa ctcactttat    240
ctgcaaatga acagcctgag agccgaggac acggctgtgt attactgtgc gagagatcga    300
agcacctcgt gggtccctta ctggttcttc gatctctggg gccgtggcac cctggtcact    360
gtctcctca                                                             369

<210> SEQ ID NO 250
<211> LENGTH: 123
<212> TYPE: PRT
<213> ORGANISM: Artificial Sequence
<220> FEATURE:
<223> OTHER INFORMATION: synthetic

<400> SEQUENCE: 250

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe His Ser Asn Arg Tyr
            20                  25                  30

Trp Met Asp Trp Val Arg Gln Ala Pro Gly Lys Gly Leu Glu Trp Val
        35                  40                  45

Ala Asn Ile Lys Gln Asp Gly Ser Glu Glu Asn Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ser Thr Ser Trp Val Pro Tyr Trp Phe Phe Asp Leu
            100                 105                 110

Trp Gly Arg Gly Thr Leu Val Thr Val Ser Ser
        115                 120

<210> SEQ ID NO 251
<211> LENGTH: 24
<212> TYPE: DNA
<213> ORGANISM: Artificial Sequence
<220> FEATURE:
<223> OTHER INFORMATION: synthetic

```
<400> SEQUENCE: 251
ggattccact ctaatagata ttgg                                              24

<210> SEQ ID NO 252
<211> LENGTH: 8
<212> TYPE: PRT
<213> ORGANISM: Artificial Sequence
<220> FEATURE:
<223> OTHER INFORMATION: synthetic

<400> SEQUENCE: 252

Gly Phe His Ser Asn Arg Tyr Trp
1               5

<210> SEQ ID NO 253
<211> LENGTH: 24
<212> TYPE: DNA
<213> ORGANISM: Artificial Sequence
<220> FEATURE:
<223> OTHER INFORMATION: synthetic

<400> SEQUENCE: 253
ataaagcaag atggaagtga ggaa                                              24

<210> SEQ ID NO 254
<211> LENGTH: 8
<212> TYPE: PRT
<213> ORGANISM: Artificial Sequence
<220> FEATURE:
<223> OTHER INFORMATION: synthetic

<400> SEQUENCE: 254

Ile Lys Gln Asp Gly Ser Glu Glu
1               5

<210> SEQ ID NO 255
<211> LENGTH: 48
<212> TYPE: DNA
<213> ORGANISM: Artificial Sequence
<220> FEATURE:
<223> OTHER INFORMATION: synthetic

<400> SEQUENCE: 255
gcgagagatc gaagcacctc gtgggtccct tactggttct tcgatctc                    48

<210> SEQ ID NO 256
<211> LENGTH: 16
<212> TYPE: PRT
<213> ORGANISM: Artificial Sequence
<220> FEATURE:
<223> OTHER INFORMATION: synthetic

<400> SEQUENCE: 256

Ala Arg Asp Arg Ser Thr Ser Trp Val Pro Tyr Trp Phe Phe Asp Leu
1               5                  10                  15

<210> SEQ ID NO 257
<211> LENGTH: 324
<212> TYPE: DNA
<213> ORGANISM: Artificial Sequence
<220> FEATURE:
<223> OTHER INFORMATION: synthetic

<400> SEQUENCE: 257
gacatccaga tgacccagtc tccatcctcc ctgtctgcat ctgtaggaga cagagtcacc       60
```

```
atcacttgcc gggcaagtca gagcattagc agctatttaa attggtatca gcagaaacca    120
gggaaagccc ctaagctcct gatctatgct gcatccagtt tgcaaagtgg ggtcccgtca    180
aggttcagtg gcagtggatc tgggacagat ttcactctca ccatcagcag tctgcaacct    240
gaagattttg caacttacta ctgtcaacag agttacagta cccctccgat caccttcggc    300
caagggacac gactggagat taaa                                            324
```

```
<210> SEQ ID NO 258
<211> LENGTH: 108
<212> TYPE: PRT
<213> ORGANISM: Artificial Sequence
<220> FEATURE:
<223> OTHER INFORMATION: synthetic

<400> SEQUENCE: 258
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

```
<210> SEQ ID NO 259
<211> LENGTH: 18
<212> TYPE: DNA
<213> ORGANISM: Artificial Sequence
<220> FEATURE:
<223> OTHER INFORMATION: synthetic

<400> SEQUENCE: 259
cagagcatta gcagctat                                                   18

<210> SEQ ID NO 260
<211> LENGTH: 6
<212> TYPE: PRT
<213> ORGANISM: Artificial Sequence
<220> FEATURE:
<223> OTHER INFORMATION: synthetic

<400> SEQUENCE: 260
```

Gln Ser Ile Ser Ser Tyr
1               5

```
<210> SEQ ID NO 261
<211> LENGTH: 9
<212> TYPE: DNA
<213> ORGANISM: Artificial Sequence
<220> FEATURE:
<223> OTHER INFORMATION: synthetic

<400> SEQUENCE: 261 gctgcatcc                                                              9
```

```
<210> SEQ ID NO 262
<211> LENGTH: 3
<212> TYPE: PRT
<213> ORGANISM: Artificial Sequence
<220> FEATURE:
<223> OTHER INFORMATION: synthetic

<400> SEQUENCE: 262

Ala Ala Ser
1

<210> SEQ ID NO 263
<211> LENGTH: 30
<212> TYPE: DNA
<213> ORGANISM: Artificial Sequence
<220> FEATURE:
<223> OTHER INFORMATION: synthetic

<400> SEQUENCE: 263
caacagagtt acagtacccc tccgatcacc                                         30

<210> SEQ ID NO 264
<211> LENGTH: 10
<212> TYPE: PRT
<213> ORGANISM: Artificial Sequence
<220> FEATURE:
<223> OTHER INFORMATION: synthetic

<400> SEQUENCE: 264

Gln Gln Ser Tyr Ser Thr Pro Pro Ile Thr
1               5                   10

<210> SEQ ID NO 265
<211> LENGTH: 360
<212> TYPE: DNA
<213> ORGANISM: Artificial Sequence
<220> FEATURE:
<223> OTHER INFORMATION: synthetic

<400> SEQUENCE: 265
gaagtgcagc tggtggagtc tgggggaggc gtggtacagc gggggagtc cctgagactc          60 tcctgttcag cctctgactt catctttaaa gattatgcca tgtactgggt ccgtcaaatt         120
ccagggaagg gtctagagtg gatctctctt attagtggtg atggtgacac tacatggtat         180
ggagactctg tgaagggccg attcaccatc tccagagaca caacgaaaa ctccctctttt         240 ctgcaaatga acgatctgag aactgaggac accgccatgt actactgtgc aagagatatg         300
gggtggaact tctttcagtt gcaatactgg ggccagggaa ccctggtcac cgtctcctca         360

<210> SEQ ID NO 266
<211> LENGTH: 120
<212> TYPE: PRT
<213> ORGANISM: Artificial Sequence
<220> FEATURE:
<223> OTHER INFORMATION: synthetic

<400> SEQUENCE: 266

Glu Val Gln Leu Val Glu Ser Gly Gly Gly Val Val Gln Arg Gly Glu
1               5                   10                  15

Ser Leu Arg Leu Ser Cys Ser Ala Ser Asp Phe Ile Phe Lys Asp Tyr
            20                  25                  30

Ala Met Tyr Trp Val Arg Gln Ile Pro Gly Lys Gly Leu Glu Trp Ile
        35                  40                  45
```

```
Ser Leu Ile Ser Gly Asp Gly Asp Thr Thr Trp Tyr Gly Asp Ser Val
    50                  55                  60
Lys Gly Arg Phe Thr Ile Ser Arg Asp Asn Asn Glu Asn Ser Leu Phe
 65                  70                  75                  80
Leu Gln Met Asn Asp Leu Arg Thr Glu Asp Thr Ala Met Tyr Tyr Cys
                 85                  90                  95
Ala Arg Asp Met Gly Trp Asn Phe Phe Gln Leu Gln Tyr Trp Gly Gln
            100                 105                 110
Gly Thr Leu Val Thr Val Ser Ser
        115                 120

<210> SEQ ID NO 267
<211> LENGTH: 24
<212> TYPE: DNA
<213> ORGANISM: Artificial Sequence
<220> FEATURE:
<223> OTHER INFORMATION: synthetic

<400> SEQUENCE: 267
gacttcatct ttaaagatta tgcc                                          24

<210> SEQ ID NO 268
<211> LENGTH: 8
<212> TYPE: PRT
<213> ORGANISM: Artificial Sequence
<220> FEATURE:
<223> OTHER INFORMATION: synthetic

<400> SEQUENCE: 268

Asp Phe Ile Phe Lys Asp Tyr Ala
 1               5

<210> SEQ ID NO 269
<211> LENGTH: 24
<212> TYPE: DNA
<213> ORGANISM: Artificial Sequence
<220> FEATURE:
<223> OTHER INFORMATION: synthetic

<400> SEQUENCE: 269
attagtggtg atggtgacac taca                                          24

<210> SEQ ID NO 270
<211> LENGTH: 8
<212> TYPE: PRT
<213> ORGANISM: Artificial Sequence
<220> FEATURE:
<223> OTHER INFORMATION: synthetic

<400> SEQUENCE: 270

Ile Ser Gly Asp Gly Asp Thr Thr
 1               5

<210> SEQ ID NO 271
<211> LENGTH: 39
<212> TYPE: DNA
<213> ORGANISM: Artificial Sequence
<220> FEATURE:
<223> OTHER INFORMATION: synthetic

<400> SEQUENCE: 271
gcaagagata tggggtggaa cttctttcag ttgcaatac                          39

<210> SEQ ID NO 272
```

<211> LENGTH: 13
<212> TYPE: PRT
<213> ORGANISM: Artificial Sequence
<220> FEATURE:
<223> OTHER INFORMATION: synthetic

<400> SEQUENCE: 272

Ala Arg Asp Met Gly Trp Asn Phe Phe Gln Leu Gln Tyr
1               5                   10

<210> SEQ ID NO 273
<211> LENGTH: 361
<212> TYPE: DNA
<213> ORGANISM: Artificial Sequence
<220> FEATURE:
<223> OTHER INFORMATION: synthetic

<400> SEQUENCE: 273

```
dcaggtgcag ctgcaggagt cgggccccgc actggtgaag ccttcacaga ccctgtccct    60
cacctgcact gtctctggtg gctccatcat cagaggtagt acctactgga gttgggtccg   120
ccaattccca gggaagggcc tggagtggat tggatacagt tattacagtg ggaccgccta   180
ctataatccg tccctcgaga gtcgagctac catttctgta gacacgtcta agaaccagtt   240
ctccctgaac ctgaagtctg tgacggccgc ggacacggcc gtgtattatt gtacaagaga   300
aataggagtg gctggtctct ttgacatctg gggccaggga accctggtca ccgtctcctc   360
a                                                                   361
```

<210> SEQ ID NO 274
<211> LENGTH: 120
<212> TYPE: PRT
<213> ORGANISM: Artificial Sequence
<220> FEATURE:
<223> OTHER INFORMATION: synthetic

<400> SEQUENCE: 274

Gln Val Gln Leu Gln Glu Ser Gly Pro Ala Leu Val Lys Pro Ser Gln
1               5                   10                  15

Thr Leu Ser Leu Thr Cys Thr Val Ser Gly Gly Ser Ile Ile Arg Gly
            20                  25                  30

Ser Thr Tyr Trp Ser Trp Val Arg Gln Phe Pro Gly Lys Gly Leu Glu
        35                  40                  45

Trp Ile Gly Tyr Ser Tyr Tyr Ser Gly Thr Ala Tyr Tyr Asn Pro Ser
    50                  55                  60

Leu Glu Ser Arg Ala Thr Ile Ser Val Asp Thr Ser Lys Asn Gln Phe
65                  70                  75                  80

Ser Leu Asn Leu Lys Ser Val Thr Ala Ala Asp Thr Ala Val Tyr Tyr
                85                  90                  95

Cys Thr Arg Glu Ile Gly Val Ala Gly Leu Phe Asp Ile Trp Gly Gln
            100                 105                 110

Gly Thr Leu Val Thr Val Ser Ser
        115                 120

<210> SEQ ID NO 275
<211> LENGTH: 30
<212> TYPE: DNA
<213> ORGANISM: Artificial Sequence
<220> FEATURE:
<223> OTHER INFORMATION: synthetic

<400> SEQUENCE: 275
ggtggctcca tcatcagagg tagtacctac                    30

<210> SEQ ID NO 276
<211> LENGTH: 10
<212> TYPE: PRT
<213> ORGANISM: Artificial Sequence
<220> FEATURE:
<223> OTHER INFORMATION: synthetic

<400> SEQUENCE: 276

Gly Gly Ser Ile Ile Arg Gly Ser Thr Tyr
1               5                   10

<210> SEQ ID NO 277
<211> LENGTH: 21
<212> TYPE: DNA
<213> ORGANISM: Artificial Sequence
<220> FEATURE:
<223> OTHER INFORMATION: synthetic

<400> SEQUENCE: 277
agttattaca gtgggaccgc c                             21

<210> SEQ ID NO 278
<211> LENGTH: 7
<212> TYPE: PRT
<213> ORGANISM: Artificial Sequence
<220> FEATURE:
<223> OTHER INFORMATION: synthetic

<400> SEQUENCE: 278

Ser Tyr Tyr Ser Gly Thr Ala
1               5

<210> SEQ ID NO 279
<211> LENGTH: 36
<212> TYPE: DNA
<213> ORGANISM: Artificial Sequence
<220> FEATURE:
<223> OTHER INFORMATION: synthetic

<400> SEQUENCE: 279
acaagagaaa taggagtggc tggtctcttt gacatc             36

<210> SEQ ID NO 280
<211> LENGTH: 12
<212> TYPE: PRT
<213> ORGANISM: Artificial Sequence
<220> FEATURE:
<223> OTHER INFORMATION: synthetic

<400> SEQUENCE: 280

Thr Arg Glu Ile Gly Val Ala Gly Leu Phe Asp Ile
1               5                   10

<210> SEQ ID NO 281
<211> LENGTH: 324
<212> TYPE: DNA
<213> ORGANISM: Artificial Sequence
<220> FEATURE:
<223> OTHER INFORMATION: synthetic

<400> SEQUENCE: 281
gaaatagttt tgacacagag tcccggcaca ctgtcactct ctcccgggga aagagccacc    60
ttgtcatgta gagcaagtca gtcagtctct agctcttatc tcgcctggta ccagcagaag   120

```
ccgggacagg ccctagact gctgatctac ggggcaagtt ccagggccac cggaatcccc      180
gaccggttca gtggaagcgg aagcggaacc gatttactt tgacgatttc tagactggag      240
ccagaggatt tcgccgttta ctattgtcaa cagtacggaa gcagcccgtg acgtttggc      300 cagggcacga aggtagaaat caag                                            324
```

<210> SEQ ID NO 282
<211> LENGTH: 108
<212> TYPE: PRT
<213> ORGANISM: Artificial Sequence
<220> FEATURE:
<223> OTHER INFORMATION: synthetic

<400> SEQUENCE: 282

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105
```

<210> SEQ ID NO 283
<211> LENGTH: 36
<212> TYPE: DNA
<213> ORGANISM: Artificial Sequence
<220> FEATURE:
<223> OTHER INFORMATION: synthetic

<400> SEQUENCE: 283

```
agagcaagtc agtcagtctc tagctcttat ctcgcc                                36
```

<210> SEQ ID NO 284
<211> LENGTH: 12
<212> TYPE: PRT
<213> ORGANISM: Artificial Sequence
<220> FEATURE:
<223> OTHER INFORMATION: synthetic

<400> SEQUENCE: 284

```
Arg Ala Ser Gln Ser Val Ser Ser Ser Tyr Leu Ala
1               5                   10
```

<210> SEQ ID NO 285
<211> LENGTH: 21
<212> TYPE: DNA
<213> ORGANISM: Artificial Sequence
<220> FEATURE:
<223> OTHER INFORMATION: synthetic

<400> SEQUENCE: 285

```
ggggcaagtt ccagggccac c                                                21
```

<210> SEQ ID NO 286
<211> LENGTH: 7

<212> TYPE: PRT
<213> ORGANISM: Artificial Sequence
<220> FEATURE:
<223> OTHER INFORMATION: synthetic

<400> SEQUENCE: 286

Gly Ala Ser Ser Arg Ala Thr
1               5

<210> SEQ ID NO 287
<211> LENGTH: 27
<212> TYPE: DNA
<213> ORGANISM: Artificial Sequence
<220> FEATURE:
<223> OTHER INFORMATION: synthetic

<400> SEQUENCE: 287
caacagtacg gaagcagccc gtggacg                                           27

<210> SEQ ID NO 288
<211> LENGTH: 9
<212> TYPE: PRT
<213> ORGANISM: Artificial Sequence
<220> FEATURE:
<223> OTHER INFORMATION: synthetic

<400> SEQUENCE: 288

Gln Gln Tyr Gly Ser Ser Pro Trp Thr
1               5

<210> SEQ ID NO 289
<211> LENGTH: 357
<212> TYPE: DNA
<213> ORGANISM: Artificial Sequence
<220> FEATURE:
<223> OTHER INFORMATION: synthetic

<400> SEQUENCE: 289
caggagcagt tggtgcagtc tggggctgag gtgaagaagc ctggggcctc agtgaaggtc      60
tcctgtaagg cttctggata caccttcacc ggctactata tacattgggt gcgacaggcc     120
cctggactag gcttgaatg gatgggatgg atcaacccta cagtggtgg cacaaaatat      180
gcacagaagt tcagggcag ggtcaccatg accagggaca cgtccatcaa tacagcctac     240
atggagctga aaagactgaa atctgacgac tcggccgtat attactgtgc gagagacgcc     300
cctccccatg atgtttttga tatctggggc caagggacat tggtcaccgt ctcttca       357

<210> SEQ ID NO 290
<211> LENGTH: 119
<212> TYPE: PRT
<213> ORGANISM: Artificial Sequence
<220> FEATURE:
<223> OTHER INFORMATION: synthetic

<400> SEQUENCE: 290

Gln Glu Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Leu Gly Leu Glu Trp Met
        35                  40                  45

Gly Trp Ile Asn Pro Asn Ser Gly Gly Thr Lys Tyr Ala Gln Lys Phe
    50                  55                  60

Gln Gly Arg Val Thr Met Thr Arg Asp Thr Ser Ile Asn Thr Ala Tyr
65                  70                  75                  80

Met Glu Leu Lys Arg Leu Lys Ser Asp Asp Ser Ala Val Tyr Tyr Cys
                85                  90                  95

Ala Arg Asp Ala Pro Pro His Asp Val Phe Asp Ile Trp Gly Gln Gly
            100                 105                 110

Thr Leu Val Thr Val Ser Ser
        115

<210> SEQ ID NO 291
<211> LENGTH: 24
<212> TYPE: DNA
<213> ORGANISM: Artificial Sequence
<220> FEATURE:
<223> OTHER INFORMATION: synthetic

<400> SEQUENCE: 291
ggatacacct tcaccggcta ctat                                    24

<210> SEQ ID NO 292
<211> LENGTH: 8
<212> TYPE: PRT
<213> ORGANISM: Artificial Sequence
<220> FEATURE:
<223> OTHER INFORMATION: synthetic

<400> SEQUENCE: 292

Gly Tyr Thr Phe Thr Gly Tyr Tyr
1               5

<210> SEQ ID NO 293
<211> LENGTH: 24
<212> TYPE: DNA
<213> ORGANISM: Artificial Sequence
<220> FEATURE:
<223> OTHER INFORMATION: synthetic

<400> SEQUENCE: 293
atcaacccta acagtggtgg caca                                    24

<210> SEQ ID NO 294
<211> LENGTH: 8
<212> TYPE: PRT
<213> ORGANISM: Artificial Sequence
<220> FEATURE:
<223> OTHER INFORMATION: synthetic

<400> SEQUENCE: 294

Ile Asn Pro Asn Ser Gly Gly Thr
1               5

<210> SEQ ID NO 295
<211> LENGTH: 36
<212> TYPE: DNA
<213> ORGANISM: Artificial Sequence
<220> FEATURE:
<223> OTHER INFORMATION: synthetic

<400> SEQUENCE: 295
gcgagagacg cccctcccca tgatgttttt gatatc                       36

<210> SEQ ID NO 296
<211> LENGTH: 12
<212> TYPE: PRT
<213> ORGANISM: Artificial Sequence

```
<220> FEATURE:
<223> OTHER INFORMATION: synthetic

<400> SEQUENCE: 296

Ala Arg Asp Ala Pro Pro His Asp Val Phe Asp Ile
1               5                   10

<210> SEQ ID NO 297
<211> LENGTH: 321
<212> TYPE: DNA
<213> ORGANISM: Artificial Sequence
<220> FEATURE:
<223> OTHER INFORMATION: synthetic

<400> SEQUENCE: 297
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaattgg ggtcccatca   180
aggttcagcg gcagtggatc tgggacagaa ttcactctca caatcagcag cctgcagcct   240
gaagattttg caacttatta ctgtctacag cataatagtt acccgctcac tttcggcgga   300
gggaccaagg tggagatcaa a                                              321

<210> SEQ ID NO 298
<211> LENGTH: 107
<212> TYPE: PRT
<213> ORGANISM: Artificial Sequence
<220> FEATURE:
<223> OTHER INFORMATION: synthetic

<400> SEQUENCE: 298

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ile Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
            100                 105

<210> SEQ ID NO 299
<211> LENGTH: 18
<212> TYPE: DNA
<213> ORGANISM: Artificial Sequence
<220> FEATURE:
<223> OTHER INFORMATION: synthetic

<400> SEQUENCE: 299
cagggcatta gaaatgat                                                   18

<210> SEQ ID NO 300
<211> LENGTH: 6
<212> TYPE: PRT
<213> ORGANISM: Artificial Sequence
<220> FEATURE:
```

<223> OTHER INFORMATION: synthetic

<400> SEQUENCE: 300

Gln Gly Ile Arg Asn Asp
1               5

<210> SEQ ID NO 301
<211> LENGTH: 9
<212> TYPE: DNA
<213> ORGANISM: Artificial Sequence
<220> FEATURE:
<223> OTHER INFORMATION: synthetic

<400> SEQUENCE: 301 gctgcatcc                                                                    9

<210> SEQ ID NO 302
<211> LENGTH: 3
<212> TYPE: PRT
<213> ORGANISM: Artificial Sequence
<220> FEATURE:
<223> OTHER INFORMATION: synthetic

<400> SEQUENCE: 302

Ala Ala Ser
1

<210> SEQ ID NO 303
<211> LENGTH: 27
<212> TYPE: DNA
<213> ORGANISM: Artificial Sequence
<220> FEATURE:
<223> OTHER INFORMATION: synthetic

<400> SEQUENCE: 303
ctacagcata atagttaccc gctcact                                               27

<210> SEQ ID NO 304
<211> LENGTH: 9
<212> TYPE: PRT
<213> ORGANISM: Artificial Sequence
<220> FEATURE:
<223> OTHER INFORMATION: synthetic

<400> SEQUENCE: 304

Leu Gln His Asn Ser Tyr Pro Leu Thr
1               5

<210> SEQ ID NO 305
<211> LENGTH: 357
<212> TYPE: DNA
<213> ORGANISM: Artificial Sequence
<220> FEATURE:
<223> OTHER INFORMATION: synthetic

<400> SEQUENCE: 305
caggtgcagc tgcaagagtc gggcccagga ctggtgaagc cttcacagac cctgtccctc          60
acctgcactg tctctggtgg ctccatcagt agtggtgctt accactggag ctggatccgc         120
cagcacccag ggaagggcct agagtggatt ggatacatct attacaatgg ggacacctac         180
tataatccgt ccctcaagag tcgcgttacc atttcagtgg acacgtctaa gaaccaattc         240
ttcctgaagg tgacctctgt gactgccgcg gacacggcca tgtattactg tgcgggagaa         300
aagcagctga ctgcttttga tatctggggc caagggacat tggtcaccgt ctcttca            357

<210> SEQ ID NO 306
<211> LENGTH: 119
<212> TYPE: PRT
<213> ORGANISM: Artificial Sequence
<220> FEATURE:
<223> OTHER INFORMATION: synthetic

<400> SEQUENCE: 306

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Ala Tyr His Trp Ser Trp Ile Arg Gln His Pro Gly Lys Gly Leu Glu
        35                  40                  45

Trp Ile Gly Tyr Ile Tyr Tyr Asn Gly Asp Thr Tyr Tyr Asn Pro Ser
    50                  55                  60

Leu Lys Ser Arg Val Thr Ile Ser Val Asp Thr Ser Lys Asn Gln Phe
65                  70                  75                  80

Phe Leu Lys Val Thr Ser Val Thr Ala Ala Asp Thr Ala Met Tyr Tyr
                85                  90                  95

Cys Ala Gly Glu Lys Gln Leu Thr Ala Phe Asp Ile Trp Gly Gln Gly
            100                 105                 110

Thr Leu Val Thr Val Ser Ser
        115
```

<210> SEQ ID NO 307
<211> LENGTH: 30
<212> TYPE: DNA
<213> ORGANISM: Artificial Sequence
<220> FEATURE:
<223> OTHER INFORMATION: synthetic

<400> SEQUENCE: 307
ggtggctcca tcagtagtgg tgcttaccac                                     30

<210> SEQ ID NO 308
<211> LENGTH: 10
<212> TYPE: PRT
<213> ORGANISM: Artificial Sequence
<220> FEATURE:
<223> OTHER INFORMATION: synthetic

<400> SEQUENCE: 308

```
Gly Gly Ser Ile Ser Ser Gly Ala Tyr His
1               5                   10
```

<210> SEQ ID NO 309
<211> LENGTH: 21
<212> TYPE: DNA
<213> ORGANISM: Artificial Sequence
<220> FEATURE:
<223> OTHER INFORMATION: synthetic

<400> SEQUENCE: 309
atctattaca atggggacac c                                              21

<210> SEQ ID NO 310
<211> LENGTH: 7
<212> TYPE: PRT
<213> ORGANISM: Artificial Sequence
<220> FEATURE:
<223> OTHER INFORMATION: synthetic

<400> SEQUENCE: 310

Ile Tyr Tyr Asn Gly Asp Thr
1               5

<210> SEQ ID NO 311
<211> LENGTH: 33
<212> TYPE: DNA
<213> ORGANISM: Artificial Sequence
<220> FEATURE:
<223> OTHER INFORMATION: synthetic

<400> SEQUENCE: 311
gcgggagaaa agcagctgac tgcttttgat atc                                    33

<210> SEQ ID NO 312
<211> LENGTH: 11
<212> TYPE: PRT
<213> ORGANISM: Artificial Sequence
<220> FEATURE:
<223> OTHER INFORMATION: synthetic

<400> SEQUENCE: 312

Ala Gly Glu Lys Gln Leu Thr Ala Phe Asp Ile
1               5                  10

<210> SEQ ID NO 313
<211> LENGTH: 321
<212> TYPE: DNA
<213> ORGANISM: Artificial Sequence
<220> FEATURE:
<223> OTHER INFORMATION: synthetic

<400> SEQUENCE: 313
gtcatccaga tgacccagtc tccatcctcc ctgtctgcat ctgttggaga cagagtcacc        60
ataacttgcc gggcgagtca ggacattaat aattttttaa attggtatca acagaaatta      120
gggaaagccc ctaaactcct gatctccgat gcatccaatt tgcagacagg agtcccgtca      180
aggttcagtg gaagtggatc tgggacagat tttactttca ccatcagcag cctgcagcct      240
gaagatattg ctgcatatta ctgtcaacaa tatgatcatt tcccgtatac ttttggccag      300
gggaccagac tggagaacaa t                                                321

<210> SEQ ID NO 314
<211> LENGTH: 107
<212> TYPE: PRT
<213> ORGANISM: Artificial Sequence
<220> FEATURE:
<223> OTHER INFORMATION: synthetic

<400> SEQUENCE: 314

Val Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Phe
            20                  25                  30

Leu Asn Trp Tyr Gln Gln Lys Leu Gly Lys Ala Pro Lys Leu Leu Ile
        35                  40                  45

Ser Asp Ala Ser Asn Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Ala Tyr Tyr Cys Gln Gln Tyr Asp His Phe Pro Tyr
                85                  90                  95

Thr Phe Gly Gln Gly Thr Arg Leu Glu Asn Asn
            100                 105

<210> SEQ ID NO 315
<211> LENGTH: 18
<212> TYPE: DNA
<213> ORGANISM: Artificial Sequence
<220> FEATURE:
<223> OTHER INFORMATION: synthetic

<400> SEQUENCE: 315
caggacatta ataatttt                                                  18

<210> SEQ ID NO 316
<211> LENGTH: 6
<212> TYPE: PRT
<213> ORGANISM: Artificial Sequence
<220> FEATURE:
<223> OTHER INFORMATION: synthetic

<400> SEQUENCE: 316

Gln Asp Ile Asn Asn Phe
1               5

<210> SEQ ID NO 317
<211> LENGTH: 9
<212> TYPE: DNA
<213> ORGANISM: Artificial Sequence
<220> FEATURE:
<223> OTHER INFORMATION: synthetic

<400> SEQUENCE: 317 gatgcatcc                                                             9

<210> SEQ ID NO 318
<211> LENGTH: 3
<212> TYPE: PRT
<213> ORGANISM: Artificial Sequence
<220> FEATURE:
<223> OTHER INFORMATION: synthetic

<400> SEQUENCE: 318

Asp Ala Ser
1

<210> SEQ ID NO 319
<211> LENGTH: 27
<212> TYPE: DNA
<213> ORGANISM: Artificial Sequence
<220> FEATURE:
<223> OTHER INFORMATION: synthetic

<400> SEQUENCE: 319
caacaatatg atcatttccc gtatact                                        27

<210> SEQ ID NO 320
<211> LENGTH: 9
<212> TYPE: PRT
<213> ORGANISM: Artificial Sequence
<220> FEATURE:
<223> OTHER INFORMATION: synthetic

<400> SEQUENCE: 320

Gln Gln Tyr Asp His Phe Pro Tyr Thr
1               5

<210> SEQ ID NO 321
<211> LENGTH: 357
<212> TYPE: DNA
<213> ORGANISM: Artificial Sequence
<220> FEATURE:
<223> OTHER INFORMATION: synthetic

<400> SEQUENCE: 321

```
gaggtgcagt tggtggagtc tggggggaggt gtggttcggc ctgggggtc cctgagactc      60
tcctgtgcag cctctggatt cacctttgat gattatggca tgacctgggt ccgccaagct    120
ccagggaagg ggctggagtg gtctctggt attaattgga atggcgatag cacagagtat    180
tcagactctg tgaagggccg attcaccatc tccagagaca acgccaagaa ctccctgtat    240
ctgcaaatga acagtctgag agccgaggac acggccttct atcactgtgc gagagagaat    300
aactggaact tctactttga ctactggggc cagggaaccc tggtcaccgt ctcctca       357
```

<210> SEQ ID NO 322
<211> LENGTH: 119
<212> TYPE: PRT
<213> ORGANISM: Artificial Sequence
<220> FEATURE:
<223> OTHER INFORMATION: synthetic

<400> SEQUENCE: 322

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Thr Trp Val Arg Gln Ala Pro Gly Lys Gly Leu Glu Trp Val
        35                  40                  45

Ser Gly Ile Asn Trp Asn Gly Asp Ser Thr Glu Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Phe Tyr His Cys
                85                  90                  95

Ala Arg Glu Asn Asn Trp Asn Phe Tyr Phe Asp Tyr Trp Gly Gln Gly
            100                 105                 110

Thr Leu Val Thr Val Ser Ser
        115

<210> SEQ ID NO 323
<211> LENGTH: 24
<212> TYPE: DNA
<213> ORGANISM: Artificial Sequence
<220> FEATURE:
<223> OTHER INFORMATION: synthetic

<400> SEQUENCE: 323

```
ggattcacct ttgatgatta tggc                                             24
```

<210> SEQ ID NO 324
<211> LENGTH: 8
<212> TYPE: PRT
<213> ORGANISM: Artificial Sequence
<220> FEATURE:
<223> OTHER INFORMATION: synthetic

<400> SEQUENCE: 324

Gly Phe Thr Phe Asp Asp Tyr Gly

```
<210> SEQ ID NO 325
<211> LENGTH: 24
<212> TYPE: DNA
<213> ORGANISM: Artificial Sequence
<220> FEATURE:
<223> OTHER INFORMATION: synthetic

<400> SEQUENCE: 325
attaattgga atggcgatag caca                                          24

<210> SEQ ID NO 326
<211> LENGTH: 8
<212> TYPE: PRT
<213> ORGANISM: Artificial Sequence
<220> FEATURE:
<223> OTHER INFORMATION: synthetic

<400> SEQUENCE: 326

Ile Asn Trp Asn Gly Asp Ser Thr
1               5

<210> SEQ ID NO 327
<211> LENGTH: 36
<212> TYPE: DNA
<213> ORGANISM: Artificial Sequence
<220> FEATURE:
<223> OTHER INFORMATION: synthetic

<400> SEQUENCE: 327
gcgagagaga ataactggaa cttctacttt gactac                             36

<210> SEQ ID NO 328
<211> LENGTH: 12
<212> TYPE: PRT
<213> ORGANISM: Artificial Sequence
<220> FEATURE:
<223> OTHER INFORMATION: synthetic

<400> SEQUENCE: 328

Ala Arg Glu Asn Asn Trp Asn Phe Tyr Phe Asp Tyr
1               5                   10

<210> SEQ ID NO 329
<211> LENGTH: 321
<212> TYPE: DNA
<213> ORGANISM: Artificial Sequence
<220> FEATURE:
<223> OTHER INFORMATION: synthetic

<400> SEQUENCE: 329
gaaatagtga tgacgcagtc tccagccacc ctgtctgtgt ctcgagggga aagagccacc    60
ctctcctgta gggccagtca gagtgttagc agcaacttag cctggtacca gcagaaactt   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ttgtcagcag tataataact ggccgtggac gttcggccaa   300
gggaccaagg tggaaatcaa a                                             321

<210> SEQ ID NO 330
<211> LENGTH: 107
<212> TYPE: PRT
<213> ORGANISM: Artificial Sequence
```

<220> FEATURE:
<223> OTHER INFORMATION: synthetic

<400> SEQUENCE: 330

Glu Ile Val Met Thr Gln Ser Pro Ala Thr Leu Ser Val Ser Arg Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Leu Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
                85                  90                  95

Thr Phe Gly Gln Gly Thr Lys Val Glu Ile Lys
            100                 105

<210> SEQ ID NO 331
<211> LENGTH: 18
<212> TYPE: DNA
<213> ORGANISM: Artificial Sequence
<220> FEATURE:
<223> OTHER INFORMATION: synthetic

<400> SEQUENCE: 331
cagagtgtta gcagcaac                                              18

<210> SEQ ID NO 332
<211> LENGTH: 6
<212> TYPE: PRT
<213> ORGANISM: Artificial Sequence
<220> FEATURE:
<223> OTHER INFORMATION: synthetic

<400> SEQUENCE: 332

Gln Ser Val Ser Ser Asn
1               5

<210> SEQ ID NO 333
<211> LENGTH: 9
<212> TYPE: DNA
<213> ORGANISM: Artificial Sequence
<220> FEATURE:
<223> OTHER INFORMATION: synthetic

<400> SEQUENCE: 333 ggtgcatcc                                                         9

<210> SEQ ID NO 334
<211> LENGTH: 3
<212> TYPE: PRT
<213> ORGANISM: Artificial Sequence
<220> FEATURE:
<223> OTHER INFORMATION: synthetic

<400> SEQUENCE: 334

Gly Ala Ser
1

<210> SEQ ID NO 335
<211> LENGTH: 27

<212> TYPE: DNA
<213> ORGANISM: Artificial Sequence
<220> FEATURE:
<223> OTHER INFORMATION: synthetic

<400> SEQUENCE: 335
cagcagtata ataactggcc gtggacg 27

<210> SEQ ID NO 336
<211> LENGTH: 9
<212> TYPE: PRT
<213> ORGANISM: Artificial Sequence
<220> FEATURE:
<223> OTHER INFORMATION: synthetic

<400> SEQUENCE: 336

Gln Gln Tyr Asn Asn Trp Pro Trp Thr
1               5

<210> SEQ ID NO 337
<211> LENGTH: 351
<212> TYPE: DNA
<213> ORGANISM: Artificial Sequence
<220> FEATURE:
<223> OTHER INFORMATION: synthetic

<400> SEQUENCE: 337
caggtccacc tggtacagtc tggggctgag gtgaagaagc ctggggcctc agtgaaggtc      60
tcctgcaagg tttccggaaa caccctcact gaattatcca tgcactgggt gcgacaggct     120
cctggaaaag gcttgagtg gatgggaggt tttgatcctg aagatggtga cacaatctac     180
tcacagaagt tccagggcag agtcaccttg accgaggaca tctctcacaga cacagcctac   240
atggagctga gcagcctgag atctgaggac acggccgtgt attactgttc aacagtgggg   300
ggacctacct ctgactgctg ggccaggga accctggtca ccgtctcctc a              351

<210> SEQ ID NO 338
<211> LENGTH: 117
<212> TYPE: PRT
<213> ORGANISM: Artificial Sequence
<220> FEATURE:
<223> OTHER INFORMATION: synthetic

<400> SEQUENCE: 338

Gln Val His Leu Val Gln Ser Gly Ala Glu Val Lys Lys Pro Gly Ala
1               5                   10                  15

Ser Val Lys Val Ser Cys Lys Val Ser Gly Asn Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Asp Thr Ile Tyr Ser Gln Lys Phe
    50                  55                  60

Gln Gly Arg Val Thr Leu Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ser Thr Val Gly Gly Pro Thr Ser Asp Cys Trp Gly Gln Gly Thr Leu
            100                 105                 110

Val Thr Val Ser Ser
        115

<210> SEQ ID NO 339
<211> LENGTH: 24
<212> TYPE: DNA
<213> ORGANISM: Artificial Sequence
<220> FEATURE:
<223> OTHER INFORMATION: synthetic

<400> SEQUENCE: 339
ggaaacaccc tcactgaatt atcc                                          24

<210> SEQ ID NO 340
<211> LENGTH: 8
<212> TYPE: PRT
<213> ORGANISM: Artificial Sequence
<220> FEATURE:
<223> OTHER INFORMATION: synthetic

<400> SEQUENCE: 340

Gly Asn Thr Leu Thr Glu Leu Ser
1               5

<210> SEQ ID NO 341
<211> LENGTH: 24
<212> TYPE: DNA
<213> ORGANISM: Artificial Sequence
<220> FEATURE:
<223> OTHER INFORMATION: synthetic

<400> SEQUENCE: 341
tttgatcctg aagatggtga caca                                          24

<210> SEQ ID NO 342
<211> LENGTH: 8
<212> TYPE: PRT
<213> ORGANISM: Artificial Sequence
<220> FEATURE:
<223> OTHER INFORMATION: synthetic

<400> SEQUENCE: 342

Phe Asp Pro Glu Asp Gly Asp Thr
1               5

<210> SEQ ID NO 343
<211> LENGTH: 30
<212> TYPE: DNA
<213> ORGANISM: Artificial Sequence
<220> FEATURE:
<223> OTHER INFORMATION: synthetic

<400> SEQUENCE: 343
tcaacagtgg ggggacctac ctctgactgc                                    30

<210> SEQ ID NO 344
<211> LENGTH: 10
<212> TYPE: PRT
<213> ORGANISM: Artificial Sequence
<220> FEATURE:
<223> OTHER INFORMATION: synthetic

<400> SEQUENCE: 344

Ser Thr Val Gly Gly Pro Thr Ser Asp Cys
1               5                   10

<210> SEQ ID NO 345
<211> LENGTH: 321
<212> TYPE: DNA
<213> ORGANISM: Artificial Sequence
<220> FEATURE:
<223> OTHER INFORMATION: synthetic

<400> SEQUENCE: 345

```
gacatccaga tgacccagtc tccatcctcc ctgtctgcat ctgtaggaga cagagtcacc    60
atcacttgcc aggcgagtca ggacattagc aactatttaa attggtatca gcagaaacca   120
gggaaagccc ctaaggtcct gatcttcgat gcatccaatt tagaaccagg ggtcccatca   180
aggttcagtg aagtggatc tgggacagat tttactttca ccatcatcag cctgcagcct   240
gaagatattg caacatatta ctgtcaacaa tatgataatc tcccgatcac cttcggccag   300
gggacacgac tggacattaa a                                             321
```

<210> SEQ ID NO 346
<211> LENGTH: 107
<212> TYPE: PRT
<213> ORGANISM: Artificial Sequence
<220> FEATURE:
<223> OTHER INFORMATION: synthetic

<400> SEQUENCE: 346

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Phe Asp Ala Ser Asn Leu Glu Pro Gly Val Pro Ser Arg Phe Ser Gly
    50                  55                  60

Ser Gly Ser Gly Thr Asp Phe Thr Phe Thr Ile Ile Ser Leu Gln Pro
65                  70                  75                  80

Glu Asp Ile Ala Thr Tyr Tyr Cys Gln Gln Tyr Asp Asn Leu Pro Ile
                85                  90                  95

Thr Phe Gly Gln Gly Thr Arg Leu Asp Ile Lys
            100                 105
```

<210> SEQ ID NO 347
<211> LENGTH: 18
<212> TYPE: DNA
<213> ORGANISM: Artificial Sequence
<220> FEATURE:
<223> OTHER INFORMATION: synthetic

<400> SEQUENCE: 347

```
caggacatta gcaactat                                                  18
```

<210> SEQ ID NO 348
<211> LENGTH: 6
<212> TYPE: PRT
<213> ORGANISM: Artificial Sequence
<220> FEATURE:
<223> OTHER INFORMATION: synthetic

<400> SEQUENCE: 348

```
Gln Asp Ile Ser Asn Tyr
1               5
```

<210> SEQ ID NO 349
<211> LENGTH: 9
<212> TYPE: DNA
<213> ORGANISM: Artificial Sequence
<220> FEATURE:

<223> OTHER INFORMATION: synthetic

<400> SEQUENCE: 349 gatgcatcc                                                                                       9

<210> SEQ ID NO 350
<211> LENGTH: 3
<212> TYPE: PRT
<213> ORGANISM: Artificial Sequence
<220> FEATURE:
<223> OTHER INFORMATION: synthetic

<400> SEQUENCE: 350

Asp Ala Ser
1

<210> SEQ ID NO 351
<211> LENGTH: 27
<212> TYPE: DNA
<213> ORGANISM: Artificial Sequence
<220> FEATURE:
<223> OTHER INFORMATION: synthetic

<400> SEQUENCE: 351
caacaatatg ataatctccc gatcacc                                                                  27

<210> SEQ ID NO 352
<211> LENGTH: 9
<212> TYPE: PRT
<213> ORGANISM: Artificial Sequence
<220> FEATURE:
<223> OTHER INFORMATION: synthetic

<400> SEQUENCE: 352

Gln Gln Tyr Asp Asn Leu Pro Ile Thr
1               5

<210> SEQ ID NO 353
<211> LENGTH: 447
<212> TYPE: PRT
<213> ORGANISM: Artificial Sequence
<220> FEATURE:
<223> OTHER INFORMATION: HC

<400> SEQUENCE: 353

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Val Ser Ser Ser
            20                  25                  30

Tyr Trp Thr Trp Ile Arg Gln Pro Pro Gly Lys Gly Leu Glu Trp Ile
        35                  40                  45

Gly Tyr Ile Tyr Tyr Ser Gly Ser Ser Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Asn Val Asp Thr Thr Met Ile Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala

```
            130                 135                 140
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 354
<211> LENGTH: 214
<212> TYPE: PRT
<213> ORGANISM: Artificial Sequence
<220> FEATURE:
<223> OTHER INFORMATION: LC

<400> SEQUENCE: 354

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ala Gly
```

```
        50                  55                  60
Arg Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Phe Asn Tyr Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 355
<211> LENGTH: 1676
<212> TYPE: PRT
<213> ORGANISM: Artificial Sequence
<220> FEATURE:
<223> OTHER INFORMATION: human C5

<400> SEQUENCE: 355
```

```
Met Gly Leu Leu Gly Ile Leu Cys Phe Leu Ile Phe Leu Gly Lys Thr
  1               5                  10                  15

Trp Gly Gln Glu Gln Thr Tyr Val Ile Ser Ala Pro Lys Ile Phe Arg
                 20                  25                  30

Val Gly Ala Ser Glu Asn Ile Val Ile Gln Val Tyr Gly Tyr Thr Glu
             35                  40                  45

Ala Phe Asp Ala Thr Ile Ser Ile Lys Ser Tyr Pro Asp Lys Lys Phe
         50                  55                  60

Ser Tyr Ser Ser Gly His Val His Leu Ser Ser Glu Asn Lys Phe Gln
 65                  70                  75                  80

Asn Ser Ala Ile Leu Thr Ile Gln Pro Lys Gln Leu Pro Gly Gly Gln
                 85                  90                  95

Asn Pro Val Ser Tyr Val Tyr Leu Glu Val Val Ser Lys His Phe Ser
            100                 105                 110

Lys Ser Lys Arg Met Pro Ile Thr Tyr Asp Asn Gly Phe Leu Phe Ile
        115                 120                 125

His Thr Asp Lys Pro Val Tyr Thr Pro Asp Gln Ser Val Lys Val Arg
    130                 135                 140

Val Tyr Ser Leu Asn Asp Asp Leu Lys Pro Ala Lys Arg Glu Thr Val
145                 150                 155                 160

Leu Thr Phe Ile Asp Pro Glu Gly Ser Glu Val Asp Met Val Glu Glu
                165                 170                 175

Ile Asp His Ile Gly Ile Ile Ser Phe Pro Asp Phe Lys Ile Pro Ser
            180                 185                 190

Asn Pro Arg Tyr Gly Met Trp Thr Ile Lys Ala Lys Tyr Lys Glu Asp
```

```
                195                 200                 205
Phe Ser Thr Thr Gly Thr Ala Tyr Phe Glu Val Lys Glu Tyr Val Leu
    210                 215                 220

Pro His Phe Ser Val Ser Ile Glu Pro Glu Tyr Asn Phe Ile Gly Tyr
225                 230                 235                 240

Lys Asn Phe Lys Asn Phe Glu Ile Thr Ile Lys Ala Arg Tyr Phe Tyr
                245                 250                 255

Asn Lys Val Val Thr Glu Ala Asp Val Tyr Ile Thr Phe Gly Ile Arg
            260                 265                 270

Glu Asp Leu Lys Asp Asp Gln Lys Glu Met Met Gln Thr Ala Met Gln
        275                 280                 285

Asn Thr Met Leu Ile Asn Gly Ile Ala Gln Val Thr Phe Asp Ser Glu
    290                 295                 300

Thr Ala Val Lys Glu Leu Ser Tyr Tyr Ser Leu Glu Asp Leu Asn Asn
305                 310                 315                 320

Lys Tyr Leu Tyr Ile Ala Val Thr Val Ile Glu Ser Thr Gly Gly Phe
                325                 330                 335

Ser Glu Glu Ala Glu Ile Pro Gly Ile Lys Tyr Val Leu Ser Pro Tyr
            340                 345                 350

Lys Leu Asn Leu Val Ala Thr Pro Leu Phe Leu Lys Pro Gly Ile Pro
        355                 360                 365

Tyr Pro Ile Lys Val Gln Val Lys Asp Ser Leu Asp Gln Leu Val Gly
    370                 375                 380

Gly Val Pro Val Thr Leu Asn Ala Gln Thr Ile Asp Val Asn Gln Glu
385                 390                 395                 400

Thr Ser Asp Leu Asp Pro Ser Lys Ser Val Thr Arg Val Asp Asp Gly
                405                 410                 415

Val Ala Ser Phe Val Leu Asn Leu Pro Ser Gly Val Thr Val Leu Glu
            420                 425                 430

Phe Asn Val Lys Thr Asp Ala Pro Asp Leu Pro Glu Glu Asn Gln Ala
        435                 440                 445

Arg Glu Gly Tyr Arg Ala Ile Ala Tyr Ser Ser Leu Ser Gln Ser Tyr
    450                 455                 460

Leu Tyr Ile Asp Trp Thr Asp Asn His Lys Ala Leu Leu Val Gly Glu
465                 470                 475                 480

His Leu Asn Ile Ile Val Thr Pro Lys Ser Pro Tyr Ile Asp Lys Ile
                485                 490                 495

Thr His Tyr Asn Tyr Leu Ile Leu Ser Lys Gly Lys Ile Ile His Phe
            500                 505                 510

Gly Thr Arg Glu Lys Phe Ser Asp Ala Ser Tyr Gln Ser Ile Asn Ile
        515                 520                 525

Pro Val Thr Gln Asn Met Val Pro Ser Ser Arg Leu Leu Val Tyr Tyr
    530                 535                 540

Ile Val Thr Gly Glu Gln Thr Ala Glu Leu Val Ser Asp Ser Val Trp
545                 550                 555                 560

Leu Asn Ile Glu Glu Lys Cys Gly Asn Gln Leu Gln Val His Leu Ser
                565                 570                 575

Pro Asp Ala Asp Ala Tyr Ser Pro Gly Gln Thr Val Ser Leu Asn Met
            580                 585                 590

Ala Thr Gly Met Asp Ser Trp Val Ala Leu Ala Ala Val Asp Ser Ala
        595                 600                 605

Val Tyr Gly Val Gln Arg Gly Ala Lys Lys Pro Leu Glu Arg Val Phe
    610                 615                 620
```

```
Gln Phe Leu Glu Lys Ser Asp Leu Gly Cys Gly Ala Gly Gly Leu
625                 630                 635                 640

Asn Asn Ala Asn Val Phe His Leu Ala Gly Leu Thr Phe Leu Thr Asn
                645                 650                 655

Ala Asn Ala Asp Asp Ser Gln Glu Asn Asp Glu Pro Cys Lys Glu Ile
            660                 665                 670

Leu Arg Pro Arg Arg Thr Leu Gln Lys Lys Ile Glu Glu Ile Ala Ala
        675                 680                 685

Lys Tyr Lys His Ser Val Val Lys Cys Cys Tyr Asp Gly Ala Cys
690                 695                 700

Val Asn Asn Asp Glu Thr Cys Glu Gln Arg Ala Ala Arg Ile Ser Leu
705                 710                 715                 720

Gly Pro Arg Cys Ile Lys Ala Phe Thr Glu Cys Cys Val Val Ala Ser
                725                 730                 735

Gln Leu Arg Ala Asn Ile Ser His Lys Asp Met Gln Leu Gly Arg Leu
            740                 745                 750

His Met Lys Thr Leu Leu Pro Val Ser Lys Pro Glu Ile Arg Ser Tyr
        755                 760                 765

Phe Pro Glu Ser Trp Leu Trp Glu Val His Leu Val Pro Arg Arg Lys
770                 775                 780

Gln Leu Gln Phe Ala Leu Pro Asp Ser Leu Thr Thr Trp Glu Ile Gln
785                 790                 795                 800

Gly Val Gly Ile Ser Asn Thr Gly Ile Cys Val Ala Asp Thr Val Lys
                805                 810                 815

Ala Lys Val Phe Lys Asp Val Phe Leu Glu Met Asn Ile Pro Tyr Ser
            820                 825                 830

Val Val Arg Gly Glu Gln Ile Gln Leu Lys Gly Thr Val Tyr Asn Tyr
        835                 840                 845

Arg Thr Ser Gly Met Gln Phe Cys Val Lys Met Ser Ala Val Glu Gly
850                 855                 860

Ile Cys Thr Ser Glu Ser Pro Val Ile Asp His Gln Gly Thr Lys Ser
865                 870                 875                 880

Ser Lys Cys Val Arg Gln Lys Val Glu Gly Ser Ser His Leu Val
                885                 890                 895

Thr Phe Thr Val Leu Pro Leu Glu Ile Gly Leu His Asn Ile Asn Phe
            900                 905                 910

Ser Leu Glu Thr Trp Phe Gly Lys Glu Ile Leu Val Lys Thr Leu Arg
        915                 920                 925

Val Val Pro Glu Gly Val Lys Arg Glu Ser Tyr Ser Gly Val Thr Leu
930                 935                 940

Asp Pro Arg Gly Ile Tyr Gly Thr Ile Ser Arg Arg Lys Glu Phe Pro
945                 950                 955                 960

Tyr Arg Ile Pro Leu Asp Leu Val Pro Lys Thr Glu Ile Lys Arg Ile
                965                 970                 975

Leu Ser Val Lys Gly Leu Leu Val Gly Glu Ile Leu Ser Ala Val Leu
            980                 985                 990

Ser Gln Glu Gly Ile Asn Ile Leu Thr His Leu Pro Lys Gly Ser Ala
        995                 1000                1005

Glu Ala Glu Leu Met Ser Val Val Pro Val Phe Tyr Val Phe His Tyr
1010                1015                1020

Leu Glu Thr Gly Asn His Trp Asn Ile Phe His Ser Asp Pro Leu Ile
1025                1030                1035                1040
```

-continued

Glu Lys Gln Lys Leu Lys Lys Lys Leu Lys Glu Gly Met Leu Ser Ile
            1045                1050                1055

Met Ser Tyr Arg Asn Ala Asp Tyr Ser Tyr Ser Val Trp Lys Gly Gly
        1060                1065                1070

Ser Ala Ser Thr Trp Leu Thr Ala Phe Ala Leu Arg Val Leu Gly Gln
        1075                1080                1085

Val Asn Lys Tyr Val Glu Gln Asn Gln Asn Ser Ile Cys Asn Ser Leu
    1090                1095                1100

Leu Trp Leu Val Glu Asn Tyr Gln Leu Asp Asn Gly Ser Phe Lys Glu
1105                1110                1115                1120

Asn Ser Gln Tyr Gln Pro Ile Lys Leu Gln Gly Thr Leu Pro Val Glu
            1125                1130                1135

Ala Arg Glu Asn Ser Leu Tyr Leu Thr Ala Phe Thr Val Ile Gly Ile
        1140                1145                1150

Arg Lys Ala Phe Asp Ile Cys Pro Leu Val Lys Ile Asp Thr Ala Leu
        1155                1160                1165

Ile Lys Ala Asp Asn Phe Leu Leu Glu Asn Thr Leu Pro Ala Gln Ser
    1170                1175                1180

Thr Phe Thr Leu Ala Ile Ser Ala Tyr Ala Leu Ser Leu Gly Asp Lys
1185                1190                1195                1200

Thr His Pro Gln Phe Arg Ser Ile Val Ser Ala Leu Lys Arg Glu Ala
        1205                1210                1215

Leu Val Lys Gly Asn Pro Pro Ile Tyr Arg Phe Trp Lys Asp Asn Leu
        1220                1225                1230

Gln His Lys Asp Ser Ser Val Pro Asn Thr Gly Thr Ala Arg Met Val
    1235                1240                1245

Glu Thr Thr Ala Tyr Ala Leu Leu Thr Ser Leu Asn Leu Lys Asp Ile
    1250                1255                1260

Asn Tyr Val Asn Pro Val Ile Lys Trp Leu Ser Glu Glu Gln Arg Tyr
1265                1270                1275                1280

Gly Gly Gly Phe Tyr Ser Thr Gln Asp Thr Ile Asn Ala Ile Glu Gly
            1285                1290                1295

Leu Thr Glu Tyr Ser Leu Leu Val Lys Gln Leu Arg Leu Ser Met Asp
        1300                1305                1310

Ile Asp Val Ser Tyr Lys His Lys Gly Ala Leu His Asn Tyr Lys Met
        1315                1320                1325

Thr Asp Lys Asn Phe Leu Gly Arg Pro Val Glu Val Leu Leu Asn Asp
    1330                1335                1340

Asp Leu Ile Val Ser Thr Gly Phe Gly Ser Gly Leu Ala Thr Val His
1345                1350                1355                1360

Val Thr Thr Val Val His Lys Thr Ser Thr Ser Glu Glu Val Cys Ser
            1365                1370                1375

Phe Tyr Leu Lys Ile Asp Thr Gln Asp Ile Glu Ala Ser His Tyr Arg
        1380                1385                1390

Gly Tyr Gly Asn Ser Asp Tyr Lys Arg Ile Val Ala Cys Ala Ser Tyr
        1395                1400                1405

Lys Pro Ser Arg Glu Glu Ser Ser Ser Gly Ser Ser His Ala Val Met
    1410                1415                1420

Asp Ile Ser Leu Pro Thr Gly Ile Ser Ala Asn Glu Glu Asp Leu Lys
1425                1430                1435                1440

Ala Leu Val Glu Gly Val Asp Gln Leu Phe Thr Asp Tyr Gln Ile Lys
        1445                1450                1455

Asp Gly His Val Ile Leu Gln Leu Asn Ser Ile Pro Ser Ser Asp Phe

```
                1460                1465                1470
Leu Cys Val Arg Phe Arg Ile Phe Glu Leu Phe Glu Val Gly Phe Leu
                1475                1480                1485

Ser Pro Ala Thr Phe Thr Val Tyr Glu Tyr His Arg Pro Asp Lys Gln
            1490                1495                1500

Cys Thr Met Phe Tyr Ser Thr Ser Asn Ile Lys Ile Gln Lys Val Cys
1505                1510                1515                1520

Glu Gly Ala Ala Cys Lys Cys Val Glu Ala Asp Cys Gly Gln Met Gln
                1525                1530                1535

Glu Glu Leu Asp Leu Thr Ile Ser Ala Glu Thr Arg Lys Gln Thr Ala
            1540                1545                1550

Cys Lys Pro Glu Ile Ala Tyr Ala Tyr Lys Val Ser Ile Thr Ser Ile
        1555                1560                1565

Thr Val Glu Asn Val Phe Val Lys Tyr Lys Ala Thr Leu Leu Asp Ile
    1570                1575                1580

Tyr Lys Thr Gly Glu Ala Val Ala Glu Lys Asp Ser Glu Ile Thr Phe
1585                1590                1595                1600

Ile Lys Lys Val Thr Cys Thr Asn Ala Glu Leu Val Lys Gly Arg Gln
                1605                1610                1615

Tyr Leu Ile Met Gly Lys Glu Ala Leu Gln Ile Lys Tyr Asn Phe Ser
            1620                1625                1630

Phe Arg Tyr Ile Tyr Pro Leu Asp Ser Leu Thr Trp Ile Glu Tyr Trp
        1635                1640                1645

Pro Arg Asp Thr Thr Cys Ser Ser Cys Gln Ala Phe Leu Ala Asn Leu
    1650                1655                1660

Asp Glu Phe Ala Glu Asp Ile Phe Leu Asn Gly Cys
1665                1670                1675

<210> SEQ ID NO 356
<211> LENGTH: 1686
<212> TYPE: PRT
<213> ORGANISM: Artificial Sequence
<220> FEATURE:
<223> OTHER INFORMATION: hC5 R885H
      aa 1-1658: hC5 (aa 19-1676 of NM_001735.2 with
      R885H change)
      aa 1659-1686: myc-myc-hexahistidine tag

<400> SEQUENCE: 356

Gln Glu Gln Thr Tyr Val Ile Ser Ala Pro Lys Ile Phe Arg Val Gly
1               5                   10                  15

Ala Ser Glu Asn Ile Val Ile Gln Val Tyr Gly Tyr Thr Glu Ala Phe
            20                  25                  30

Asp Ala Thr Ile Ser Ile Lys Ser Tyr Pro Asp Lys Lys Phe Ser Tyr
        35                  40                  45

Ser Ser Gly His Val His Leu Ser Ser Glu Asn Lys Phe Gln Asn Ser
    50                  55                  60

Ala Ile Leu Thr Ile Gln Pro Lys Gln Leu Pro Gly Gly Gln Asn Pro
65                  70                  75                  80

Val Ser Tyr Val Tyr Leu Glu Val Val Ser Lys His Phe Ser Lys Ser
                85                  90                  95

Lys Arg Met Pro Ile Thr Tyr Asp Asn Gly Phe Leu Phe Ile His Thr
            100                 105                 110

Asp Lys Pro Val Tyr Thr Pro Asp Gln Ser Val Lys Val Arg Val Tyr
        115                 120                 125

Ser Leu Asn Asp Asp Leu Lys Pro Ala Lys Arg Glu Thr Val Leu Thr
```

-continued

```
            130                 135                 140
Phe Ile Asp Pro Glu Gly Ser Glu Val Asp Met Val Glu Ile Asp
145                 150                 155                 160

His Ile Gly Ile Ile Ser Phe Pro Asp Phe Lys Ile Pro Ser Asn Pro
                165                 170                 175

Arg Tyr Gly Met Trp Thr Ile Lys Ala Lys Tyr Lys Glu Asp Phe Ser
                180                 185                 190

Thr Thr Gly Thr Ala Tyr Phe Glu Val Lys Glu Tyr Val Leu Pro His
                195                 200                 205

Phe Ser Val Ser Ile Glu Pro Glu Tyr Asn Phe Ile Gly Tyr Lys Asn
                210                 215                 220

Phe Lys Asn Phe Glu Ile Thr Ile Lys Ala Arg Tyr Phe Tyr Asn Lys
225                 230                 235                 240

Val Val Thr Glu Ala Asp Val Tyr Ile Thr Phe Gly Ile Arg Glu Asp
                245                 250                 255

Leu Lys Asp Asp Gln Lys Glu Met Met Gln Thr Ala Met Gln Asn Thr
                260                 265                 270

Met Leu Ile Asn Gly Ile Ala Gln Val Thr Phe Asp Ser Glu Thr Ala
                275                 280                 285

Val Lys Glu Leu Ser Tyr Tyr Ser Leu Glu Asp Leu Asn Asn Lys Tyr
                290                 295                 300

Leu Tyr Ile Ala Val Thr Val Ile Glu Ser Thr Gly Gly Phe Ser Glu
305                 310                 315                 320

Glu Ala Glu Ile Pro Gly Ile Lys Tyr Val Leu Ser Pro Tyr Lys Leu
                325                 330                 335

Asn Leu Val Ala Thr Pro Leu Phe Leu Lys Pro Gly Ile Pro Tyr Pro
                340                 345                 350

Ile Lys Val Gln Val Lys Asp Ser Leu Asp Gln Leu Val Gly Gly Val
                355                 360                 365

Pro Val Thr Leu Asn Ala Gln Thr Ile Asp Val Asn Gln Glu Thr Ser
                370                 375                 380

Asp Leu Asp Pro Ser Lys Ser Val Thr Arg Val Asp Asp Gly Val Ala
385                 390                 395                 400

Ser Phe Val Leu Asn Leu Pro Ser Gly Val Thr Val Leu Glu Phe Asn
                405                 410                 415

Val Lys Thr Asp Ala Pro Asp Leu Pro Glu Glu Asn Gln Ala Arg Glu
                420                 425                 430

Gly Tyr Arg Ala Ile Ala Tyr Ser Ser Leu Ser Gln Ser Tyr Leu Tyr
                435                 440                 445

Ile Asp Trp Thr Asp Asn His Lys Ala Leu Leu Val Gly Glu His Leu
450                 455                 460

Asn Ile Ile Val Thr Pro Lys Ser Pro Tyr Ile Asp Lys Ile Thr His
465                 470                 475                 480

Tyr Asn Tyr Leu Ile Leu Ser Lys Gly Lys Ile Ile His Phe Gly Thr
                485                 490                 495

Arg Glu Lys Phe Ser Asp Ala Ser Tyr Gln Ser Ile Asn Ile Pro Val
                500                 505                 510

Thr Gln Asn Met Val Pro Ser Ser Arg Leu Leu Val Tyr Tyr Ile Val
                515                 520                 525

Thr Gly Glu Gln Thr Ala Glu Leu Val Ser Asp Ser Val Trp Leu Asn
                530                 535                 540

Ile Glu Glu Lys Cys Gly Asn Gln Leu Gln Val His Leu Ser Pro Asp
545                 550                 555                 560
```

Ala Asp Ala Tyr Ser Pro Gly Gln Thr Val Ser Leu Asn Met Ala Thr
                565                 570                 575

Gly Met Asp Ser Trp Val Ala Leu Ala Ala Val Asp Ser Ala Val Tyr
                580                 585                 590

Gly Val Gln Arg Gly Ala Lys Lys Pro Leu Glu Arg Val Phe Gln Phe
            595                 600                 605

Leu Glu Lys Ser Asp Leu Gly Cys Gly Ala Gly Gly Leu Asn Asn
        610                 615                 620

Ala Asn Val Phe His Leu Ala Gly Leu Thr Phe Leu Thr Asn Ala Asn
625                 630                 635                 640

Ala Asp Asp Ser Gln Glu Asn Asp Glu Pro Cys Lys Glu Ile Leu Arg
                645                 650                 655

Pro Arg Arg Thr Leu Gln Lys Lys Ile Glu Glu Ile Ala Ala Lys Tyr
                660                 665                 670

Lys His Ser Val Val Lys Lys Cys Cys Tyr Asp Gly Ala Cys Val Asn
675                 680                 685

Asn Asp Glu Thr Cys Glu Gln Arg Ala Ala Arg Ile Ser Leu Gly Pro
        690                 695                 700

Arg Cys Ile Lys Ala Phe Thr Glu Cys Val Val Ala Ser Gln Leu
705                 710                 715                 720

Arg Ala Asn Ile Ser His Lys Asp Met Gln Leu Gly Arg Leu His Met
                725                 730                 735

Lys Thr Leu Leu Pro Val Ser Lys Pro Glu Ile Arg Ser Tyr Phe Pro
                740                 745                 750

Glu Ser Trp Leu Trp Glu Val His Leu Val Pro Arg Arg Lys Gln Leu
            755                 760                 765

Gln Phe Ala Leu Pro Asp Ser Leu Thr Thr Trp Glu Ile Gln Gly Val
    770                 775                 780

Gly Ile Ser Asn Thr Gly Ile Cys Val Ala Asp Thr Val Lys Ala Lys
785                 790                 795                 800

Val Phe Lys Asp Val Phe Leu Glu Met Asn Ile Pro Tyr Ser Val Val
                805                 810                 815

Arg Gly Glu Gln Ile Gln Leu Lys Gly Thr Val Tyr Asn Tyr Arg Thr
                820                 825                 830

Ser Gly Met Gln Phe Cys Val Lys Met Ser Ala Val Glu Gly Ile Cys
            835                 840                 845

Thr Ser Glu Ser Pro Val Ile Asp His Gln Gly Thr Lys Ser Ser Lys
        850                 855                 860

Cys Val His Gln Lys Val Glu Gly Ser Ser Ser His Leu Val Thr Phe
865                 870                 875                 880

Thr Val Leu Pro Leu Glu Ile Gly Leu His Asn Ile Asn Phe Ser Leu
                885                 890                 895

Glu Thr Trp Phe Gly Lys Glu Ile Leu Val Lys Thr Leu Arg Val Val
                900                 905                 910

Pro Glu Gly Val Lys Arg Glu Ser Tyr Ser Gly Val Thr Leu Asp Pro
            915                 920                 925

Arg Gly Ile Tyr Gly Thr Ile Ser Arg Arg Lys Glu Phe Pro Tyr Arg
        930                 935                 940

Ile Pro Leu Asp Leu Val Pro Lys Thr Glu Ile Lys Arg Ile Leu Ser
945                 950                 955                 960

Val Lys Gly Leu Leu Val Gly Glu Ile Leu Ser Ala Val Leu Ser Gln
                965                 970                 975

```
Glu Gly Ile Asn Ile Leu Thr His Leu Pro Lys Gly Ser Ala Glu Ala
            980                 985                 990

Glu Leu Met Ser Val Val Pro Val Phe Tyr Val Phe His Tyr Leu Glu
        995                 1000                1005

Thr Gly Asn His Trp Asn Ile Phe His Ser Asp Pro Leu Ile Glu Lys
    1010                1015                1020

Gln Lys Leu Lys Lys Lys Leu Lys Glu Gly Met Leu Ser Ile Met Ser
1025                1030                1035                1040

Tyr Arg Asn Ala Asp Tyr Ser Tyr Ser Val Trp Lys Gly Gly Ser Ala
                1045                1050                1055

Ser Thr Trp Leu Thr Ala Phe Ala Leu Arg Val Leu Gly Gln Val Asn
            1060                1065                1070

Lys Tyr Val Glu Gln Asn Gln Asn Ser Ile Cys Asn Ser Leu Leu Trp
        1075                1080                1085

Leu Val Glu Asn Tyr Gln Leu Asp Asn Gly Ser Phe Lys Glu Asn Ser
        1090                1095                1100

Gln Tyr Gln Pro Ile Lys Leu Gln Gly Thr Leu Pro Val Glu Ala Arg
1105                1110                1115                1120

Glu Asn Ser Leu Tyr Leu Thr Ala Phe Thr Val Ile Gly Ile Arg Lys
                1125                1130                1135

Ala Phe Asp Ile Cys Pro Leu Val Lys Ile Asp Thr Ala Leu Ile Lys
            1140                1145                1150

Ala Asp Asn Phe Leu Leu Glu Asn Thr Leu Pro Ala Gln Ser Thr Phe
        1155                1160                1165

Thr Leu Ala Ile Ser Ala Tyr Ala Leu Ser Leu Gly Asp Lys Thr His
    1170                1175                1180

Pro Gln Phe Arg Ser Ile Val Ser Ala Leu Lys Arg Glu Ala Leu Val
1185                1190                1195                1200

Lys Gly Asn Pro Pro Ile Tyr Arg Phe Trp Lys Asp Asn Leu Gln His
                1205                1210                1215

Lys Asp Ser Ser Val Pro Asn Thr Gly Thr Ala Arg Met Val Glu Thr
            1220                1225                1230

Thr Ala Tyr Ala Leu Leu Thr Ser Leu Asn Leu Lys Asp Ile Asn Tyr
        1235                1240                1245

Val Asn Pro Val Ile Lys Trp Leu Ser Glu Glu Gln Arg Tyr Gly Gly
        1250                1255                1260

Gly Phe Tyr Ser Thr Gln Asp Thr Ile Asn Ala Ile Glu Gly Leu Thr
1265                1270                1275                1280

Glu Tyr Ser Leu Leu Val Lys Gln Leu Arg Leu Ser Met Asp Ile Asp
                1285                1290                1295

Val Ser Tyr Lys His Lys Gly Ala Leu His Asn Tyr Lys Met Thr Asp
            1300                1305                1310

Lys Asn Phe Leu Gly Arg Pro Val Glu Val Leu Leu Asn Asp Asp Leu
        1315                1320                1325

Ile Val Ser Thr Gly Phe Gly Ser Gly Leu Ala Thr Val His Val Thr
    1330                1335                1340

Thr Val Val His Lys Thr Ser Thr Ser Glu Glu Val Cys Ser Phe Tyr
1345                1350                1355                1360

Leu Lys Ile Asp Thr Gln Asp Ile Glu Ala Ser His Tyr Arg Gly Tyr
                1365                1370                1375

Gly Asn Ser Asp Tyr Lys Arg Ile Val Ala Cys Ala Ser Tyr Lys Pro
            1380                1385                1390

Ser Arg Glu Glu Ser Ser Ser Gly Ser Ser His Ala Val Met Asp Ile
```

-continued

```
            1395                1400                1405

Ser Leu Pro Thr Gly Ile Ser Ala Asn Glu Glu Asp Leu Lys Ala Leu
            1410                1415                1420

Val Glu Gly Val Asp Gln Leu Phe Thr Asp Tyr Gln Ile Lys Asp Gly
1425                1430                1435                1440

His Val Ile Leu Gln Leu Asn Ser Ile Pro Ser Ser Asp Phe Leu Cys
                1445                1450                1455

Val Arg Phe Arg Ile Phe Glu Leu Phe Glu Val Gly Phe Leu Ser Pro
                1460                1465                1470

Ala Thr Phe Thr Val Tyr Glu Tyr His Arg Pro Asp Lys Gln Cys Thr
                1475                1480                1485

Met Phe Tyr Ser Thr Ser Asn Ile Lys Ile Gln Lys Val Cys Glu Gly
                1490                1495                1500

Ala Ala Cys Lys Cys Val Glu Ala Asp Cys Gly Gln Met Gln Glu Glu
1505                1510                1515                1520

Leu Asp Leu Thr Ile Ser Ala Glu Thr Arg Lys Gln Thr Ala Cys Lys
                1525                1530                1535

Pro Glu Ile Ala Tyr Ala Tyr Lys Val Ser Ile Thr Ser Ile Thr Val
                1540                1545                1550

Glu Asn Val Phe Val Lys Tyr Lys Ala Thr Leu Leu Asp Ile Tyr Lys
                1555                1560                1565

Thr Gly Glu Ala Val Ala Glu Lys Asp Ser Glu Ile Thr Phe Ile Lys
                1570                1575                1580

Lys Val Thr Cys Thr Asn Ala Glu Leu Val Lys Gly Arg Gln Tyr Leu
1585                1590                1595                1600

Ile Met Gly Lys Glu Ala Leu Gln Ile Lys Tyr Asn Phe Ser Phe Arg
                1605                1610                1615

Tyr Ile Tyr Pro Leu Asp Ser Leu Thr Trp Ile Glu Tyr Trp Pro Arg
                1620                1625                1630

Asp Thr Thr Cys Ser Ser Cys Gln Ala Phe Leu Ala Asn Leu Asp Glu
                1635                1640                1645

Phe Ala Glu Asp Ile Phe Leu Asn Gly Cys Glu Gln Lys Leu Ile Ser
                1650                1655                1660

Glu Glu Asp Leu Gly Gly Glu Gln Lys Leu Ile Ser Glu Glu Asp Leu
1665                1670                1675                1680

His His His His His His
                1685

<210> SEQ ID NO 357
<211> LENGTH: 1686
<212> TYPE: PRT
<213> ORGANISM: Artificial Sequence
<220> FEATURE:
<223> OTHER INFORMATION: hC5 R885C
      aa 1-1658: hC5 (aa 19-1676 of NM_001735.2 with
      R885C change)
      aa 1659-1686: myc-myc-hexahistidine tag

<400> SEQUENCE: 357

Gln Glu Gln Thr Tyr Val Ile Ser Ala Pro Lys Ile Phe Arg Val Gly
1               5                   10                  15

Ala Ser Glu Asn Ile Val Ile Gln Val Tyr Gly Tyr Thr Glu Ala Phe
                20                  25                  30

Asp Ala Thr Ile Ser Ile Lys Ser Tyr Pro Asp Lys Lys Phe Ser Tyr
            35                  40                  45

Ser Ser Gly His Val His Leu Ser Ser Glu Asn Lys Phe Gln Asn Ser
```

```
            50                  55                  60
Ala Ile Leu Thr Ile Gln Pro Lys Gln Leu Pro Gly Gly Gln Asn Pro
 65                  70                  75                  80

Val Ser Tyr Val Tyr Leu Glu Val Val Ser Lys His Phe Ser Lys Ser
                     85                  90                  95

Lys Arg Met Pro Ile Thr Tyr Asp Asn Gly Phe Leu Phe Ile His Thr
                100                 105                 110

Asp Lys Pro Val Tyr Thr Pro Asp Gln Ser Val Lys Val Arg Val Tyr
                115                 120                 125

Ser Leu Asn Asp Asp Leu Lys Pro Ala Lys Arg Glu Thr Val Leu Thr
130                 135                 140

Phe Ile Asp Pro Glu Gly Ser Glu Val Asp Met Val Glu Glu Ile Asp
145                 150                 155                 160

His Ile Gly Ile Ile Ser Phe Pro Asp Phe Lys Ile Pro Ser Asn Pro
                165                 170                 175

Arg Tyr Gly Met Trp Thr Ile Lys Ala Lys Tyr Lys Glu Asp Phe Ser
                180                 185                 190

Thr Thr Gly Thr Ala Tyr Phe Glu Val Lys Glu Tyr Val Leu Pro His
                195                 200                 205

Phe Ser Val Ser Ile Glu Pro Glu Tyr Asn Phe Ile Gly Tyr Lys Asn
210                 215                 220

Phe Lys Asn Phe Glu Ile Thr Ile Lys Ala Arg Tyr Phe Tyr Asn Lys
225                 230                 235                 240

Val Val Thr Glu Ala Asp Val Tyr Ile Thr Phe Gly Ile Arg Glu Asp
                245                 250                 255

Leu Lys Asp Asp Gln Lys Glu Met Met Gln Thr Ala Met Gln Asn Thr
                260                 265                 270

Met Leu Ile Asn Gly Ile Ala Gln Val Thr Phe Asp Ser Glu Thr Ala
                275                 280                 285

Val Lys Glu Leu Ser Tyr Tyr Ser Leu Glu Asp Leu Asn Asn Lys Tyr
                290                 295                 300

Leu Tyr Ile Ala Val Thr Val Ile Glu Ser Thr Gly Gly Phe Ser Glu
305                 310                 315                 320

Glu Ala Glu Ile Pro Gly Ile Lys Tyr Val Leu Ser Pro Tyr Lys Leu
                325                 330                 335

Asn Leu Val Ala Thr Pro Leu Phe Leu Lys Pro Gly Ile Pro Tyr Pro
                340                 345                 350

Ile Lys Val Gln Val Lys Asp Ser Leu Asp Gln Leu Val Gly Gly Val
                355                 360                 365

Pro Val Thr Leu Asn Ala Gln Thr Ile Asp Val Asn Gln Glu Thr Ser
370                 375                 380

Asp Leu Asp Pro Ser Lys Ser Val Thr Arg Val Asp Asp Gly Val Ala
385                 390                 395                 400

Ser Phe Val Leu Asn Leu Pro Ser Gly Val Thr Val Leu Glu Phe Asn
                405                 410                 415

Val Lys Thr Asp Ala Pro Asp Leu Pro Glu Glu Asn Gln Ala Arg Glu
                420                 425                 430

Gly Tyr Arg Ala Ile Ala Tyr Ser Ser Leu Ser Gln Ser Tyr Leu Tyr
                435                 440                 445

Ile Asp Trp Thr Asp Asn His Lys Ala Leu Leu Val Gly Glu His Leu
                450                 455                 460

Asn Ile Ile Val Thr Pro Lys Ser Pro Tyr Ile Asp Lys Ile Thr His
465                 470                 475                 480
```

```
Tyr Asn Tyr Leu Ile Leu Ser Lys Gly Lys Ile Ile His Phe Gly Thr
            485                 490                 495

Arg Glu Lys Phe Ser Asp Ala Ser Tyr Gln Ser Ile Asn Ile Pro Val
            500                 505                 510

Thr Gln Asn Met Val Pro Ser Ser Arg Leu Leu Val Tyr Tyr Ile Val
            515                 520                 525

Thr Gly Glu Gln Thr Ala Glu Leu Val Ser Asp Ser Val Trp Leu Asn
        530                 535                 540

Ile Glu Glu Lys Cys Gly Asn Gln Leu Gln Val His Leu Ser Pro Asp
545                 550                 555                 560

Ala Asp Ala Tyr Ser Pro Gly Gln Thr Val Ser Leu Asn Met Ala Thr
                565                 570                 575

Gly Met Asp Ser Trp Val Ala Leu Ala Ala Val Asp Ser Ala Val Tyr
            580                 585                 590

Gly Val Gln Arg Gly Ala Lys Lys Pro Leu Glu Arg Val Phe Gln Phe
        595                 600                 605

Leu Glu Lys Ser Asp Leu Gly Cys Gly Ala Gly Gly Gly Leu Asn Asn
        610                 615                 620

Ala Asn Val Phe His Leu Ala Gly Leu Thr Phe Leu Thr Asn Ala Asn
625                 630                 635                 640

Ala Asp Asp Ser Gln Glu Asn Asp Glu Pro Cys Lys Glu Ile Leu Arg
                645                 650                 655

Pro Arg Arg Thr Leu Gln Lys Lys Ile Glu Glu Ile Ala Ala Lys Tyr
                660                 665                 670

Lys His Ser Val Val Lys Lys Cys Cys Tyr Asp Gly Ala Cys Val Asn
            675                 680                 685

Asn Asp Glu Thr Cys Glu Gln Arg Ala Ala Arg Ile Ser Leu Gly Pro
690                 695                 700

Arg Cys Ile Lys Ala Phe Thr Glu Cys Cys Val Val Ala Ser Gln Leu
705                 710                 715                 720

Arg Ala Asn Ile Ser His Lys Asp Met Gln Leu Gly Arg Leu His Met
                725                 730                 735

Lys Thr Leu Leu Pro Val Ser Lys Pro Glu Ile Arg Ser Tyr Phe Pro
            740                 745                 750

Glu Ser Trp Leu Trp Glu Val His Leu Val Pro Arg Arg Lys Gln Leu
        755                 760                 765

Gln Phe Ala Leu Pro Asp Ser Leu Thr Thr Trp Glu Ile Gln Gly Val
        770                 775                 780

Gly Ile Ser Asn Thr Gly Ile Cys Val Ala Asp Thr Val Lys Ala Lys
785                 790                 795                 800

Val Phe Lys Asp Val Phe Leu Glu Met Asn Ile Pro Tyr Ser Val Val
                805                 810                 815

Arg Gly Glu Gln Ile Gln Leu Lys Gly Thr Val Tyr Asn Tyr Arg Thr
                820                 825                 830

Ser Gly Met Gln Phe Cys Val Lys Met Ser Ala Val Glu Gly Ile Cys
            835                 840                 845

Thr Ser Glu Ser Pro Val Ile Asp His Gln Gly Thr Lys Ser Ser Lys
850                 855                 860

Cys Val Cys Gln Lys Val Glu Gly Ser Ser Ser His Leu Val Thr Phe
865                 870                 875                 880

Thr Val Leu Pro Leu Glu Ile Gly Leu His Asn Ile Asn Phe Ser Leu
                885                 890                 895
```

Glu Thr Trp Phe Gly Lys Glu Ile Leu Val Lys Thr Leu Arg Val Val
                900                 905                 910

Pro Glu Gly Val Lys Arg Glu Ser Tyr Ser Gly Val Thr Leu Asp Pro
            915                 920                 925

Arg Gly Ile Tyr Gly Thr Ile Ser Arg Arg Lys Glu Phe Pro Tyr Arg
        930                 935                 940

Ile Pro Leu Asp Leu Val Pro Lys Thr Glu Ile Lys Arg Ile Leu Ser
945                 950                 955                 960

Val Lys Gly Leu Leu Val Gly Glu Ile Leu Ser Ala Val Leu Ser Gln
                965                 970                 975

Glu Gly Ile Asn Ile Leu Thr His Leu Pro Lys Gly Ser Ala Glu Ala
            980                 985                 990

Glu Leu Met Ser Val Val Pro Val Phe Tyr Val Phe His Tyr Leu Glu
        995                 1000                1005

Thr Gly Asn His Trp Asn Ile Phe His Ser Asp Pro Leu Ile Glu Lys
    1010                1015                1020

Gln Lys Leu Lys Lys Leu Lys Glu Gly Met Leu Ser Ile Met Ser
1025                1030                1035                1040

Tyr Arg Asn Ala Asp Tyr Ser Tyr Ser Val Trp Lys Gly Gly Ser Ala
                1045                1050                1055

Ser Thr Trp Leu Thr Ala Phe Ala Leu Arg Val Leu Gly Gln Val Asn
            1060                1065                1070

Lys Tyr Val Glu Gln Asn Gln Asn Ser Ile Cys Asn Ser Leu Leu Trp
        1075                1080                1085

Leu Val Glu Asn Tyr Gln Leu Asp Asn Gly Ser Phe Lys Glu Asn Ser
    1090                1095                1100

Gln Tyr Gln Pro Ile Lys Leu Gln Gly Thr Leu Pro Val Glu Ala Arg
1105                1110                1115                1120

Glu Asn Ser Leu Tyr Leu Thr Ala Phe Thr Val Ile Gly Ile Arg Lys
                1125                1130                1135

Ala Phe Asp Ile Cys Pro Leu Val Lys Ile Asp Thr Ala Leu Ile Lys
            1140                1145                1150

Ala Asp Asn Phe Leu Leu Glu Asn Thr Leu Pro Ala Gln Ser Thr Phe
        1155                1160                1165

Thr Leu Ala Ile Ser Ala Tyr Ala Leu Ser Leu Gly Asp Lys Thr His
    1170                1175                1180

Pro Gln Phe Arg Ser Ile Val Ser Ala Leu Lys Arg Glu Ala Leu Val
1185                1190                1195                1200

Lys Gly Asn Pro Pro Ile Tyr Arg Phe Trp Lys Asp Asn Leu Gln His
                1205                1210                1215

Lys Asp Ser Ser Val Pro Asn Thr Gly Thr Ala Arg Met Val Glu Thr
            1220                1225                1230

Thr Ala Tyr Ala Leu Leu Thr Ser Leu Asn Leu Lys Asp Ile Asn Tyr
        1235                1240                1245

Val Asn Pro Val Ile Lys Trp Leu Ser Glu Glu Gln Arg Tyr Gly Gly
    1250                1255                1260

Gly Phe Tyr Ser Thr Gln Asp Thr Ile Asn Ala Ile Glu Gly Leu Thr
1265                1270                1275                1280

Glu Tyr Ser Leu Leu Val Lys Gln Leu Arg Leu Ser Met Asp Ile Asp
                1285                1290                1295

Val Ser Tyr Lys His Lys Gly Ala Leu His Asn Tyr Lys Met Thr Asp
            1300                1305                1310

Lys Asn Phe Leu Gly Arg Pro Val Glu Val Leu Leu Asn Asp Asp Leu

```
                1315                1320                1325
Ile Val Ser Thr Gly Phe Gly Ser Gly Leu Ala Thr Val His Val Thr
            1330                1335                1340

Thr Val Val His Lys Thr Ser Thr Ser Glu Glu Val Cys Ser Phe Tyr
1345                1350                1355                1360

Leu Lys Ile Asp Thr Gln Asp Ile Glu Ala Ser His Tyr Arg Gly Tyr
                1365                1370                1375

Gly Asn Ser Asp Tyr Lys Arg Ile Val Ala Cys Ala Ser Tyr Lys Pro
            1380                1385                1390

Ser Arg Glu Glu Ser Ser Gly Ser Ser His Ala Val Met Asp Ile
        1395                1400                1405

Ser Leu Pro Thr Gly Ile Ser Ala Asn Glu Glu Asp Leu Lys Ala Leu
    1410                1415                1420

Val Glu Gly Val Asp Gln Leu Phe Thr Asp Tyr Gln Ile Lys Asp Gly
1425                1430                1435                1440

His Val Ile Leu Gln Leu Asn Ser Ile Pro Ser Ser Asp Phe Leu Cys
                1445                1450                1455

Val Arg Phe Arg Ile Phe Glu Leu Phe Glu Val Gly Phe Leu Ser Pro
            1460                1465                1470

Ala Thr Phe Thr Val Tyr Glu Tyr His Arg Pro Asp Lys Gln Cys Thr
        1475                1480                1485

Met Phe Tyr Ser Thr Ser Asn Ile Lys Ile Gln Lys Val Cys Glu Gly
    1490                1495                1500

Ala Ala Cys Lys Cys Val Glu Ala Asp Cys Gly Gln Met Gln Glu Glu
1505                1510                1515                1520

Leu Asp Leu Thr Ile Ser Ala Glu Thr Arg Lys Gln Thr Ala Cys Lys
                1525                1530                1535

Pro Glu Ile Ala Tyr Ala Tyr Lys Val Ser Ile Thr Ser Ile Thr Val
            1540                1545                1550

Glu Asn Val Phe Val Lys Tyr Lys Ala Thr Leu Leu Asp Ile Tyr Lys
        1555                1560                1565

Thr Gly Glu Ala Val Ala Glu Lys Asp Ser Glu Ile Thr Phe Ile Lys
    1570                1575                1580

Lys Val Thr Cys Thr Asn Ala Glu Leu Val Lys Gly Arg Gln Tyr Leu
1585                1590                1595                1600

Ile Met Gly Lys Glu Ala Leu Gln Ile Lys Tyr Asn Phe Ser Phe Arg
                1605                1610                1615

Tyr Ile Tyr Pro Leu Asp Ser Leu Thr Trp Ile Glu Tyr Trp Pro Arg
            1620                1625                1630

Asp Thr Thr Cys Ser Ser Cys Gln Ala Phe Leu Ala Asn Leu Asp Glu
        1635                1640                1645

Phe Ala Glu Asp Ile Phe Leu Asn Gly Cys Glu Gln Lys Leu Ile Ser
    1650                1655                1660

Glu Glu Asp Leu Gly Gly Glu Gln Lys Leu Ile Ser Glu Glu Asp Leu
1665                1670                1675                1680

His His His His His His
            1685

<210> SEQ ID NO 358
<211> LENGTH: 1686
<212> TYPE: PRT
<213> ORGANISM: Artificial Sequence
<220> FEATURE:
<223> OTHER INFORMATION: M. fascicularis C5 R885H
      aa 1-1658: M. fascicularis C5 (determined
``` in-house; NTBK#12480)
aa 1659-1686: myc-myc-hexahistidine tag

<400> SEQUENCE: 358

Gln Glu Gln Thr Tyr Val Ile Ser Ala Pro Lys Ile Phe Arg Val Gly
1               5                   10                  15

Ala Ser Glu Asn Ile Val Ile Gln Val Tyr Gly Tyr Thr Glu Ala Phe
            20                  25                  30

Asp Ala Thr Ile Ser Ile Lys Ser Tyr Pro Asp Lys Lys Phe Ser Tyr
        35                  40                  45

Ser Ser Gly His Val His Leu Ser Ser Glu Asn Lys Phe Gln Asn Ser
    50                  55                  60

Ala Val Leu Thr Ile Gln Pro Lys Gln Leu Pro Gly Gln Asn Gln
65                  70                  75                  80

Val Ser Tyr Val Tyr Leu Glu Val Ser Lys His Phe Ser Lys Ser
            85                  90                  95

Lys Lys Ile Pro Ile Thr Tyr Asp Asn Gly Phe Leu Phe Ile His Thr
            100                 105                 110

Asp Lys Pro Val Tyr Thr Pro Asp Gln Ser Val Lys Val Arg Val Tyr
        115                 120                 125

Ser Leu Asn Asp Asp Leu Lys Pro Ala Lys Arg Glu Thr Val Leu Thr
    130                 135                 140

Phe Ile Asp Pro Glu Gly Ser Glu Ile Asp Met Val Glu Glu Ile Asp
145                 150                 155                 160

His Ile Gly Ile Ile Ser Phe Pro Asp Phe Lys Ile Pro Ser Asn Pro
                165                 170                 175

Arg Tyr Gly Met Trp Thr Ile Gln Ala Lys Tyr Lys Glu Asp Phe Ser
            180                 185                 190

Thr Thr Gly Thr Ala Phe Phe Glu Val Lys Glu Tyr Val Leu Pro His
        195                 200                 205

Phe Ser Val Ser Val Glu Pro Glu Ser Asn Phe Ile Gly Tyr Lys Asn
    210                 215                 220

Phe Lys Asn Phe Glu Ile Thr Ile Lys Ala Arg Tyr Phe Tyr Asn Lys
225                 230                 235                 240

Val Val Thr Glu Ala Asp Val Tyr Ile Thr Phe Gly Ile Arg Glu Asp
                245                 250                 255

Leu Lys Asp Asp Gln Lys Glu Met Met Gln Thr Ala Met Gln Asn Thr
            260                 265                 270

Met Leu Ile Asn Gly Ile Ala Gln Val Thr Phe Asp Ser Glu Thr Ala
        275                 280                 285

Val Lys Glu Leu Ser Tyr Tyr Ser Leu Glu Asp Leu Asn Asn Lys Tyr
    290                 295                 300

Leu Tyr Ile Ala Val Thr Val Ile Glu Ser Thr Gly Gly Phe Ser Glu
305                 310                 315                 320

Glu Ala Glu Ile Pro Gly Ile Lys Tyr Val Leu Ser Pro Tyr Lys Leu
                325                 330                 335

Asn Leu Val Ala Thr Pro Leu Phe Leu Lys Pro Gly Ile Pro Tyr Ser
            340                 345                 350

Ile Lys Val Gln Val Lys Asp Ala Leu Asp Gln Leu Val Gly Gly Val
        355                 360                 365

Pro Val Thr Leu Asn Ala Gln Thr Ile Asp Val Asn Gln Glu Thr Ser
    370                 375                 380

Asp Leu Glu Pro Arg Lys Ser Val Thr Arg Val Asp Asp Gly Val Ala
385                 390                 395                 400

```
Ser Phe Val Val Asn Leu Pro Ser Gly Val Thr Val Leu Glu Phe Asn
            405                 410                 415

Val Lys Thr Asp Ala Pro Asp Leu Pro Asp Glu Asn Gln Ala Arg Glu
        420                 425                 430

Gly Tyr Arg Ala Ile Ala Tyr Ser Ser Leu Ser Gln Ser Tyr Leu Tyr
            435                 440                 445

Ile Asp Trp Thr Asp Asn His Lys Ala Leu Leu Val Gly Glu Tyr Leu
        450                 455                 460

Asn Ile Ile Val Thr Pro Lys Ser Pro Tyr Ile Asp Lys Ile Thr His
465                 470                 475                 480

Tyr Asn Tyr Leu Ile Leu Ser Lys Gly Lys Ile Ile His Phe Gly Thr
                485                 490                 495

Arg Glu Lys Leu Ser Asp Ala Ser Tyr Gln Ser Ile Asn Ile Pro Val
                500                 505                 510

Thr Gln Asn Met Val Pro Ser Ser Arg Leu Leu Val Tyr Tyr Ile Val
                515                 520                 525

Thr Gly Glu Gln Thr Ala Glu Leu Val Ser Asp Ser Val Trp Leu Asn
            530                 535                 540

Ile Glu Glu Lys Cys Gly Asn Gln Leu Gln Val His Leu Ser Pro Asp
545                 550                 555                 560

Ala Asp Thr Tyr Ser Pro Gly Gln Thr Val Ser Leu Asn Met Val Thr
                565                 570                 575

Gly Met Asp Ser Trp Val Ala Leu Thr Ala Val Asp Ser Ala Val Tyr
                580                 585                 590

Gly Val Gln Arg Arg Ala Lys Lys Pro Leu Glu Arg Val Phe Gln Phe
            595                 600                 605

Leu Glu Lys Ser Asp Leu Gly Cys Gly Ala Gly Gly Gly Leu Asn Asn
        610                 615                 620

Ala Asn Val Phe His Leu Ala Gly Leu Thr Phe Leu Thr Asn Ala Asn
625                 630                 635                 640

Ala Asp Asp Ser Gln Glu Asn Asp Glu Pro Cys Lys Glu Ile Ile Arg
                645                 650                 655

Pro Arg Arg Met Leu Gln Glu Lys Ile Glu Ile Ala Ala Lys Tyr
                660                 665                 670

Lys His Leu Val Val Lys Lys Cys Cys Tyr Asp Gly Val Arg Ile Asn
            675                 680                 685

His Asp Glu Thr Cys Glu Gln Arg Ala Ala Arg Ile Ser Val Gly Pro
        690                 695                 700

Arg Cys Val Lys Ala Phe Thr Glu Cys Cys Val Val Ala Ser Gln Leu
705                 710                 715                 720

Arg Ala Asn Asn Ser His Lys Asp Leu Gln Leu Gly Arg Leu His Met
                725                 730                 735

Lys Thr Leu Leu Pro Val Ser Lys Pro Glu Ile Arg Ser Tyr Phe Pro
                740                 745                 750

Glu Ser Trp Leu Trp Glu Val His Leu Val Pro Arg Arg Lys Gln Leu
            755                 760                 765

Gln Phe Ala Leu Pro Asp Ser Val Thr Thr Trp Glu Ile Gln Gly Val
        770                 775                 780

Gly Ile Ser Asn Ser Gly Ile Cys Val Ala Asp Thr Ile Lys Ala Lys
785                 790                 795                 800

Val Phe Lys Asp Val Phe Leu Glu Met Asn Ile Pro Tyr Ser Val Val
                805                 810                 815
```

```
Arg Gly Glu Gln Val Gln Leu Lys Gly Thr Val Tyr Asn Tyr Arg Thr
            820                 825                 830

Ser Gly Met Gln Phe Cys Val Lys Met Ser Ala Val Glu Gly Ile Cys
        835                 840                 845

Thr Ser Glu Ser Pro Val Ile Asp His Gln Gly Thr Lys Ser Ser Lys
    850                 855                 860

Cys Val Arg Gln Lys Val Glu Gly Ser Ser Asn His Leu Val Thr Phe
865                 870                 875                 880

Thr Val Leu Pro Leu Glu Ile Gly Leu Gln Asn Ile Asn Phe Ser Leu
                885                 890                 895

Glu Thr Ser Phe Gly Lys Glu Ile Leu Val Lys Ser Leu Arg Val Val
            900                 905                 910

Pro Glu Gly Val Lys Arg Glu Ser Tyr Ser Gly Ile Thr Leu Asp Pro
        915                 920                 925

Arg Gly Ile Tyr Gly Thr Ile Ser Arg Arg Lys Glu Phe Pro Tyr Arg
    930                 935                 940

Ile Pro Leu Asp Leu Val Pro Lys Thr Glu Ile Lys Arg Ile Leu Ser
945                 950                 955                 960

Val Lys Gly Leu Leu Val Gly Glu Ile Leu Ser Ala Val Leu Ser Arg
                965                 970                 975

Glu Gly Ile Asn Ile Leu Thr His Leu Pro Lys Gly Ser Ala Glu Ala
            980                 985                 990

Glu Leu Met Ser Val Val Pro Val Phe Tyr Val Phe His Tyr Leu Glu
        995                 1000                1005

Thr Gly Asn His Trp Asn Ile Phe His Ser Asp Pro Leu Ile Glu Lys
    1010                1015                1020

Arg Asn Leu Glu Lys Lys Leu Lys Glu Gly Met Val Ser Ile Met Ser
1025                1030                1035                1040

Tyr Arg Asn Ala Asp Tyr Ser Tyr Ser Val Trp Lys Gly Gly Ser Ala
                1045                1050                1055

Ser Thr Trp Leu Thr Ala Phe Ala Leu Arg Val Leu Gly Gln Val His
            1060                1065                1070

Lys His Val Glu Gln Asn Gln Asn Ser Ile Cys Asn Ser Leu Leu Trp
        1075                1080                1085

Leu Val Glu Asn Tyr Gln Leu Asp Asn Gly Ser Phe Lys Glu Asn Ser
    1090                1095                1100

Gln Tyr Gln Pro Ile Lys Leu Gln Gly Thr Leu Pro Val Glu Ala Arg
1105                1110                1115                1120

Glu Asn Ser Leu Tyr Leu Thr Ala Phe Thr Val Ile Gly Ile Arg Lys
                1125                1130                1135

Ala Phe Asp Ile Cys Pro Leu Val Lys Ile Asn Thr Ala Leu Ile Lys
            1140                1145                1150

Ala Asp Thr Phe Leu Leu Glu Asn Thr Leu Pro Ala Gln Ser Thr Phe
        1155                1160                1165

Thr Leu Ala Ile Ser Ala Tyr Ala Leu Ser Leu Gly Asp Lys Thr His
    1170                1175                1180

Pro Gln Phe Arg Ser Ile Val Ser Ala Leu Lys Arg Glu Ala Leu Val
1185                1190                1195                1200

Lys Gly Asn Pro Pro Ile Tyr Arg Phe Trp Lys Asp Ser Leu Gln His
                1205                1210                1215

Lys Asp Ser Ser Val Pro Asn Thr Gly Thr Ala Arg Met Val Glu Thr
            1220                1225                1230

Thr Ala Tyr Ala Leu Leu Thr Ser Leu Asn Leu Lys Asp Ile Asn Tyr
```

```
                1235                1240                1245

Val Asn Pro Ile Ile Lys Trp Leu Ser Glu Glu Gln Arg Tyr Gly Gly
                1250                1255                1260

Gly Phe Tyr Ser Thr Gln Asp Thr Ile Asn Ala Ile Glu Gly Leu Thr
1265                1270                1275                1280

Glu Tyr Ser Leu Leu Val Lys Gln Leu Arg Leu Asn Met Asp Ile Asp
                1285                1290                1295

Val Ala Tyr Lys His Lys Gly Pro Leu His Asn Tyr Lys Met Thr Asp
                1300                1305                1310

Lys Asn Phe Leu Gly Arg Pro Val Glu Val Leu Leu Asn Asp Asp Leu
                1315                1320                1325

Val Val Ser Thr Gly Phe Gly Ser Gly Leu Ala Thr Val His Val Thr
                1330                1335                1340

Thr Val Val His Lys Thr Ser Thr Ser Glu Glu Val Cys Ser Phe Tyr
1345                1350                1355                1360

Leu Lys Ile Asp Thr Gln Asp Ile Glu Ala Ser His Tyr Arg Gly Tyr
                1365                1370                1375

Gly Asn Ser Asp Tyr Lys Arg Ile Val Ala Cys Ala Ser Tyr Lys Pro
                1380                1385                1390

Ser Arg Glu Glu Ser Ser Ser Gly Ser Ser His Ala Val Met Asp Ile
                1395                1400                1405

Ser Leu Pro Thr Gly Ile Asn Ala Asn Glu Glu Asp Leu Lys Ala Leu
                1410                1415                1420

Val Glu Gly Val Asp Gln Leu Phe Thr Asp Tyr Gln Ile Lys Asp Gly
1425                1430                1435                1440

His Val Ile Leu Gln Leu Asn Ser Ile Pro Ser Ser Asp Phe Leu Cys
                1445                1450                1455

Val Arg Phe Arg Ile Phe Glu Leu Phe Glu Val Gly Phe Leu Ser Pro
                1460                1465                1470

Ala Thr Phe Thr Val Tyr Glu Tyr His Arg Pro Asp Lys Gln Cys Thr
                1475                1480                1485

Met Phe Tyr Ser Thr Ser Asn Ile Lys Ile Gln Lys Val Cys Glu Gly
                1490                1495                1500

Ala Thr Cys Lys Cys Ile Glu Ala Asp Cys Gly Gln Met Gln Lys Glu
1505                1510                1515                1520

Leu Asp Leu Thr Ile Ser Ala Glu Thr Arg Lys Gln Thr Ala Cys Asn
                1525                1530                1535

Pro Glu Ile Ala Tyr Ala Tyr Lys Val Ile Ile Thr Ser Ile Thr Thr
                1540                1545                1550

Glu Asn Val Phe Val Lys Tyr Lys Ala Thr Leu Leu Asp Ile Tyr Lys
                1555                1560                1565

Thr Gly Glu Ala Val Ala Glu Lys Asp Ser Glu Ile Thr Phe Ile Lys
                1570                1575                1580

Lys Val Thr Cys Thr Asn Ala Glu Leu Val Lys Gly Arg Gln Tyr Leu
1585                1590                1595                1600

Ile Met Gly Lys Glu Ala Leu Gln Ile Lys Tyr Asn Phe Thr Phe Arg
                1605                1610                1615

Tyr Ile Tyr Pro Leu Asp Ser Leu Thr Trp Ile Glu Tyr Trp Pro Arg
                1620                1625                1630

Asp Thr Thr Cys Ser Ser Cys Gln Ala Phe Leu Ala Asn Leu Asp Glu
                1635                1640                1645

Phe Ala Glu Asp Ile Phe Leu Asn Gly Cys Glu Gln Lys Leu Ile Ser
                1650                1655                1660
```

Glu Glu Asp Leu Gly Gly Glu Gln Lys Leu Ile Ser Glu Glu Asp Leu
1665                1670                1675                1680

His His His His His His
            1685

<210> SEQ ID NO 359
<211> LENGTH: 1676
<212> TYPE: PRT
<213> ORGANISM: Artificial Sequence
<220> FEATURE:
<223> OTHER INFORMATION: hC5 P01031

<400> SEQUENCE: 359

Met Gly Leu Leu Gly Ile Leu Cys Phe Leu Ile Phe Leu Gly Lys Thr
1               5                   10                  15

Trp Gly Gln Glu Gln Thr Tyr Val Ile Ser Ala Pro Lys Ile Phe Arg
            20                  25                  30

Val Gly Ala Ser Glu Asn Ile Val Ile Gln Val Tyr Gly Tyr Thr Glu
        35                  40                  45

Ala Phe Asp Ala Thr Ile Ser Ile Lys Ser Tyr Pro Asp Lys Lys Phe
    50                  55                  60

Ser Tyr Ser Ser Gly His Val His Leu Ser Ser Glu Asn Lys Phe Gln
65                  70                  75                  80

Asn Ser Ala Ile Leu Thr Ile Gln Pro Lys Gln Leu Pro Gly Gly Gln
                85                  90                  95

Asn Pro Val Ser Tyr Val Tyr Leu Glu Val Val Ser Lys His Phe Ser
            100                 105                 110

Lys Ser Lys Arg Met Pro Ile Thr Tyr Asp Asn Gly Phe Leu Phe Ile
        115                 120                 125

His Thr Asp Lys Pro Val Tyr Thr Pro Asp Gln Ser Val Lys Val Arg
    130                 135                 140

Val Tyr Ser Leu Asn Asp Asp Leu Lys Pro Ala Lys Arg Glu Thr Val
145                 150                 155                 160

Leu Thr Phe Ile Asp Pro Glu Gly Ser Glu Val Asp Met Val Glu Glu
                165                 170                 175

Ile Asp His Ile Gly Ile Ile Ser Phe Pro Asp Phe Lys Ile Pro Ser
            180                 185                 190

Asn Pro Arg Tyr Gly Met Trp Thr Ile Lys Ala Lys Tyr Lys Glu Asp
        195                 200                 205

Phe Ser Thr Thr Gly Thr Ala Tyr Phe Glu Val Lys Glu Tyr Val Leu
    210                 215                 220

Pro His Phe Ser Val Ser Ile Glu Pro Glu Tyr Asn Phe Ile Gly Tyr
225                 230                 235                 240

Lys Asn Phe Lys Asn Phe Glu Ile Thr Ile Lys Ala Arg Tyr Phe Tyr
                245                 250                 255

Asn Lys Val Val Thr Glu Ala Asp Val Tyr Ile Thr Phe Gly Ile Arg
            260                 265                 270

Glu Asp Leu Lys Asp Asp Gln Lys Glu Met Met Gln Thr Ala Met Gln
        275                 280                 285

Asn Thr Met Leu Ile Asn Gly Ile Ala Gln Val Thr Phe Asp Ser Glu
    290                 295                 300

Thr Ala Val Lys Glu Leu Ser Tyr Tyr Ser Leu Glu Asp Leu Asn Asn
305                 310                 315                 320

Lys Tyr Leu Tyr Ile Ala Val Thr Val Ile Glu Ser Thr Gly Gly Phe
                325                 330                 335

```
Ser Glu Glu Ala Glu Ile Pro Gly Ile Lys Tyr Val Leu Ser Pro Tyr
                340                 345                 350

Lys Leu Asn Leu Val Ala Thr Pro Leu Phe Leu Lys Pro Gly Ile Pro
                355                 360                 365

Tyr Pro Ile Lys Val Gln Val Lys Asp Ser Leu Asp Gln Leu Val Gly
                370                 375                 380

Gly Val Pro Val Thr Leu Asn Ala Gln Thr Ile Asp Val Asn Gln Glu
385                 390                 395                 400

Thr Ser Asp Leu Asp Pro Ser Lys Ser Val Thr Arg Val Asp Asp Gly
                405                 410                 415

Val Ala Ser Phe Val Leu Asn Leu Pro Ser Gly Val Thr Val Leu Glu
                420                 425                 430

Phe Asn Val Lys Thr Asp Ala Pro Asp Leu Pro Glu Glu Asn Gln Ala
                435                 440                 445

Arg Glu Gly Tyr Arg Ala Ile Ala Tyr Ser Ser Leu Ser Gln Ser Tyr
                450                 455                 460

Leu Tyr Ile Asp Trp Thr Asp Asn His Lys Ala Leu Leu Val Gly Glu
465                 470                 475                 480

His Leu Asn Ile Ile Val Thr Pro Lys Ser Pro Tyr Ile Asp Lys Ile
                485                 490                 495

Thr His Tyr Asn Tyr Leu Ile Leu Ser Lys Gly Lys Ile Ile His Phe
                500                 505                 510

Gly Thr Arg Glu Lys Phe Ser Asp Ala Ser Tyr Gln Ser Ile Asn Ile
                515                 520                 525

Pro Val Thr Gln Asn Met Val Pro Ser Ser Arg Leu Leu Val Tyr Tyr
                530                 535                 540

Ile Val Thr Gly Glu Gln Thr Ala Glu Leu Val Ser Asp Ser Val Trp
545                 550                 555                 560

Leu Asn Ile Glu Glu Lys Cys Gly Asn Gln Leu Gln Val His Leu Ser
                565                 570                 575

Pro Asp Ala Asp Ala Tyr Ser Pro Gly Gln Thr Val Ser Leu Asn Met
                580                 585                 590

Ala Thr Gly Met Asp Ser Trp Val Ala Leu Ala Ala Val Asp Ser Ala
                595                 600                 605

Val Tyr Gly Val Gln Arg Gly Ala Lys Lys Pro Leu Glu Arg Val Phe
                610                 615                 620

Gln Phe Leu Glu Lys Ser Asp Leu Gly Cys Gly Ala Gly Gly Gly Leu
625                 630                 635                 640

Asn Asn Ala Asn Val Phe His Leu Ala Gly Leu Thr Phe Leu Thr Asn
                645                 650                 655

Ala Asn Ala Asp Asp Ser Gln Glu Asn Asp Glu Pro Cys Lys Glu Ile
                660                 665                 670

Leu Arg Pro Arg Arg Thr Leu Gln Lys Lys Ile Glu Glu Ile Ala Ala
                675                 680                 685

Lys Tyr Lys His Ser Val Val Lys Lys Cys Cys Tyr Asp Gly Ala Cys
                690                 695                 700

Val Asn Asn Asp Glu Thr Cys Glu Gln Arg Ala Ala Arg Ile Ser Leu
705                 710                 715                 720

Gly Pro Arg Cys Ile Lys Ala Phe Thr Glu Cys Cys Val Val Ala Ser
                725                 730                 735

Gln Leu Arg Ala Asn Ile Ser His Lys Asp Met Gln Leu Gly Arg Leu
                740                 745                 750
```

```
His Met Lys Thr Leu Leu Pro Val Ser Lys Pro Glu Ile Arg Ser Tyr
            755                 760                 765

Phe Pro Glu Ser Trp Leu Trp Glu Val His Leu Val Pro Arg Arg Lys
770                 775                 780

Gln Leu Gln Phe Ala Leu Pro Asp Ser Leu Thr Thr Trp Glu Ile Gln
785                 790                 795                 800

Gly Val Gly Ile Ser Asn Thr Gly Ile Cys Val Ala Asp Thr Val Lys
                805                 810                 815

Ala Lys Val Phe Lys Asp Val Phe Leu Glu Met Asn Ile Pro Tyr Ser
                820                 825                 830

Val Val Arg Gly Glu Gln Ile Gln Leu Lys Gly Thr Val Tyr Asn Tyr
                835                 840                 845

Arg Thr Ser Gly Met Gln Phe Cys Val Lys Met Ser Ala Val Glu Gly
                850                 855                 860

Ile Cys Thr Ser Glu Ser Pro Val Ile Asp His Gln Gly Thr Lys Ser
865                 870                 875                 880

Ser Lys Cys Val Arg Gln Lys Val Glu Gly Ser Ser His Leu Val
                885                 890                 895

Thr Phe Thr Val Leu Pro Leu Glu Ile Gly Leu His Asn Ile Asn Phe
                900                 905                 910

Ser Leu Glu Thr Trp Phe Gly Lys Glu Ile Leu Val Lys Thr Leu Arg
                915                 920                 925

Val Val Pro Glu Gly Val Lys Arg Glu Ser Tyr Ser Gly Val Thr Leu
                930                 935                 940

Asp Pro Arg Gly Ile Tyr Gly Thr Ile Ser Arg Arg Lys Glu Phe Pro
945                 950                 955                 960

Tyr Arg Ile Pro Leu Asp Leu Val Pro Lys Thr Glu Ile Lys Arg Ile
                965                 970                 975

Leu Ser Val Lys Gly Leu Leu Val Gly Glu Ile Leu Ser Ala Val Leu
                980                 985                 990

Ser Gln Glu Gly Ile Asn Ile Leu Thr His Leu Pro Lys Gly Ser Ala
                995                 1000                1005

Glu Ala Glu Leu Met Ser Val Val Pro Val Phe Tyr Val Phe His Tyr
                1010                1015                1020

Leu Glu Thr Gly Asn His Trp Asn Ile Phe His Ser Asp Pro Leu Ile
1025                1030                1035                1040

Glu Lys Gln Lys Leu Lys Lys Leu Lys Glu Gly Met Leu Ser Ile
                1045                1050                1055

Met Ser Tyr Arg Asn Ala Asp Tyr Ser Tyr Ser Val Trp Lys Gly Gly
                1060                1065                1070

Ser Ala Ser Thr Trp Leu Thr Ala Phe Ala Leu Arg Val Leu Gly Gln
                1075                1080                1085

Val Asn Lys Tyr Val Glu Gln Asn Gln Asn Ser Ile Cys Asn Ser Leu
                1090                1095                1100

Leu Trp Leu Val Glu Asn Tyr Gln Leu Asp Asn Gly Ser Phe Lys Glu
1105                1110                1115                1120

Asn Ser Gln Tyr Gln Pro Ile Lys Leu Gln Gly Thr Leu Pro Val Glu
                1125                1130                1135

Ala Arg Glu Asn Ser Leu Tyr Leu Thr Ala Phe Thr Val Ile Gly Ile
                1140                1145                1150

Arg Lys Ala Phe Asp Ile Cys Pro Leu Val Lys Ile Asp Thr Ala Leu
                1155                1160                1165

Ile Lys Ala Asp Asn Phe Leu Leu Glu Asn Thr Leu Pro Ala Gln Ser
```

```
            1170            1175            1180
Thr Phe Thr Leu Ala Ile Ser Ala Tyr Ala Leu Ser Leu Gly Asp Lys
1185            1190            1195            1200
Thr His Pro Gln Phe Arg Ser Ile Val Ser Ala Leu Lys Arg Glu Ala
            1205            1210            1215
Leu Val Lys Gly Asn Pro Pro Ile Tyr Arg Phe Trp Lys Asp Asn Leu
            1220            1225            1230
Gln His Lys Asp Ser Ser Val Pro Asn Thr Gly Thr Ala Arg Met Val
            1235            1240            1245
Glu Thr Thr Ala Tyr Ala Leu Leu Thr Ser Leu Asn Leu Lys Asp Ile
            1250            1255            1260
Asn Tyr Val Asn Pro Val Ile Lys Trp Leu Ser Glu Glu Gln Arg Tyr
1265            1270            1275            1280
Gly Gly Gly Phe Tyr Ser Thr Gln Asp Thr Ile Asn Ala Ile Glu Gly
            1285            1290            1295
Leu Thr Glu Tyr Ser Leu Leu Val Lys Gln Leu Arg Leu Ser Met Asp
            1300            1305            1310
Ile Asp Val Ser Tyr Lys His Lys Gly Ala Leu His Asn Tyr Lys Met
            1315            1320            1325
Thr Asp Lys Asn Phe Leu Gly Arg Pro Val Glu Val Leu Leu Asn Asp
            1330            1335            1340
Asp Leu Ile Val Ser Thr Gly Phe Gly Ser Gly Leu Ala Thr Val His
1345            1350            1355            1360
Val Thr Thr Val Val His Lys Thr Ser Thr Ser Glu Glu Val Cys Ser
            1365            1370            1375
Phe Tyr Leu Lys Ile Asp Thr Gln Asp Ile Glu Ala Ser His Tyr Arg
            1380            1385            1390
Gly Tyr Gly Asn Ser Asp Tyr Lys Arg Ile Val Ala Cys Ala Ser Tyr
            1395            1400            1405
Lys Pro Ser Arg Glu Glu Ser Ser Ser Gly Ser Ser His Ala Val Met
            1410            1415            1420
Asp Ile Ser Leu Pro Thr Gly Ile Ser Ala Asn Glu Glu Asp Leu Lys
1425            1430            1435            1440
Ala Leu Val Glu Gly Val Asp Gln Leu Phe Thr Asp Tyr Gln Ile Lys
            1445            1450            1455
Asp Gly His Val Ile Leu Gln Leu Asn Ser Ile Pro Ser Ser Asp Phe
            1460            1465            1470
Leu Cys Val Arg Phe Arg Ile Phe Glu Leu Phe Glu Val Gly Phe Leu
            1475            1480            1485
Ser Pro Ala Thr Phe Thr Val Tyr Glu Tyr His Arg Pro Asp Lys Gln
            1490            1495            1500
Cys Thr Met Phe Tyr Ser Thr Ser Asn Ile Lys Ile Gln Lys Val Cys
1505            1510            1515            1520
Glu Gly Ala Ala Cys Lys Cys Val Glu Ala Asp Cys Gly Gln Met Gln
            1525            1530            1535
Glu Glu Leu Asp Leu Thr Ile Ser Ala Glu Thr Arg Lys Gln Thr Ala
            1540            1545            1550
Cys Lys Pro Glu Ile Ala Tyr Ala Tyr Lys Val Ser Ile Thr Ser Ile
            1555            1560            1565
Thr Val Glu Asn Val Phe Val Lys Tyr Lys Ala Thr Leu Leu Asp Ile
            1570            1575            1580
Tyr Lys Thr Gly Glu Ala Val Ala Glu Lys Asp Ser Glu Ile Thr Phe
1585            1590            1595            1600
```

```
Ile Lys Lys Val Thr Cys Thr Asn Ala Glu Leu Val Lys Gly Arg Gln
            1605                1610                1615

Tyr Leu Ile Met Gly Lys Glu Ala Leu Gln Ile Lys Tyr Asn Phe Ser
            1620                1625                1630

Phe Arg Tyr Ile Tyr Pro Leu Asp Ser Leu Thr Trp Ile Glu Tyr Trp
            1635                1640                1645

Pro Arg Asp Thr Thr Cys Ser Ser Cys Gln Ala Phe Leu Ala Asn Leu
            1650                1655                1660

Asp Glu Phe Ala Glu Asp Ile Phe Leu Asn Gly Cys
1665                1670                1675

<210> SEQ ID NO 360
<211> LENGTH: 9
<212> TYPE: PRT
<213> ORGANISM: Artificial Sequence
<220> FEATURE:
<223> OTHER INFORMATION: human C5 peptide aa591-599

<400> SEQUENCE: 360

Asn Met Ala Thr Gly Met Asp Ser Trp
1               5

<210> SEQ ID NO 361
<211> LENGTH: 20
<212> TYPE: PRT
<213> ORGANISM: Artificial Sequence
<220> FEATURE:
<223> OTHER INFORMATION: human C5 peptide aa775-794

<400> SEQUENCE: 361

Trp Glu Val His Leu Val Pro Arg Arg Lys Gln Leu Gln Phe Ala Leu
1               5                   10                  15

Pro Asp Ser Leu
            20

<210> SEQ ID NO 362
<211> LENGTH: 121
<212> TYPE: PRT
<213> ORGANISM: Artificial Sequence
<220> FEATURE:
<223> OTHER INFORMATION: HCVR of M1M17628N

<400> SEQUENCE: 362

Glu Val Gln Leu Gln Glu Ser Gly Pro Gly Leu Ala Lys Pro Ser Gln
1               5                   10                  15

Thr Leu Ser Leu Thr Cys Ser Val Thr Gly Tyr Ser Ile Thr Arg Asp
            20                  25                  30

Tyr Trp Asn Trp Ile Arg Lys Phe Pro Gly Asn Lys Leu Asp Tyr Met
            35                  40                  45

Gly Tyr Ile Ser Tyr Ser Gly Gly Thr Tyr Tyr Asn Pro Ser Leu Lys
        50                  55                  60

Ser Arg Phe Ser Ile Ser Arg Asp Thr Ser Lys Asn Gln Phe Tyr Leu
65                  70                  75                  80

Gln Leu Asn Ser Val Thr Phe Glu Asp Thr Ala Thr Tyr Tyr Cys Ala
                85                  90                  95

Arg Gly Val Ser Tyr Tyr Gly Ser Thr Tyr Tyr Phe Asp Tyr Trp Gly
            100                 105                 110

Gln Gly Thr Thr Leu Thr Val Ser Ser
            115                 120
```

<210> SEQ ID NO 363
<211> LENGTH: 107
<212> TYPE: PRT
<213> ORGANISM: Artificial Sequence
<220> FEATURE:
<223> OTHER INFORMATION: LCVR of M1M17628N

<400> SEQUENCE: 363

```
Asp Ile Gln Met Asn Gln Ser Pro Ser Leu Ser Ala Ser Leu Gly
1               5                   10                  15

Asp Thr Ile Thr Ile Thr Cys His Ala Ser Gln Asn Ile His Val Trp
            20                  25                  30

Leu Asn Trp Tyr Gln Gln Thr Pro Gly Asn Ile Pro Lys Leu Leu Ile
        35                  40                  45

Tyr Lys Ala Ser Asn Leu His Thr Gly Val Pro Ser Arg Phe Ser Ala
    50                  55                  60

Ser Gly Ser Gly Thr Gly Phe Thr Leu Thr Ile Ser Ser Leu Gln Ser
65                  70                  75                  80

Glu Asp Ile Ala Thr Tyr Tyr Cys Gln Gln Gly Gln Ser Tyr Pro Leu
                85                  90                  95

Thr Phe Gly Gly Gly Thr Lys Leu Glu Ile Lys
            100                 105
```

<210> SEQ ID NO 364
<211> LENGTH: 20
<212> TYPE: PRT
<213> ORGANISM: Artificial Sequence
<220> FEATURE:
<223> OTHER INFORMATION: IRBP peptide

<400> SEQUENCE: 364

```
Gly Pro Thr His Leu Phe Gln Pro Ser Leu Val Leu Asp Met Ala Lys
1               5                   10                  15

Val Leu Leu Asp
            20
```

<210> SEQ ID NO 365
<211> LENGTH: 127
<212> TYPE: PRT
<213> ORGANISM: Artificial Sequence
<220> FEATURE:
<223> OTHER INFORMATION: HCVR of M1M17627N

<400> SEQUENCE: 365

```
Gln Val Gln Leu Gln Gln Pro Gly Ala Glu Leu Val Lys Pro Gly Ala
1               5                   10                  15

Ser Val Lys Val Ser Cys Lys Ala Ser Gly Tyr Thr Phe Thr Ser Tyr
            20                  25                  30

Trp Ile His Trp Met Arg Gln Arg Pro Gly Gln Gly Leu Glu Trp Ile
        35                  40                  45

Gly Arg Ile His Pro Ser Asp Ser Asp Thr Asn Tyr Asn Gln Lys Phe
    50                  55                  60

Lys Gly Lys Ala Thr Leu Thr Val Asp Thr Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ile Leu Pro Pro Pro Pro Tyr Tyr Tyr Ala Asn Tyr Gly Gly Gly
            100                 105                 110

Thr Met Asp Tyr Trp Gly Arg Gly Thr Ser Val Thr Val Ser Ser
```

```
                115                 120                 125

<210> SEQ ID NO 366
<211> LENGTH: 107
<212> TYPE: PRT
<213> ORGANISM: Artificial Sequence
<220> FEATURE:
<223> OTHER INFORMATION: LCVR of M1M17627N

<400> SEQUENCE: 366

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Val Trp Tyr Gln Gln Lys Pro Gly Gln Ser Pro Lys Ala Leu Ile
        35                  40                  45

Tyr Ser Ala Ser Tyr Arg Tyr Ser Gly Val Pro Ala Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Ala Glu Tyr Ile Cys Gln Gln Tyr Asn Arg Ser Pro Tyr
                85                  90                  95

Thr Phe Gly Gly Gly Thr Lys Leu Glu Thr Lys
            100                 105
```

ANTI-C5 ANTIBODIES

CROSS-REFERENCE TO RELATED APPLICATIONS

This application claims the benefit under 35 U.S.C. § 119(e) of U.S. provisional application No. 62/349,705, filed on Jun. 14, 2016; 62/405,561, filed on Oct. 7, 2016; and 62/422,107, filed on Nov. 15, 2016, the disclosures of each herein incorporated by reference in their entireties.

FIELD OF THE INVENTION

The present invention is related to antibodies and antigen-binding fragments of antibodies that specifically bind to complement factor C5, and therapeutic and diagnostic methods of using those antibodies.

BACKGROUND OF THE INVENTION

The complement system is a group of plasma proteins that when activated lead to target cell lysis and facilitate phagocytosis through opsonization. Complement is activated through a series of proteolytic steps by three major pathways: the classical pathway, which is typically activated by immune-complexes, the alternative pathway that can be induced by unprotected cell surfaces, and the mannose binding lectin pathway. All three pathways of complement cascade converge on proteolytic cleavage of complement component 5 (C5) protein. Cleavage of complement component 5 (C5) results in the production of fragments C5a and C5b, a process that is critical during the activation of the complement cascade. C5a can generate pleiotropic physiological responses through binding to its receptors (Monk et al 2007, Br. J. Pharmacol. 152: 429-448). C5a is a potent pro-inflammatory mediator that induces chemotactic migration, enhances cell adhesion, stimulates the oxidative burst, and induces the release of various inflammatory mediators such as histamine or cytokines. C5b mediates the formation of the membrane-attack complex (MAC, or C5b-9) leading to cell lysis in the late phases of the complement dependent cytotoxicity (CDC). Further, in nucleated cells that are resistant to cytolysis by C5b-9, sublytic quantities of C5b-9 can cause cellular activation which results in cell proliferation, generation of pro-inflammatory mediators and production of extracellular matrix.

Monoclonal antibodies to C5 are known in the art and have been described, for example, in US Patent/Publication Nos. 9206251, 9107861, 9079949, 9051365, 8999340, 8883158, 8241628, 7999081, 7432356, 7361339, 7279158, 6534058, 6355245, 6074642, 20160299305, 20160051673, 20160031975, 20150158936, 20140056888, 20130022615, 20120308559, and in WO2015198243, WO2015134894, WO2015120130, EP2563813B1, EP2328616B1, and EP2061810B1.

Fully human antibodies that specifically bind to C5 protein with high affinity and have improved pharmacokinetic properties could be important in the prevention and treatment of various C5-associated diseases (e.g., atypical hemolytic uremic syndrome).

BRIEF SUMMARY OF THE INVENTION

The present invention provides antibodies and antigen-binding fragments thereof that specifically bind complement factor 5 (C5) protein. The antibodies of the present invention are useful, inter alia, for inhibiting or neutralizing the activity of C5 protein. In certain embodiments, the antibodies are useful in preventing, treating or ameliorating at least one symptom or indication of a C5-associated disease or disorder in a subject. In certain embodiments, the antibodies may be administered prophylactically or therapeutically to a subject having or at risk of having a C5-associated disease or disorder. In certain embodiments, the anti-C5 antibodies are fully human antibodies that bind to C5 with high affinity and have improved pharmacokinetic (PK) and pharmacodynamic (PD) properties. Such high-affinity antibodies with improved PK/PD can be used to provide superior efficacy, along with less frequent dosing in a subject with a C5-associated disease or disorder.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to increase persistence in the host or to eliminate residual effector functions (Reddy et al., 2000, J. Immunol. 164:1925-1933). In certain embodiments, the antibodies may be bispecific.

In a first aspect, the present invention provides isolated recombinant monoclonal antibodies or antigen-binding fragments thereof that bind specifically to the C5 protein. In some embodiments, the antibodies are fully human monoclonal antibodies.

Exemplary anti-C5 antibodies of the present invention are listed in Tables 1 and 2 herein. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of exemplary anti-C5 antibodies. Table 2 sets forth the nucleic acid sequence identifiers of the HCVRs, LCVRs, HCDR1, HCDR2 HCDR3, LCDR1, LCDR2 and LCDR3 of the exemplary anti-C5 antibodies.

The present invention provides antibodies, or antigen-binding fragments thereof, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides antibodies, or antigen-binding fragments thereof, comprising an HCVR/LCVR amino acid sequence pair contained within any of the exemplary anti-C5 antibodies listed in Table 1. In certain embodiments, the HCVR/LCVR amino acid sequence pair is selected from the group consisting of SEQ ID NOs: 2/10, 18/26, 34/42, 50/58, 66/74, 82/90, 98/106, 98/114, 122/106, 98/130, 138/106, 146/106, 122/130, 146/114, 146/130, 138/130, 154/162, 170/178, 186/194, 202/210, 218/226, 234/242, 250/258, 266/258, 274/282, 290/298, 306/314, 322/330, and 338/346. In certain embodiments, the HCVR/LCVR amino acid sequence pair is selected from one of SEQ ID NOs: 50/58 (e.g., H4H12161P), 98/106 (e.g., H4H12166P), 138/106 (e.g., H4H12166P5), or 202/210 (e.g., H4H12170P). In certain embodiments, the present invention provides anti-C5 antibodies or antigen-binding fragments thereof comprising a HCVR and a LCVR, said HCVR comprising an amino acid sequence listed in Table 1 having no more than five amino acid substitutions, and said LCVR comprising an amino acid sequence listed in Table 1 having no more than two amino acid substitutions. For example, the present invention provides anti-C5 antibodies or antigen-binding fragments thereof comprising a HCVR and a LCVR, said HCVR comprising an amino acid sequence of SEQ ID NO: 98 having no more than five amino acid substitutions, and said LCVR comprising an amino acid sequence of SEQ ID NO: 106 having no more than two amino acid substitutions. In another embodiment, the present invention provides anti-C5 antibodies or antigen-binding fragments thereof comprising a HCVR and a LCVR, said HCVR comprising an amino acid sequence of SEQ ID NO: 98 having at least one amino acid substitution, and said LCVR comprising an amino acid sequence of SEQ ID NO: 106 having one amino acid substitution.

The present invention also provides antibodies, or antigen-binding fragments thereof, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antibodies, or antigen-binding fragments thereof, comprising an HCDR3/LCDR3 amino acid sequence pair contained within any of the exemplary anti-C5 antibodies listed in Table 1. In certain embodiments, the HCDR3/LCDR3 amino acid sequence pair is selected from the group consisting of SEQ ID NOs: 56/64 (e.g., H4H12161P), 104/112 (e.g., H4H12166P), 144/112 (e.g., H4H12166P5), and 208/216 (e.g., H4H12170P).

The present invention also provides antibodies, or antigen-binding fragments thereof, comprising a HCVR and a LCVR, said HCVR comprising HCDR1 comprising an amino acid sequence differing from an amino acid sequence listed in Table 1 by 1 amino acid, HCDR2 comprising an amino acid sequence differing from an amino acid sequence listed in Table 1 by 1 amino acid, and HCDR3 comprising an amino acid sequence differing from an amino acid sequence listed in Table 1 by 1 amino acid. In certain embodiments, the present invention provides antibodies, or antigen-binding fragments thereof, comprising a HCVR and a LCVR, said LCVR comprising LCDR1 comprising an amino acid sequence differing from an amino acid sequence listed in Table 1 by 1 amino acid, LCDR2 comprising an amino acid sequence differing from an amino acid sequence listed in Table 1 by 1 amino acid, and LCDR3 comprising an amino acid sequence differing from an amino acid sequence listed in Table 1 by 1 amino acid. For example, the present invention provides anti-C5 antibodies, or antigen-binding fragments thereof, comprising a HCVR and a LCVR, said HCVR comprising HCDR1 comprising an amino acid sequence of SEQ ID NO: 100 or an amino acid sequence differing from SEQ ID NO: 100 by 1 amino acid, HCDR2 comprising an amino acid sequence of SEQ ID NO: 102 or an amino acid sequence differing from SEQ ID NO: 102 by 1 amino acid, and HCDR3 comprising an amino acid sequence of SEQ ID NO: 104 or an amino acid sequence differing from SEQ ID NO: 104 by 1 amino acid. In another exemplary embodiment, the present invention provides antibodies, or antigen-binding fragments thereof, comprising a HCVR and a LCVR, said LCVR comprising LCDR1 comprising an amino acid sequence of SEQ ID NO: 108 or an amino acid sequence differing from SEQ ID NO: 108 by 1 amino acid, LCDR2 comprising an amino acid sequence of SEQ ID NO: 110 or an amino acid sequence differing from SEQ ID NO: 110 by 1 amino acid, and LCDR3 comprising an amino acid sequence of SEQ ID NO: 112 or an amino acid sequence differing from SEQ ID NO: 112 by 1 amino acid.

The present invention provides antibodies, or antigen-binding fragments thereof, comprising a heavy chain comprising an amino acid sequence of SEQ ID NO: 353, or a substantially similar sequence thereof having at least 80%, at least 85%, at least 90%, at least 95%, at least 98% or at least 99% sequence identity thereto.

The present invention also provides antibodies, or antigen-binding fragments thereof, comprising a light chain comprising an amino acid sequence of SEQ ID NO: 354, or a substantially similar sequence thereof having at least 80%, at least 85%, at least 90%, at least 95%, at least 98% or at least 99% sequence identity thereto.

In certain embodiments, the present invention provides antibodies, or antigen-binding fragments thereof, comprising a heavy chain comprising an amino acid sequence of SEQ ID NO: 353, or a substantially similar sequence thereof having at least 80%, or at least 90% sequence identity thereto; and a light chain comprising an amino acid sequence of SEQ ID NO: 354, or a substantially similar sequence thereof having at least 80%, or at least 90% sequence identity thereto.

The present invention also provides antibodies, or antigen-binding fragments thereof, comprising a set of six CDRs (i.e., HCDR1-HCDR2-HCDR3-LCDR1-LCDR2-LCDR3) contained within any of the exemplary anti-C5 antibodies listed in Table 1. In certain embodiments, the HCDR1-HCDR2-HCDR3-LCDR1-LCDR2-LCDR3 amino acid sequence set is selected from the group consisting of SEQ ID NOs: 52-54-56-60-62-64 (e.g., H4H12161P), 100-102-104-108-110-112 (e.g., H4H12166P), 140-142-144-108-110-112 (e.g., H4H12166P5), and 204-206-208-212-214-216 (e.g., H4H12170P).

In a related embodiment, the present invention provides antibodies, or antigen-binding fragments thereof, comprising a set of six CDRs (i.e., HCDR1-HCDR2-HCDR3-LCDR1-LCDR2-LCDR3) contained within an HCVR/LCVR amino acid sequence pair as defined by any of the exemplary anti-C5 antibodies listed in Table 1. For example, the present invention includes antibodies, or antigen-binding fragments thereof, comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 50/58 (e.g., H4H12161P), 98/106 (e.g., H4H12166P), 138/106 (e.g., H4H12166P5), or 202/210 (e.g., H4H12170P). Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In certain embodiments, the present invention includes an antibody or antigen-binding fragment thereof that binds specifically to C5, wherein the antibody or antigen-binding fragment thereof comprises three heavy chain complementarity determining regions (CDRs) (HCDR1, HCDR2 and HCDR3) contained within a heavy chain variable region (HCVR) and three light chain CDRs (LCDR1, LCDR2 and LCDR3) contained within a light chain variable region (LCVR), wherein the HCVR comprises: (i) the amino acid sequence of SEQ ID NO: 98, (ii) an amino acid sequence having at least 90% identity to SEQ ID NO: 98, (iii) an amino acid sequence having at least 95% identity to SEQ ID NO: 98; or (iv) the amino acid sequence of SEQ ID NO: 98 having no more than 5 amino acid substitutions; and the LCVR comprises: (i) the amino acid sequence of SEQ ID NO: 106, (ii) an amino acid sequence having at least 90% identity to SEQ ID NO: 106, (iii) an amino acid sequence having at least 95% identity to SEQ ID NO: 106; or (iv) the amino acid sequence of SEQ ID NO: 106 having no more than 5 amino acid substitutions.

The present invention includes anti-C5 antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In certain embodiments, the present invention provides antibodies and antigen-binding fragments thereof that exhibit pH-dependent binding to C5. For example, the present invention includes antibodies and antigen-binding fragment thereof that bind C5 with higher affinity at neutral pH than at acidic pH (i.e., reduced binding at acidic pH).

In certain embodiments, the present invention provides antibodies and antigen-binding fragments that exhibit improved pharmacokinetic and pharmacodynamic properties, for example, the present invention provides anti-C5 antibodies that have extended serum half-life. In certain embodiments, the anti-C5 antibodies of the present invention have serum concentration of more than 10 μg/mL through day 40 in C5-humanized mice. In certain embodiments, the anti-C5 antibodies of the present invention block CP- and AP hemolysis through day 35 upon administration to C5-humanized mice.

The present invention also provides for antibodies and antigen-binding fragments thereof that compete for specific binding to C5 with an antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

The present invention also provides antibodies and antigen-binding fragments thereof that cross-compete for binding to C5 with a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

The present invention also provides antibodies and antigen-binding fragments thereof that bind to the same epitope as a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 1. In certain embodiments, the present invention provides antibodies and antigen-binding fragments thereof that bind to the same epitope as a reference antibody or antigen-binding fragment thereof comprising the CDRs of a HCVR and the CDRs of a LCVR, wherein the HCVR/LCVR amino acid sequence pair has SEQ ID NOs: 98/106.

The present invention also includes anti-C5 antibodies and antigen-binding fragments thereof that bind to one or more amino acid residues comprised in the alpha chain and/or the beta chain of C5. In certain embodiments, the present invention provides antibodies and antigen-binding fragments thereof that bind to one or more amino acids in the alpha chain of C5 and one or more amino acids in the beta chain of C5. In certain embodiments, the present invention provides antibodies and antigen-binding fragments thereof that bind to one or more amino acids in the alpha and beta chains of C5, wherein the antibodies do not bind to the C5a anaphylatoxin domain. In certain embodiments, the present invention provides anti-C5 antibodies that interact with one or more amino acids contained within human C5 (SEQ ID NO: 359). In certain embodiments, the present invention provides anti-C5 antibodies that interact with one or more amino acids contained within human C5 (SEQ ID NO: 359), wherein the antibodies do not bind to the C5a anaphylatoxin domain of C5. In certain embodiments, the present invention provides anti-C5 antibodies and antigen-binding fragments thereof that interact with an amino acid sequence selected from the group consisting of (a) amino acids 591 to 599 of SEQ ID NO: 359; (b) amino acids 593 to 599 of SEQ ID NO: 359; (c) amino acids 775 to 787 of SEQ ID NO: 359; (d) amino acids 775 to 794 of SEQ ID NO: 359; and (e) amino acids 779 to 787 of SEQ ID NO: 359. In certain embodiments, the present invention provides anti-C5 antibodies and antigen-binding fragments thereof that interact with one or more amino acids contained within SEQ ID NO: 359, for example, the present invention provides anti-C5 antibodies and antigen-binding fragments thereof that interact with at least 5 amino acids, at least 10 amino acids, or at least 15 amino acids contained within SEQ ID NO: 361.

In certain embodiments, the present invention provides anti-C5 antibodies and antigen-binding fragments thereof that interact with one or more amino acids contained within SEQ ID NO: 359, for example, the present invention provides anti-C5 antibodies and antigen-binding fragments thereof that interact with at least 5 amino acids contained within SEQ ID NO: 360. In certain embodiments, the present invention provides anti-C5 antibodies and antigen-binding fragments thereof that interact with at least 5 amino acids contained within SEQ ID NOs: 360 and 361. In certain embodiments, the present invention provides anti-C5 antibodies and antigen-binding fragments thereof that interact with the amino acid sequence of SEQ ID NO: 360 (corresponding to amino acids 591 to 599 of SEQ ID NO: 359) and with the amino acid sequence of SEQ ID NO: 361 (corresponding to amino acids 775 to 794 of SEQ ID NO: 359).

In some embodiments, the antibody or antigen binding fragment thereof may bind specifically to C5 in an agonist manner, i.e., it may enhance or stimulate C5 binding and/or activity; in other embodiments, the antibody may bind specifically to C5 in an antagonist manner, i.e., it may block C5 binding and/or activity.

The present invention also provides isolated antibodies and antigen-binding fragments thereof that block C5 binding to C5 convertase. In some embodiments, the antibody or antigen-binding fragment thereof that blocks C5 binding to C5 convertase may bind to the same epitope on C5 as C5 convertase or may bind to a different epitope on C5 as C5 convertase. In some embodiments, the present invention provides antibodies or antigen-binding fragments thereof that block the binding of C5 to monkey C5 convertase.

In certain embodiments, the antibodies or antigen-binding fragments of the present invention are bispecific comprising a first binding specificity to a first epitope of C5 protein and a second binding specificity to a second epitope of C5 protein wherein the first and second epitopes are distinct and non-overlapping.

In certain embodiments, the antibodies and antigen-binding fragments of the present invention bind to C5a with an $IC_{50}$ of less than 0.5 nM. In certain embodiments, the antibodies comprise an HCVR comprising an amino acid sequence selected from the group consisting of SEQ ID NOs: 290, 306, 322, and 338. In certain embodiments, the antibodies comprise an LCVR comprising an amino acid sequence selected from the group consisting of SEQ ID NOs: 298, 314, 330, and 346.

In certain embodiments, the present invention provides an isolated antibody or antigen-binding fragment thereof that has one or more of the following characteristics: (a) is a fully human monoclonal antibody; (b) binds to human C5 with a dissociation constant ($K_D$) of less than 0.9 nM at 25° C., as measured in a surface plasmon resonance assay; (c) binds to human C5 with a $K_D$ of less than 0.3 nM at 37° C., as measured in a surface plasmon resonance assay; (d) binds to monkey C5 with a $K_D$ of less than 65 nM, as measured in a surface plasmon resonance assay; (e) binds to human C5 variant R885H (SEQ ID NO: 356) with a $K_D$ of less than 0.5 nM, as measured in a surface plasmon resonance assay; (f) binds to human C5 variant R885C (SEQ ID NO: 357) with a $K_D$ of less than 0.5 nM, as measured in a surface plasmon resonance assay; (g) blocks human C5-mediated classical pathway (CP) hemolysis by more than 95% and with $IC_{50}$ less than 6 nM, as measured in a CP hemolysis assay; (h) blocks human C5-mediated alternative pathway (AP) hemolysis by more than 70% and with $IC_{50}$ less than 165 nM, as measured in a AP hemolysis assay; (i) inhibits African green monkey C5-mediated CP hemolysis with $IC_{50}$ less than 185 nM, as measured in a CP hemolysis assay; (j) inhibits African green monkey C5-mediated AP hemolysis with $IC_{50}$ less than 235 nM, as measured in a AP hemolysis assay; (k) inhibits cynomolgus monkey C5-mediated CP hemolysis with $IC_{50}$ less than 145 nM, as measured in a CP hemolysis assay; and (l) inhibits cynomolgus monkey C5-mediated AP hemolysis with $IC_{50}$ less than 30 nM, as measured in a AP hemolysis assay.

In certain embodiments, the present invention provides an isolated recombinant monoclonal anti-C5 antibody or antigen-binding fragment thereof that has one or more of the following characteristics: (a) comprises a set of six CDRs comprising the amino acid sequences of SEQ ID NOs: 100-102-104-108-110-112; (b) binds to human C5 with a dissociation constant ($K_D$) of less than 0.2 nM at 25° C., as measured in a surface plasmon resonance assay; (c) binds to human C5 with a $K_D$ of less than 0.3 nM at 37° C., as measured in a surface plasmon resonance assay; (d) binds to a human C5 variant (R885H) with a $K_D$ of less than 0.4 nM at 37° C., as measured in a surface plasmon resonance assay; (e) inhibits classical pathway (CP)-mediated hemolysis of human serum with an $IC_{50}$ of less than 3 nM; (f) inhibits alternative pathway (AP)-mediated hemolysis of human serum with an $IC_{50}$ of less than 27 nM; (g) inhibits CP-mediated hemolysis of monkey serum with an $IC_{50}$ of less than 21 nM; (g) inhibits AP-mediated hemolysis of monkey serum with an $IC_{50}$ of less than 10 nM; (h) has serum half-life ($t_{1/2}$) of more than 10 days in C5-humanized mice; (i) has serum concentration of more than 10 µg/mL through day 40 upon administering to C5-humanized mice; (j) blocks CP-mediated hemolysis through day 50 in C5-humanized mice; and (k) binds to one or more amino acids comprised in the alpha chain and/or the beta chain of SEQ ID NO: 359, wherein the antibody does not bind to the C5a anaphylatoxin domain of C5.

In a second aspect, the present invention provides nucleic acid molecules encoding anti-C5 antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-C5 antibodies listed in Table 1.

The present invention also provides nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-C5 antibodies listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 1, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-C5 antibody listed in Table 1.

In a related aspect, the present invention provides recombinant expression vectors capable of expressing a polypeptide comprising a heavy or light chain variable region of an anti-C5 antibody. For example, the present invention includes recombinant expression vectors comprising any of the nucleic acid molecules mentioned above, i.e., nucleic acid molecules encoding any of the HCVR, LCVR, and/or CDR sequences as set forth in Table 2. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

In a third aspect, the invention provides a pharmaceutical composition comprising a therapeutically effective amount of at least one recombinant monoclonal antibody or antigen-binding fragment thereof which specifically binds C5 and a pharmaceutically acceptable carrier. In a related aspect, the invention features a composition which is a combination of an anti-C5 antibody and a second therapeutic agent. In one embodiment, the second therapeutic agent is any agent that is advantageously combined with an anti-C5 antibody. Exemplary agents that may be advantageously combined with an anti-C5 antibody include, without limitation, other agents that bind and/or inhibit C5 activity (including other antibodies or antigen-binding fragments thereof, etc.) and/or agents which do not directly bind C5 but nonetheless treat or ameliorate at least one symptom or indication of a C5-associated disease or disorder. Additional combination therapies and co-formulations involving the anti-C5 antibodies of the present invention are disclosed elsewhere herein.

In a fourth aspect, the invention provides therapeutic methods for treating a disease or disorder associated with C5 in a subject using an anti-C5 antibody or antigen-binding portion of an antibody of the invention, wherein the therapeutic methods comprise administering a therapeutically effective amount of a pharmaceutical composition comprising an antibody or antigen-binding fragment of an antibody of the invention to the subject in need thereof. The disorder treated is any disease or condition which is improved, ameliorated, inhibited or prevented by inhibition of C5 activity. In certain embodiments, the invention provides methods to prevent, treat or ameliorate at least one symptom of atypical hemolytic uremic syndrome (aHUS), the method comprising administering a therapeutically effective amount of an anti-C5 antibody or antigen-binding fragment thereof of the invention to a subject in need thereof. In some embodiments, the present invention provides methods to ameliorate or reduce the severity of at least one symptom or indication of paroxysmal nocturnal hemoglobinuria (PNH) in a subject by administering an anti-C5 antibody of the invention. In some embodiments, the antibody or antigen-binding fragment thereof may be administered prophylactically or therapeutically to a subject having or at risk of having a C5-associated disease or disorder. In certain embodiments, the antibody or antigen-binding fragment thereof the invention is administered in combination with a second therapeutic agent to the subject in need thereof. The second therapeutic agent may be selected from the group consisting of an anti-inflammatory drug (such as corticosteroids, and non-steroidal anti-inflammatory drugs), a different antibody to C5 protein, a dietary supplement such as anti-oxidants and any other drug or therapy known in the art. In certain embodiments, the second therapeutic agent may be an agent that helps to counteract or reduce any possible side effect(s) associated with an antibody or antigen-binding fragment thereof of the invention, if such side effect(s) should occur. The antibody or fragment thereof may be administered subcutaneously, intravenously, intradermally, intraperitoneally, orally, or intramuscularly. The antibody or fragment thereof may be administered at a dose of about 0.1 mg/kg of body weight to about 100 mg/kg of body weight of the subject. In certain embodiments, an antibody of the present invention may be administered at one or more doses comprising between 50 mg to 600 mg.

The present invention also includes use of an anti-C5 antibody or antigen-binding fragment thereof of the invention in the manufacture of a medicament for the treatment of a disease or disorder that would benefit from the blockade of C5 binding and/or activity.

Other embodiments will become apparent from a review of the ensuing detailed description.

DETAILED DESCRIPTION

Figure 1:
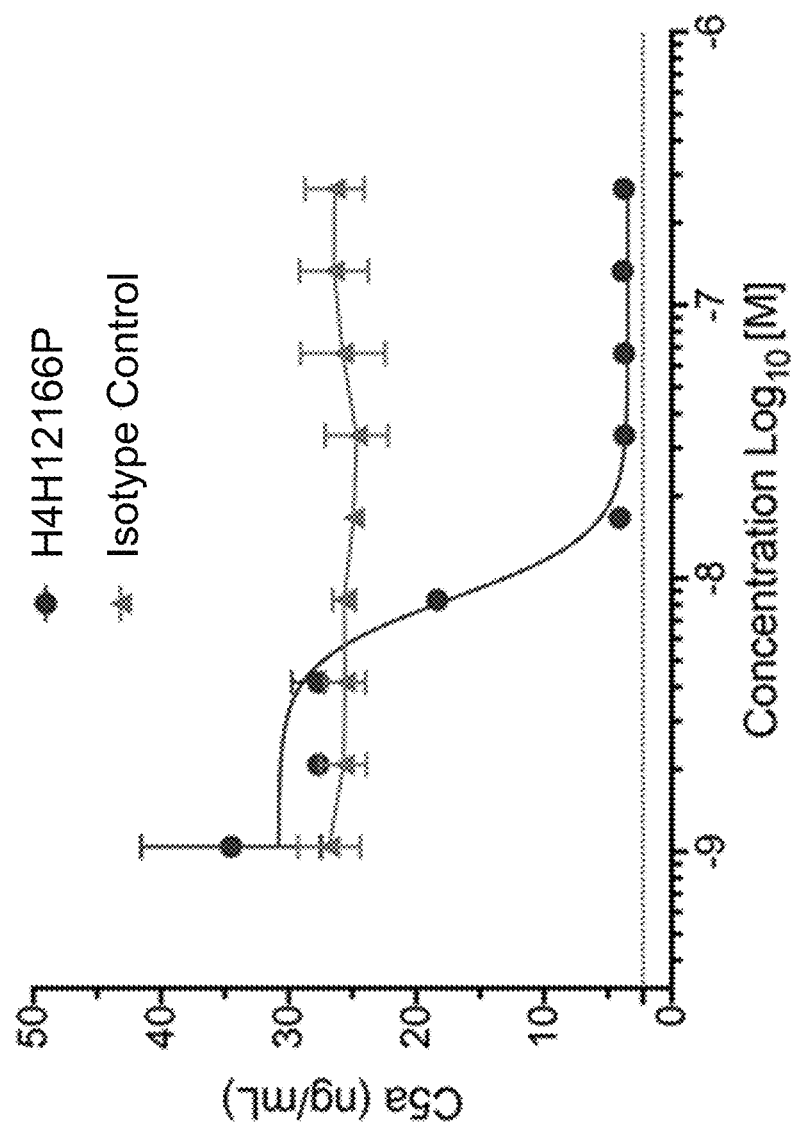
FIG. 1 shows inhibition of C5a levels by anti-C5 antibody H4H12166P in a dose-dependent manner, as determined by ELISA (described in Example 9 herein).

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

Definitions

The term "C05", also called "complement component 5" or "complement factor 5" refers to the serum protein of the complement cascade. The C5 protein is a 1676 amino acid protein comprising two chains, alpha and beta. The protein represents the convergence point for three complement activation pathways: classical pathway, alternative pathway and the mannose binding lectin pathway. The amino acid sequence of full-length C5 protein is exemplified by the amino acid sequence provided in GenBank as accession number NP_001726.2 (SEQ ID NO: 355). The term "C5" includes recombinant C5 protein or a fragment thereof. The term also encompasses C5 protein or a fragment thereof coupled to, for example, histidine tag, mouse or human Fc, or a signal sequence such as ROR1. For example, the term includes sequences exemplified by the sequence shown in SEQ ID NO: 356 or 357, comprising a histidine tag at the C-terminal, coupled to amino acid residues 19-1676 of full-length C5 protein. The term also includes protein variants that comprise a histidine tag at the C-terminal, coupled to amino acid residues 19-1676 of full-length C5 protein with a R885H change or a R885C change.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$).

Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human anti-C5 monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes fully human anti-C5 monoclonal antibodies comprising variants of any of the HCVR, LCVR, and/or CDR amino acid sequences disclosed herein having one or more conservative substitutions. For example, the present invention includes anti-C5 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

The term "recombinant", as used herein, refers to antibodies or antigen-binding fragments thereof of the invention created, expressed, isolated or obtained by technologies or methods known in the art as recombinant DNA technology which include, e.g., DNA splicing and transgenic expression. The term refers to antibodies expressed in a non-human mammal (including transgenic non-human mammals, e.g., transgenic mice), or a cell (e.g., CHO cells) expression system or isolated from a recombinant combinatorial human antibody library.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1 \times 10^{-8}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to C5. Moreover, multi-specific antibodies that bind to one domain in C5 and one or more additional antigens or a bi-specific that binds to two different regions of C5 are nonetheless considered antibodies that "specifically bind", as used herein.

The term "high affinity" antibody refers to those mAbs having a binding affinity to C5, expressed as $K_D$, of at least $10^{-8}$ M; preferably $10^{-9}$ M; more preferably $10^{-10}$ M, even more preferably $10^{-11}$ M, even more preferably $10^{-12}$ M, as measured by surface plasmon resonance, e.g., BIACORE™ or solution-affinity ELISA.

By the term "slow off rate", "Koff" or "kd" is meant an antibody that dissociates from C5, with a rate constant of $1 \times 10^{-3}$ s$^{-1}$ or less, preferably $1 \times 10^{-4}$ s$^{-1}$ or less, as determined by surface plasmon resonance, e.g., BIACORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to C5 protein.

In specific embodiments, antibody or antibody fragments of the invention may be conjugated to a moiety such a ligand or a therapeutic moiety ("immunoconjugate"), a second anti-C5 antibody, or any other therapeutic moiety useful for treating a C5-associated disease or disorder.

An "isolated antibody", as used herein, is intended to refer to an antibody that is substantially free of other antibodies (Abs) having different antigenic specificities (e.g., an isolated antibody that specifically binds C5, or a fragment thereof, is substantially free of Abs that specifically bind antigens other than C5.

A "blocking antibody" or a "neutralizing antibody", as used herein (or an "antibody that neutralizes C5 activity" or "antagonist antibody"), is intended to refer to an antibody whose binding to C5 results in inhibition of at least one biological activity of C5. For example, an antibody of the invention may prevent or block complement-mediated hemolysis by classical pathway or alternative pathway.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "cross-competes", as used herein, means an antibody or antigen-binding fragment thereof binds to an antigen and inhibits or blocks the binding of another antibody or antigen-binding fragment thereof. The term also includes competition between two antibodies in both orientations, i.e., a first antibody that binds and blocks binding of second antibody and vice-versa. In certain embodiments, the first antibody and second antibody may bind to the same epitope. Alternatively, the first and second antibodies may bind to different, but overlapping epitopes such that binding of one inhibits or blocks the binding of the second antibody, e.g., via steric hindrance. Cross-competition between antibodies may be measured by methods known in the art, for example, by a real-time, label-free bio-layer interferometry assay. Cross-competition between two antibodies may be expressed as the binding of the second antibody that is less than the background signal due to self-self binding (wherein first and second antibodies is the same antibody). Cross-competition between 2 antibodies may be expressed, for example, as % binding of the second antibody that is less than the baseline self-self background binding (wherein first and second antibodies is the same antibody).

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402, each of which is herein incorporated by reference.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

As used herein, the term "subject" refers to an animal, preferably a mammal, more preferably a human, in need of amelioration, prevention and/or treatment of a C5-associated disease or disorder such as atypical hemolytic uremic syndrome (aHUS) or paroxysmal nocturnal hemoglobinuria (PNH). The term includes human subjects who have or are at risk of having such a disease or disorder.

As used herein, the terms "treat", "treating", or "treatment" refer to the reduction or amelioration of the severity of at least one symptom or indication of a C5-associated disease or disorder due to the administration of a therapeutic agent such as an antibody of the present invention to a subject in need thereof. The terms include inhibition of progression of disease or of worsening of a symptom/indication. The terms also include positive prognosis of disease, i.e., the subject may be free of disease or may have reduced disease upon administration of a therapeutic agent such as an antibody of the present invention. The therapeutic agent may be administered at a therapeutic dose to the subject.

The terms "prevent", "preventing" or "prevention" refer to inhibition of manifestation of a C5-associated disease or disorder or any symptoms or indications of such a disease or disorder upon administration of an antibody of the present invention.

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to C5 protein. An antibody fragment may include a Fab fragment, a F(ab')$_2$ fragment, a Fv fragment, a dAb fragment, a fragment containing a CDR, or an isolated CDR. In certain embodiments, the term "antigen-binding fragment" refers to a polypeptide fragment of a multi-specific antigen-binding molecule. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$—$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

Preparation of Human Antibodies

Methods for generating human antibodies in transgenic mice are known in the art. Any such known methods can be used in the context of the present invention to make human antibodies that specifically bind to C5 protein.

An immunogen comprising any one of the following can be used to generate antibodies to C5 protein. In certain embodiments, the antibodies of the invention are obtained from mice immunized with a full length, native C5 protein (See, for example, GenBank accession number NP_001726.2) (SEQ ID NO: 355), or with DNA encoding the protein or fragment thereof. Alternatively, the protein or a fragment thereof may be produced using standard biochemical techniques and modified and used as immunogen. In certain embodiments of the invention, the immunogen is a fragment of C5 protein that ranges from about amino acid residues 19-1676 of SEQ ID NO: 355.

In some embodiments, the immunogen may be a recombinant C5 protein or fragment thereof expressed in E. coli or in any other eukaryotic or mammalian cells such as Chinese hamster ovary (CHO) cells.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to C5 are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

Bioequivalents

The anti-C5 antibodies and antibody fragments of the present invention encompass proteins having amino acid sequences that vary from those of the described antibodies, but that retain the ability to bind C5 protein. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present invention encompass sequences that comprise one or more additions, deletions, or substitutions of nucleotides when compared to the disclosed sequence, but that encode an antibody or antibody fragment that is essentially bioequivalent to an antibody or antibody fragment of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, or potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Anti-C5 Antibodies Comprising Fc Variants

According to certain embodiments of the present invention, anti-C5 antibodies are provided comprising an Fc domain comprising one or more mutations which enhance or diminish antibody binding to the FcRn receptor, e.g., at acidic pH as compared to neutral pH. For example, the present invention includes anti-C5 antibodies comprising a mutation in the $C_{H2}$ or a $C_{H}3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present invention includes anti-C5 antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). All possible combinations of the foregoing Fc domain mutations and other mutations within the antibody variable domains disclosed herein, are contemplated within the scope of the present invention.

The present invention also includes anti-C5 antibodies comprising a chimeric heavy chain constant ($C_H$) region, wherein the chimeric $C_H$ region comprises segments derived from the $C_H$ regions of more than one immunoglobulin isotype. For example, the antibodies of the invention may comprise a chimeric $C_H$ region comprising part or all of a $C_{H2}$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the invention comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., U.S. Patent Application Publication 2014/0243504, the disclosure of which is hereby incorporated by reference in its entirety).

Biological Characteristics of the Antibodies

In general, the antibodies of the present invention function by binding to C5 protein and preventing its cleavage to C5a and C5b. For example, the present invention includes antibodies and antigen-binding fragments of antibodies that bind C5 protein (e.g., at 25° C. or at 37° C.) with a $K_D$ of less than 9 nM as measured by surface plasmon resonance, e.g., using the assay format as defined in Example 3 herein. In certain embodiments, the antibodies or antigen-binding fragments thereof bind C5 with a $K_D$ of less than about 9 nM, less than about 5 nM, less than about 2 nM, less than about 1 nM, less than about 500 pM, less than 250 pM, or less than 100 pM, as measured by surface plasmon resonance, e.g., using the assay format as defined in Example 3 herein, or a substantially similar assay.

The present invention also includes antibodies and antigen-binding fragments thereof that bind human C5 protein with a dissociative half-life (t ½) of greater than about 2 minutes as measured by surface plasmon resonance at 25° C., e.g., using an assay format as defined in Example 4 herein, or a substantially similar assay. In certain embodiments, the antibodies or antigen-binding fragments of the present invention bind C5 protein with a t % of greater than about 5 minutes, greater than about 10 minutes, greater than about 30 minutes, greater than about 50 minutes, greater than about 100 minutes, greater than about 150 minutes, greater than about 200 minutes, or greater than about 250 minutes, as measured by surface plasmon resonance at 25° C., e.g., using an assay format as defined in Example 3 herein (e.g., mAb-capture or antigen-capture format), or a substantially similar assay.

The present invention also includes antibodies and antigen-binding fragments thereof that bind human C5 protein with a dissociative half-life (t %) of greater than about 1.5 minutes as measured by surface plasmon resonance at 37° C., e.g., using an assay format as defined in Example 4 herein, or a substantially similar assay. In certain embodiments, the antibodies or antigen-binding fragments of the present invention bind C5 protein with a t % of greater than about 2 minutes, greater than about 5 minutes, greater than about 10 minutes, greater than about 25 minutes, greater than about 50 minutes, greater than about 100 minutes, greater than about 150 minutes, or greater than about 200 minutes, as measured by surface plasmon resonance at 37° C., e.g., using an assay format as defined in Example 3 herein (e.g., mAb-capture or antigen-capture format), or a substantially similar assay.

The present invention also includes antibodies and antigen-binding fragments of antibodies that bind monkey C5 protein (e.g., at 25° C. or at 37° C.) with a $K_D$ of less than 120 nM as measured by surface plasmon resonance, e.g., using the assay format as defined in Example 3 herein. In certain embodiments, the antibodies or antigen-binding fragments thereof bind monkey C5 with a $K_D$ of less than about 120 nM, less than about 100 nM, less than about 50 nM, less than about 25 nM, less than about 10 nM, less than about 5 nM, less than about 1 nM, less than about 500 pM, or less than 250 pM, as measured by surface plasmon resonance, e.g., using the assay format as defined in Example 3 herein, or a substantially similar assay.

The present invention also includes antibodies and antigen-binding fragments of antibodies that bind modified human C5 protein with R885H change (exemplified by SEQ ID NO: 356) with a $K_D$ of less than 70 nM as measured by surface plasmon resonance, e.g., using the assay format as defined in Example 3 herein. C5 variants have shown poor response to anti-C5 antibodies previously disclosed in the art (e.g., Nishimura et al 2014, New Engl. J. Med. 370: 632-639). In certain embodiments, the antibodies or antigen-binding fragments thereof bind the modified human C5 with a $K_D$ of less than about 65 nM, less than about 50 nM, less than about 20 nM, less than about 10 nM, less than about 5 nM, less than about 3 nM, or less than 2 nM, as measured by surface plasmon resonance, e.g., using the assay format as defined in Example 3 herein, or a substantially similar assay.

The present invention also includes antibodies and antigen-binding fragments of antibodies that bind modified human C5 protein with R885C change (exemplified by SEQ ID NO: 357) with a $K_D$ of less than 160 nM as measured by surface plasmon resonance, e.g., using the assay format as defined in Example 3 herein. C5 variants have shown poor response to anti-C5 antibodies previously disclosed in the art (e.g., Nishimura et al 2014, New Engl. J. Med. 370: 632-639). In certain embodiments, the antibodies or antigen-binding fragments thereof bind the modified human C5 with a $K_D$ of less than about 150 nM, less than about 100 nM, less than about 50 nM, less than about 20 nM, less than about 10 nM, less than about 5 nM, or less than 2 nM, as measured by surface plasmon resonance, e.g., using the assay format as defined in Example 3 herein, or a substantially similar assay.

The present invention also includes antibodies and antigen-binding fragments of antibodies that inhibit complement dependent cytotoxicity (CDC) with $IC_{50}$ less than 10 nM as measured by a luminescence assay, e.g., using the assay format as defined in Example 6 herein. In certain embodiments, the antibodies or antigen-binding fragments thereof inhibit CDC with $IC_{50}$ less than about 5 nM, less than about 3.5 nM, or less than about 2 nM, as measured by a B-cell luminescence assay, e.g., using the assay format as defined in Example 6 herein, or a substantially similar assay.

The present invention also includes antibodies and antigen-binding fragments that block human C5-mediated classical pathway (CP) hemolysis by more than 94% and with an $IC_{50}$ less than 6 nM, as measured by a CP hemolysis assay, e.g., using the assay format as defined in Example 8 herein. In certain embodiments, the antibodies or antigen-binding fragments thereof block CP hemolysis with $IC_{50}$ less than about 6 nM, less than about 5 nM, less than about 4 nM, less than about 3 nM, or less than about 2 nM, as measured by CP hemolysis assay, e.g., using the assay format as defined in Example 8 herein, or a substantially similar assay.

The present invention also includes antibodies and antigen-binding fragments that block human C5-mediated alternative pathway (AP) hemolysis by more than 70% and with an $IC_{50}$ less than 165 nM, as measured by a AP hemolysis assay, e.g., using the assay format as defined in Example 8 herein. In certain embodiments, the antibodies or antigen-binding fragments thereof block AP hemolysis with $IC_{50}$ less than about 160 nM, less than about 150 nM, less than about 100 nM, less than about 50 nM, or less than about 20 nM, as measured by AP hemolysis assay, e.g., using the assay format as defined in Example 8 herein, or a substantially similar assay.

The present invention also includes antibodies and antigen-binding fragments that block African green monkey C5-mediated classical pathway (CP) hemolysis by more than 40% and with an $IC_{50}$ less than 185 nM, as measured by a CP hemolysis assay, e.g., using the assay format as defined in Example 8 herein. In certain embodiments, the antibodies or antigen-binding fragments thereof block CP hemolysis with $IC_{50}$ less than about 180 nM, less than about 150 nM, less than about 100 nM, less than about 75 nM, or less than about 50 nM, as measured by CP hemolysis assay, e.g., using the assay format as defined in Example 8 herein, or a substantially similar assay.

The present invention also includes antibodies and antigen-binding fragments that block African green monkey C5-mediated alternative pathway (AP) hemolysis with an $IC_{50}$ less than 235 nM, as measured by a AP hemolysis assay, e.g., using the assay format as defined in Example 8 herein. In certain embodiments, the antibodies or antigen-binding fragments thereof block AP hemolysis with $IC_{50}$ less than about 200 nM, less than about 150 nM, less than about 100 nM, less than about 50 nM, or less than about 20 nM, as measured by AP hemolysis assay, e.g., using the assay format as defined in Example 8 herein, or a substantially similar assay.

The present invention also includes antibodies and antigen-binding fragments that block more than 90% of cynomolgus monkey C5-mediated classical pathway (CP) hemolysis with an $IC_{50}$ less than 145 nM, as measured by a CP hemolysis assay, e.g., using the assay format as defined in Example 8 herein. In certain embodiments, the antibodies or antigen-binding fragments thereof block CP hemolysis with $IC_{50}$ less than about 140 nM, less than about 120 nM, less than about 100 nM, less than about 75 nM, or less than about 50 nM, as measured by CP hemolysis assay, e.g., using the assay format as defined in Example 8 herein, or a substantially similar assay.

The present invention also includes antibodies and antigen-binding fragments that block cynomolgus monkey C5-mediated alternative pathway (AP) hemolysis with an $IC_{50}$ less than 30 nM, as measured by an AP hemolysis assay, e.g., using the assay format as defined in Example 8 herein. In certain embodiments, the antibodies or antigen-binding fragments thereof block AP hemolysis with $IC_{50}$ less than about 25 nM, less than about 20 nM, less than about 10 nM, less than about 5 nM, or less than about 2 nM, as measured by AP hemolysis assay, e.g., using the assay format as defined in Example 8 herein, or a substantially similar assay.

The present invention also includes antibodies and antigen-binding fragments that show improved pharmacokinetic (PK) and pharmacodynamic (PD) properties as compared to anti-C5 antibodies in the art. The anti-C5 antibodies of the present invention show less susceptibility to target-mediated clearance upon administration, as shown in Examples 9 and 10 herein. In certain embodiments, the present invention includes anti-C5 antibodies and antigen-binding fragments thereof that show serum concentrations for extended periods, e.g., more than 20 days, more than 25 days, more than 30 days, more than 35 days, more than 40 days, more than 45 days, more than 50 days, more than 55 days, or more than 60 days, as described in Examples 9 and 10 herein. In certain embodiments, the anti-C5 antibodies of the present invention show an extended serum half-life of more than 10 days, as compared to anti-C5 antibodies in the art.

In certain embodiments, the present invention provides anti-C5 antibodies and antigen-binding fragments thereof that have high affinity for human C5 (e.g., $K_D$ less than 0.3 nM) and a lower clearance (e.g., extended serum half-life, improved pharmacodynamic activity over more days than previously known anti-C5 antibodies). Such antibodies of the present invention may be advantageously used with less frequent dosing in a subject with a C5-associated disease or disorder.

In one embodiment, the present invention provides an isolated recombinant antibody or antigen-binding fragment thereof that binds specifically to C5 protein, wherein the antibody or fragment thereof exhibits one or more of the following characteristics: (a) is a fully human monoclonal antibody; (b) binds to human C5 with a dissociation constant ($K_D$) of less than 0.9 nM at 25° C., as measured in a surface plasmon resonance assay; (c) binds to human C5 with a $K_D$ of less than 0.3 nM at 37° C., as measured in a surface plasmon resonance assay; (d) has serum concentration of more than 10 µg/mL through day 70 upon administration to cynomolgus monkey; (e) blocks CP- and AP hemolysis through day 35 upon administration to cynomolgus monkey, as measured in an ex vivo hemolysis assay; (f) has serum half-life of more than 10 days in cynomolgus monkey; (g) has serum concentration of more than 10 µg/mL through day 40 upon administration to C5-humanized mice; (h) blocks CP hemolysis through day 30 upon administration to C5-humanized mice, as measured in an ex vivo hemolysis assay; and (i) has serum half-life of more than 10 days in C5-humanized mice.

In one embodiment, the present invention provides an isolated recombinant antibody or antigen-binding fragment thereof that binds specifically to C5 protein, wherein the antibody or fragment thereof exhibits one or more of the following characteristics: (a) is a fully human monoclonal antibody; (b) binds to human C5 with a dissociation constant ($K_D$) of less than 0.9 nM at 25° C., as measured in a surface plasmon resonance assay; (c) binds to human C5 with a $K_D$ of less than 0.3 nM at 37° C., as measured in a surface plasmon resonance assay; (d) binds to monkey C5 with a $K_D$ of less than 65 nM, as measured in a surface plasmon resonance assay; (e) binds to human C5 variant R885H (SEQ ID NO: 356) with a $K_D$ of less than 0.5 nM, as measured in a surface plasmon resonance assay; (f) binds to human C5 variant R885C (SEQ ID NO: 357) with a $K_D$ of less than 0.5 nM, as measured in a surface plasmon resonance assay; (g) blocks human C5-mediated classical pathway (CP) hemolysis by more than 95% and with $IC_{50}$ less than 6 nM, as measured in a CP hemolysis assay; (h) blocks human C5-mediated alternative pathway (AP) hemolysis by more than 70% and with $IC_{50}$ less than 165 nM, as measured in a AP hemolysis assay; (i) inhibits African green monkey C5-mediated CP hemolysis with $IC_{50}$ less than 185 nM, as measured in a CP hemolysis assay; (j) inhibits African green monkey C5-mediated AP hemolysis with $IC_{50}$ less than 235 nM, as measured in a AP hemolysis assay; (k) inhibits cynomolgus monkey C5-mediated CP hemolysis with $IC_{50}$ less than 145 nM, as measured in a CP hemolysis assay; and (I) inhibits cynomolgus monkey C5-mediated AP hemolysis with $IC_{50}$ less than 30 nM, as measured in a AP hemolysis assay.

The antibodies of the present invention may possess one or more of the aforementioned biological characteristics, or any combinations thereof. Other biological characteristics of the antibodies of the present invention will be evident to a person of ordinary skill in the art from a review of the present disclosure including the working Examples herein.

Epitope Mapping and Related Technologies

The present invention includes anti-C5 antibodies which interact with one or more amino acids found within one or more regions of the C5 protein molecule including, the alpha polypeptide and beta polypeptide. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within any of the aforementioned domains of the C5 protein molecule (e.g. a linear epitope in a domain). Alternatively, the epitope may consist of a plurality of non-contiguous amino acids (or amino acid sequences) located within either or both of the aforementioned domains of the protein molecule (e.g. a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Other methods include alanine scanning mutational analysis, peptide blot analysis (Reineke (2004) Methods Mol. Biol. 248: 443-63), peptide cleavage analysis crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267: 252-259; Engen and Smith (2001) Anal. Chem. 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the invention into groups of antibodies binding different epitopes.

In certain embodiments, the anti-C5 antibodies or antigen-binding fragments thereof bind an epitope within any one or more of the regions exemplified in C5 protein, either in natural form, as exemplified in SEQ ID NO: 355, or recombinantly produced, or to a fragment thereof. In some embodiments, the antibodies of the invention bind to a region comprising one or more amino acids selected from the group consisting of amino acid residues 19-1676 of human C5 protein.

In certain embodiments, the antibodies of the invention, interact with at least one amino acid sequence selected from the group consisting of amino acid residues ranging from about position 19 to about position 750; or amino acid residues ranging from about position 751 to about position 1676 of SEQ ID NO: 355.

In certain embodiments, the present invention includes anti-C5 antibodies and antigen-binding fragments thereof that interact with one or more epitopes found within the alpha and/or the beta chain of C5 (SEQ ID NO: 359). The epitope(s) may consist of one or more contiguous sequences of 3 or more (e.g., 3, 4, 5, 6, 7, 8, 9, 10, 11, 12, 13, 14, 15, 16, 17, 18, 19, 20 or more) amino acids located within alpha chain and/or beta chain of C5. Alternatively, the epitope may consist of a plurality of non-contiguous amino acids (or amino acid sequences) located within C5. As shown in Example 11 herein, the epitope of C5 with which the exemplary antibody of the invention H4H12166P interacts is defined by: (i) the amino acid sequence NMATGMDSW (SEQ ID NO: 360) which corresponds to amino acids 591 to 599 comprised in the beta chain of SEQ ID NO: 359; and (ii) the amino acid sequence WEVHLVPRRKQLQFALPDSL (SEQ ID NO: 361), which corresponds to amino acids 775 to 794 comprised in the alpha chain of SEQ ID NO: 359. Accordingly, the present invention includes anti-C5 antibodies that interact with one or more amino acids contained within the region consisting of (i) the amino acid sequence NMATGMDSW (SEQ ID NO: 360), which corresponds to amino acids 591 to 599 of SEQ ID NO: 359; and (ii) the amino acid sequence WEVHLVPRRKQLQFALPDSL (SEQ ID NO: 361), which corresponds to amino acids 775 to 794 of SEQ ID NO: 359.

The present invention includes anti-C5 antibodies that bind to the same epitope, or a portion of the epitope, as any of the specific exemplary antibodies listed in Table 1. Likewise, the present invention also includes anti-C5 antibodies that compete for binding to C5 protein or a fragment thereof with any of the specific exemplary antibodies listed in Table 1. For example, the present invention includes anti-C5 antibodies that cross-compete for binding to C5 protein with one or more antibodies listed in Table 1.

One can easily determine whether an antibody binds to the same epitope as, or competes for binding with, a reference anti-C5 antibody by using routine methods known in the art. For example, to determine if a test antibody binds to the same epitope as a reference anti-C5 antibody of the invention, the reference antibody is allowed to bind to a C5 protein or peptide under saturating conditions. Next, the ability of a test antibody to bind to the C5 protein molecule is assessed. If the test antibody is able to bind to C5 following saturation binding with the reference anti-C5 antibody, it can be concluded that the test antibody binds to a different epitope than the reference anti-C5 antibody. On the other hand, if the test antibody is not able to bind to the C5 protein following saturation binding with the reference anti-C5 antibody, then the test antibody may bind to the same epitope as the epitope bound by the reference anti-C5 antibody of the invention.

To determine if an antibody competes for binding with a reference anti-C5 antibody, the above-described binding methodology is performed in two orientations: In a first orientation, the reference antibody is allowed to bind to a C5 protein under saturating conditions followed by assessment of binding of the test antibody to the C5 molecule. In a second orientation, the test antibody is allowed to bind to a C5 molecule under saturating conditions followed by assessment of binding of the reference antibody to the C5 molecule. If, in both orientations, only the first (saturating) antibody is capable of binding to the C5 molecule, then it is concluded that the test antibody and the reference antibody compete for binding to C5. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The invention encompasses a human anti-C5 monoclonal antibody conjugated to a therapeutic moiety ("immunoconjugate"), to treat a C5-associated disease or disorder (e.g., atypical hemolytic uremic syndrome). As used herein, the term "immunoconjugate" refers to an antibody which is chemically or biologically linked to a radioactive agent, a cytokine, an interferon, a target or reporter moiety, an enzyme, a peptide or protein or a therapeutic agent. The antibody may be linked to the radioactive agent, cytokine, interferon, target or reporter moiety, enzyme, peptide or therapeutic agent at any location along the molecule so long as it is able to bind its target. Examples of immunoconjugates include antibody drug conjugates and antibody-toxin fusion proteins. In one embodiment, the agent may be a second different antibody to C5 protein. The type of therapeutic moiety that may be conjugated to the anti-C5 antibody and will take into account the condition to be treated and the desired therapeutic effect to be achieved. Examples of suitable agents for forming immunoconjugates are known in the art; see for example, WO 05/103081.

Multi-Specific Antibodies

The antibodies of the present invention may be monospecific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244.

Any of the multi-specific antigen-binding molecules of the invention, or variants thereof, may be constructed using standard molecular biological techniques (e.g., recombinant DNA and protein expression technology), as will be known to a person of ordinary skill in the art.

In some embodiments, C5-specific antibodies are generated in a bi-specific format (a "bi-specific") in which variable regions binding to distinct domains of C5 protein are linked together to confer dual-domain specificity within a single binding molecule. Appropriately designed bi-specifics may enhance overall C5-protein inhibitory efficacy through increasing both specificity and binding avidity. Variable regions with specificity for individual domains, (e.g., segments of the N-terminal domain), or that can bind to different regions within one domain, are paired on a structural scaffold that allows each region to bind simultaneously to the separate epitopes, or to different regions within one domain. In one example for a bi-specific, heavy chain variable regions ($V_H$) from a binder with specificity for one domain are recombined with light chain variable regions ($V_L$) from a series of binders with specificity for a second domain to identify non-cognate $V_L$ partners that can be paired with an original $V_H$ without disrupting the original specificity for that $V_H$. In this way, a single $V_L$ segment (e.g., $V_L1$) can be combined with two different $V_H$ domains (e.g., $V_H1$ and $V_H2$) to generate a bi-specific comprised of two binding "arms" ($V_H1$-$V_L1$ and $V_H2$-$V_L1$). Use of a single $V_L$ segment reduces the complexity of the system and thereby simplifies and increases efficiency in cloning, expression, and purification processes used to generate the bi-specific (See, for example, U.S. Ser. No. 13/022,759 and US2010/0331527).

Alternatively, antibodies that bind more than one domains and a second target, such as, but not limited to, for example, a second different anti-C5 antibody, may be prepared in a bi-specific format using techniques described herein, or other techniques known to those skilled in the art. Antibody variable regions binding to distinct regions may be linked together with variable regions that bind to relevant sites on, for example, the extracellular domain of C5, to confer dual-antigen specificity within a single binding molecule. Appropriately designed bi-specifics of this nature serve a dual function. Variable regions with specificity for the extracellular domain are combined with a variable region with specificity for outside the extracellular domain and are paired on a structural scaffold that allows each variable region to bind to the separate antigens.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., J. Am. Chem. Soc. [Epub: Dec. 4, 2012]).

Therapeutic Administration and Formulations

The invention provides therapeutic compositions comprising the anti-C5 antibodies or antigen-binding fragments thereof of the present invention. Therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When an antibody of the present invention is used for treating a disease or disorder in an adult patient, or for preventing such a disease, it is advantageous to administer the antibody of the present invention normally at a single dose of about 0.1 to about 100 mg/kg body weight, more preferably about 5 to about 80, about 10 to about 70, or about 20 to about 50 mg/kg body weight. Depending on the severity of the condition, the frequency and the duration of the treatment can be adjusted. In certain embodiments, the antibody or antigen-binding fragment thereof of the invention can be administered as an initial dose of at least about 0.1 mg to about 800 mg, about 1 to about 600 mg, about 5 to about 500 mg, or about 10 to about 400 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer (1990) Science 249: 1527-1533).

The use of nanoparticles to deliver the antibodies of the present invention is also contemplated herein. Antibody-conjugated nanoparticles may be used both for therapeutic and diagnostic applications. Antibody-conjugated nanoparticles and methods of preparation and use are described in detail by Arruebo, M., et al. 2009 ("Antibody-conjugated nanoparticles for biomedical applications" in J. Nanomat. Volume 2009, Article ID 439389, 24 pages, doi: 10.1155/2009/439389), incorporated herein by reference. Nanoparticles may be developed and conjugated to antibodies contained in pharmaceutical compositions to target cells. Nanoparticles for drug delivery have also been described in, for example, U.S. Pat. No. 8,257,740, or U.S. Pat. No. 8,246,995, each incorporated herein in its entirety.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous, intracranial, intraperitoneal and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but certainly are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.) and the HUMIRA™ Pen (Abbott Labs, Abbott Park, Ill.), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the antibody contained is generally about 5 to about 500 mg per dosage form in a unit dose; especially in the form of injection, it is preferred that the antibody is contained in about 5 to about 300 mg and in about 10 to about 300 mg for the other dosage forms.

Therapeutic Uses of the Antibodies

The antibodies of the present invention are useful for the treatment, and/or prevention of a disease or disorder or condition associated with C5 and/or for ameliorating at least one symptom associated with such disease, disorder or condition. In certain embodiments, an antibody or antigen-binding fragment thereof of the invention may be administered at a therapeutic dose to a patient with a disease or disorder or condition associated with C5.

In certain embodiments, the antibodies of the present invention are useful in treating or preventing a symptom or indication of atypical hemolytic uremic syndrome (aHUS). Symptoms and indications of aHUS include, but are not limited to, platelet activation, hemolysis, systemic thrombotic microangiopathy (formation of blood clots in small blood vessels throughout the body) leading to stroke, heart attack, kidney failure and/or death, end-stage renal disease, permanent renal damage, abdominal pain, confusion, edema, fatigue, nausea/vomiting, diarrhea, and microangiopathic anemia.

In certain embodiments, the antibodies of the present invention are useful in treating or preventing a symptom or indication of paroxysmal nocturnal hemoglobinuria (PNH). Symptoms and indications of PNH include, but are not limited to, destruction of red blood cells, thrombosis (including deep vein thrombosis, pulmonary embolism), intravascular hemolytic anemia, red discoloration of urine, symptoms of anemia such as tiredness, shortness of breath, and palpitations, abdominal pain and difficulty swallowing.

In certain embodiments, the antibodies of the present invention are useful for treating or preventing at least one symptom or indication of a C5-associated disease or disorder selected from the group consisting of neurological disorders, renal disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, thermal injury including burns or frostbite, post-ischemic reperfusion conditions, myocardial infarction, capillary leak syndrome, obesity, diabetes, Alzheimer's disease, schizophrenia, stroke, epilepsy, atherosclerosis, vasculitis, bullous pemphigoid, C3 glomerulopathy, membraneproliferative glomerulonephritis, balloon angioplasty, post-pump syndrome in cardiopulmonary bypass or renal bypass, hemodialysis, renal ischemia, mesenteric artery reperfusion after aortic reconstruction, infectious disease or sepsis, immune complex disorders and autoimmune diseases, diabetic nephropathy, Alport's syndrome, progressive kidney failure, proteinuric kidney diseases, renal ischemia-reperfusion injury, lupus nephritis, glomerulopathy, rheumatoid arthritis, systemic lupus erythematosus (SLE), SLE nephritis, membrano-proliferative nephritis, hemolytic anemia, neuromyelitis optica, renal transplant, inherited CD59 deficiency, psoriasis, and myasthenia gravis. In certain other embodiments, the antibodies of the present invention are useful for treating or preventing at least one symptom or indication of a C5-associated disease or disorder selected from the group consisting of lung disease and disorders such as dyspnea, hemoptysis, ARDS, asthma, chronic obstructive pulmonary disease (COPD), emphysema, pulmonary embolisms and infarcts, pneumonia, fibrogenic dust diseases, injury due to inert dusts and minerals (e.g., silicon, coal dust, beryllium, and asbestos), pulmonary fibrosis, organic dust diseases, chemical injury (due to irritant gasses and chemicals, e.g., chlorine, phosgene, sulfur dioxide, hydrogen sulfide, nitrogen dioxide, ammonia, and hydrochloric acid), smoke injury, thermal injury (e.g., burn, freeze), asthma, allergy, bronchoconstriction, hypersensitivity pneumonitis, parasitic diseases, Goodpasture's Syndrome, pulmonary vasculitis, hereditary angioedema, and immune complex-associated inflammation.

In certain embodiments, the antibodies of the invention are useful to treat subjects suffering from an ocular disease such as age-related macular degeneration (AMD), diabetic macular edema (DME), diabetic retinopathy, ocular angiogenesis (ocular neovascularization affecting choroidal, corneal or retinal tissue), geographic atrophy (GA), uveitis and neuromyelitis optica. The antibodies of the present invention may be used to treat or to ameliorate at least one symptom or indication of dry AMD or wet AMD. In some embodiments, the antibodies of the invention are useful in preventing or slowing rate of loss of vision. In one embodiment, the antibodies of the present invention are useful in reducing drusen in the eye of a subject with dry AMD. In one embodiment, the antibodies of the present invention are useful in preventing or reducing/slowing loss of vision in a subject with AMD.

One or more antibodies of the present invention may be administered to relieve or prevent or decrease the severity of one or more of the symptoms or conditions/indications of the ocular disease or disorder. The antibodies may be used to ameliorate or reduce the severity of at least one symptom including, but not limited to loss of vision, visual distortion, difficulty adapting to low light levels, crooked central vision, increase in haziness of central/overall vision, presence of drusen (tiny accumulations of extracellular material that build up on the retina), pigmentary changes, distorted vision in the form of metamorphopsia, in which a grid of straight lines appears wavy and parts of the grid may appear blank, exudative changes (hemorrhages in the eye, hard exudates, subretinal/sub-RPE/intraretinal fluid), slow recovery of visual function after exposure to bright light (photostress test), incipient and geographic atrophy, visual acuity drastically decreasing (two levels or more), e.g., 20/20 to 20/80, preferential hyperacuity perimetry changes (for wet AMD), blurred vision, gradual loss of central vision (for those with non-exudative macular degeneration, rapid onset of vision loss (often caused by leakage and bleeding of abnormal blood vessels in subjects with exudative macular degeneration, central scotomas (shadows or missing areas of vision), trouble discerning colors, specifically dark ones from dark ones and light ones from light ones, loss in contrast sensitivity, straight lines appear curved in an Amsler grid.

It is also contemplated herein to use one or more antibodies of the present invention prophylactically to subjects at risk for developing macular degeneration such as subjects over the age of 50, subjects with a family history of macular degeneration, smokers, and subjects with obesity, high cholesterol, cardiovascular disease, or unhealthy diet.

In a further embodiment of the invention the present antibodies are used for the preparation of a pharmaceutical composition or medicament for treating patients suffering from a disease or disorder associated with C5. In another embodiment of the invention, the present antibodies are used as adjunct therapy with any other agent or any other therapy known to those skilled in the art useful for treating or ameliorating a disease or disorder associated with C5.

Combination Therapies

Combination therapies may include an anti-C5 antibody of the invention and any additional therapeutic agent that may be advantageously combined with an antibody of the invention, or with a biologically active fragment of an antibody of the invention. The antibodies of the present invention may be combined synergistically with one or more drugs or therapy used to treat a disease or disorder associated with C5. In some embodiments, the antibodies of the invention may be combined with a second therapeutic agent to ameliorate one or more symptoms of said disease.

Depending upon the C5-associated disease or disorder, the antibodies of the present invention may be used in combination with one or more additional therapeutic agents including, but not limited to, an anti-coagulant (e.g., warfarin, aspirin, heparin, phenindione, fondaparinux, idraparinux, and thrombin inhibitors such as argatroban, lepirudin, bivalirudin, or dabigatran) an anti-inflammatory drug (e.g., corticosteroids, and non-steroidal anti-inflammatory drugs), an antihypertensive (e.g., an angiotensin-converting enzyme inhibitor), an immunosuppressive agent (e.g., vincristine, cyclosporine A, or methotrexate), a fibrinolytic agent (e.g., ancrod, E-aminocaproic acid, antiplasmin-$a_1$, prostacyclin, and defibrotide), a lipid-lowering agent such as an inhibitor of hydroxymethylglutaryl CoA reductase, an anti-CD20 agent such as rituximab, an anti-TNF agent such as infliximab, an anti-seizure agent (e.g., magnesium sulfate), a C3 inhibitor, or an anti-thrombotic agent.

In certain embodiments, the second therapeutic agent is another antibody to C5 protein. It is contemplated herein to use a combination ("cocktail") of antibodies with broad neutralization or inhibitory activity against C5. In some embodiments, non-competing antibodies may be combined and administered to a subject in need thereof. In some embodiments, the antibodies comprising the combination bind to distinct non-overlapping epitopes on the protein. The antibodies comprising the combination may block the C5 binding to C5 convertase and/or may prevent/inhibit cleavage of C5 into C5a and C5b. In certain embodiments, the second antibody may possess longer half-life in human serum.

As used herein, the term "in combination with" means that additional therapeutically active component(s) may be administered prior to, concurrent with, or after the administration of the anti-C5 antibody of the present invention. The term "in combination with" also includes sequential or concomitant administration of an anti-C5 antibody and a second therapeutic agent.

The additional therapeutically active component(s) may be administered to a subject prior to administration of an anti-C5 antibody of the present invention. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the additional therapeutically active component(s) may be administered to a subject after administration of an anti-C5 antibody of the present invention. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration of the second component. In yet other embodiments, the additional therapeutically active component(s) may be administered to a subject concurrent with administration of an anti-C5 antibody of the present invention. "Concurrent" administration, for purposes of the present invention, includes, e.g., administration of an anti-C5 antibody and an additional therapeutically active component to a subject in a single dosage form, or in separate dosage forms administered to the subject within about 30 minutes or less of each other. If administered in separate dosage forms, each dosage form may be administered via the same route (e.g., both the anti-C5 antibody and the additional therapeutically active component may be administered intravenously, etc.); alternatively, each dosage form may be administered via a different route (e.g., the anti-C5 antibody may be administered intravenously, and the additional therapeutically active component may be administered orally). In any event, administering the components in a single dosage from, in separate dosage forms by the same route, or in separate dosage forms by different routes are all considered "concurrent administration," for purposes of the present disclosure. For purposes of the present disclosure, administration of an anti-C5 antibody "prior to", "concurrent with," or "after" (as those terms are defined herein above) administration of an additional therapeutically active component is considered administration of an anti-C5 antibody "in combination with" an additional therapeutically active component.

The present invention includes pharmaceutical compositions in which an anti-C5 antibody of the present invention is co-formulated with one or more of the additional therapeutically active component(s) as described elsewhere herein.

Administration Regimens

According to certain embodiments, a single dose of an anti-C5 antibody of the invention (or a pharmaceutical composition comprising a combination of an anti-C5 antibody and any of the additional therapeutically active agents mentioned herein) may be administered to a subject in need thereof. According to certain embodiments of the present invention, multiple doses of an anti-C5 antibody (or a pharmaceutical composition comprising a combination of an anti-C5 antibody and any of the additional therapeutically active agents mentioned herein) may be administered to a subject over a defined time course. The methods according to this aspect of the invention comprise sequentially administering to a subject multiple doses of an anti-C5 antibody of the invention. As used herein, "sequentially administering" means that each dose of anti-C5 antibody is administered to the subject at a different point in time, e.g., on different days separated by a predetermined interval (e.g., hours, days, weeks or months). The present invention includes methods which comprise sequentially administering to the patient a single initial dose of an anti-C5 antibody, followed by one or more secondary doses of the anti-C5 antibody, and optionally followed by one or more tertiary doses of the anti-C5 antibody.

The terms "initial dose," "secondary doses," and "tertiary doses," refer to the temporal sequence of administration of the anti-C5 antibody of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-C5 antibody, but generally may differ from one another in terms of frequency of administration. In certain embodiments, however, the amount of anti-C5 antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present invention, each secondary and/or tertiary dose is administered 1 to 48 hours (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) after the immediately preceding dose. The phrase "the immediately preceding dose," as used herein, means, in a sequence of multiple administrations, the dose of anti-C5 antibody which is administered to a patient prior to the administration of the very next dose in the sequence with no intervening doses.

The methods according to this aspect of the invention may comprise administering to a patient any number of secondary and/or tertiary doses of an anti-C5 antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In certain embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

Diagnostic Uses of the Antibodies

The anti-C5 antibodies of the present invention may be used to detect and/or measure C5 in a sample, e.g., for diagnostic purposes. Some embodiments contemplate the use of one or more antibodies of the present invention in assays to detect a C5-associated-disease or disorder. Exemplary diagnostic assays for C5 may comprise, e.g., contacting a sample, obtained from a patient, with an anti-C5 antibody of the invention, wherein the anti-C5 antibody is labeled with a detectable label or reporter molecule or used as a capture ligand to selectively isolate C5 from patient samples. Alternatively, an unlabeled anti-C5 antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure C5 in a sample include enzyme-linked immunosorbent assay (ELISA), radioimmunoassay (RIA), and fluorescence-activated cell sorting (FACS).

Samples that can be used in C5 diagnostic assays according to the present invention include any tissue or fluid sample obtainable from a patient, which contains detectable quantities of either C5 protein, or fragments thereof, under normal or pathological conditions. Generally, levels of C5 protein in a particular sample obtained from a healthy patient (e.g., a patient not afflicted with a disease associated with C5) will be measured to initially establish a baseline, or standard, level of C5. This baseline level of C5 can then be compared against the levels of C5 measured in samples obtained from individuals suspected of having a C5-associated condition, or symptoms associated with such condition.

The antibodies specific for C5 protein may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

Selected Embodiments

Selected embodiments of the present disclosure include the following:

In Embodiment 1, the present invention includes an isolated antibody or antigen-binding fragment thereof that binds specifically to complement factor 5 (C05) protein, wherein the antibody or antigen-binding fragment thereof interacts with one or more amino acids contained within C5 (SEQ ID NO: 359), as determined by hydrogen/deuterium exchange.

In Embodiment 2, the present invention includes the isolated antibody of antigen-binding fragment of Embodiment 1, wherein the antibody or antigen-binding fragment thereof interacts with one or more amino acids contained within the alpha chain and/or the beta chain of C5, as determined by hydrogen/deuterium exchange.

In Embodiment 3, the present invention includes the isolated antibody of antigen-binding fragment of Embodiments 1 or 2, wherein the antibody or antigen-binding fragment thereof does not interact with an amino acid of the C5a anaphylatoxin region of C5, as determined by hydrogen/deuterium exchange.

In Embodiment 4, the present invention includes the isolated antibody of antigen-binding fragment of any one of Embodiments 1 to 3, wherein the antibody or antigen-binding fragment thereof interacts with one or more amino acids contained within SEQ ID NO: 360 and/or SEQ ID NO: 361, as determined by hydrogen/deuterium exchange.

In Embodiment 5, the present invention includes the isolated antibody or antigen-binding fragment of any one of Embodiments 1 to 4, wherein the antibody or antigen-binding fragment thereof interacts with an amino acid sequence selected from the group consisting of (a) amino acids 591 to 599 of SEQ ID NO: 359; (b) amino acids 593 to 599 of SEQ ID NO: 359; (c) amino acids 775 to 787 of SEQ ID NO: 359; (d) amino acids 775 to 794 of SEQ ID NO: 359; and (e) amino acids 779 to 787 of SEQ ID NO: 359.

In Embodiment 6, the present invention includes the isolated antibody or antigen-binding fragment thereof of any one of Embodiments 1 to 5, wherein the antibody or antigen-binding fragment thereof interacts with at least five amino acids contained within an amino acid sequence selected from the group consisting of SEQ ID NOs: 360 and 361.

In Embodiment 7, the present invention includes the isolated antibody or antigen-binding fragment thereof of any one of Embodiments 1 to 5, wherein the antibody or antigen-binding fragment thereof interacts with the amino acid sequences of SEQ ID NOs: 360 and 361.

In Embodiment 8, the present invention includes an isolated antibody or antigen-binding fragment thereof that binds specifically to complement factor 5 (C5) protein, wherein the antibody or antigen-binding fragment thereof interacts with at least one of the following amino acid residues: N591, M592, A593, T594, G595, M596, D597, S598, W599, W775, E776, V777, H778, L779, V780, P781, R782, R783, K784, Q785, L786, Q787, F788, A789, L790, P791, D792, S793, or L794 of SEQ ID NO: 359.

In Embodiment 9, the present invention includes the isolated antibody or antigen-binding fragment thereof of any one of Embodiments 1 to 8, wherein the antibody has one or more of the following characteristics: (a) has serum concentration of more than 10 µg/mL through day 70 upon administration to cynomolgus monkey; (b) blocks classical pathway (CP) hemolysis through day 35 upon administration to cynomolgus monkey, as measured in an ex vivo hemolysis assay; (c) blocks alternative pathway (AP) hemolysis through day 35 upon administration to cynomolgus monkey, as measured in an ex vivo hemolysis assay; (d) has serum half-life of more than 10 days in cynomolgus monkey; (e) has serum concentration of more than 10 µg/mL through day 40 upon administration to C5-humanized mice; (f) blocks CP hemolysis through day 30 upon administration to C5-humanized mice, as measured in an ex vivo hemolysis assay; and (g) has serum half-life of more than 10 days in C5-humanized mice.

In Embodiment 10, the present invention includes the isolated antibody or antigen-binding fragment thereof of any one of Embodiments 1 to 9, wherein the antibody has an additional characteristic selected from the group consisting of: (a) is a fully human monoclonal antibody; (b) binds to human C5 with a dissociation constant ($K_D$) of less than 0.9 nM at 25° C., as measured in a surface plasmon resonance assay; (c) binds to human C5 with a $K_D$ of less than 0.3 nM at 37° C., as measured in a surface plasmon resonance assay; (d) binds to monkey C5 with a $K_D$ of less than 65 nM, as measured in a surface plasmon resonance assay; (e) binds to human 05 variant R885H (SEQ ID NO: 356) with a $K_D$ of less than 0.5 nM, as measured in a surface plasmon resonance assay; (f) binds to human C5 variant R885C (SEQ ID NO: 357) with a $K_D$ of less than 0.5 nM, as measured in a surface plasmon resonance assay; (g) blocks human C5-mediated classical pathway (CP) hemolysis by more than 95% and with $IC_{50}$ less than 6 nM, as measured in a CP hemolysis assay; (h) blocks human C5-mediated alternative pathway (AP) hemolysis by more than 70% and with $IC_{50}$ less than 165 nM, as measured in a AP hemolysis assay; (i) inhibits African green monkey C5-mediated CP hemolysis with $IC_{50}$ less than 185 nM, as measured in a CP hemolysis assay; (j) inhibits African green monkey C5-mediated AP hemolysis with $IC_{50}$ less than 235 nM, as measured in a AP hemolysis assay; (k) inhibits cynomolgus monkey C5-mediated CP hemolysis with $IC_{50}$ less than 145 nM, as measured in a CP hemolysis assay; and (I) inhibits cynomolgus monkey C5-mediated AP hemolysis with $IC_{50}$ less than 30 nM, as measured in a AP hemolysis assay.

In Embodiment 11, the present invention includes the isolated antibody or antigen-binding fragment of any one of Embodiments 1 to 10, wherein the antibody or antigen-binding fragment comprises three heavy chain complementarity determining regions (CDRs) (HCDR1, HCDR2 and HCDR3) contained within any one of the heavy chain variable region (HCVR) sequences listed in Table 1; and three light chain CDRs (LCDR1, LCDR2 and LCDR3) contained within any one of the light chain variable region (LCVR) sequences listed in Table 1.

In Embodiment 12, the present invention includes the isolated antibody or antigen-binding fragment thereof of any one of Embodiments 1 to 11, comprising: (a) a HCDR1 domain having an amino acid sequence selected from the group consisting of SEQ ID NOs: 4, 20, 36, 52, 68, 84, 100, 124, 140, 148, 156, 172, 188, 204, 220, 236, 252, 268, 276, 292, 308, 324, and 340; (b) a HCDR2 domain having an amino acid sequence selected from the group consisting of SEQ ID NOs: 6, 22, 38, 54, 70, 86, 102, 126, 142, 150, 158, 174, 190, 206, 222, 238, 254, 270, 278, 294, 310, 326, and 342; (c) a HCDR3 domain having an amino acid sequence selected from the group consisting of SEQ ID NOs: 8, 24, 40, 56, 72, 88, 104, 128, 144, 152, 160, 176, 192, 208, 224, 240, 256, 272, 280, 296, 312, 328, and 344; (d) a LCDR1 domain having an amino acid sequence selected from the group consisting of SEQ ID NOs: 12, 28, 44, 60, 76, 92, 108, 116, 132, 164, 180, 196, 212, 228, 244, 260, 284, 300, 316, 332, and 348; (e) a LCDR2 domain having an amino acid sequence selected from the group consisting of SEQ ID NOs: 14, 30, 46, 62, 78, 94, 110, 118, 134, 166, 182, 198, 214, 230, 246, 262, 286, 302, 318, 334, and 350; and (f) a LCDR3 domain having an amino acid sequence selected from the group consisting of SEQ ID NOs: 16, 32, 48, 64, 80, 96, 112, 120, 136, 168, 184, 200, 216, 232, 248, 264, 288, 304, 320, 336, and 352.

In Embodiment 13, the present invention includes the isolated antibody or antigen-binding fragment thereof of any one of Embodiments 1 to 12 comprising a HCVR having an amino acid sequence selected from the group consisting of HCVR sequences listed in Table 1.

In Embodiment 14, the present invention includes an isolated antibody or antigen-binding fragment thereof of Embodiment 13 comprising a LCVR having an amino acid sequence selected from the group consisting of LCVR sequences listed in Table 1.

In Embodiment 15, the present invention includes the isolated antibody or antigen-binding fragment of any one of Embodiments 11 to 14 comprising a HCVR/LCVR amino acid sequence pair selected from the group consisting of SEQ ID NOs: 2/10, 18/26, 34/42, 50/58, 66/74, 82/90, 98/106, 98/114, 122/106, 98/130, 138/106, 146/106, 122/130, 146/114, 146/130, 138/130, 154/162, 170/178, 186/194, 202/210, 218/226, 234/242, 250/258, 266/258, 274/282, 290/298, 306/314, 322/330, and 338/346.

In Embodiment 16, the present invention includes the isolated antibody or antigen-binding fragment thereof of any one of Embodiments 11 to 15 comprising three CDRs contained within a HCVR selected from the group consisting of SEQ ID NOs: 50, 98, 138, and 202; and three CDRs contained within a LCVR selected from the group consisting of SEQ ID NOs: 58, 106, and 210.

In Embodiment 17, the present invention includes the isolated antibody or antigen-binding fragment thereof of Embodiment 16 comprising CDRs selected from the group consisting of: (a) SEQ ID NOs: 52, 54, 56, 60, 62, and 64; (b) SEQ ID NOs: 100, 102, 104, 108, 110, and 112; (c) SEQ ID NOs: 140, 142, 144, 108, 110, and 112; and (d) SEQ ID NOs: 204, 206, 208, 212, 214, and 216.

In Embodiment 18, the present invention includes the isolated antibody or antigen-binding fragment thereof of Embodiment 17 comprising a HCVR/LCVR amino acid sequence pair selected from the group consisting of SEQ ID NOs: 50/58, 98/106, 138/106, and 202/210.

In Embodiment 19, the present invention includes an antibody or antigen-binding fragment thereof that competes for binding to C5 with the antibody or antigen-binding fragment thereof of Embodiment 17.

In Embodiment 20, the present invention includes an antibody or antigen-binding fragment thereof that binds to the same epitope as an antibody or antigen-binding fragment thereof of Embodiment 17.

In Embodiment 21, the present invention includes the antibody or antigen-binding fragment thereof of Embodiment 9 or 10 comprising a heavy chain variable region comprising an amino acid sequence listed in Table 1 having no more than 5 amino acid substitutions.

In Embodiment 22, the present invention includes the antibody or antigen-binding fragment thereof of Embodiment 21, comprising a light chain variable region comprising an amino acid sequence listed in Table 1 having no more than 5 amino acid substitutions.

In Embodiment 23, the present invention includes the antibody or antigen-binding fragment thereof of Embodiment 9 or 10 comprising a heavy chain variable region having at least 90% sequence identity to SEQ ID NO: 98.

In Embodiment 24, the present invention includes an antibody or antigen-binding fragment thereof of Embodiment 23 comprising a light chain variable region having at least 90% sequence identity to SEQ ID NO: 106.

In Embodiment 25, the present invention includes an isolated monoclonal antibody or antigen-binding fragment thereof that blocks C5 cleavage to C5a and C5b comprising three CDRs of a HCVR, wherein the HCVR has an amino acid sequence selected from the group consisting of SEQ ID NOs: 2, 18, 34, 50, 66, 82, 98, 122, 138, 146, 154, 170, 186, 202, 218, 234, 250, 266, 274, 290, 306, 322, and 338; and three CDRs of a LCVR, wherein the LCVR has an amino acid sequence selected from the group consisting of SEQ ID NOs: 10, 26, 42, 58, 74, 90, 106, 114, 130, 162, 178, 194, 210, 226, 242, 258, 282, 298, 314, 330, and 346.

In Embodiment 26, the present invention includes a pharmaceutical composition comprising an isolated antibody or antigen-binding fragment thereof that binds to C5 according to any one of Embodiments 1 to 25 and a pharmaceutically acceptable carrier or diluent.

In Embodiment 27, the present invention includes an isolated polynucleotide molecule comprising a polynucleotide sequence that encodes a HCVR of an antibody as set forth in any one of Embodiments 1 to 25.

In Embodiment 28, the present invention includes an isolated polynucleotide molecule comprising a polynucleotide sequence that encodes a LCVR of an antibody as set forth in any one of Embodiments 1 to 25.

In Embodiment 29, the present invention includes a vector comprising the polynucleotide sequence of Embodiment 27 or 28.

In Embodiment 30, the present invention includes a cell expressing the vector of Embodiment 29.

In Embodiment 31, the present invention includes a method of preventing, treating or ameliorating at least one symptom or indication of a disease or disorder associated with C5, the method comprising administering an antibody or antigen-binding fragment of any one of Embodiments 1 to 25 to a subject in need thereof.

In Embodiment 32, the present invention includes the method of Embodiment 31, wherein the disease or disorder is selected from the group consisting of atypical hemolytic uremic syndrome (aHUS), paroxysmal nocturnal hemoglobinuria (PNH), age-related macular degeneration, geographic atrophy, uveitis, neuromyelitis optica, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, thermal injury including burns or frostbite, post-ischemic reperfusion conditions, myocardial infarction, capillary leak syndrome, obesity, diabetes, Alzheimer's disease, schizophrenia, stroke, epilepsy, atherosclerosis, vasculitis, bullous pemphigoid, C3 glomerulopathy, membraneproliferative glomerulonephritis, diabetic nephropathy, Alport's syndrome, progressive kidney failure, proteinuric kidney diseases, renal ischemia-reperfusion injury, lupus nephritis, balloon angioplasty, post-pump syndrome in cardiopulmonary bypass or renal bypass, hemodialysis, renal ischemia, mesenteric artery reperfusion after aortic reconstruction, infectious disease or sepsis, immune complex disorders and autoimmune diseases, renal disorders, rheumatoid arthritis, systemic lupus erythematosus (SLE), SLE nephritis, proliferative nephritis, hemolytic anemia, asthma, chronic obstructive pulmonary disease (COPD), emphysema, pulmonary embolisms and infarcts, pneumonia, and myasthenia gravis.

In Embodiment 33, the present invention includes the method of Embodiment 31, wherein the disease or disorder is aHUS.

In Embodiment 34, the present invention includes the method of Embodiment 31, wherein the disease or disorder is PNH.

In Embodiment 35, the present invention includes the method of any one of Embodiments 31-34, wherein the pharmaceutical composition is administered prophylactically or therapeutically to the subject in need thereof.

In Embodiment 36, the present invention includes the method of any one of Embodiments 31 to 35, wherein the pharmaceutical composition is administered in combination with a second therapeutic agent.

In Embodiment 37, the present invention includes the method of Embodiment 36, wherein the second therapeutic agent is selected from the group consisting of an anticoagulant, an anti-inflammatory drug, an antihypertensive, an immunosuppressive agent, a lipid-lowering agent, an anti-CD20 agent such as rituximab, an anti-TNF agent such as infliximab, an anti-seizure agent, a C3 inhibitor, a second anti-C5 antibody, and an anti-thrombotic agent.

In Embodiment 38, the present invention includes the method of any one of Embodiments 31 to 37, wherein the pharmaceutical composition is administered subcutaneously, intravenously, intradermally, intraperitoneally, orally, intramuscularly or intracranially.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Generation of Human Antibodies to Complement Factor 5 (C5) Protein

Human antibodies to C5 protein were generated in a VELOCIMMUNE® mouse comprising DNA encoding human Immunoglobulin heavy and kappa light chain variable regions. The mice were immunized with serum purified human C5 protein (CALBIOCHEM® Cat #20-4888).

The antibody immune response was monitored by a C5-specific immunoassay. When a desired immune response was achieved splenocytes were harvested and fused with mouse myeloma cells to preserve their viability and form hybridoma cell lines. The hybridoma cell lines were screened and selected to identify cell lines that produce C5-specific antibodies. The cell lines were used to obtain several anti-C5 chimeric antibodies (i.e., antibodies possessing human variable domains and mouse constant domains); exemplary antibodies generated in this manner were designated as H2M11683N and H2M11686N.

Anti-C5 antibodies were also isolated directly from antigen-positive mouse B cells without fusion to myeloma cells, as described in U.S. Pat. No. 7,582,298, herein specifically incorporated by reference in its entirety. Using this method, several fully human anti-C5 antibodies (i.e., antibodies possessing human variable domains and human constant domains) were obtained; exemplary antibodies generated in this manner were designated as H4H12159P, H4H12161P, H4H12163P, H4H12164P, H4H12166P, H4H12167P, H4H12168P, H4H12169P, H4H12170P, H4H12171P, H4H12175P, H4H12176P2, H4H12177P2 and H4H12183P2.

The biological properties of the exemplary antibodies generated in accordance with the methods of this Example are described in detail in the Examples set forth below.

Example 2: Heavy and Light Chain Variable Region Amino Acid and Nucleotide Sequences Table 1 sets forth the amino acid sequence identifiers of the heavy and light chain variable regions and CDRs of selected anti-C5 antibodies of the invention.

TABLE 1

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H2M11683N | 2 | 4 | 6 | 8 | 10 | 12 | 14 | 16 |
| H2M11686N | 18 | 20 | 22 | 24 | 26 | 28 | 30 | 32 |
| H4H12159P | 34 | 36 | 38 | 40 | 42 | 44 | 46 | 48 |
| H4H12161P | 50 | 52 | 54 | 56 | 58 | 60 | 62 | 64 |
| H4H12163P | 66 | 68 | 70 | 72 | 74 | 76 | 78 | 80 |
| H4H12164P | 82 | 84 | 86 | 88 | 90 | 92 | 94 | 96 |
| H4H12166P | 98 | 100 | 102 | 104 | 106 | 108 | 110 | 112 |
| H4H12166P2 | 98 | 100 | 102 | 104 | 114 | 116 | 118 | 120 |
| H4H12166P3 | 122 | 124 | 126 | 128 | 106 | 108 | 110 | 112 |

TABLE 1-continued

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H4H12166P4 | 98 | 100 | 102 | 104 | 130 | 132 | 134 | 136 |
| H4H12166P5 | 138 | 140 | 142 | 144 | 106 | 108 | 110 | 112 |
| H4H12166P6 | 146 | 148 | 150 | 152 | 106 | 108 | 110 | 112 |
| H4H12166P7 | 122 | 124 | 126 | 128 | 130 | 132 | 134 | 136 |
| H4H12166P8 | 146 | 148 | 150 | 152 | 114 | 116 | 118 | 120 |
| H4H12166P9 | 146 | 148 | 150 | 152 | 130 | 132 | 134 | 136 |
| H4H12166P10 | 138 | 140 | 142 | 144 | 130 | 132 | 134 | 136 |
| H4H12167P | 154 | 156 | 158 | 160 | 162 | 164 | 166 | 168 |
| H4H12168P | 170 | 172 | 174 | 176 | 178 | 180 | 182 | 184 |
| H4H12169P | 186 | 188 | 190 | 192 | 194 | 196 | 198 | 200 |
| H4H12170P | 202 | 204 | 206 | 208 | 210 | 212 | 214 | 216 |
| H4H12171P | 218 | 220 | 222 | 224 | 226 | 228 | 230 | 232 |
| H4H12175P | 234 | 236 | 238 | 240 | 242 | 244 | 246 | 248 |
| H4H12176P2 | 250 | 252 | 254 | 256 | 258 | 260 | 262 | 264 |
| H4H12177P2 | 266 | 268 | 270 | 272 | 258 | 260 | 262 | 264 |
| H4H12183P2 | 274 | 276 | 278 | 280 | 282 | 284 | 286 | 288 |
| H2M11682N | 290 | 292 | 294 | 296 | 298 | 300 | 302 | 304 |
| H2M11684N | 306 | 308 | 310 | 312 | 314 | 316 | 318 | 320 |
| H2M11694N | 322 | 324 | 326 | 328 | 330 | 332 | 334 | 336 |
| H2M11695N | 338 | 340 | 342 | 344 | 346 | 348 | 350 | 352 |

The corresponding nucleic acid sequence identifiers are set forth in Table 2.

TABLE 2

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H2M11683N | 1 | 3 | 5 | 7 | 9 | 11 | 13 | 15 |
| H2M11686N | 17 | 19 | 21 | 23 | 25 | 27 | 29 | 31 |
| H4H12159P | 33 | 35 | 37 | 39 | 41 | 43 | 45 | 47 |
| H4H12161P | 49 | 51 | 53 | 55 | 57 | 59 | 61 | 63 |
| H4H12163P | 65 | 67 | 69 | 71 | 73 | 75 | 77 | 79 |
| H4H12164P | 81 | 83 | 85 | 87 | 89 | 91 | 93 | 95 |
| H4H12166P | 97 | 99 | 101 | 103 | 105 | 107 | 109 | 111 |
| H4H12166P2 | 97 | 99 | 101 | 103 | 113 | 115 | 117 | 119 |
| H4H12166P3 | 121 | 123 | 125 | 127 | 105 | 107 | 109 | 111 |
| H4H12166P4 | 97 | 99 | 101 | 103 | 129 | 131 | 133 | 135 |
| H4H12166P5 | 137 | 139 | 141 | 143 | 105 | 107 | 109 | 111 |
| H4H12166P6 | 145 | 147 | 149 | 151 | 105 | 107 | 109 | 111 |
| H4H12166P7 | 121 | 123 | 125 | 127 | 129 | 131 | 133 | 135 |
| H4H12166P8 | 145 | 147 | 149 | 151 | 113 | 115 | 117 | 119 |
| H4H12166P9 | 145 | 147 | 149 | 151 | 129 | 131 | 133 | 135 |
| H4H12166P10 | 137 | 139 | 141 | 143 | 129 | 131 | 133 | 135 |
| H4H12167P | 153 | 155 | 157 | 159 | 161 | 163 | 165 | 167 |
| H4H12168P | 169 | 171 | 173 | 175 | 177 | 179 | 181 | 183 |
| H4H12169P | 185 | 187 | 189 | 191 | 193 | 195 | 197 | 199 |
| H4H12170P | 201 | 203 | 205 | 207 | 209 | 211 | 213 | 215 |
| H4H12171P | 217 | 219 | 221 | 223 | 225 | 227 | 229 | 231 |
| H4H12175P | 233 | 235 | 237 | 239 | 241 | 243 | 245 | 247 |
| H4H12176P2 | 249 | 251 | 253 | 255 | 257 | 259 | 261 | 263 |
| H4H12177P2 | 265 | 267 | 269 | 271 | 257 | 259 | 261 | 263 |
| H4H12183P2 | 273 | 275 | 277 | 279 | 281 | 283 | 285 | 287 |
| H2M11682N | 289 | 291 | 293 | 295 | 297 | 299 | 301 | 303 |
| H2M11684N | 305 | 307 | 309 | 311 | 313 | 315 | 317 | 319 |
| H2M11694N | 321 | 323 | 325 | 327 | 329 | 331 | 333 | 335 |
| H2M11695N | 337 | 339 | 341 | 343 | 345 | 347 | 349 | 351 |

Antibodies are typically referred to herein according to the following nomenclature: Fc prefix (e.g. "H4H," "H2M," etc.), followed by a numerical identifier (e.g. "11686," "12166," "12183," etc., as shown in Table 2), followed by a "P," "P2," or "N" suffix. Thus, according to this nomenclature, an antibody may be referred to herein as, e.g., "H2M11686N," "H4H12183P2," "H4H12168P," etc. The H4H and H2M prefixes on the antibody designations used herein indicate the particular Fc region isotype of the antibody. For example, an "H4H" antibody has a human IgG4 Fc comprising a serine to proline mutation in the hinge region (S108P) to promote dimer stabilization, and an "H2M" antibody has a mouse IgG2 Fc (a or b isotype) (all variable regions are fully human as denoted by the first 'H' in the antibody designation). As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Table 2—will remain the same, and the binding properties to antigen are expected to be identical or substantially similar regardless of the nature of the Fc domain.

In certain embodiments, selected antibodies with a mouse IgG1 Fc were converted to antibodies with human IgG4 Fc. In one embodiment, the IgG4 Fc domain comprises 2 or more amino acid changes as disclosed in US20100331527.

To generate mutated antibodies, various residues in the complementary determining regions (CDRs) of H4H12166P were mutated to histidine to generate 9 mutated antibodies, identified as H4H12166P2 to H4H12166P10. Histidine mutations in the CDRs have been shown to confer pH-dependence of binding to target antigen leading to improved pharmacokinetics (Igawa et al. 2010, Nat. Biotechnol. 28: 1203-1207).

Control Constructs Used in the Following Examples

The following control constructs (anti-C5 antibodies) were included in the experiments disclosed herein, for comparative purposes: "Comparator 1," a monoclonal antibody against human C5 having $V_H/V_L$ sequences of antibody "h5G1.1" according to U.S. Pat. No. 6,355,245 (Alexion Pharmaceuticals, Inc.); and "Comparator 2," a human monoclonal antibody against human C5 having $V_H/V_L$ sequences of antibody "8109" according to US Patent Application Publication No. 2013/0022615 (Novartis).

Example 3: Antibody Binding to C5 as Determined by Surface Plasmon Resonance Equilibrium dissociation constants ($K_D$ values) for C5 binding to purified anti-C5 antibodies were determined using a real-time surface plasmon resonance biosensor assay on a BIACORE™ T200 instrument. The BIACORE™ sensor surface was derivatized by amine coupling with a monoclonal mouse anti-human Fc antibody (GE Healthcare, # BR-1008-39) to capture anti-C5 antibodies expressed with human Fc constant regions. BIACORE™ binding studies were conducted in HBST running buffer (0.01M HEPES pH 7.4, 0.15M NaCl, 3 mM EDTA, 0.05% v/v Surfactant P20). Human C5 was obtained from a commercial source (EMD). Other C5 reagents were expressed with a C-terminal myc-myc-hexahistidine tag (subsequently referred to as C5-mmh). Human C5-mmh reagents were also expressed containing histidine and cysteine point mutations at arginine 885 (subsequently referred to as C5 R885H-mmh and C5 R885C-mmh, respectively). Different concentrations of human C5, human C5 R885H-mmh (SEQ ID No: 356), human C5 R885C-mmh (SEQ ID No: 357) and monkey C5-mmh (SEQ ID No: 358) (ranging from 100 nM to 1.23 nM, 3-fold dilutions) prepared in HBST running buffer were injected over the anti-C5 antibody captured surface at a flow rate of 30 μL/min. Association of all the C5 reagents to each of the captured monoclonal antibodies was monitored for 3 minutes and their dissociation in HBST running buffer was monitored for 8 minutes. All the binding kinetics experiments were performed at either 25° C. or 37° C. Kinetic association ($k_a$) and dissociation ($k_d$) rate constants were determined by fitting the real-time sensorgrams to a 1:1 binding model using Scrubber 2.0c curve fitting software. Binding dissociation equilibrium constants ($K_D$) and dissociative half-lives (t1/2) were calculated from the kinetic rate constants as: $K_D$ (M)=$k_d/k_a$ and t1/2 (min)=ln 2/(60×$k_d$)

Binding kinetic parameters for human C5 binding to anti-C5 antibodies at 25° C. and 37° C. are shown in Tables 3 and 4.

TABLE 3

Binding Kinetics parameters of anti-C5 monoclonal antibodies binding to human C5 at 25° C.

| Antibody | Amount of Antibody Captured (RU) | 100 nM Human C5 Bound (RU) | $k_a$ (1/Ms) | $k_d$ (1/s) | KD (M) | t½ (min) |
|---|---|---|---|---|---|---|
| H4H11683N | 231 | 439 | 4.17E+05 | 5.14E−05 | 1.23E−10 | 225 |
| H4H12171P | 51 | 64 | 1.49E+05 | 8.16E−05 | 5.49E−10 | 142 |
| H4H12161P | 38 | 64 | 2.58E+05 | 4.37E−05 | 1.70E−10 | 264 |
| H4H12176P2 | 50 | 96 | 3.36E+05 | 6.75E−05 | 2.01E−10 | 171 |
| H4H12163P | 51 | 108 | 6.43E+05 | 2.08E−04 | 3.24E−10 | 55 |
| H4H12167P | 52 | 116 | 1.09E+06 | 1.31E−04 | 1.21E−10 | 88 |
| H4H12175P | 51 | 100 | 2.16E+05 | 1.96E−04 | 9.10E−10 | 59 |
| H4H12159P | 53 | 118 | 9.75E+05 | 7.13E−05 | 7.31E−11 | 162 |
| H4H12164P | 52 | 103 | 2.92E+05 | 8.84E−05 | 3.02E−10 | 131 |
| H4H12168P | 50 | 113 | 4.23E+05 | 4.75E−05 | 1.12E−10 | 243 |
| H4H12169P | 51 | 18 | 2.24E+05 | 4.40E−04 | 1.96E−09 | 26 |
| H4H11686N | 200 | 341 | 2.20E+05 | 3.31E−05 | 1.50E−10 | 349 |
| H4H12170P | 51 | 119 | 5.25E+05 | 6.79E−05 | 1.29E−10 | 170 |
| H4H12177P2 | 47 | 60 | 6.56E+04 | 6.29E−05 | 9.59E−10 | 184 |
| H4H12183P2 | 46 | 50 | 1.66E+05 | 2.70E−04 | 1.63E−10 | 427 |
| H4H12166P | 53 | 105 | 6.42E+05 | 1.10E−04 | 1.71E−10 | 105 |
| H4H12166P2 | 53 | 95 | 8.26E+05 | 3.61E−04 | 4.38E−10 | 32 |
| H4H12166P3 | 59 | 124 | 4.03E+05 | 4.65E−04 | 1.15E−09 | 25 |
| H4H12166P4 | 49 | 92 | 4.46E+05 | 1.76E−04 | 3.95E−10 | 66 |
| H4H12166P5 | 59 | 110 | 2.85E+05 | 3.28E−04 | 1.15E−09 | 35 |
| H4H12166P6 | 64 | 131 | 4.89E+05 | 1.84E−04 | 3.75E−10 | 63 |
| H4H12166P7 | 50 | 92 | 2.74E+05 | 1.01E−03 | 3.67E−09 | 11 |
| H4H12166P8 | 50 | 91 | 4.84E+05 | 6.86E−04 | 1.42E−09 | 17 |
| H4H12166P9 | 52 | 100 | 3.32E+05 | 2.64E−04 | 7.94E−10 | 44 |
| H4H12166P10 | 49 | 69 | 1.57E+05 | 1.32E−03 | 8.38E−09 | 9 |

TABLE 3-continued

Binding Kinetics parameters of anti-C5 monoclonal antibodies binding to human C5 at 25° C.

| Antibody | Amount of Antibody Captured (RU) | 100 nM Human C5 Bound (RU) | $k_a$ (1/Ms) | $k_d$ (1/s) | KD (M) | $t½$ (min) |
|---|---|---|---|---|---|---|
| Comparator 1 | 232 | 250 | 9.69E+04 | 1.46E−04 | 1.51E−09 | 79 |
| Comparator 2 | 117 | 170 | 2.62E+05 | 2.39E−04 | 9.12E−10 | 48 |

TABLE 4

Binding Kinetics parameters of anti-C5 monoclonal antibodies binding to human C5 at 37° C.

| Antibody | Amount of Antibody Captured (RU) | 100 nM Human C5 Bound (RU) | $k_a$ (1/Ms) | $k_d$ (1/s) | $K_D$ (M) | $t½$ (min) |
|---|---|---|---|---|---|---|
| H4H11683N | 257 | 492 | 4.54E+05 | 2.41E−04 | 5.32E−10 | 48 |
| H4H12171P | 59 | 58 | 1.22E+05 | 7.62E−04 | 6.27E−09 | 15 |
| H4H12161P | 40 | 66 | 1.16E+05 | 1.15E−04 | 9.90E−10 | 101 |
| H4H12176P2 | 38 | 71 | 1.47E+05 | 2.34E−04 | 1.59E−09 | 49 |
| H4H12163P | 65 | 139 | 9.11E+05 | 6.65E−04 | 7.29E−10 | 17 |
| H4H12167P | 75 | 153 | 1.29E+06 | 3.81E−04 | 2.95E−10 | 30 |
| H4H12175P | 74 | 132 | 2.96E+05 | 6.37E−04 | 2.15E−09 | 18 |
| H4H12159P | 70 | 145 | 1.04E+06 | 1.07E−04 | 1.03E−10 | 108 |
| H4H12164P | 66 | 140 | 3.96E+05 | 1.28E−04 | 3.23E−10 | 90 |
| H4H12168P | 34 | 12 | 2.50E+04 | 4.64E−04 | 1.85E−08 | 25 |
| H4H12169P | 59 | 65 | 1.15E+05 | 3.52E−04 | 3.06E−09 | 33 |
| H4H11686N | 206 | 406 | 3.33E+05 | 1.56E−04 | 4.69E−10 | 74 |
| H4H12170P | 34 | 55 | 2.97E+05 | 4.15E−04 | 1.40E−09 | 28 |
| H4H12177P2 | 41 | 37 | 4.42E+04 | 5.78E−04 | 1.31E−08 | 20 |
| H4H12183P2 | 29 | 30 | 4.30E+04 | 2.50E−04 | 5.81E−09 | 46 |
| H4H12166P | 69 | 127 | 8.80E+05 | 2.30E−04 | 2.62E−10 | 50 |
| H4H12166P2 | 68 | 110 | 9.50E+05 | 1.23E−03 | 1.29E−09 | 9 |
| H4H12166P3 | 86 | 147 | 6.12E+05 | 1.27E−03 | 2.07E−09 | 9 |
| H4H12166P4 | 63 | 108 | 5.05E+05 | 4.69E−04 | 9.30E−10 | 25 |
| H4H12166P5 | 76 | 129 | 4.40E+05 | 1.22E−03 | 2.77E−09 | 9 |
| H4H12166P6 | 90 | 157 | 5.42E+05 | 4.74E−04 | 8.75E−10 | 24 |
| H4H12166P7 | 64 | 105 | 3.49E+05 | 2.58E−03 | 7.39E−09 | 4 |
| H4H12166P8 | 65 | 98 | 6.75E+05 | 2.09E−03 | 3.10E−09 | 6 |
| H4H12166P9 | 76 | 122 | 3.75E+05 | 6.39E−04 | 1.70E−09 | 18 |
| H4H12166P10 | 64 | 82 | 2.27E+05 | 3.14E−03 | 1.38E−08 | 4 |
| Comparator 1 | 185 | 246 | 1.47E+05 | 5.30E−04 | 3.61E−09 | 22 |
| Comparator 2 | 119 | 205 | 2.85E+05 | 6.57E−04 | 2.30E−10 | 18 |

Monkey C5-mmh binding to anti-C5 antibodies at 25° C. and 37° C. are shown in Tables 5 and 6.

TABLE 5

Binding Kinetics parameters of anti-C5 monoclonal antibodies binding to monkey C5-mmh at 25° C.

| Antibody | Amount of Antibody Captured (RU) | 100 nM monkey C5-mmh Bound (RU) | ka (1/Ms) | kd (1/s) | $K_D$ (M) | $t½$ (min) |
|---|---|---|---|---|---|---|
| H4H11683N | 228 | 403 | 3.86E+05 | 2.47E−04 | 6.40E−10 | 47 |
| H4H12171P | 51 | 17 | 4.60E+04 | 2.26E−04 | 4.92E−09 | 51 |
| H4H12161P | 38 | 45 | 6.33E+04 | 2.48E−05 | 3.92E−10 | 465 |
| H4H12176P2 | 50 | 69 | 1.82E+05 | 5.88E−05 | 3.22E−10 | 196 |
| H4H12163P | 50 | 98 | 3.11E+05 | 7.75E−04 | 2.49E−09 | 15 |
| H4H12167P | 52 | 111 | 4.19E+05 | 1.32E−04 | 3.15E−10 | 88 |
| H4H12175P | 51 | 59 | 6.42E+04 | 1.65E−03 | 2.57E−08 | 7 |
| H4H12159P | 53 | 116 | 3.54E+05 | 4.69E−05 | 1.33E−10 | 246 |
| H4H12164P | 51 | 66 | 1.27E+05 | 1.53E−03 | 1.20E−08 | 8 |
| H4H12168P | 50 | 86 | 1.73E+05 | 1.14E−04 | 6.60E−10 | 101 |

TABLE 5-continued

Binding Kinetics parameters of anti-C5 monoclonal antibodies binding to monkey C5-mmh at 25° C.

| Antibody | Amount of Antibody Captured (RU) | 100 nM monkey C5-mmh Bound (RU) | ka (1/Ms) | kd (1/s) | $K_D$ (M) | t½ (min) |
|---|---|---|---|---|---|---|
| H4H12169P | 51 | 22 | 1.64E+05 | 4.55E-03 | 2.78E-08 | 3 |
| H4H11686N | 196 | 247 | 1.57E+05 | 4.89E-04 | 3.11E-09 | 24 |
| H4H12170P | 51 | 92 | 2.62E+05 | 5.21E-05 | 1.99E-10 | 222 |
| H4H12177P2 | 47 | 32 | 4.62E+04 | 9.92E-04 | 2.15E-08 | 12 |
| H4H12183P2 | 47 | 23 | 4.88E+04 | 4.94E-04 | 1.01E-08 | 23 |
| H4H12166P | 52 | 90 | 2.05E+05 | 1.06E-03 | 5.15E-09 | 11 |
| H4H12166P2 | 53 | 71 | 3.00E+05 | 3.16E-03 | 1.05E-08 | 4 |
| H4H12166P3 | 59 | 72 | 1.68E+05 | 4.47E-03 | 2.66E-08 | 3 |
| H4H12166P4 | 49 | 69 | 2.10E+05 | 1.78E-03 | 8.50E-09 | 6 |
| H4H12166P5 | 59 | 56 | 1.44E+05 | 3.46E-03 | 2.40E-08 | 3 |
| H4H12166P6 | 64 | 94 | 2.39E+05 | 2.66E-03 | 1.11E-08 | 4 |
| H4H12166P7 | 50 | 36 | 1.36E+05 | 6.33E-03 | 4.65E-08 | 2 |
| H4H12166P8 | 50 | 47 | 2.31E+05 | 4.99E-03 | 2.16E-08 | 2 |
| H4H12166P9 | 52 | 55 | 1.70E+05 | 3.18E-03 | 1.87E-08 | 4 |
| H4H12166P10 | 49 | 15 | 9.56E+04 | 6.16E-03 | 6.44E-08 | 2 |
| Comparator 1* | 228 | 11 | N/A | N/A | 3.11E-07 | N/A |

N/A = Not Available;
*SS = steady state analysis

TABLE 6

Binding Kinetics parameters of anti-C5 monoclonal antibodies binding to monkey C5-mmh at 37° C.

| Antibody | Amount of Antibody Captured (RU) | 100 nM monkey C5-mmh Bound (RU) | ka (1/Ms) | kd (1/s) | KD (M) | t½ (min) |
|---|---|---|---|---|---|---|
| H4H11683N | 192 | 303 | 5.35E+05 | 1.15E-03 | 2.16E-09 | 10 |
| H4H12171P | 59 | 78 | 5.56E+05 | 1.03E-03 | 1.85E-09 | 11 |
| H4H12161P | 41 | 53 | 1.34E+05 | 7.45E-04 | 5.56E-09 | 16 |
| H4H12176P2 | 36 | 47 | 1.35E+05 | 1.29E-03 | 9.60E-09 | 9 |
| H4H12163P | 64 | 129 | 3.90E+05 | 1.25E-03 | 3.20E-09 | 9 |
| H4H12167P | 74 | 146 | 5.37E+05 | 2.89E-04 | 5.39E-10 | 40 |
| H4H12175P | 74 | 74 | 1.77E+05 | 2.76E-03 | 1.56E-08 | 4 |
| H4H12159P | 70 | 137 | 4.12E+05 | 5.50E-05 | 1.33E-10 | 210 |
| H4H12164P | 65 | 99 | 1.86E+05 | 1.17E-03 | 6.30E-09 | 10 |
| H4H12168P | 34 | 29 | 5.33E+04 | 6.76E-04 | 1.27E-08 | 17 |
| H4H12169P | 59 | 64 | 2.51E+05 | 3.61E-03 | 1.43E-08 | 3 |
| H4H11686N | 145 | 195 | 2.33E+05 | 2.07E-03 | 8.88E-09 | 6 |
| H4H12170P | 34 | 60 | 5.21E+05 | 8.71E-04 | 1.67E-09 | 13 |
| H4H12177P2 | 41 | 27 | 1.50E+05 | 7.17E-03 | 4.77E-08 | 2 |
| H4H12183P2 | 28 | 13 | 5.40E+04 | 6.37E-03 | 1.18E-07 | 2 |
| H4H12166P | 68 | 110 | 2.19E+05 | 1.87E-03 | 8.55E-09 | 6 |
| H4H12166P2 | 68 | 83 | 3.93E+05 | 2.97E-03 | 7.56E-09 | 4 |
| H4H12166P3 | 85 | 92 | 2.23E+05 | 2.92E-03 | 1.31E-08 | 4 |
| H4H12166P4 | 62 | 80 | 2.23E+05 | 1.83E-03 | 8.20E-09 | 6 |
| H4H12166P5 | 75 | 70 | 1.50E+05 | 3.13E-03 | 2.09E-08 | 4 |
| H4H12166P6 | 90 | 112 | 2.53E+05 | 2.32E-03 | 9.18E-09 | 5 |
| H4H12166P7 | 63 | 48 | 1.25E+05 | 2.41E-03 | 1.93E-08 | 5 |
| H4H12166P8 | 64 | 53 | 2.03E+05 | 2.69E-03 | 1.33E-08 | 4 |
| H4H12166P9 | 75 | 69 | 1.81E+05 | 2.61E-03 | 1.44E-08 | 4 |
| H4H12166P10 | 63 | 24 | 6.60E+04 | 2.79E-03 | 4.22E-08 | 4 |
| Comparator 1 | 132 | 4 | NB | NB | NB | NB |

Human C5 R885H-mmh and human C5 R885C-mmh binding to anti-C5 antibodies at 25° C. are shown in Tables 7 and 8, respectively.

TABLE 7

Binding Kinetics parameters of anti-C5 monoclonal antibodies binding to human C5 R885H-mmh at 25° C.

| Antibody | Amount of Antibody Captured (RU) | 100 nM Human C5 R885H-mmh Bound (RU) | $k_a$ (1/Ms) | $k_d$ (1/s) | $K_D$ (M) | $t^{1/2}$ (min) |
|---|---|---|---|---|---|---|
| H4H11683N | 183 | 118 | 5.26E+05 | 2.46E−04 | 4.68E−10 | 47 |
| H4H12171P | 119 | 51 | 6.59E+05 | 1.42E−04 | 2.16E−10 | 81 |
| H4H12161P | 105 | 199 | 8.36E+04 | 8.32E−05 | 9.96E−10 | 139 |
| H4H12176P2 | 170 | 65 | 1.78E+05 | 2.17E−04 | 1.22E−09 | 53 |
| H4H12163P | 111 | 214 | 6.72E+05 | 4.34E−04 | 6.46E−10 | 27 |
| H4H12167P | 93 | 187 | 6.89E+05 | 2.98E−04 | 4.33E−10 | 39 |
| H4H12175P | 104 | 207 | 1.81E+05 | 1.98E−03 | 1.09E−08 | 6 |
| H4H12159P | 101 | 177 | 7.06E+05 | 1.76E−04 | 2.50E−10 | 66 |
| H4H12164P | 143 | 295 | 1.58E+05 | 1.87E−04 | 1.19E−09 | 62 |
| H4H12168P | 138 | 197 | 5.29E+04 | 2.14E−04 | 4.05E−09 | 54 |
| H4H12169P | 116 | 173 | 4.84E+05 | 7.09E−05 | 1.47E−10 | 163 |
| H4H11686N | 145 | 259 | 2.16E+05 | 1.06E−04 | 4.91E−10 | 109 |
| H4H12170P | 244 | 442 | 4.09E+05 | 1.61E−04 | 3.94E−10 | 72 |
| H4H12177P2 | 137 | 232 | 1.48E+05 | 5.92E−04 | 4.01E−09 | 20 |
| H4H12183P2 | 158 | 99 | 3.77E+04 | 4.37E−05 | 1.16E−09 | 264 |
| H4H12166P | 188 | 366 | 5.28E+05 | 2.12E−04 | 4.02E−10 | 54 |
| Comparator 1 | 87 | 11 | NB | NB | NB | NB |
| Comparator 2 | 118 | 249 | 1.08E+06 | 6.53E−04 | 6.06E−10 | 18 |

TABLE 8

Binding Kinetics parameters of anti-C5 monoclonal antibodies binding to human C5 R885C-mmh at 25° C.

| Antibody | Amount of Antibody Captured (RU) | 100 nM Human C5 R885C-mmh Bound (RU) | $k_a$ (1/Ms) | $k_d$ (1/s) | $K_D$ (M) | $t^{1/2}$ (min) |
|---|---|---|---|---|---|---|
| H4H11683N | 174 | 116 | 4.99E+05 | 2.39E−04 | 4.79E−10 | 48 |
| H4H12171P | 109 | 51 | 3.79E+05 | 1.39E−04 | 3.66E−10 | 83 |
| H4H12161P | 103 | 147 | 1.30E+05 | 8.71E−05 | 6.72E−10 | 133 |
| H4H12176P2 | 164 | 63 | 1.07E+05 | 2.18E−04 | 2.03E−09 | 53 |
| H4H12163P | 110 | 211 | 5.04E+05 | 4.32E−04 | 8.58E−10 | 27 |
| H4H12167P | 85 | 163 | 7.11E+05 | 2.94E−04 | 4.13E−10 | 39 |
| H4H12175P | 99 | 128 | 8.18E+04 | 1.55E−02 | 1.90E−07 | 1 |
| H4H12159P | 93 | 168 | 5.86E+05 | 1.69E−04 | 2.89E−10 | 68 |
| H4H12164P | 139 | 249 | 1.53E+05 | 1.82E−04 | 1.19E−09 | 63 |
| H4H12168P | 128 | 144 | 6.09E+04 | 1.99E−04 | 3.27E−09 | 58 |
| H4H12169P | 108 | 168 | 2.78E+05 | 6.99E−05 | 2.51E−10 | 165 |
| H4H11686N | 143 | 253 | 1.78E+05 | 9.49E−05 | 5.34E−10 | 122 |
| H4H12170P | 244 | 427 | 3.57E+05 | 1.60E−04 | 4.47E−10 | 72 |
| H4H12177P2 | 138 | 177 | 1.00E+05 | 1.32E−03 | 1.32E−08 | 9 |
| H4H12183P2 | 158 | 80 | 2.99E+04 | 2.20E−05 | 7.37E−10 | 525 |
| H4H12166P | 188 | 356 | 4.26E+05 | 2.07E−04 | 4.87E−10 | 56 |
| Comparator 1 | 87 | 9 | NB | NB | NB | NB |
| Comparator 2 | 117 | 241 | 1.17E+06 | 6.19E−04 | 5.30E−10 | 19 |

Human C5 R885H-mmh and human C5 R885C-mmh binding to anti-C5 antibodies at 37° C. are shown in Tables 9 and 10, respectively.

TABLE 9

Binding Kinetics parameters of anti-C5 monoclonal antibodies binding to human C5 R885H-mmh at 37° C.

| Antibody | Amount of Antibody Captured (RU) | 100 nM Human C5 R885H-mmh Bound (RU) | $k_a$ (1/Ms) | $k_d$ (1/s) | $K_D$ (M) | t½ (min) |
|---|---|---|---|---|---|---|
| H4H11683N | 49 | 81 | 5.48E+05 | 1.47E−03 | 2.69E−09 | 8 |
| H4H12171P | 59 | 80 | 5.92E+05 | 9.63E−04 | 1.63E−09 | 12 |
| H4H12161P | 41 | 54 | 1.18E+05 | 9.25E−04 | 7.84E−09 | 12 |
| H4H12176P2 | 45 | 69 | 2.57E+05 | 9.58E−04 | 3.73E−09 | 12 |
| H4H12163P | 60 | 85 | 7.24E+05 | 2.90E−03 | 4.00E−09 | 4 |
| H4H12167P | 38 | 65 | 8.81E+05 | 2.57E−03 | 2.91E−09 | 5 |
| H4H12175P | 25 | 30 | 1.37E+05 | 9.50E−03 | 6.94E−08 | 1 |
| H4H12159P | 51 | 82 | 6.38E+05 | 9.48E−04 | 1.49E−09 | 12 |
| H4H12164P | 59 | 68 | 1.95E+05 | 1.06E−03 | 5.46E−09 | 11 |
| H4H12168P | 34 | 29 | 2.43E+04 | 1.23E−03 | 5.04E−08 | 9 |
| H4H12169P | 61 | 79 | 4.29E+05 | 7.39E−04 | 1.72E−09 | 16 |
| H4H11686N | 40 | 74 | 4.19E+05 | 8.00E−04 | 1.91E−09 | 14 |
| H4H12170P | 36 | 64 | 5.59E+05 | 8.39E−04 | 1.50E−09 | 14 |
| H4H12177P2 | 45 | 51 | 2.76E+05 | 2.76E−03 | 1.00E−08 | 4 |
| H4H12183P2 | 33 | 36 | 9.58E+04 | 7.12E−04 | 7.43E−09 | 16 |
| H4H12166P | 71 | 58 | 6.24E+05 | 1.31E−03 | 2.09E−09 | 9 |
| Comparator 1 | 41 | 5 | NB | NB | NB | NB |
| Comparator 2 | 23 | 47 | 8.39E+05 | 1.05E−03 | 1.25E−09 | 11 |

TABLE 10

Binding Kinetics parameters of anti-C5 monoclonal antibodies binding to human C5 R885C-mmh at 37° C.

| Antibody | Amount of Antibody Captured (RU) | 100 nM Human C5 R885C-mmh Bound (RU) | $k_a$ (1/Ms) | $k_d$ (1/s) | $K_D$ (M) | t½ (min) |
|---|---|---|---|---|---|---|
| H4H11683N | 48 | 78 | 4.38E+05 | 1.43E−03 | 3.25E−09 | 8 |
| H4H12171P | 59 | 78 | 4.77E+05 | 9.57E−04 | 2.01E−09 | 12 |
| H4H12161P | 41 | 49 | 1.10E+05 | 9.01E−04 | 8.17E−09 | 13 |
| H4H12176P2 | 44 | 55 | 1.41E+05 | 1.03E−03 | 7.32E−09 | 11 |
| H4H12163P | 59 | 83 | 5.66E+05 | 2.81E−03 | 4.97E−09 | 4 |
| H4H12167P | 38 | 64 | 6.84E+05 | 2.49E−03 | 3.64E−09 | 5 |
| H4H12175P | 25 | 4 | 1.12E+05 | 1.79E−02 | 1.59E−07 | 1 |
| H4H12159P | 51 | 68 | 5.61E+05 | 9.75E−04 | 1.74E−09 | 12 |
| H4H12164P | 59 | 64 | 1.77E+05 | 1.04E−03 | 5.85E−09 | 11 |
| H4H12168P | 34 | 21 | 6.38E+04 | 5.69E−04 | 8.90E−09 | 20 |
| H4H12169P | 61 | 75 | 3.29E+05 | 7.37E−04 | 2.24E−09 | 16 |
| H4H11686N | 39 | 69 | 2.84E+05 | 7.91E−04 | 2.78E−09 | 15 |
| H4H12170P | 36 | 61 | 4.24E+05 | 8.70E−04 | 2.05E−09 | 13 |
| H4H12177P2 | 43 | 31 | 1.07E+05 | 5.07E−03 | 4.76E−08 | 2 |
| H4H12183P2 | 31 | 25 | 5.12E+04 | 9.97E−04 | 1.95E−08 | 12 |
| H4H12166P | 72 | 54 | 4.91E+05 | 1.26E−03 | 2.56E−09 | 9 |
| Comparator 1 | 41 | 2 | NB | NB | NB | NB |
| Comparator 2 | 23 | 42 | 7.34E+05 | 1.07E−03 | 1.45E−09 | 11 |

At 25° C., all 25 anti-C5 antibodies of the invention bound to human C5 with $K_D$ values ranging from 73 pM to 8.4 nM as shown in Table 3. At 37° C., the anti-C5 antibodies of the invention bound to human C5 with $K_D$ values ranging from 103 pM to 18.5 nM as shown in Table 4. At 25° C., 25 out of the 25 anti-C5 antibodies of the invention tested bound to monkey C5-mmh with $K_D$ values ranging from 133 pM to 64 nM as shown in Table 5. At 37° C., 25 out of the 25 anti-C5 antibodies of the invention tested bound to monkey C5-mmh with $K_D$ values ranging from 133 pM to 118 nM as shown in Table 6. At 25° C., 16 out of the 16 anti-C5 antibodies of the invention tested bound to human C5 R885H-mmh with $K_D$ values ranging from 147 pM to 10.9 nM as shown in Table 7. At 25° C., 16 out of the 16 anti-C5 antibodies of the invention tested bound to human C5 R885C-mmh with $K_D$ values ranging from 251 pM to 190 nM as shown in Table 8. At 37° C., 16 out of the 16 anti-C5 antibodies of the invention tested bound to human C5 R885H-mmh with $K_D$ values ranging from 1.49 nM to 69.4 nM as shown in Table 9. At 25° C., 16 out of the 16 anti-C5 antibodies of the invention tested bound to human C5 R885C-mmh with $K_D$ values ranging from 1.74 nM to 159 nM as shown in Table 10.

Example 4: Antibody Binding to C5 Through Different pH

Effect of pH on the rate of dissociation of recombinant human C5 bound to purified anti-C5 monoclonal antibodies was determined using a real-time surface plasmon resonance biosensor using a BIACORE™ T200 instrument. The BIACORE™ sensor surface was first derivatized by amine coupling with a monoclonal mouse anti-human Fc antibody (GE, # BR-1008-39) to capture anti-C5 monoclonal antibodies expressed with human IgG4 Fc. All BIACORE™ binding studies were performed using two running buffers PBS-T, pH7.4 (0.01M $Na_2HPO_4/NaH_2PO_4$, 0.15M NaCl, 0.05% v/v Tween-20, adjusted to pH7.4) and PBS-T, pH6.0 (0.01M $Na_2HPO_4/NaH_2PO_4$, 0.15M NaCl, 0.05% v/v Tween-20, adjusted to pH6.0). Different concentrations of human C5 (EMD, Catalog #204888) or monkey C5.mmh (prepared in PBS-T, pH7.4 running buffer (ranging from 100 nM to 11.11 nM, 3-fold dilutions) were injected over the anti-C5 monoclonal antibody captured surface for 3 minutes at a flow rate of 50 μL/minute and their dissociation in two running buffers PBS-T, pH7.4 and PBS-T, pH6.0 was monitored for 6 minutes. All the binding kinetics experiments were performed at 25° C. and 37° C. Kinetic dissociation constant ($k_d$) were determined by fitting the real-time sensorgrams to a 1:1 binding model using Scrubber 2.0c curve fitting software. Binding dissociative half-lives (t1/2) were calculated from $k_d$ as:

$$t1/2(min) = \frac{\ln(2)}{60 * kd}$$

Half-life ratios for human C5 binding to different anti-C5 monoclonal antibodies at 25° C. and 37° C. in two running buffers PBS-T, pH7.4 and PBS-T, pH6.0 are shown in Tables 11 and 12.

TABLE 11

Half-life ratios of selected anti-C5 antibodies for human C5 at 25° C.

| mAb Captured | t½ Ratio pH7.4/pH6.0 |
|---|---|
| H4H12169P | IC |
| H4H12176P2 | IC |
| H4H12161P | IC |
| H4H12159P | ≤0.3 |
| H4H12170P | ≤0.5 |
| H4H12166P | 4.5 |
| H4H12183P2 | IC |
| H4H12167P | 0.6 |
| H4H12164P | 0.3 |
| H4H12163P | 1.2 |
| H4H12175P | 0.9 |
| H4H12177P2 | ≤0.5 |
| H4H12171P | 0.6 |
| H4H12168P | 1.5 |
| H4H12166P2 | 9.3 |
| H4H12166P3 | 7.9 |
| H4H12166P4 | 7.8 |
| H4H12166P5 | 8.3 |
| H4H12166P6 | 7.8 |
| H4H12166P7 | 35 |
| H4H12166P8 | 47 |
| H4H12166P9 | 31 |
| H4H12166P10 | 33 |
| H4H11683N | 2 |
| H4H11686N | 2 |

IC = inconclusive

TABLE 12

Half-life ratios of selected anti-C5 antibodies on human C5 at 37° C.

| mAb Captured | t½ Ratio pH7.4/pH6.0 |
|---|---|
| H4H12169P | IC |
| H4H12176P2 | ≤0.4 |
| H4H12161P | ≤0.7 |
| H4H12159P | ≤0.2 |
| H4H12170P | ≤0.2 |
| H4H12166P | 3.8 |
| H4H12183P2 | IC |
| H4H12167P | 0.2 |
| H4H12164P | ≤0.1 |
| H4H12163P | 0.8 |
| H4H12175P | 0.9 |
| H4H12177P2 | 1.3 |
| H4H12171P | 3.7 |
| H4H12168P | 1 |
| H4H12166P2 | 7.3 |
| H4H12166P3 | 6.6 |
| H4H12166P4 | 7.6 |
| H4H12166P5 | 7.6 |
| H4H12166P6 | 8.2 |
| H4H12166P7 | 21 |
| H4H12166P8 | 36 |
| H4H12166P9 | 28 |
| H4H12166P10 | 19 |
| H4H11683N | 1.4 |
| H4H11686N | 0.8 |

IC = inconclusive

Half-life ratios for monkey C5 binding to different anti-C5 monoclonal antibodies at 25° C. and 37° C. in two running buffers PBS-T, pH7.4 and PBS-T, pH6.0 are shown in Tables 13 and 14.

TABLE 13

Half-life ratios of selected anti-C5 antibodies on monkey C5 at 25° C.

| mAb Captured | t½ Ratio pH7.4/pH6.0 |
|---|---|
| H4H12169P | 3.4 |
| H4H12176P2 | ≤9.1 |
| H4H12161P | IC |
| H4H12159P | 1.2 |
| H4H12170P | ≤1.7 |
| H4H12166P | 18.5 |
| H4H12183P2 | 5.8 |
| H4H12167P | 9.2 |
| H4H12164P | 2.9 |
| H4H12163P | 9.7 |
| H4H12175P | 3.6 |
| H4H12177P2 | 3.7 |
| H4H12171P | 2.1 |
| H4H12168P | 3.8 |
| H4H11683N | 0.34 |
| H4H11686N | 0.37 |

IC = inconclusive

TABLE 14

Half-life ratios of selected anti-C5 antibodies on monkey C5 at 37° C.

| mAb Captured | t½ Ratio pH7.4/pH6.0 |
|---|---|
| H4H12169P | 2 |
| H4H12176P2 | 2.8 |
| H4H12161P | 10.7 |
| H4H12159P | 6.3 |
| H4H12170P | 4.7 |
| H4H12166P | 7.1 |

TABLE 14-continued

Half-life ratios of selected anti-C5 antibodies on monkey C5 at 37° C.

| mAb Captured | t½ Ratio pH7.4/pH6.0 |
|---|---|
| H4H12183P2 | 2.4 |
| H4H12167P | 4.4 |
| H4H12164P | 1.1 |
| H4H12163P | 3.3 |
| H4H12175P | 0.4 |
| H4H12177P2 | 1.5 |
| H4H12171P | 4.7 |
| H4H12168P | 4 |
| H4H11683N | 0.7 |
| H4H11686N | 0.5 |

IC = inconclusive

As shown in Tables 11-14, selected anti-C5 antibodies showed pH-dependent binding, as seen by the t % ratios.

Example 5: OCTET® Cross-Competition Between Anti-C5 Antibodies

Binding competition between anti-C5 monoclonal antibodies (mAbs) was determined using a real time, label-free bio-layer interferometry assay on an OCTET™ RED384 biosensor (Pall ForteBio Corp.). The entire experiment was performed at 25° C. in 0.01 M HEPES pH7.4, 0.15M NaCl, 0.05% v/v Surfactant Tween-20, 0.1 mg/mL BSA (OCTET™ HBS-P buffer) with the plate shaking at the speed of 1000 rpm. To assess whether 2 antibodies were able to compete with one another for binding to their respective epitopes on a human C5 (hC5 purified from plasma, EMD), around 1.5 nm of anti-human C5 mAb was first captured onto anti-hFc antibody coated OCTET™® biosensor tips (Pall ForteBio Corp., #18-5060) by submerging the tips for 3 minutes into wells containing a 50 μg/mL solution of anti-human C5 mAb (subsequently referred to as mAb1). The antibody captured biosensor tips were then saturated with a blocking H4H isotype control mAb (subsequently referred to as blocking mAb) by dipping into wells containing 200 μg/mL solution of blocking mAb for 4 minutes. The biosensor tips were then subsequently dipped into wells containing a co-complexed solution of 50 nM hC5 and 1 μM of a second anti-human C5 mAb (subsequently referred to as mAb2), that had been preincubated for 2 hours, for 4 minutes. The bio sensor tips were washed in OCTET™ HBS-P buffer in between every step of the experiment. The real-time binding response was monitored during the course of the experiment and the binding response at the end of every step was recorded. The response of human C5 pre-complexed mAb2 binding to mAb1 was corrected for background binding, compared and competitive/non-competitive behavior of different anti-C5 monoclonal antibodies was determined.

Table 15 explicitly defines the relationships of antibodies competing in both directions, independent of the order of binding.

TABLE 15

Cross-competition between pairs of selected anti-C5 antibodies

| First mAb (mAb1) Captured using AHC Octet Biosensors | mAb2 Antibodies Shown to Compete with mAb1 |
|---|---|
| H4H12183P2 | H4H12167P; H4H12166P; H4H12163P |
| H4H12167P | H4H12183P2; H4H12166P; H4H12163P |
| H4H12166P | H4H12183P2; H4H12167P; H4H12163P |
| H4H12163P | H4H12183P2; H4H12167P; H4H12166P |

TABLE 15-continued

Cross-competition between pairs of selected anti-C5 antibodies

| First mAb (mAb1) Captured using AHC Octet Biosensors | mAb2 Antibodies Shown to Compete with mAb1 |
|---|---|
| H4H12159P | H4H12169P; H4H11683N; H4H12170P |
| H4H12169P | H4H12159P; H4H11683N; H4H12170P |
| H4H11683N | H4H12159P; H4H12169P; H4H12170P |
| H4H12170P | H4H12159P; H4H12169P; H4H11683N |
| H4H12175P | H4H12177P2 |
| H4H12177P2 | H4H12175P |
| H4H12176P2 | H4H12164P |
| H4H12164P | H4H12176P2 |
| H4H12168P | none |
| H4H12161P | none |
| H4H11686N | none |

Example 6: Inhibition of C5-Mediated Complement-Dependent Cytotoxicity in a B-Cell Bioassay This Example describes a bioassay to test the role of C5 using an anti-CD20 antibody in the classical complement pathway. Therapeutic anti-CD20 antibodies against the B-cell specific cell-surface antigen CD20, have been shown to lead to CDC of B-cells (Glennie et al. 2007, Mol. Immunol. 44: 3823-3837) and CDC assay using cell lines expressing CD20 has been described previously (Flieger et al. 2000, Cell. Immunol. 204: 55-63). Daudi cells, a human B cell line expressing CD20, complement preserved serum or C5 depleted serum with exogenous C5 variants and an anti-CD20 antibody (antibody comprising VH/VL of "2F2" from U.S. Pat. No. 8,529,902) were used to assess the role of C5 activity in CDC.

For the C5 CDC bioassay, Daudi cells were seeded onto a 96-well assay plates at 10,000 cells/well in either RPMI containing 10% FBS, penicillin/streptomycin, L-glutamine, sodium pyruvate and Non-Essential Amino Acids (RPMI Complete media) or RPMI containing 1% BSA, penicillin/streptomycin and L-glutamine (RPMI/BSA). All assays testing mutated anti-hC5 antibodies, along with testing of the non-mutated antibodies with C5 containing human serum were tested in RPMI Complete media, while assays testing the non-mutated antibodies with African Green monkey serum and human C5 variants were tested in RPMI/BSA media. To measure CDC with human or monkey serum, the anti-CD20 antibody was diluted 1:3 from 100 nM to 2 pM (including a control sample containing no antibody) and incubated with cells for 10 minutes at 25° C. followed by addition of 1.66% serum or 1.66% of C5 depleted serum and 6.6 nM C5 variant proteins. The amount of C5 protein to be added to the C5 depleted serum was based on the reported value of C5 concentration in human serum of 0.37 uM (Rawal et al 2008, J. Biol. Chem. 283: 7853-7863). To test C5 antibody inhibition of CDC, C5 antibodies were diluted 1:3 from 100 nM to 2 pM (including a control sample containing no antibody) and incubated with 1.66% serum or 1.66% of C5 depleted serum and 6.6 nM C5 variant proteins for 30 minutes. Ten minutes prior to addition of antibodies with serum to cells, the anti-CD20 antibody was added to cells at 1 nM, 2 nM, 3 nM, 3.5 nM, 7 nM, 10 nM, or 30 nM. At the conclusion of the incubation with the anti-CD20 antibody, the antibody/serum mixture was added to cells.

Cytotoxicity was measured after 3.5 hours of incubation at 37° C. and in 5% $CO_2$, followed by 15 minute incubation at 25° C., and addition of CYTOTOX-GLO™ reagent (Promega PROMEGA™, # G9292). CYTOTOX-GLO™ is a luminescence-based reagent that measures cell killing such that increased luminescence is observed with increased cytotoxicity (measured in relative light units, RLUs). Untreated cells in control wells were lysed by treatment with digitonin immediately after addition of CYTOTOX-GLO™ reagent to determine maximal killing of cells. Plates were read for luminescence by a VICTOR™ X instrument (Perkin Elmer) 15 minutes following the addition of CYTOTOX-GLO™. Where calculated, the percentage of cytotoxicity was calculated with the RLU values by using the following equation:

$$\% \text{ Cytotoxicity} = 100 \times \frac{(\text{Experimental Cell Lysis} - \text{Background Cell Lysis})}{(\text{Maximum Cell Lysis} - \text{Background Cell Lysis})}$$

In this equation "background cell lysis" is the luminescence from the cells treated with media and serum alone without any anti-CD20 antibody and the "maximum cell lysis" is the luminescence from the cells treated with digitonin. The results, expressed as % cytotoxicity or RLUs, were analyzed using nonlinear regression (4-parameter logistics) with PRISM™ 5 software (GRAPHPAD™) to obtain $EC_{50}$ and $IC_{50}$ values. Inhibition of antibodies was calculated such that 0-100% inhibition is the range of inhibition of the concentration of anti-CD20 antibody used in the assay without inhibitor to 0 nM anti-CD20 antibody.

Results

A total of 25 anti-human C5 antibodies, 16 non-mutated and 9 mutated, were tested for their ability to inhibit C5 in the CDC assay using Daudi cells with an anti-CD20 antibody and either human sera (with normal hC5 or C5 variants) or African green monkey sera. Various residues in the complementary determining regions (CDRs) of H4H12166P were mutated to histidines to generate 9 mutated antibodies, H4H12166P2-H4H12166P10. Histidine mutations in the CDRs have been shown to confer pH-dependence of binding to target antigen leading to improved pharmacokinetics (Igawa et al. 2010, Nat. Biotechnol. 28: 1203-1207).

TABLE 16

Non-mutated anti-hC5 antibody inhibition of CDC with 1.66% serum and anti-CD20 antibody in Daudi Cells

| Serum | Human | Human | African Green monkey | C5 depleted Human and 6.6 nM C5 Variant R885H | C5 depleted Human and 6.6 nM C5 Variant R885C |
|---|---|---|---|---|---|
| EC50 [M] of anti-CD20 antibody (with 1.66% Serum) | 1.0E−09 | 1.4E−09 | 2.4E−09 | 1.9E−09 | 2.7E−09 |
| Constant anti-CD20 antibody (with 1.66% serum) | 1 nM | | 3 nM | 3.5 nM | 30 nM |

| Antibody | IC50 [M] | IC50 [M] (Max % Inhibition)* | IC50 [M] | IC50 [M] (Max % Inhibition)* |
|---|---|---|---|---|
| H4H11683N | Not Tested | 1.2E−09 | 4.0E−09 | 1.3E−09 | 9.0E−10 |
| H4H11686N | Not Tested | 1.5E−09 | 4.4E−09 | 1.1E−09 | 4.5E−10 |
| H4H12159P | 3.2E−09 | Not Tested | 3.4E−09 | 1.4E−09 | 1.0E−09 |
| H4H12161P | 2.4E−09 | Not Tested | 2.6E−09 | 1.8E−09 | 1.0E−09 |
| H4H12163P | 3.4E−09 | Not Tested | 3.7E−09 | 2.1E−09 | 1.1E−09 |
| H4H12164P | 2.4E−09 | Not Tested | 5.8E−09 | 1.8E−09 | 8.2E−10 |
| H4H12166P | 2.6E−09 | Not Tested | 4.5E−09 | 1.3E−09 | 4.6E−10 |
| H4H12167P | 2.5E−09 | Not Tested | 3.5E−09 | 1.9E−09 | 1.0E−09 |
| H4H12168P | 1.5E−09 | Not Tested | 2.0E−09 | 2.3E−09 | 8.6E−10 |
| H4H12169P | 1.7E−09 | Not Tested | 2.9E−09 | 1.3E−09 | 6.7E−10 |
| H4H12170P | 2.0E−09 | Not Tested | 3.7E−09 | 4.8E−10 | 4.3E−10 |
| H4H12171P | 1.9E−09 | Not Tested | 3.3E−09 | 1.6E−09 | 6.5E−10 |
| H4H12175P | 2.2E−09 | Not Tested | 5.2E−09 | 4.2E−09 | >2.0E−08 (67%) |
| H4H12176P2 | 2.7E−09 | Not Tested | 3.5E−09 | 2.1E−09 | 1.3E−09 |
| H4H12177P2 | 2.2E−09 | Not Tested | 6.1E−09 | 2.4E−09 | 1.6E−09 |
| H4H12183P2 | 1.7E−09 | Not Tested | 1.4E−08 | 1.2E−09 | 4.5E−10 |
| Comparator 1 | 2.3E−09 | 1.8E−09 | >9.0E−08 (49%) | No inhibition | No inhibition |
| Control mAb 1 | No Inhibition | No Inhibition | Not Tested | Not Tested | Not Tested |
| Control mAb 2 | Not Tested | Not Tested | No Inhibition | No Inhibition | No Inhibition |

*Unless otherwise noted, all inhibition is ~100%

As shown in Tables 16 and 17, all 25 anti-hC5 antibodies showed complete inhibition of CDC mediated by C5 present in 1.66% of human serum. The $IC_{50}$s of the non-mutated antibodies ranged from 1.2 to 3.4 nM. The $IC_{50}$s of the mutated antibodies ranged from 3.0 nM to 12 nM. The parental, non-mutated antibody H4H12166P gave complete inhibition with $IC_{50}$s of 2.6 nM and 2.9 nM.

TABLE 17

Mutated anti-hC5 antibody inhibition of CDC with 1.66% serum and anti-CD20 antibody in Daudi Cells

| Serum | Human | African Green monkey | C5 depleted Human and 6.6 nM C5 Variant R885H | C5 depleted Human and 6.6 nM C5 Variant R885C |
|---|---|---|---|---|
| EC50 [M] of anti-CD20 antibody (with 1.66% Serum) | 1.9E−09 | 2.6E−09 | 6.3E−09 | 9.5E−09 |
| Constant anti-CD20 antibody (with 1.66% serum) | 2 nM | 10 nM | 7 nM | 30 nM |

| Antibody | IC50 [M] | IC50 [M] (Max % Inhibition)* | IC50 [M] | IC50 [M] |
|---|---|---|---|---|
| H4H12166P | 2.9E−09 | 5.6E−09 | 1.3E−09 | 7.6E−10 |
| H4H12166P2 | 3.7E−09 | 9.7E−09 | 1.7E−09 | 1.2E−09 |
| H4H12166P3 | 7.8E−09 | >3.0E−08 (64%) | 2.9E−09 | 1.7E−09 |
| H4H12166P4 | 3.5E−09 | 7.9E−09 | 1.5E−09 | 9.6E−10 |
| H4H12166P5 | 4.9E−09 | >3.0E−08 (75%) | 2.1E−09 | 1.4E−09 |
| H4H12166P6 | 3.0E−09 | 9.9E−09 | 1.3E−09 | 7.9E−10 |
| H4H12166P7 | 7.3E−09 | >6.0E−08 (61%) | 4.2E−09 | 2.3E−09 |
| H4H12166P8 | 4.1E−09 | >2.0E−08 (79%) | 2.1E−09 | 1.2E−09 |
| H4H12166P9 | 3.9E−09 | >1.0E−08 (85%) | 1.7E−09 | 7.7E−10 |
| H4H12166P10 | 1.2E−08 | >1.0E−07 (34%) | 7.0E−09 | 3.5E−09 |
| Comparator 1 | 2.7E−09 | >1.0E−07 (35%) | No Inhibition | No Inhibition |
| Control mAb 2 | No Inhibition | No Inhibition | No Inhibition | No Inhibition |

*Unless otherwise noted, all inhibition is ~100%

The sixteen non-mutated anti-hC5 antibodies showed complete inhibition of CDC mediated by African Green monkey C5 with $IC_{50}$s ranging from 2.0 nM to 14 nM.

Four of the 9 mutated antibodies showed complete inhibition of CDC mediated by African Green monkey C5 with $IC_{50}$s ranging from 7.1 nM to 9.9 nM. The remaining six mutated antibodies were blockers with $IC_{50}$s greater than 10 nM, and maximum inhibition (at 100 nM antibody) ranging from 34% to 85%. The parental, non-mutated antibody H4H12166P gave complete inhibition with $IC_{50}$s of 4.5 nM and 5.6 nM.

To test whether the anti-hC5 antibodies inhibit human C5 variants, R885H and R885C, C5-Depleted Human Serum was tested with 6.6 nM of each C5 variant. All 25 anti-hC5 antibodies showed complete inhibition of CDC mediated by C5 variant R885H, with $IC_{50}$s of the non-mutated antibodies ranging from 0.48 nM to 4.2 nM, while $IC_{50}$s of the mutated antibodies ranged from 1.3 nM to 7.0 nM. The parental, non-mutated antibody H4H12166P gave complete inhibition with $IC_{50}$s of 1.3 nM and 1.3 nM.

Fifteen out of 16 non-mutated anti-hC5 antibodies showed complete inhibition of CDC mediated by C5 variant R885C with $IC_{50}$s ranging from 0.43 nM to 1.6 nM. One non-mutated antibody showed weak inhibition of CDC with maximum inhibition of 67% (at 100 nM antibody) and an $IC_{50>20}$ nM. All nine mutated antibodies showed complete inhibition of CDC mediated by C5 variant R885C with $IC_{50}$s ranging from 0.77 nM to 3.5 nM. The parental, non-mutated antibody H4H12166P gave complete inhibition with an $IC_{50}$s of 0.46 nM and 0.76 nM.

Anti-CD20 antibody showed CDC of Daudi cells with 1.66% serum with EC50s of 1.0 nM, 1.4 nM, and 1.9 nM for human serum, 2.4 nM and 2.6 nM for African Green monkey serum, 1.9 nM and 6.3 nM for hC5 depleted serum with hC5 variant R885H, and 2.7 nM and 9.5 nM for hC5 depleted serum with hC5 variant R885C. Neither of the irrelevant IgG control antibodies, Control mAb1 and Control mAb2, demonstrated any inhibition of CDC.

Example 7: Inhibition of C5a Activity as Determined by Luciferase Assay

This Example describes an assay to test the activation of C5a through one of its receptors, C5aR1. C5aR1 is a G-protein coupled receptor (GPCR) and can initiate various GPCR coupled signaling pathways (Monk et al. 2007, Br. J. Pharmacol. 152: 429-448). A bioassay was established using HEK293 cells stably transfected with human C5aR1 (Accession No. NP_001727.1) and human Gα16 (Accession No. NP_002059.3) along with a luciferase reporter [NFAT response element (4×)-luciferase]. Gα16 is a relatively promiscuous G protein that can couple to different types of GPCRs leading to PLC-β activation and subsequent elevation of $Ca^{++}$, which in turn activates NFAT translocation and reporter gene transcription (Kostenis et al. 2005, Trends Pharmacol. Sci. 26: 595-602). The resulting cell line, HEK293/hGα16/hC5aR1/NFAT-luc, was isolated and maintained in 10% DMEM containing 10% FBS, NEAA, penicillin/streptomycin, 500 µg/mL G418, 100 µg/mL hygromycin B, and 7 µg/mL blasticidin.

For the C5a luciferase bioassay, HEK293/hGα16/hC5aR1/NFAT-luc cells were seeded into 96-well assay plates at 20,000 cells/well in OPTI-MEM™ reduced serum medium (Invitrogen, #31985-070) supplemented with 0.5% BSA, penicillin/streptomycin and L-glutamine, and then incubated at 37° C. and 5% $CO_2$ overnight. BSA was used instead of FBS, since serum has been shown to cleave and inactivate hC5a (Klos et al., 2013, Pharmacol. Rev. 65: 500-543). The next morning, hC5a was titrated from 100 nM to 2 pM (including a control sample containing no hC5a) and added to cells to determine the dose response titration curve for the cell line. To test hC5a antibody inhibition of hC5a, 500 pM of hC5a was added to cells. Immediately afterwards, antibodies diluted 1:3 from 100 nM to 2 pM (including a control sample containing no antibody) were added to cells. Cells were incubated for 5.5 hours at 37° C. in the presence of 5% $CO_2$ The luciferase activity was detected after the incubation with ONEGLO™ reagent (PROMEGA™, # E6051). ONEGLO™ is a luminescence-based reagent that measures the amount of luciferase present in cells. In this assay, increased hC5a activation leads to increased luciferase production and luminescence (measured in relative light units, RLUs). Measurement of luminescence was performed using a VICTOR™ X instrument (Perkin Elmer). The results were analyzed using nonlinear regression (4-parameter logistics) with PRISM™ 5 software (GRAPHPAD™) to obtain $EC_{50}$ and $IC_{50}$ values. Inhibition of antibodies was calculated such that 0-100% inhibition is the range of inhibition from 500 pM hC5a without inhibitor to 0 nM hC5a.

Four anti-hC5 antibodies were tested for their ability to inhibit hC5a activation of its receptor, hC5aR1, by measuring the extent of inhibition of 500 pM hC5a activation of HEK293/hGα16/hC5aR1/NFAT-luc cells.

TABLE 18

Anti-hC5 antibody inhibition of 500 pM hC5a in HEK293/Gα16/hC5aR1/NFAT-luc cells

| mAb PID or REGN # | $EC_{50}$[M] hC5a<br>3.9E−10<br>Inhibition of 500 pM hC5a<br>$IC_{50}$ [NA] |
|---|---|
| H2aM11682N | 4.6E−10 |
| H2aM11684N | 3.5E−11 |
| H2aM11694N | 1.4E−10 |
| H2aM11695N | 4.2E−11 |
| Control mAb | No Inhibition |

As shown in Table 18, all four antibodies of the invention, showed complete inhibition of 500 pM hC5a with $IC_{50}$s ranging from 0.035 nM to 0.46 nM. An Irrelevant IgG control antibody, Control mAb3, did not demonstrate any inhibition of hC5a. hC5a activated HEK293/Gα16/hC5aR1/NFAT-luc cells with an EC50 of 0.39 nM.

Example 8: Hemolysis Bioassay

Classical pathway hemolysis assay (CH) and alternative pathway hemolysis assay (AH) were developed to test the antibody activity.

The CH is a screening assay for the activation of the classical complement pathway, which is sensitive to the decrease, absence, and/or inactivity of any component of the pathway. The CH tests the functional capability of serum complement components of the classical pathway to lyse sheep red blood cells (SRBC) pre-coated with rabbit anti-sheep red blood cell antibody (hemolysin). When antibody-coated SRBC are incubated with test serum, the classical pathway of complement is activated and hemolysis results. If a complement component is absent, the CH level will be zero; if one or more components of the classical pathway are decreased, the CH will be decreased. (Nilsson et al 1984, J. Immunol. Meth. 72: 49-59). This assay is used for characterization and screening of high-affinity anti-human C5 antibodies.

Methods (A) Classical Pathway Complement Hemolysis Assay

Desired number of sheep red blood cells (SRBCs) were washed in GVB++ buffer and re suspended at 1×10^9 cells/mL. To sensitize the SRBCs, were mixed with equal volume of the 1:50 diluted rabbit anti-sheep hemolysin (1.5 mg/mL) at 37° C. for 20 minutes. Sensitized SRBC cells were diluted to 2×10^8 cells/ml in GVB++ prior to using in hemolysis assay. Normal human serum or cynomolgus monkey serum was diluted to 2% or 10% in GVB++ buffer. To test the inhibition of C5 mediated hemolysis activity, test antibodies were pre-incubated for 20 minutes at 4° C., at concentrations ranging from 0.6 nM to 800 nM in 2%-10% normal human or 10% cynomolgus monkey serum or African green monkey serum. Round bottom 96 well plates were used to measure hemolysis activity. A total of 100 ul sensitized sheep RBCs (2×10^8 cells/ml) were plated into 96-well plate followed by addition of 100 ul of respective serum samples that was pre-incubated with the test antibodies. Cells were gently mixed and incubated at 37° C. for 60 minutes. After the incubation time, cells were spun down by centrifugation at 1250×g at 4° C. A total of 100 uL of the supernatant was transferred to a fresh 96 flat bottom plate and read at 412 nm on Spectramax microplate reader. The hemolytic activity was calculated at final serum concentration of 1-5% for treatments.

Percent hemolysis was calculated as follows:

$$\% \text{ Hemolysis} = 100 \times \frac{(\text{Experimental Cell Lysis} - \text{Background Cell Lysis})}{(\text{Maximum Cell Lysis} - \text{Background Cell Lysis})}$$

In this equation "background cell lysis" is the OD at A412 nm from the cells incubated in GVB++ buffer only containing no serum. The "maximum cell lysis" is the OD at A412 nm from the cells treated with water. The results, expressed as % hemolysis were analyzed using nonlinear regression (4-parameter logistics) with PRISM™ 5 software (GRAPHPAD™) to obtain $IC_{50}$ values. Data represented as mean±Standard error of mean.

(B) Alternative Complement Assay

Desired number of rabbit red blood cells (RbRBCs) were washed in GVB-$Mg^{2+}$/EGTA buffer and re suspended at 2×10^8 cells/ml. Normal human or cynomolgus monkey serum was diluted to 10% in GVB-$Mg^{2+}$/EGTA buffer. To test the inhibition of C5 mediated hemolysis activity, antibodies at concentrations ranging from 3 nM to 800 nM were pre-incubated for 20 minutes at 4° C. in 5-10% normal human serum or cynomolgus monkey serum. Round bottom 96 well plates were used to measure hemolysis activity. A total of 100 ul RbRBCs (2×10^8 cells/ml) were plated into 96-well plate followed by addition of 100 ul of 10% normal human serum or cynomolgus monkey serum or African green monkey serum that was pre-incubated with the anti-C5 antibodies. Cells were gently mixed and incubated at 37° C. for 60 minutes. After incubation time, the cells were spun down by centrifugation at 1250×g at 4° C. A total of 100 uL of the supernatant was transferred to a fresh 96 flat bottom plate and read at 412 nm on Spectramax microplate reader. The hemolytic activity was calculated at final serum concentration of 5% serum.

Percent hemolysis was calculated as follows:

$$\% \text{ Hemolysis} = 100 \times \frac{(\text{Experimental Cell Lysis} - \text{Background Cell Lysis})}{(\text{Maximum Cell Lysis} - \text{Background Cell Lysis})}$$

In this equation "background cell lysis" is the OD at A412 nm from the cells incubated in GVB-Mg/EGTA buffer only containing no serum or without any anti-C5 antibody. The "maximum cell lysis" is the OD at A412 nm from the cells treated with water. Inhibition by anti-C5 antibodies, $IC_{50}$ values were calculated using nonlinear regression (4-parameter logistics) with PRISM™ 6 software (GRAPHPAD™)

Results (A) Inhibition of Human C5 Hemolysis

A total of 25 anti-human C5 (hC5) antibodies, 16 non-mutated and 9 mutated, were tested for their ability to inhibit C5 from normal human serum (NHS) in the CH50 assay using sensitized sheep red blood (SRBCs) and AH50 assay using rabbit red blood cells (RRBCs).

TABLE 19

Anti-hC5 antibody inhibition of CP and AP activity in 1% or 5% normal human serum (NHS)

| mAb PID | Human CP $IC_{50}$ [M] | Human AP $IC_{50}$ [M] | Human CP % Max Inhibition | Human AP % Max Inhibition |
|---|---|---|---|---|
| H4H12183P2 | 5.88E−09 | 1.60E−07 | 99.9% | 78.9% |
| H4H12176P2 | 4.58E−09 | 1.65E−08 | 94.1% | 69.9% |
| H4H12168P | 3.33E−09 | 2.85E−08 | 97.5% | 66.2% |
| H4H11686N | 3.09E−09 | 1.30E−08 | 97.4% | 76.2% |

TABLE 19-continued

Anti-hC5 antibody inhibition of CP and AP activity in 1% or 5% normal human serum (NHS)

| mAb PID | Human CP IC$_{50}$ [M] | Human AP IC$_{50}$ [M] | Human CP % Max Inhibition | Human AP % Max Inhibition |
|---|---|---|---|---|
| H4H12167P | 3.68E−09 | 1.55E−08 | 99.9% | 64.8% |
| H4H12161P | 2.56E−09 | 2.55E−08 | 93.7% | 56.1% |
| H4H12163P | 2.72E−09 | 2.05E−08 | 96.1% | 66.0% |
| H4H12166P | 2.80E−09 | 2.60E−08 | 95.0% | 70.9% |
| H4H11683N | 2.54E−09 | 3.40E−08 | 98.1% | 73.2% |
| H4H12159P | 2.50E−09 | 1.75E−08 | 97.9% | 73.4% |
| H4H12177P2 | 2.34E−09 | 1.70E−08 | 97.5% | 71.0% |
| H4H12170P | 2.39E−09 | 1.80E−08 | 98.2% | 81.1% |
| H4H12175P | 2.36E−09 | 2.00E−08 | 98.0% | 80.2% |
| H4H12171P | 2.33E−09 | 1.55E−08 | 94.9% | 42.0% |
| H4H12164P | 2.10E−09 | 1.45E−08 | 95.9% | 69.7% |
| H4H12169P | 2.36E−09 | 2.00E−08 | 98.3% | 44.5% |
| Isotype control | No Activity | No Activity | No Activity | No Activity |

As shown in Table 19, sixteen anti-hC5 antibodies of this invention showed more than 94% inhibition of hemolysis in classical pathway (CP) mediated by C5 present in 1% of human serum. The IC$_{50}$s of antibodies ranged from 2.1 to 5.9 nM and the percent inhibition ranged from 95%-99%. All 16 anti-C5 antibodies showed more than 60% inhibition (except H4H12169P) in the alternative pathway (AP) hemolysis assay mediated by C5 present in 5% NHS. The IC$_{50}$s of antibodies ranged from 13 to 160 nM and the percent inhibition activity ranged from 44% to 81%.

TABLE 20

Anti-hC5 antibody inhibition of CP and AP activity in 5% normal human serum (NHS)

| mAb PID | Human CP IC$_{50}$ [M] | Human AP IC$_{50}$ [M] | Human CP % Max Inhibition | Human AP % Max Inhibition |
|---|---|---|---|---|
| H4H12166P | 1.09E−08 | 2.09E−08 | 99.4% | 86.9% |
| H4H12166P2 | 1.59E−08 | 4.78E−08 | 98.2% | 81.3% |
| H4H12166P3 | 1.34E−08 | 6.00E−08 | 95.9% | 78.3% |
| H4H12166P4 | 1.32E−08 | 3.17E−08 | 98.6% | 77.0% |
| H4H12166P5 | 1.49E−08 | 6.55E−08 | 97.1% | 77.7% |
| H4H12166P6 | 1.03E−08 | 2.84E−08 | 98.1% | 82.4% |
| H4H12166P7 | 2.43E−08 | 1.56E−07 | 93.7% | 83.2% |
| H4H12166P8 | 1.41E−08 | 7.30E−08 | 95.7% | 73.3% |
| H4H12166P9 | 1.16E−08 | 5.35E−08 | 93.7% | 72.2% |
| H4H12166P10 | 4.44E−08 | No Activity | 74.0% | No Activity |
| Isotype control | No Activity | No Activity | No Activity | No Activity |

As shown in Table 20, all 9 mutated anti-hC5 antibodies showed inhibition of CP and AP hemolysis activity mediated by C5 present in 5% of human serum. In the CP hemolysis assay, the parental, non-mutated antibody H4H12166P showed more than 98% inhibition with IC$_{50}$ of 10.9 nM. Eight mutated anti-hC5 antibodies showed more than 90% inhibition with IC$_{50}$ ranging from 10.3 nM to 24.3 nM. Mutant anti-C5 antibody 12166P10 showed partial inhibition of 74%. In the AP hemolysis assay the parental, non-mutated antibody H4H12166P showed more than 85% inhibition with IC$_{50}$s of 20.9 nM. The mutated anti-hC5 antibodies showed inhibition range from 72-83% and the IC$_{50}$s antibodies ranged from 28 nM to 0.15 pM.

(B) Inhibition of Monkey C5 Hemolysis

A total of 25 anti-human C5 (hC5) antibodies, 16 non-mutated and 9 mutated, were tested for their ability to inhibit C5 from Cynomolgus monkey and African green monkey in the CH50 assay using sensitized sheep red blood (SRBCs) and AH50 assay using rabbit red blood cells (RRBCs).

TABLE 21

Anti-hC5 antibody inhibition of CP and AP activity in 5% normal African green monkey (AGM) sera

| mAb PID | AGM Serum CP IC$_{50}$ [M] | AGM Serum AP IC$_{50}$ [M] | AGM CP % Max Inhibition | AGM AP % Max Inhibition |
|---|---|---|---|---|
| H4H12183P2 | No Activity | No Activity | No Activity | No Activity |
| H4H12176P2 | 3.04E−08 | 4.77E−08 | 91.0% | 83.2% |
| H4H12168P | 2.80E−08 | 2.25E−08 | 90.8% | 88.2% |
| H4H11686N | 4.82E−08 | 1.63E−07 | 49.3% | 50.4% |
| H4H12167P | 6.95E−08 | 6.95E−08 | 90.5% | 53.4% |
| H4H12161P | 3.19E−08 | 4.75E−08 | 78.9% | 35.7% |
| H4H12163P | 6.90E−08 | 2.16E−07 | 83.2% | 58.5% |
| H4H12166P | 1.30E−07 | 2.33E−07 | 81.0% | 44.2% |
| H4H11683N | 2.92E−08 | 4.08E−08 | 81.1% | 88.1% |
| H4H12159P | 2.58E−08 | 2.70E−08 | 93.4% | 93.5% |
| H4H12177P2 | 1.80E−07 | 1.01E−07 | 80.6% | 8.80% |
| H4H12170P | 2.54E−08 | 2.69E−08 | 94.9% | 90.9% |
| H4H12175P | 1.18E−07 | 9.85E−08 | 84.5% | 17.4% |
| H4H12171P | No Activity | 2.33E−08 | 17.8% | 69.70% |
| H4H12164P | 2.47E−07 | 1.78E−07 | 85.8% | 15.60% |
| H4H12169P | 3.44E−08 | 9.15E−08 | 43.3% | 45.70% |

As shown in Table 21, the anti-hC5 antibodies showed different levels of inhibition of CP or AP hemolysis activity in 5% African green monkey sera. In the CP assay, two of the 16 anti-hC5 antibodies showed no inhibition of the hemolysis activity. Fourteen antibodies showed inhibition ranging from 43-94%, with IC$_{50}$s ranging from 25 nM to 180 nM. In the AP hemolysis assay, thirteen of the 17 antibodies showed inhibition activity ranging from 17%-93% with IC$_{50}$s ranging from 22.5 nM to 233 nM.

TABLE 22

Anti-hC5 antibody inhibition of CP and AP activity in 5% normal Cynomolgus (Cyno) monkey sera

| mAb PID | Cyno Serum CP IC$_{50}$ [M] | Cyno Serum AP IC$_{50}$ [M] | Cyno CP % Max Inhibition | Cyno AP % Max Inhibition |
|---|---|---|---|---|
| H4H12183P2 | 1.42E−07 | 2.96E−08 | 64.6% | 100.0% |
| H4H12171P | 8.70E−09 | 7.20E−09 | 92.9% | 98.8% |
| H4H12170P | 8.20E−09 | 7.00E−09 | 99.0% | 99.2% |
| H4H12159P | 7.75E−09 | 7.05E−09 | 99.3% | 99.6% |
| H4H12168P | 1.03E−08 | 5.45E−09 | 99.0% | 99.7% |
| H4H11683N | 9.00E−09 | 7.15E−09 | 98.8% | 98.9% |
| H4H12176P2 | 1.47E−08 | 7.70E−09 | 97.5% | 99.3% |
| H4H12161P | 2.79E−08 | 7.80E−09 | 100.0% | 98.4% |
| H4H12169P | 1.99E−08 | 7.95E−09 | 92.8% | 96.30% |
| H4H11686N | 1.41E−08 | 9.00E−09 | 94.5% | 98.7% |
| H4H12163P | 1.65E−08 | 1.02E−08 | 96.4% | 98.5% |
| H4H12167P | 2.13E−08 | 7.60E−09 | 100.0% | 98.30% |
| H4H12175P | 1.09E−08 | 8.05E−09 | 96.7% | 98.10% |
| H4H12166P | 2.01E−08 | 8.85E−09 | 94.2% | 98.60% |
| H4H12177P2 | 1.71E−08 | 8.80E−09 | 94.90% | 98.10% |
| H4H12164P | 1.96E−08 | 9.10E−09 | 94.7% | 98.70% |
| Isotype control | No Activity | No Activity | No Activity | No Activity |

As shown in Table 22, anti-hC5 antibodies (except H4H12183P2, which showed 64% CP inhibition) showed more than 90% inhibition of CP or AP hemolysis assay in 5% of Cynomolgus monkey serum. In CP hemolysis assay, the IC$_{50}$s of antibodies ranged from 7.15 nM to 142 nM. In AP hemolysis assay, the IC$_{50}$s of antibodies ranged from 5.4 to 29.6 nM.

(C) Inhibition of Variant Human C5 Hemolysis

Selected anti-C5 antibodies were tested for their ability to inhibit variant human C5 (see Example 3 herein) from C5-depleted human serum in the CH50 assay. In C5-depleted human serum supplemented with exogenous C5 variant R885H, H4H12166P, and Comparator 2 blocked CP hemolysis with $IC_{50}$ values of 6.0 nM and 4.4 nM, respectively, and IC80 values of 7.6 nM and 5.5 nM, respectively. For variant R885C, H4H12166P and Comparator 2 blocked CP hemolysis in C5-depleted human serum with exogenous C5 variants with an $IC_{50}$ of 9.3 nM and 6.8 nM, respectively, and IC80 values of 1 nM and 8.2 nM, respectively. As expected, Comparator 1 did not block the hemolytic activity of human C5 variants.

(D) Inhibition of Human C5b-6 Complex

Selected anti-C5 antibodies were tested for their ability to inhibit human C5b-6 complex from C5-depleted human serum in CH50 assay. H4H12166P potently blocked CP hemolysis in C5-depleted human serum supplemented with exogenous huC5b-6 complex with an $IC_{50}$ of 3.8 nM and IC80 value of 5.8 nM. In contrast, Comparator 1 blocked C5b-6 complex-mediated hemolysis with lower potency, with $IC_{50}$ values of 5.0 nM and IC80 value of 46 nM respectively. Comparator 1 inhibited only 70% total hemolysis at the highest concentrations tested. Comparator 2 did not block human C5b-6 complex hemolytic activity.

Example 9: Anti-C5 Antibodies Block Generation of C5a in CP Hemolysis Assay

To assess whether anti-C5 antibodies inhibit the generation of C5a, supernatants from the assay for classical pathway (CP) hemolysis were analyzed for C5a levels by ELISA.

C5a, generated as the result of C5 cleavage, is a protein fragment of 74 amino acids. C5a is rapidly metabolized by serum carboxypeptidases to a more stable, less active, 73 amino acid form, C5a des-Arg, by removal of the C-terminal arginine. The quantitation of C5a des-Arg therefore provides a reliable measurement for monitoring the generation of C5a in vivo and in vitro. The MicroVue C5a ELISA kit used here detects C5a des-Arg according to information provided by the manufacturer. Preliminary experiments (data not shown) indicate that the primary 74 amino acid form of C5a is also detected. For the purpose of this Example, both forms will be collectively referred to as "C5a".

C5a protein levels were determined in supernatants from the CP hemolysis assay using complement-preserved normal human serum (NHS) pre-incubated with H4H12166P or isotype control antibody as described in Example 8. C5a protein levels were measured using the MicroVue C5a ELISA kit according to the manufacturer's instructions. Briefly, samples were diluted and incubated on plates pre-coated with capture antibody (mouse anti-C5a specific for a neo-epitope on human C5a). Human C5a protein provided by the manufacturer was used as a standard for calibration. C5a in the supernatants was detected by HRP-conjugated detection antibody (mouse monoclonal antibody to the C5a region of C5). The chromogenic HRP-substrate, 3,3',5,5'-tetramethylbenzidine (TMB), was added to detect HRP activity. A solution of IN hydrochloric acid was used to stop the reaction, and the optical density at 450 nm (OD450) was measured on a SPECTRAMAX™ plate reader. Data were analyzed using nonlinear regression (4-parameter logistics) in GRAPHPAD™ PRISM™. C5a concentration was expressed as ng/mL of supernatant.

In the assay using 5% NHS, H4H12166P potently blocked increases in C5a protein levels in a dose-dependent manner with an $IC_{50}$ of 8.5 nM, while the isotype control antibody had no effect on C5a levels (FIG. 1). Maximal blockade at the highest tested H4H12166P concentration (267 nM) resulted in a ~10-fold decrease in C5a levels to 3.8 ng/mL (0.3 nM), compared with 34 ng/mL (2.8 nM) observed at the lowest tested H4H12166P concentration (1 nM) in 5% serum. The C5a concentration observed for maximal blockade was close to the baseline C5a level of 2.3 ng/mL (0.2 nM) in untreated 5% NHS.

Example 10: Characterization of Pharmacokinetics and Pharmacodynamics of Anti-C5 Antibodies in Cynomolgus Monkey This Example describes the characterization of the pharmacokinetics (PK) and pharmacodynamics (PD) of selected anti-C5 antibodies conducted in male cynomolgus monkeys. Endogenous C5 levels were determined prior to anti-C5 antibody dosing and used to stratify animal dose groups.

Total circulating C5 levels in cynomolgus monkeys were determined using a Human Complement C5 ELISA (Abcam, cat # ab125963), which was performed according to the manufacturer's recommendations. Average concentrations of C5 protein in monkeys were determined to be 90.85 µg/mL±19.17 µg/mL.

For each anti-C5 antibody, 4 cynomolgus monkeys were each administered a single intravenous (IV) injection at a dose of 15 mg/kg. Blood samples were collected from each animal from pre-dose through 1680 hours (70 days), processed into serum and frozen at −80° C. until analyzed for PK and PD.

Total IG Antibody Level Analysis by ELISA Immunoassay

Total antibody concentrations in monkey serum samples were measured using a non-validated direct ELISA. The ELISA procedure employed a microtiter plate coated with a mouse anti-human IgG1/IgG4 Fc monoclonal antibody. Different anti-C5 antibodies were added to the plate and the anti-C5 antibodies captured on the plate were detected using a biotinylated mouse anti-human IgG4 Fc monoclonal antibody, followed by NeutrAvidin conjugated with Horseradish Peroxidase (NeutrAvidin HRP). A luminol-based substrate specific for peroxidase was then added to achieve a signal intensity that is proportional to the concentration of total captured anti-C5 antibody. The relative light unit (RLU) measurements of the calibration standards and their respective nominal concentrations were fitted using a weighted 4 Parameter Logistic equation to generate a calibration equation that described the concentration of anti-C5 antibodies and response relationship of the assay. The lower limit of quantitation (LLOQ) was 1.56 ng/mL in the assay (2% monkey serum) and 78 ng/mL in neat monkey serum.

Determination of PK Parameters

PK parameters were determined by non-compartmental analysis (NCA) using Phoenix®WinNonlin® software (Version 6.4, Certara, L.P.) and an IV bolus dosing model.

All PK parameters were derived from the respective mean concentration values, including the observed maximum concentration in serum ($C_{max}$), the time of observed peak concentration, $t_{max}$, and the estimated half-life observed ($T_{1/2}$). For each antibody, the area under the concentration versus time curve up to the last measurable concentration ($AUC_{last}$) and extrapolated from time zero to infinity ($AUC_{inf}$) were determined using a linear trapezoidal rule with linear interpolation and uniform weighting.

PD Analysis by Ex Vivo Hemolysis Assay

Pharmacodynamics of selected anti-C5 antibodies was analyzed using ex vivo classical pathway and alternative pathway hemolysis assays.

Classical Pathway Hemolysis Assay:

Sheep red blood cells (SRBCs) were washed in GVB++ buffer (Gelatin Veronal Buffer with CaCl2 and MgCl2)

(Boston BioProducts) and re-suspended at 1×10^9 cells/mL. To sensitize the SRBCs, a total of 1×10^9/mL of SRBCs were mixed with equal volume of the 1:50 diluted rabbit anti-sheep hemolysin (1.5 mg/mL) at 37° C. for 20 minutes. Sensitized SRBCs were diluted to 2×10^8 cells/mL in GVB++ buffer prior to using in the hemolysis assay. Blood from cynomolgus monkeys was collected prior to dosing and at 5 minutes, 4 and 8 hours, and 1, 2, 3, 5, 7, 10, 14, 18, 21, 28, 35, 42, 49, 56, 63 and 70 days post dose for PD analysis. Serum was prepared and frozen until further use. On day of the assay, cynomolgus serum from respective time points was diluted to 10% in GVB++ buffer. Round bottom 96 well plates were used to measure hemolysis activity. A total of 100 μl of sensitized SRBCs (2×10^8 cells/mL) were plated into 96-well plate at 37° C. followed by addition of 100 ul of 10% cynomolgus monkey serum from respective time points. SRBCs were gently mixed and incubated at 37° C. for 10 minutes. After incubation time, the cells were centrifuged at 1250×g at 4° C. A total of 100 μL of the supernatant was transferred to a fresh 96 flat bottom plate and read at 412 nm on a Spectramax microplate reader. The hemolytic activity was calculated at final serum concentration of 5%. The percent hemolysis was calculated with the absorbance values by using the following equation:

$$\% \text{ Hemolysis} = 100 \times \frac{(\text{Experimental Cell Lysis} - \text{Background Cell Lysis})}{(\text{Maximum Cell Lysis} - \text{Background Cell Lysis})}$$

In this equation "background cell lysis" is the OD at A412 nm from the SRBCs incubated in GVB++ buffer only containing no serum. The "maximum cell lysis" is the OD at A412 nm from SRBCs treated with water. The results, expressed as % hemolysis were analyzed using nonlinear regression (4-parameter logistics) with PRISM™5 software (GRAPHPAD™) to obtain $IC_{50}$ values. Data are represented as mean±Standard Error of Mean.

Alternative Pathway Hemolysis Assay:

The desired number of rabbit red blood cells (RbRBCs) were washed in GVB-$Mg^{2+}$/EGTA buffer and re suspended at 2×10^8 cells/mL. Blood from cynomolgus monkeys was collected prior to dosing and at 5 minutes, 4 and 8 hours, and 1, 2, 3, 5, 7, 10, 14, 18, 21, 28, 35, 42 and 49 days post dose for PD analysis. Serum was prepared and frozen until further use. Round bottom 96 well plates were used to measure hemolysis activity. A total of 100 μl RbRBCs (2×10^8 cells/mL) were plated into 96-well plate at 37° C. followed by addition of 100 μl of 10% cynomolgus monkey serum from the respective time points listed above. RbRBCs were gently mixed and incubated at 37° C. for 60 minutes. After incubation time, the cells were centrifuged at 1250×g at 4° C. A total of 100 μL of the supernatant was transferred to a fresh 96 flat bottom plate which was read at 412 nm on a Spectramax microplate reader. The hemolytic activity was calculated for final serum concentration of 5% and expressed as percentage of total hemolysis of RBCs by water. The percent of hemolysis was calculated as described above.

Results

Selected anti-C5 antibodies (listed in Table 1) were tested in initial experiments for prolonged pharmacokinetic profiles in cynomolgus monkeys and C5-humanized mice (described in Example 10). H4H12166P and H4H12161P were selected as having high affinity coupled with prolonged PK and used in subsequent experiments herein with Comparator 1 and Comparator 2.

Figure 2:
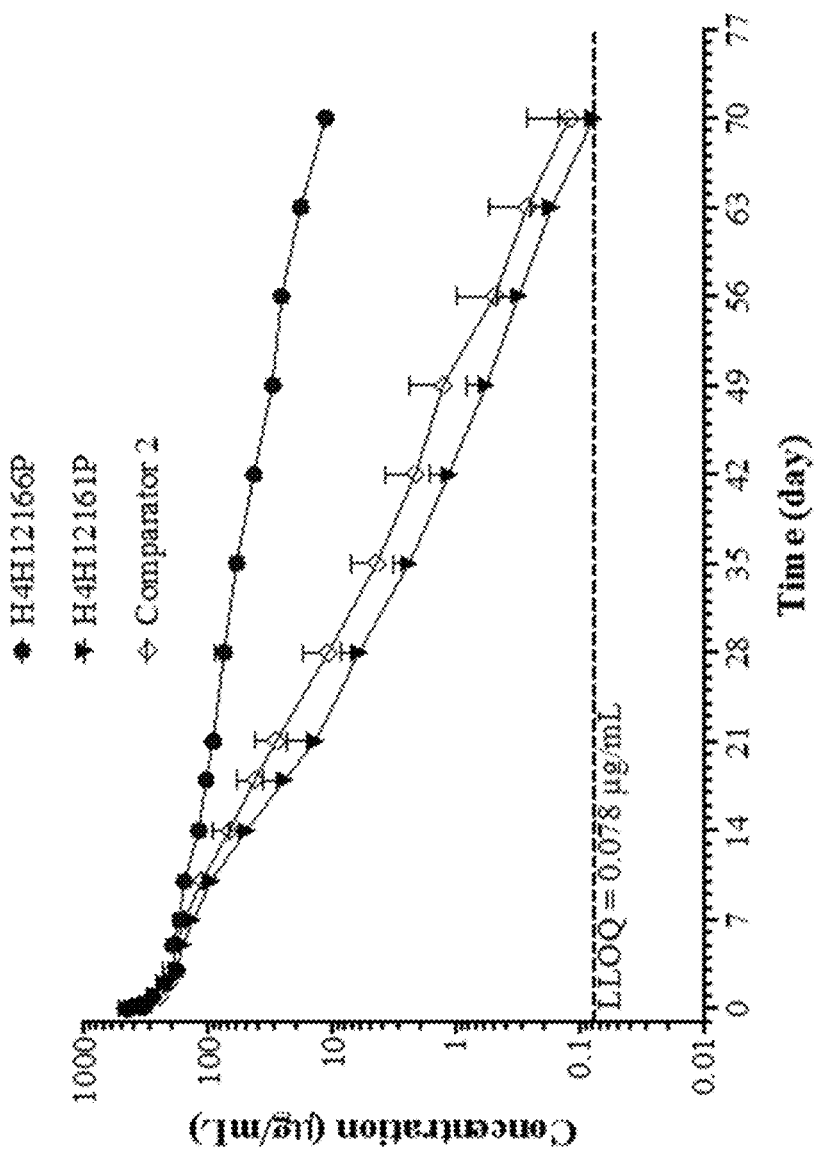
FIG. 2 shows total serum concentration vs. time following a single 15 mg/kg intravenous injection of H4H12166P, H4H12161P, or Comparator 2 to male cynomolgus monkeys (described in Example 10 herein). Concentration-time profiles were plotted through the first post dose below the limit of quantitation (BLQ) result, if applicable, which was imputed as LLOQ/2. Each data point represents Mean (±SD) (n=4 animals/group); concentrations considered to be impacted by ADA were excluded from 1 animal in the H4H12166P group and 1 animal in the H4H12161P group starting at Day 36 and Day 29, respectively. LLOQ=Lower limit of quantification

Cynomolgus monkeys were administered a single 15 mg/kg IV bolus dose of H4H12166P, H4H12161P, or Comparator 2. Serum concentrations of total antibody and percent classical pathway (CP) hemolysis activity were determined at 19 time points during a 70-day in-life period. Alternative pathway (AP) hemolysis was determined at 17 time points during a 50-day in-life period. Table 23 summarizes the mean antibody concentrations for all 3 antibodies. Mean total antibody concentrations versus time profiles are shown in FIG. 2. Mean PK parameters are described in Table 24.

TABLE 23

Mean Concentrations of Total IgG in Serum Following a Single 15 mg/kg Intravenous Injection of Selected Anti-C5 Antibodies to Male Cynomolgus Monkeys

| Time (hours post-dose) | # | Serum concentration of Ab (μg/mL) Mean ± SD | | |
|---|---|---|---|---|
| | | H4H12166P | H4H12161P | Comparator 2 |
| 0 | 4 | BLQ | BLQ | BLQ |
| 0.083 | 4 | 445 ± 30 | 456 ± 26.2 | 459 ± 55.2 |
| 4 | 4 | 328 ± 27 | 360 ± 28.2 | 363 ± 43.8 |
| 8 | 4 | 353 ± 29.9 | 316 ± 21.5 | 357 ± 16.1 |
| 24 | 4 | 282 ± 43.6 | 276 ± 32.4 | 248 ± 19.6 |
| 48 | 4 | 225 ± 15.2 | 221 ± 21.5 | 212 ± 19.3 |
| 72 | 4 | 180 ± 15.0 | 181 ± 17.2 | 196 ± 36.2 |
| 120 | 4 | 194 ± 20.9 | 162 ± 10.7 | 179 ± 23.3 |
| 168 | 4 | 171 ± 29.9 | 132 ± 17.0 | 157 ± 18.4 |
| 240 | 4 | 157 ± 12.7 | 96.1 ± 17.3 | 114 ± 13.0 |
| 336 | 4 | 120 ± 10.2 | 49.3 ± 18.7 | 67.9 ± 25.8 |
| 432 | 4 | 105 ± 13.9 | 24.6 ± 11.8 | 42.6 ± 15.9 |
| 504 | 4 | 92.2 ± 10.6 | 13.8 ± 9.95 | 28.6 ± 13.1 |
| 672 | 4 | 75.1 ± 15.8 | 6.16 ± 2.40 | 10.9 ± 6.25 |
| 840 | 3 | 59.6 ± 4.79 | 2.44 ± 0.85 | 4.45 ± 2.63 |
| 1008 | 3 | 43.3 ± 2.89 | 1.16 ± 0.52 | 2.17 ± 1.58 |
| 1176 | 3 | 30.6 ± 1.42 | 0.57 ± 0.25 | 1.29 ± 1.16 |
| 1344 | 3 | 25.9 ± 3.74 | 0.315 ± 0.16 | 0.492 ± 0.49 |
| 1512 | 3 | 18.2 ± 2.41 | 0.17 ± 0.08 | 0.270 ± 0.27 |
| 1680 | 3 | 11.5 ± 1.51 | 0.079 ± 0.07 | 0.123 ± 0.15 |

Time = Time in hours post single-dose injection;

SD = Standard deviation;

BLQ = Below Limit of Quantitation

Following IV bolus administration, the total IgG concentration-time profiles of H4H12166P, H4H12161P, and Comparator 2 were characterized by an initial brief distribution phase followed by single elimination phases throughout the in-life period. Peak H4H12166P, H4H12161P, and Comparator 2 concentrations were highly comparable, as corresponding $C_{max}$/Dose values between all the antibodies were within 1.1-fold (29.7, 30.4, and 30.6 [(ug/mL)/(mg/kg)], respectively) (Table 24).

TABLE 24

Mean Pharmacokinetic Parameters of Total IgG Concentrations in Serum Following a Single 15 mg/kg Intravenous Injection of Selected Anti-C5 Antibodies to Male Cynomolgus Monkeys

| Parameter | H4H12166P | | H4H12161P 15 mg/kg IV (n = 4) | | Comparator 2 | |
|---|---|---|---|---|---|---|
| | Mean | SD | Mean | SD | Mean | SD |
| $C_{max}$ (µg/mL) | 445 | 30.0 | 456 | 26.2 | 459 | 55.2 |
| $C_{max}$/Dose (µg/mL)/(mg/kg) | 29.7 | 2.00 | 30.4 | 1.75 | 30.6 | 3.68 |
| $C_0$ (µg/mL) | 448 | 30.5 | 458 | 26.6 | 461 | 55.6 |
| $t_{max}$ (hours) | 0.083 | 0 | 0.083 | 0 | 0.083 | 0 |
| $AUC_{last}$ day · (µg/mL) | 5080 | 1040 | 2350 | 357 | 2810 | 470 |
| $AUC_{last}$/Dose day · (µg/mL)/(mg/kg) | 339 | 69.3 | 157 | 23.8 | 187 | 31.3 |
| $AUC_{inf}$ day · (µg/mL) | 5550 | 671 | 2350 | 356 | 2810 | 470 |
| $AUC_{inf}$/Dose day · (µg/mL)/(mg/kg) | 370 | 44.7 | 157 | 23.7 | 188 | 31.4 |
| CL (mL/h/kg) | 0.114 | 0.0143 | 0.270 | 0.0411 | 0.228 | 0.0425 |
| $V_{ss}$ (mL/kg) | 60.4 | 4.85 | 44.0 | 4.34 | 45.3 | 3.06 |
| $t_{1/2}$ (day) | 15.6 | 1.43 | 5.50 | 2.45 | 5.91 | 1.13 |

IV = Intravenous;
n = Number of animals;
$C_{max}$ = Peak concentration;
$C_0$ = Initial concentration determined by extrapolation;
$t_{max}$ = Time to $C_{max}$;
AUC = Area under the concentration-time curve;
$AUC_{last}$ = AUC computed from time zero to the time of the last positive concentration;
$AUC_{inf}$ = AUC from time zero extrapolated to infinity;
CL = Total body clearance;
$V_{ss}$ = Volume of distribution at steady state;
$t_{1/2}$ = Half-life;
SD = Standard Deviation.
Note:
$t_{max}$ is expressed in nominal hours Assessment of concentration-time profiles revealed that H4H12166P demonstrated the slowest elimination with terminal antibody concentrations >10 µg/mL through study day 71. Kinetics of H4H12161P and of Comparator 2 were similar; both demonstrated more rapid elimination than H4H12166P, with mAb concentrations >10 µg/mL through day 22 and 29, respectively.

Consequently, dose-normalized exposures ($AUC_{last}$/Dose) indicated that H4H12166P had the highest exposure at 339 day*(µg/mL)/(mg/kg), while H4H12161P and Comparator 2 had approximately 2-fold lower exposure, 157 and 187 day*(µg/mL)/(mg/kg), respectively, than that of H4H12166P.

Antibody half-life ($t_{1/2}$) calculated during the elimination phase ranged from 5.5 to 15.6 days across the dose groups and also correlated with exposure, as H4H12166P had the correspondingly highest $t_{1/2}$ of 15.6 days, while H4H12161P and Comparator 2 had $t_{1/2}$ values of 5.5 and 5.9 days, respectively.

The pharmacologic effects of the anti-C5 antibodies from cynomolgus monkey serum samples were determined ex vivo by complement classical pathway (CP) hemolysis of sensitized sheep red blood cells (SRBCs) and alternative pathway (AP) hemolysis of rabbit red blood cells (RbRBCs). The inhibition of hemolytic activity was calculated for a final serum concentration of 5% and expressed as percentage of total hemolysis of RBCs by water. Table 25 summarizes ex vivo activity of the 3 antibodies as determined by mean percent hemolysis.

TABLE 25

Ex Vivo Classical and Alternative Pathway Percent Hemolysis Activity of Selected anti-C5 Antibodies

| Time (hours post-dose) | # | Classical Pathway % Hemolysis in cynomolgus serum, 10 min, Mean ± SEM | | | Alternative Pathway % Hemolysis in cynomolgus serum, 60 min, Mean ± SEM | | |
|---|---|---|---|---|---|---|---|
| | | H4H12166P | H4H12161P | Comparator 2 | H4H12166P | H4H12161P | Comparator 2 |
| 0 | 4 | 91.34 ± 7.6 | Not tested | 84.36 ± 20.28 | 73.44 ± 17.26 | 64.90 ± 19.51 | 55.77 ± 10.82 |
| 0.083 | 4 | 3.5 ± 1.4 | Not tested | 6.6 ± 6.5 | 5.53 ± 1.98 | 5.90 ± 3.92 | 3.83 ± 3.93 |
| 4 | 4 | 2.35 ± 1.06 | Not tested | 3.16 ± 2.2 | 7.43 ± 2.54 | 6.53 ± 2.7 | 5.30 ± 2.80 |
| 8 | 4 | 1.55 ± 0.21 | Not tested | 1.25 ± 0.21 | 3.53 ± 0.91 | 4.70 ± 2.77 | 1.98 ± 0.83 |
| 24 | 4 | 7.7 ± 6.08 | Not tested | 4.55 ± 2.05 | 13.40 ± 2.77 | 4.68 ± 1.89 | 4.65 ± 2.35 |
| 48 | 4 | 2.85 ± 2.19 | Not tested | 2.6 ± 0.7 | 5.53 ± 2.40 | 7.68 ± 5.22 | 2.28 ± 0.67 |
| 72 | 4 | 0.9 ± 0.42 | Not tested | 1.3 ± 0.28 | 7.95 ± 3.36 | 5.95 ± 2.23 | 1.45 ± 0.33 |
| 120 | 4 | 1.75 ± 0.07 | Not tested | 1.3 ± 0.14 | 16.38 ± 6.91 | 7.60 ± 1.94 | 1.68 ± 0.22 |
| 168 | 4 | 1.6 ± 1.13 | Not tested | 1.4 ± 0.56 | 21.28 ± 8.24 | 10.75 ± 2.27 | 2.15 ± 0.19 |
| 240 | 4 | 1 ± 0.14 | Not tested | 3.7 ± 2.83 | 19.18 ± 10.20 | 13.53 ± 7.17 | 14.20 ± 16.73 |

TABLE 25-continued

Ex Vivo Classical and Alternative Pathway Percent Hemolysis Activity of Selected anti-C5 Antibodies

| Time (hours post-dose) | # | Classical Pathway % Hemolysis in cynomolgus serum, 10 min, Mean ± SEM | | | Alternative Pathway % Hemolysis in cynomolgus serum, 60 min, Mean ± SEM | | |
|---|---|---|---|---|---|---|---|
| | | H4H12166P | H4H12161P | Comparator 2 | H4H12166P | H4H12161P | Comparator 2 |
| 336 | 4 | 2.55 ± 2.05 | Not tested | 37.85 ± 5.3 | 21.10 ± 7.55 | 50.58 ± 12.91 | 65.60 ± 26.04 |
| 432 | 4 | 1.35 ± 0.91 | Not tested | 105.25 ± 3.3 | 15.20 ± 10.86 | 59.75 ± 12.65 | 54.55 ± 19.11 |
| 504 | 4 | 3.55 ± 2.05 | Not tested | 107.1 ± 4.38 | 33.15 ± 8.80 | 88.55 ± 24.63 | 85.63 ± 27.48 |
| 672 | 4 | 2.2 ± 0.56 | Not tested | 88.9 ± 23.05 | 75.25 ± 18.30 | 88.55 ± 8.53 | 91.58 ± 18.55 |
| 840 | 3 | 3.075 ± 2.70 | Not tested | 105.37 ± 53.4 | 46.65 ± 5.30 | 92.33 ± 5.16 | 91.85 ± 2.33 |
| 1008 | 3 | 15.5 ± 26.6 | Not tested | 108.85 ± 2.35 | 58.60 ± 9.48 | 92.45 ± 6.27 | 92.30 ± 2.69 |
| 1176 | 3 | 58.33 ± 39.55 | Not tested | 113.85 ± 2.62 | 72.95 ± 5.87 | 104.90 ± 3.5 | 101.90 ± 0.42 |
| 1344 | 3 | 71.55 ± 43.02 | Not tested | 110.3 ± 1.98 | Not tested | Not tested | Not tested |
| 1512 | 3 | 91.375 ± 29.7 | Not tested | 110.6 ± 0.85 | Not tested | Not tested | Not tested |
| 1680 | 3 | 112.22 ± 4.06 | Not tested | 112.15 ± 0.5 | Not tested | Not tested | Not tested |

Time = Time in hours post single-dose injection;
SEM = Standard error of mean;
BLQ = Below Limit of Quantitation;
NC = Not calculated As shown in Table 25 and FIG. 2, PD effects were measured by complement CP (10 minute incubation) to Day 70. H4H12166P blocked more than 95% of CP hemolytic activity until day 35. Activity returned to pre-study maximum hemolysis levels by day 70. Comparator 2 blocked about 95% of CP hemolytic activity through day 10, and activity rapidly returned to pre-study maximum hemolysis levels by day 18.

Figure 3A:
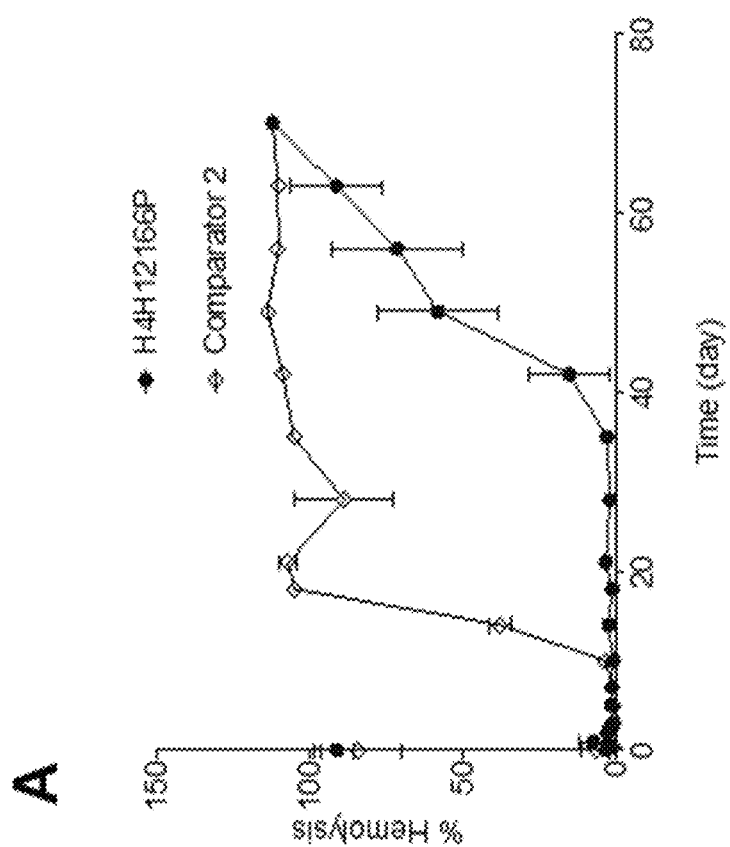
FIG. 3A and FIG. 3B show percent hemolysis vs. time in ex vivo red blood cell (A) Classical Pathway and (B) Alternative Pathway assays following a single intravenous injection of H4H12166P, H4H12161P or Comparator 2 to male cynomolgus monkeys. % hemolysis, calculated as a ratio of experimental vs. maximal lysis with % background lysis subtracted from both values, is related to the amount of C5 inhibited by the particular anti-C5 antibody present in the serum at a given time point. Each data point represents Mean (±SD).
Figure 3B:
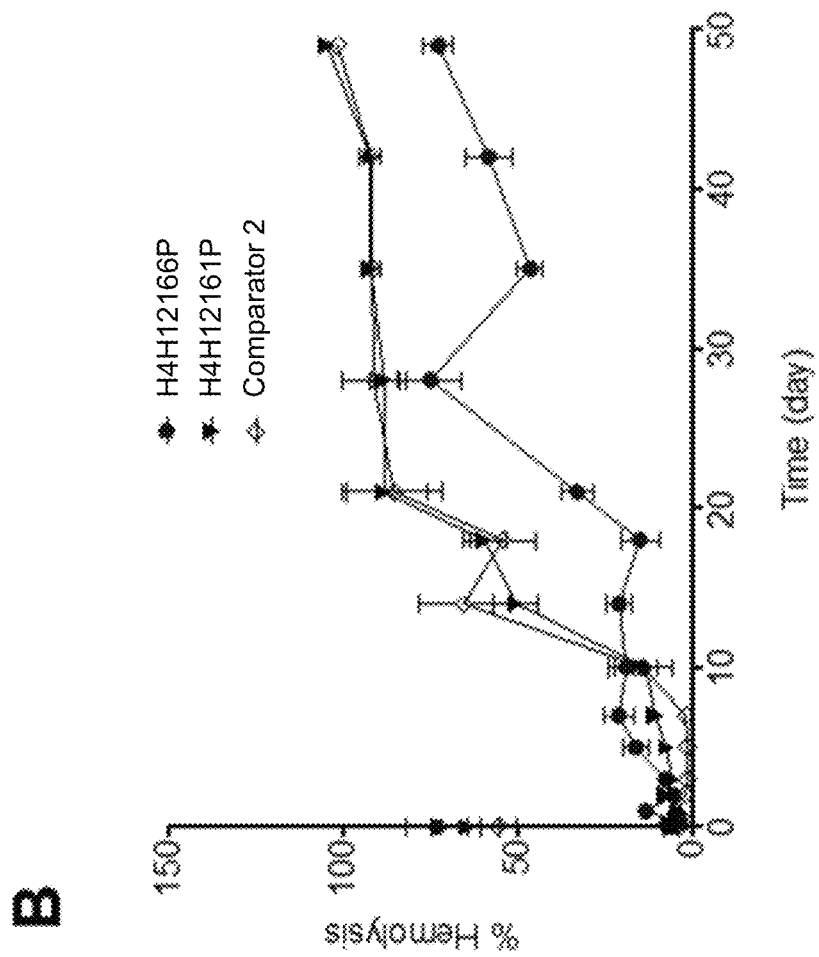

PD effects were also measured by complement AP pathway (60 minute incubation) hemolysis assays to day 49. As shown in Table 25 and FIG. 3, H4H12166P blocked 80% of the total AP hemolytic activity until day 18 and activity returned to pre-study maximum hemolysis level at day 50. H4H1216P and Comparator 2 blocked 90% of AP hemolytic activity through day 7, and activity returned to pre-study maximum hemolysis levels by day 21.

Example 11: Characterization of PK/PD of Anti-C5 Antibodies in C5-Humanized Mice In this set of experiments, the pharmacokinetics and pharmacodynamics of selected anti-C5 antibodies were assessed in mice humanized to express human C5 protein using Velocigene® technology (Valenzuela et a 2003, Nat. Biotechnol. 21: 652-659). Humanized mice were engineered to replace exon 2 through exon 41 of murine C5 gene with exons 2-42 of human C5 gene (disclosed in US Patent Application Publication 2015/0313194, herein incorporated in its entirety).

Total circulating human C5 levels were determined using a Human Complement C5 ELISA (Abcam, cat # ab125963), which was performed according to manufacturer's recommendations.

Determination of Total Drug Level in Serum by ELISA

Circulating anti-C5 antibody concentrations, both C5-bound and -unbound, were determined by total human antibody analysis using ELISA. Briefly, a goat anti-human IgG polyclonal antibody at 1 µg/mL in PBS was immobilized on 96-well plates overnight; plates were washed to remove unbound IgG and then blocked with 5% BSA. Serial dilutions of anti-C5 antibody containing serum samples (6 points) and the reference standards (12 points) of the respective antibodies were transferred to the anti-human IgG coated plates and incubated for one hour. The plate-bound anti-C5 antibodies were then detected using a goat anti-human IgG polyclonal antibody conjugated with horseradish peroxidase. Plates were developed with TMB substrate according to the manufacturer's recommended protocol and signals of optical density (OD) at 450 nm were recorded using a Perkin Elmer VICTOR™ X4 Multimode Plate Reader. Anti-05 antibody concentrations in serum were calculated based on the reference standard calibration curve generated using GRAPHPAD™ PRISM™ software.

Determination of PK Parameters

PK parameters were determined by non-compartmental analysis (NCA) using Phoenix®WinNonlin® software (Version 6.3, Certara, L.P.) and an extravascular dosing model. Using the respective mean concentration values for each antibody, all PK parameters, including estimated half-life observed ($t_1/2$), and area under the concentration versus time curve up to the last measurable concentration ($AUC_{last}$) were determined using a linear trapezoidal rule with linear interpolation and uniform weighting.

PD Analysis by Hemolysis Assay

Pharmacodynamics of selected anti-C5 antibodies was determined using a classical pathway complement hemolysis assay. Sheep red blood cells (SRBCs) (Sheep blood in Alsevers solution) were washed in GVB++ buffer (Gelatin Veronal Buffer with CaCl2 and MgCl2) (Boston BioProducts) and re suspended at $1 \times 10^{\wedge}9$ cells/mL. To sensitize, $1 \times 10^{\wedge}9$/mL of SRBCs were mixed with equal volume of the 1:50 diluted rabbit anti-sheep hemolysin (1.5 mg/mL) at 37° C. for 20 minutes. Sensitized SRBCs were diluted to $2 \times 10^{\wedge}8$ cells/mL in GVB++ prior to use in the hemolysis assay. Serum samples from pre-dosed animals or humanized C5 mice dosed with anti-C5 antibodies collected on days 10, 20, 30, 40 and 50 post-dose were diluted to 20% in GVB++ buffer. A total of 100 µl sensitized SRBCs ($2 \times 10^{\wedge}8$ cells/mL) were plated into 96-well round bottom plates at 37° C. followed by addition of 100 µl of 20% serum that was supplemented with 160-180 µg/mL human complement 3 (huC3) protein. Cells were gently mixed and incubated at 37° C. for 1 hour. After incubation, the cells were centrifuged at 1250×g at 4° C. A total of 100 µL of supernatant was transferred to a fresh 96 flat bottom plate and read at A412 nm on a Spectramax microplate reader. The percent hemolysis was calculated with the absorbance values by using the following equation:

$$\% \text{ Hemolysis} = 100 \times \frac{(\text{Experimental Cell Lysis} - \text{Background Cell Lysis})}{(\text{Maximum Cell Lysis} - \text{Background Cell Lysis})}$$

In this equation "background cell lysis" is the OD at A412 nm from SRBCs incubated in GVB++ buffer only containing no serum. The "maximum cell lysis" is the OD at A412 nm from SRBCs treated with water. The results, expressed as % hemolysis, were analyzed using nonlinear regression (4-parameter logistics) with PRISM™ 6 software (GRAPH-PAD™) to obtain $IC_{50}$ values. Data represented as Mean± (Standard Error of Mean).

Experiment 1

In this experiment, the pharmacokinetics and pharmacodynamics of exemplary antibody H4H12166P were assessed in comparison with Comparator 1 and Comparator 2 in humanized C5 mice. Total circulating human C5 levels were determined using a Human Complement C5 ELISA (Abcam, cat # ab125963), which was performed according to manufacturer's recommendations. Average concentrations of human C5 in the mice were determined to be 39.73 μg/mL±17.82 μg/mL. There was a difference between male (55.4±1.7 μg/ml, n=47) and female (24.7±0.6 μg/ml, n=49) mice.

Prior to antibody dosing, male and female humanized C5 mice were stratified according to human C5 levels that averaged 40 μg/mL. For each anti-C5 antibody, cohorts of twenty-two mice received a single 15 mg/kg dose of H4H12166P, Comparator 1 or Comparator 2 by subcutaneous (s.c.) injection. All mice were bled predose and at one day post-injection for PK analysis. In addition, at 10, 20, 30, 40 and 50 days post injection, groups of 4 or 5 mice from each cohort were euthanized and terminal bleeds were collected for PK and PD analysis. Day 1 serum samples were the mean of the entire cohort of 22 mice. Blood was processed into serum and frozen at −80° C. until analyzed.

Figure 4:
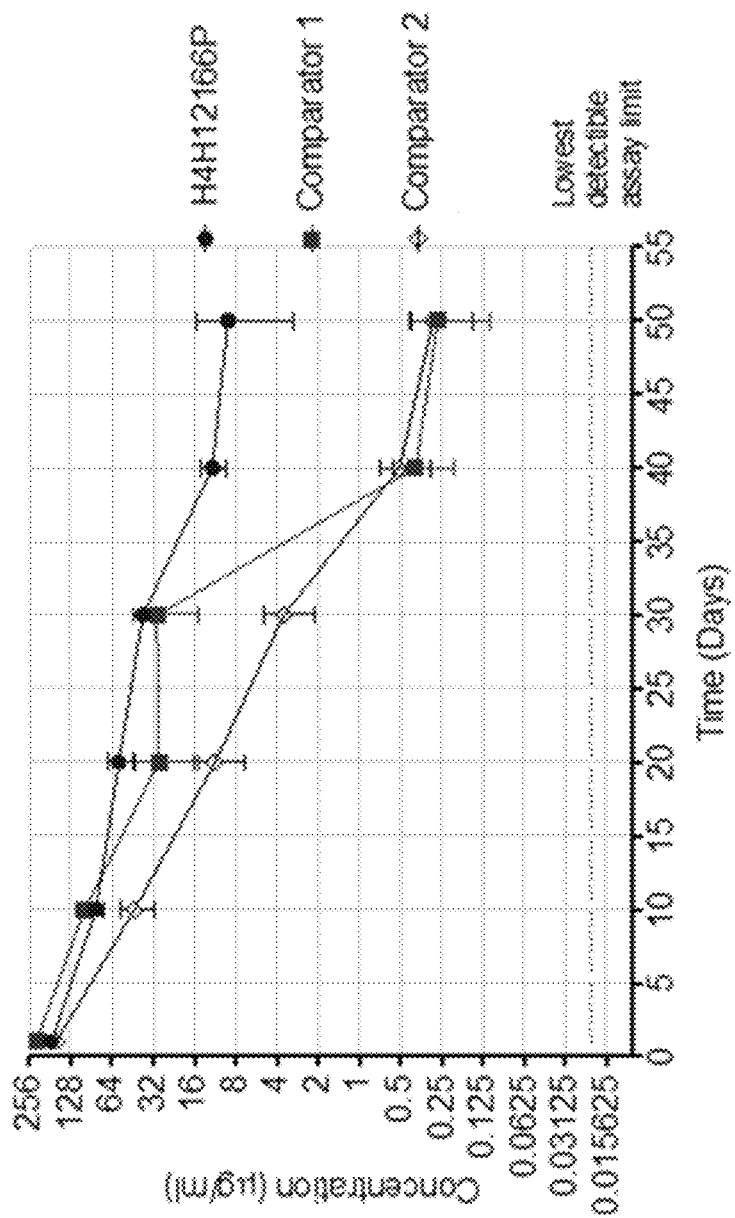
FIG. 4 shows total serum concentration vs. time profiles of selected anti-C5 antibodies in mice humanized for C5 (described in Example 11 herein). Humanized C5 mice were administered a single 15 mg/kg subcutaneous dose of H4H12166P, Comparator 1 or Comparator 2. Each data point represents the mean±s.e.m. (n=4-5 each). Antibody concentrations in sera were monitored 1, 10, 20, 30 and 40 days post injection using a sandwich ELISA.

Total antibody concentrations were determined at 7 time points and percent hemolysis activity was determined at 6 time points over the 50-day in-life period. Total anti-C5 antibody concentrations are summarized in Table 26. The mean total antibody concentrations versus time profile are shown in FIG. 4. Mean PK parameters are described in Table 27.

TABLE 26

Mean Concentrations of Total IgG in Serum Following a Single 15 mg/kg Subcutaneous Injection of anti-C5 antibodies in Humanized C5 mice

| Time | | Serum concentration of Ab (μg/mL) Mean ± SD | | |
|---|---|---|---|---|
| (Day) | # | H4H12166P | Comparator 1 | Comparator 2 |
| 1 | 22 | 178 ± 22.7 | 229 ± 40.7 | 164 ± 24.1 |
| 10 | 4 | 83.7 ± 22.2 | 102 ± 22.9 | 44 ± 24.1 |
| 20 | 5 | 57.1 ± 26.8 | 29 ± 31.3 | 11.4 ± 10.3 |
| 30 | 5 | 38.1 ± 7.6 | 30.1 ± 34.2 | 3.6 ± 3.2 |
| 40 | 4 | 11.9 ± 5.0 | 0.4 ± 0.4 | 0.5 ± 0.4 |
| 50 | 4* | 9.3 ± 12.2 | 0.3 ± 0.3 | 0.3 ± 0.2 |

Time = Time in hours post single-dose injection;
Day = Day of study;
SD = Standard deviation;
SEM = Standard error of mean;
ND = Not detected;
NS = No sample.
*For Comparator 2, day 50, n = three due to the inability of one sample to be analyzed due to technical issues.

TABLE 27

| Parameter | Units | H4H12166P | Comparator 1 | Comparator 2 |
|---|---|---|---|---|
| | | PK parameters | | |
| Day 1 mAb concentration | μg/mL | 178 | 229 | 164 |
| $AUC_{last}$ | day · μg/mL | 2801 | 2708 | 1418 |
| $t_{1/2}$ | d | 11.3 | 4.7 | 7.6 |

$C_{max}$ = Peak concentration;
AUC = Area under the concentration-time curve;
$AUC_{last}$ = AUC computed from time zero to the time of the last positive concentration;
$T_{1/2}$ = Estimated half-life observed Mean concentration versus time profiles at day 1 show that the three antibodies, H4H12166P, Comparator 1 and Comparator 2 had comparable serum concentrations of 178, 229 and 164 μg/mL, respectively. Comparator 1 had a similar elimination profile to H4H12166P up to day 30, but at days 40 and 50 exhibited a rapid increase in clearance versus H4H12166P. At day 50, H4H12166P had an average antibody serum concentration of approximately 9 μg/mL, whereas Comparator 1 and Comparator 2 both had a 30-fold lower average antibody serum concentration of 0.3 μg/mL. Comparator 2 exhibited the lowest exposure of the three antibodies tested, with an approximately 2-fold lower $AUC_{last}$ (1408 day pg/mL) as compared to H4H12166P (2801 day pg/mL) and Comparator 1 (2708 day pg/mL).

Figure 5:
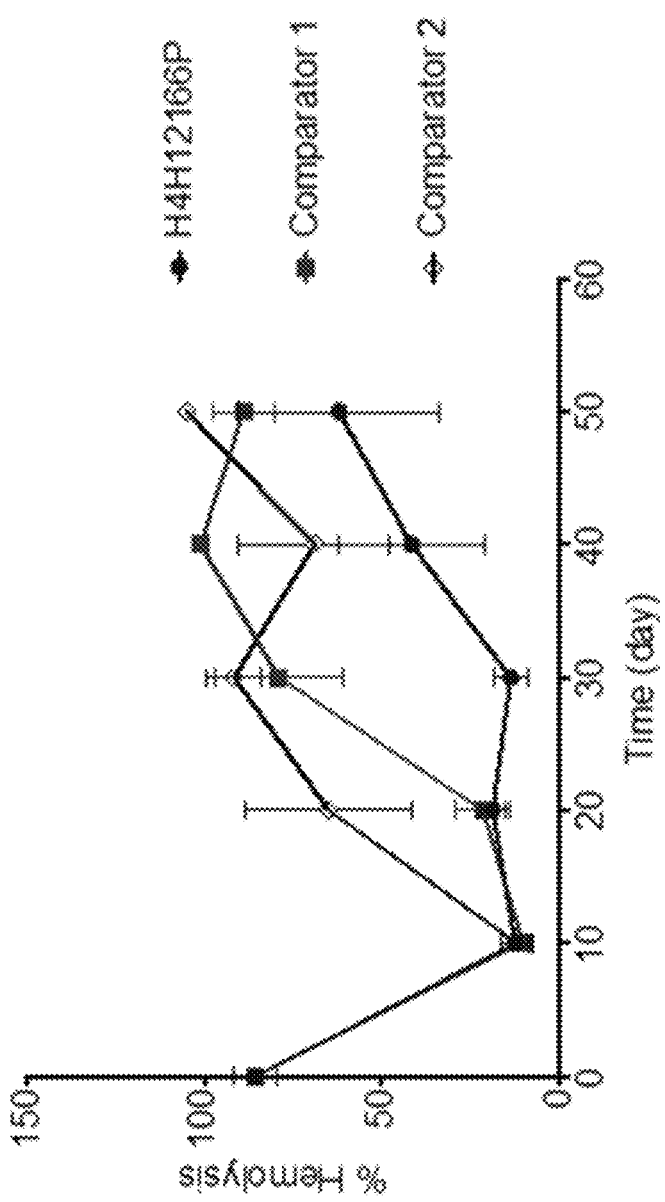
FIG. 5 shows percent hemolysis vs. time in an ex vivo complement classical pathway hemolysis assay of selected anti-C5 antibodies in mice humanized for C5. Humanized C5 mice were administered a single 15 mg/kg subcutaneous dose of H4H12166P, Comparator 1 or Comparator 2. Each data point represents the mean±s.e.m. (n=4-5 each). The percent hemolysis in serum was monitored at predose, 10, 20, 30, 40 and 50 days post injection. % hemolysis, calculated as a ratio of experimental vs. maximal lysis with % background lysis subtracted from both values, is related to the amount of C5 inhibited by the particular anti-C5 antibody present in the serum at a given time point.

The pharmacologic effects of anti-C5 antibodies H4H12166P, Comparator 1 and Comparator 2 from humanized C5 mouse serum samples supplemented with human C3 were measured out to day 50 and were determined ex vivo by complement classical pathway (CP) hemolysis of sensitized SRBC. Mean percent hemolysis for each anti-C5 antibody is summarized in Table 28 and the mean percent hemolysis versus time profile is shown in FIG. 5.

TABLE 28

Ex Vivo Classical Pathway Percent Hemolysis Activity of anti-human C5 antibodies

| Time | | Classical pathway % hemolysis in 10% mouse serum, 60 min, Mean ± SEM | | |
|---|---|---|---|---|
| (Day) | # | H4H12166P | Comparator 1 | Comparator 2 |
| 1 | 22 | NS | NS | NS |
| 10 | 4 | 12.6 ± 7.79 | 10.39 ± 2.88 | 12.06 ± 9.12 |
| 20 | 5 | 18.8 ± 8.1 | 21.59 ± 17.53 | 65.08 ± 52.87 |
| 30 | 5 | 13.76 ± 10.9 | 78.98 ± 40.3 | 91.67 ± 16.74 |
| 40 | 4 | 41.71 ± 40.7 | 101.09 ± 4.01 | 68.99 ± 42.47 |
| 50 | 4* | 62.2 ± 56.6 | 88.99 ± 17.51 | 105.14 ± 4.07 |

Time = Time in hours post single-dose injection;
Day = Day of study;
SEM = Standard error of mean;
ND = Not detected;
NS = No sample.
*For Comparator 2, day 50, n = three due to the inability of one sample to be analyzed due to technical issues H4H12166P, Comparator 1 and Comparator 2 inhibited the terminal complement hemolytic activity that appeared to correlate with antibody exposures. H4H12166P blocked more than 85% of hemolytic activity until day 30 with activity returning to predose baseline levels by day 50. Comparator 1 and Comparator 2 blocked about 80% hemolytic activity until day 20 and day 10, respectively, with activity returning to baseline levels by day 30 for both.

Experiment 2

In this experiment, the pharmacokinetics and pharmacodynamics of anti-C5 antibodies H4H12166P, H4H12161P, Comparator 1, and an isotype control was assessed in humanized C5 mice (mice homozygous for human C5 expression). Total circulating C5 levels were determined using a Human Complement C5 ELISA (Abcam, cat # ab125963), which was performed according to the manufacturer's recommendations. Average concentrations of human C5 in the mice were determined to be 48.98 µg/mL±15.1 µg/mL.

Prior to antibody dosing, humanized male and female C5 mice were stratified according to human C5 levels that averaged 50 µg/mL. For each anti-C5 mAb, cohorts of five mice received a single 15 mg/kg subcutaneous (s.c.) injection of H4H12166P, H4H12161P, Comparator 1 or an isotype control. All mice were bled predose, 6 hours, 1, 2, 3, 4, 7, 10, 13, 21, 30 and 45 days post injection for PK analysis. In addition, on day 59, all mice from each cohort were euthanized and terminal bleeds were collected for PK and PD analysis. Blood was processed into serum and frozen at −80° C. until analyzed.

Figure 6:
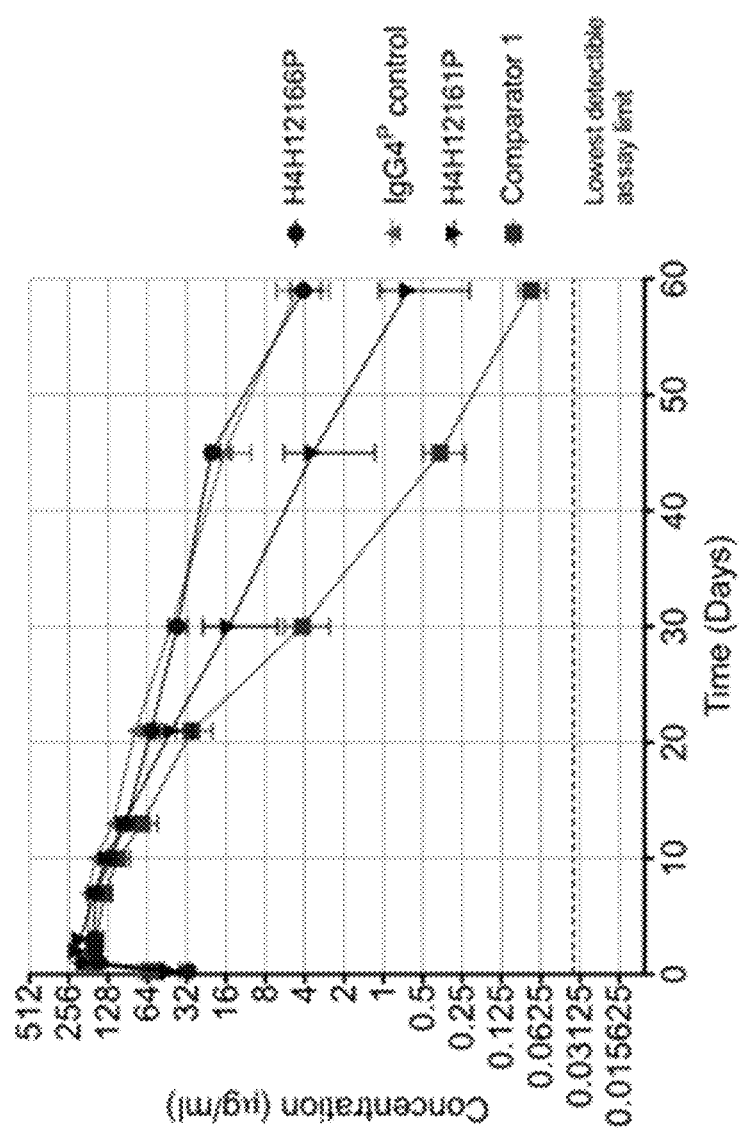
FIG. 6 shows total serum concentration vs. time profiles of selected anti-C5 antibodies in mice humanized for C5 (described in Example 11 herein). Mice were administered a single 15 mg/kg subcutaneous dose of H4H12166P, H4H12161P, Comparator 1 or IgG4$^P$ isotype control. Each data point represents the mean±s.e.m. (n=5 each). Antibody levels in sera were monitored 6 hours, 1, 2, 3, 4, 7, 10, 14, 21, 30, 45 and 59 days post injection using a sandwich ELISA.

Total antibody concentrations were determined at 12 time points and percent hemolysis activity was determined at 1 time point during a 59-day in-life period. Total serum antibody concentrations for each anti-C5 antibody are summarized in Table 29. Mean total antibody concentration versus time profiles are shown in FIG. 6. Mean PK parameters are described in Table 30.

TABLE 29

Mean Concentrations of Total IgG in Serum Following a Single 15 mg/kg Subcutaneous Injection of selected anti-C5 antibodies in Humanized C5 mice

| Time (Day) | Serum concentration of Ab (µg/mL) Mean ± SD | | | |
|---|---|---|---|---|
| | H4H12166P | H4H12161P | Comparator 1 | Isotype Control |
| 0 | ND | ND | ND | ND |
| 0.25 | 31.2 ± 4.2 | 43.5 ± 16.3 | 59.2 ± 24.1 | 61.5 ± 29.4 |
| 1 | 149.9 ± 16.1 | 193.8 ± 24.1 | 179.0 ± 9.8 | 218.1 ± 17 |
| 2 | 160.8 ± 20 | 221 ± 26.5 | 166.6 ± 22.3 | 188.8 ± 25.8 |
| 3 | 166.2 ± 12.4 | 210 ± 31.2 | 159.2 ± 33.2 | 177.9 ± 26.2 |
| 7 | 158.6 ± 8.5 | 162.5 ± 34.8 | 136.1 ± 38.1 | 184.9 ± 33.9 |
| 10 | 123.5 ± 28.7 | 133.2 ± 20.2 | 107.2 ± 45.7 | 159.5 ± 28.8 |
| 13 | 93.7 ± 23.6 | 97.2 ± 24.6 | 70.6 ± 38 | 117.2 ± 24.1 |
| 21 | 60.4 ± 14.9 | 42.4 ± 30.3 | 29.5 ± 20.6 | 80.0 ± 17.5 |
| 30 | 37.8 ± 10.8 | 15.3 ± 19.7 | 4.2 ± 3.5 | 42.1 ± 6.7 |
| 45 | 20.7 ± 5.2 | 3.5 ± 5.2 | 0.4 ± 0.3 | 16.5 ± 13.9 |
| 59 | 4.1 ± 1.9 | 0.6 ± 1.0 | 0.08 ± 0.04 | 4.6 ± 4.5 |

Time = Time in hours post single-dose injection;
Day = Day of study;
SD = Standard deviation;
SEM = Standard error of mean,;
ND = Not detected;
NS = No sample.

TABLE 30

PK parameters

| Parameter | Units | Test Antibody (mean ± SD) | | | |
|---|---|---|---|---|---|
| | | H4H12166P | H4H12161P | Comparator 1 | Isotype control |
| $C_{max}$ | µg/mL | 178 ± 10 | 225 ± 22 | 183 ± 18 | 221 ± 19 |
| $AUC_{last}$ | d · µg/mL | 3490 ± 590 | 3040 ± 900 | 2240 ± 780 | 4080 ± 480 |
| $t_{1/2}$ | D | 11 ± 1 | 5.8 ± 2 | 4.2 ± 1 | 9.9 ± 4 |

$C_{max}$ = Peak concentration;
AUC = Area under the concentration-time curve;
$AUC_{last}$ = AUC computed from time zero to the time of the last positive concentration;
$T_{1/2}$ = Estimated half-life observed.

Mean concentration versus time profiles show that H4H12166P, H4H12161P, Comparator 1 and isotype control reached a maximum serum concentration ($C_{max}$) between days 1 to 3, with comparable $C_{max}$ values within 1.3-fold (178, 225, 183 and 221) pg/mL, respectively. H4H12166P and isotype control had similar elimination profiles, with remaining drug levels of approximately 4 µg/mL at day 59. H4H12161P exhibited faster clearance than H4H12166P and isotype control but cleared more slowly than Comparator 1. At day 59, H4H12161P had mean serum drug level of 0.6 µg/mL while Comparator 1 had an almost undetectable drug level of 0.08 µg/mL.

The isotype control, H4H12166P and H4H12161P exhibited comparable exposure ($AUC_{last}$) values within 1.3-fold (4080, 3490 and 3040 day pg/mL, respectively) whereas Comparator 1 exhibited a 1.6-fold lower exposure (2240 day·µg/mL) compared to H4H12166P.

Example 12: LC-MRM-MS-Based Assay to Determine the Concentration of Total Human C5

In this Example, serum concentrations of total human C5 were determined using a liquid chromatography coupled to multiple reaction monitoring mass spectrometry (LC-MRM-MS) method in a pharmacokinetics/pharmacodynamics study of anti-C5 antibody H4H12166P.

The serum concentrations of total human C5 were determined by measuring the concentration of a 10-amino acid peptide contained in the C5 sequence LQGTLPVEAR (aa 1129-1138 of SEQ ID NO: 359) as a proxy for C5. Theoretically, this method could also detect the C5 split product, C5b. However, due to the instability of free C5b, concentrations C5b in serum are generally low with the majority of C5b being bound to cell surfaces in the form of MAC complexes (Cooper & Muller-Eberhard 1970, J. Exp. Med. 132: 775-93; Hadders et al 2012, Cell Rep. 1: 200-7). Therefore, the processed serum samples analyzed here are likely to contain only negligible amounts of C5b product, if any.

Methods

For the PK/PD study, mice received a single 15 mg/kg dose of H4H12166P by subcutaneous (s.c.) injection. All mice were bled predose and at one day post-injection for PK analysis. In addition, at 10, 20, 30, 40, 50 and 60 days post injection, mice were euthanized and terminal bleeds were collected for PK and PD analysis.

Human C5 was used as a reference standard for calibration; and a human C5 peptide produced with a C-terminal stable isotope-labeled arginine residue was used as the internal standard (LQGTLPVEAR-$^{13}C_6^{15}N_4$). Reference standard was used at concentrations ranging from 3.9 to 250 µg/mL (1:2 serial dilutions) in serum from in house-generated C5 knock-out mice, in which the mouse C5 gene was deleted (C5−/−). Serum from C5−/− mice was also used as a negative control (blank). Calibration standards, blanks, and study serum samples (10 µL each) were dried and then were denatured in 100 µL of 8M urea/20 mM Tris(2-carboxyethyl)phosphine (TCEP) buffer at 37° C. for 1 hour. Next, 10 µL of 25 nM internal standard was added to all samples. Samples were alkylated with 10 mM of 2-iodoacetamide at room temperature for 30 minutes and were diluted using 50 mM ammonium bicarbonate to a final volume of 500 µL. The samples were then digested by trypsin (1:20 w/w) overnight at 37° C. The tryptic peptide LQGTLPVEAR derived from C5 was detected and quantified by LC-MRM-MS using a Waters Xevo TQ-S with ACQUITY UPLC system. Each processed sample (10 µL)

was injected onto a pre-equilibrated ACQUITY UPLC BEH C18 Column. The flow rate was 0.6 mL/min (Mobile Phase A:water:formic acid/100:0.1 [V:V] and Mobile Phase B: acetonitrile:formic acid/100:0.1 [V:V]). Retention time and peak area were determined using Masslynx Analyst Data software (Waters). Concentrations of C5 analyte were calculated from the calibration curve which was constructed by plotting the peak area ratio of C5 reference standard (unlabeled C5 peptide LQGTLPVEAR-$^{12}C_6^{14}N_4$ generated by tryptic digest of hC5) to internal standard (stable isotope-labeled C5 peptide) versus the nominal concentration of C5 reference standard. Concentrations were calculated using linear regression. The lowest concentration of C5 reference standard (3.9 μg/mL) was within the dynamic range of the assay and was defined as the assay's LLOQ.

Results

Concentrations of total human C5 in serum were evaluated for samples collected and via tail bleed in advance of dosing (predose) and via terminal bleed on days 10, 30 and 35, from the corresponding animals. Total hC5 concentrations following H4H12166P dosing were similar (within ~1 to 0.9-fold) to predose levels on days 10, 30, and 35 post dosing. The observed minor differences were not statistically significant as assessed by Mann-Whitney test using GRAPHPAD™ PRISM™ software. Analysis of the C5/H4H12166P molar ratio demonstrated that H4H12166P remained in molar excess of C5 through day 35 post dosing (Table 31).

The labeling solution was prepared in 10 mM PBS buffer in $D_2O$ at pD 7.0 (equivalent to pH 6.6). For deuterium labeling, 3.8 μL of C5 (6 pmol/μL) or C5 premixed with the antibody in 1:1 molar ratio was incubated with 56.2 μL $D_2O$ labeling solution for various time-points (e.g., undeuterated control=0 sec, labeled for 1 min and 20 min). The deuteration was quenched by transferring 50 μL sample to 50 μL pre-chilled quench buffer (0.2 M TCEP, 6 M guanidine chloride in 100 mM phosphate buffer, pH 2.5) and the mixed sample was incubated at 1.0° C. for two minutes. The quenched sample was then injected into a Waters HDX Manager for online pepsin/protease XIII digestion. The digested peptides were trapped onto an ACQUITY UPLC BEH C18 1.7-μm, 2.1×5 mm VanGuard pre-column at 0° C. and eluted to an analytical column ACQUITY UPLC BEH C18 1.7-μm, 1.0×50 mm for a 9-minute gradient separation of 5%-40% B (mobile phase A: 0.1% formic acid in water, mobile phase B: 0.1% formic acid in acetonitrile). The mass spectrometer was set at cone voltage of 37 V, scan time of 0.5 s, and mass/charge range of 50-1700 Thomson units (Th).

For the identification of the peptides from human C5, LC-$MS^E$ data from undeuterated sample were processed and searched against the database including human C5, pepsin,

TABLE 31

Summary of PD characteristics of H4H12166P

| | % CP | | C5 (μg/mL) | | | H4H12166P | Molar ratio |
|---|---|---|---|---|---|---|---|
| Day Post dose | Hemolysis Mean ± SD | % Inhibition | Predose | Terminal | Fold Change | (μg/mL) mean ± SD | terminal C5:H4H12166P |
| 0 | 77.2 | 0 | | n/d | | n/a | n/a |
| 10 | 5.2 | 93 | 34.2 | 30.0 | 1.0 | 78.8 | 0.3 |
| 30 | 7.4 | 90 | 31.9 | 28.4 | 0.9 | 30.4 | 0.8 |
| 35 | 6.0 | 92 | 36.1 | 32.7 | 1.0 | 29.6 | 0.9 |
| 40 | 37.1 | 52 | | n/d | | 20.9 | n/d |
| 50 | | All animals in group excluded due to MAHA titers >1000 | | | | | |
| 60 | 73.57 | 5 | | n/d | | 5.9 | n/d |

$^a$Percentage of inhibition of CP hemolytic activity was calculated from mean % CP hemolysis values on the indicated day post dosing relative to the mean % CP hemolysis value on day 0.
$^b$Fold Change = terminal (indicated day post dosing) C5: predose C5.
SD = standard deviation;
MAHA = mouse anti-human antibody;
n/d = not determined
Animals with MAHA-impacted data were completely excluded from calculations (2x day 30, 1x day 35, 2x day 40, and all 4 mice on day 50)

Example 13: Epitope Mapping of H4H12166P Binding to C5 by Hydrogen/Deuterium Exchange H/D exchange epitope mapping with mass spectrometry was carried out to determine the amino acid residues of hC5 [(amino acids M1-C1676 of SEQ ID No: 359) with which H4H12166P interacts. A general description of the H/D exchange method is set forth in e.g., Ehring (1999) *Analytical Biochemistry* 267(2):252-259; and Engen and Smith (2001) *Anal. Chem.* 73:256A-265A.

HDX-MS experiments were performed on an integrated Waters HDX/MS platform, consisting of a Leaptec HDX PAL system for the deuterium labeling, a Waters Acquity M-Class (Auxiliary solvent manager) for the sample digestion and loading, a Waters Acquity M-Class (μBinary solvent manager) for the analytical column gradient, and Synapt G2-Si mass spectrometer for peptic peptide mass measurement.

and their randomized sequence via Waters ProteinLynx Global Server (PLGS) software. The identified peptides were imported to DynamX software and filtered by two criteria: (1) minimum products per amino acid=0.3 and (2) replication file threshold=3. DynamX software then automatically determined deuterium uptake of each peptide based on retention time and high mass accuracy (<10 ppm) across multiple time points with 3 replicates at each time.

Using the online pepsin/protease XIII column coupled with $MS^E$ data acquisition, total 189 peptides from human C5 were identified in the absence or presence of the antibody, representing 62% sequence coverage. Five peptides had significantly reduced deuteration uptake (centroid delta values >0.9 daltons with p-values <0.05) when bound to H4H12166P and are illustrated in the Table 32.

TABLE 32

Deuteration of Human C5 peptides upon binding to H4H12166P

| | 1 min Deuteration | | | 20 min Deuteration | | |
|---|---|---|---|---|---|---|
| Residues | C5 Centroid H$^+$ | C5 + H4H12166P Centroid MH$^+$ | Δ | C5 Centroid MH$^+$ | C5 + H4H12166P Centroid MH$^+$ | Δ |
| 591-599 | 1015.38 ± 0.09 | 1014.44 ± 0.16 | −0.93 | 1015.64 ± 0.04 | 1014.60 ± 0.08 | −1.04 |
| 593-599 | 769.41 ± 0.11 | 768.33 ± 0.05 | −1.08 | 769.65 ± 0.01 | 768.30 ± 0.004 | −1.35 |
| 775-787 | 1693.81 ± 0.11 | 1692.85 ± 0.07 | −0.96 | 1694.06 ± 0.04 | 1692.96 ± 0.02 | −1.10 |
| 775-794 | 2439.62 ± 0.29 | 2438.42 ± 0.20 | −1.20 | 2440.16 ± 0.06 | 2439.17 ± 0.21 | −0.99 |
| 779-787 | 1141.14 ± 0.04 | 1140.21 ± 0.05 | −0.93 | 1141.23 ± 0.03 | 1140.21 ± 0.02 | −1.02 |

The recorded peptide mass corresponds to the average value of the centroid MH$^+$ mass from three replicates. These peptides, corresponding to amino acids 591-599 and 775-794, had slower deuteration rate upon binding to H4H12166P. These identified residues also correspond to the residues 591-599 and 775-794 of human C5 as defined by Uniprot entry P01031 (CO5_HUMAN; SEQ ID NO: 359).

Example 14: Effect of Anti-C5 Antibodies on Ocular Inflammation in Experimental Autoimmune Uveitis in Mice The present study was undertaken to evaluate the role of C5 in experimental autoimmune uveitis (EAU). Both genetic [C5 knockout (KO), C3/C5 double KO mice], and pharmacologic (anti-C5 antibody) experimental approaches were used.

Methods

Adult C57BL/6J mice (n=25, Jackson labs), C5 KO (n=13) and C3/C5 KO (n=8) mice (Regeneron Pharmaceuticals Inc.) were used. EAU was induced by subcutaneous injection of human interphotoreceptor retinoid-binding protein peptide (IRBP, New England Peptide) in complete Freund's adjuvant and intraperitoneal injection of pertussis toxin. Anti-mouse C5 mAb or isotype control mAb was administered through subcutaneous injections every 3 days from day 5 to 28. The anti-mouse C5 antibody used in this study (M1M17628N) comprised a HCVR/LCVR of SEQ ID NOs: 362/363. SPECTRALIS® HRA+OCT (Heidelberg Engineering, Inc.) was used to assess levels of inflammation on days −1, 7, 14, 21 and 28. All animals were euthanized on day 28 for eye and blood collection. Hemolysis assay with/without human C3 was performed to validate complement inhibition. Data were analyzed by ANOVA.

Results

Figure 7:
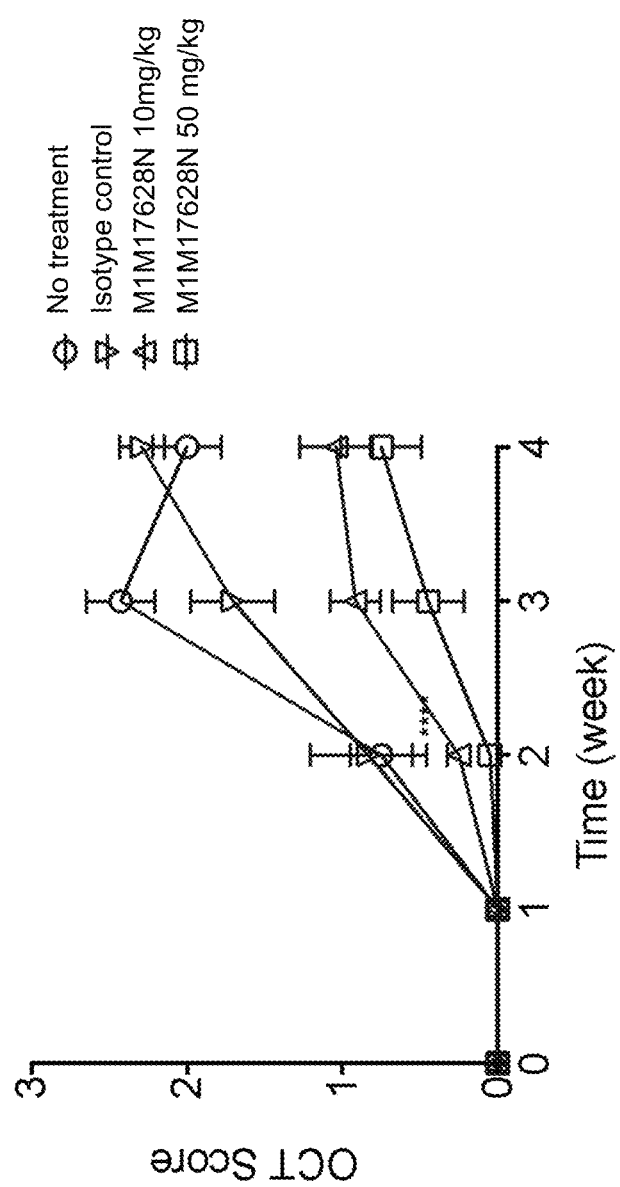
FIG. 7 is a graph showing optical coherence tomography (OCT) scores in mice treated with isotype control or with anti-C5 antibody M1M17628N at 10 mg/kg or 50 mg/kg (described in Example 14 herein). ****$p<0.0001$, two-way ANOVA treatment with anti-C5 antibody at 50 mg/kg vs. no treatment or treatment with isotype control.
Figure 8:
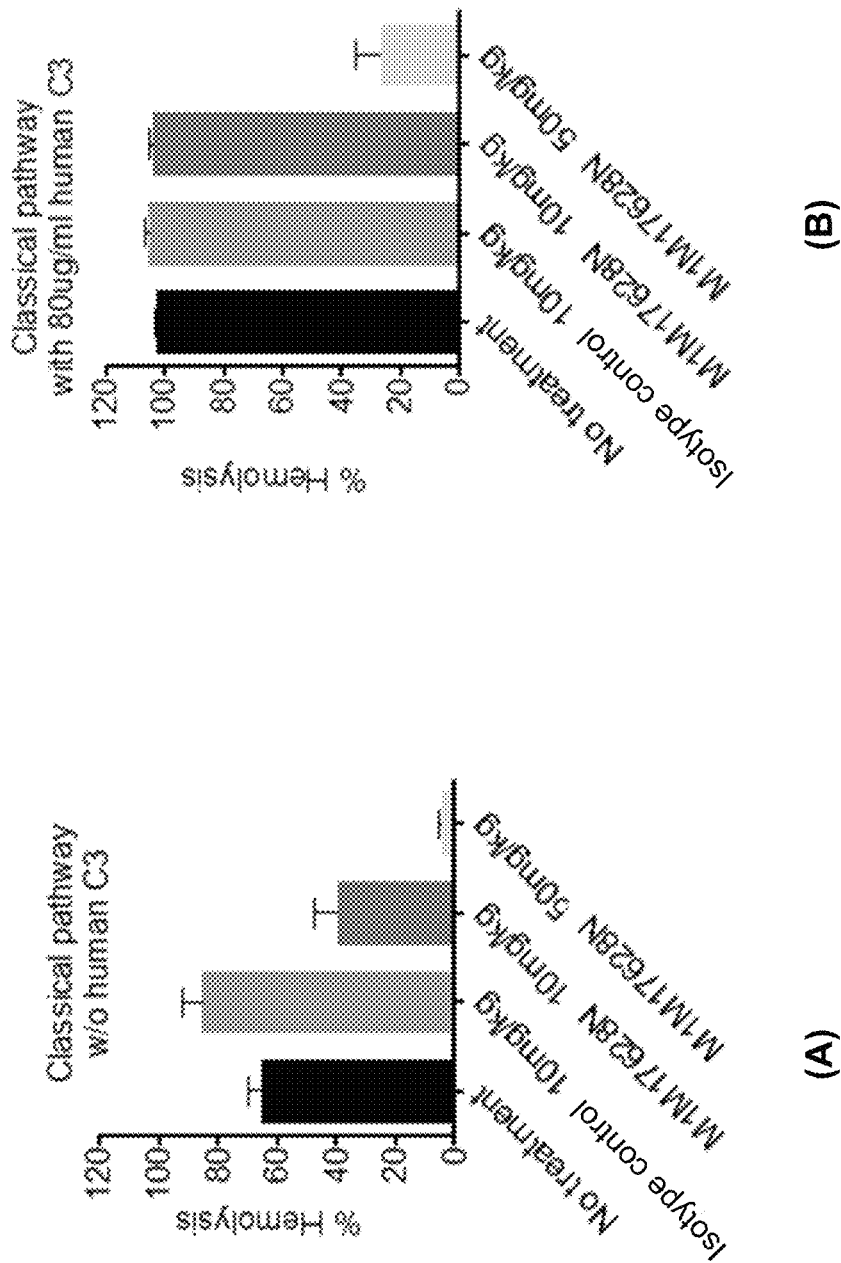
FIG. 8 shows inhibition of classical pathway hemolysis by anti-C5 antibody M1M17628N in the absence of C3 (A); and in the presence of 80 μg/mL of human C3 (B) (described in Example 14 herein).

Compared to wild type mice, inflammation occurrence (30-50%) and vitreous cell cluster counts were significantly decreased in C5 KO mice (p<0.01). Optical coherence tomography (OCT) scores in C5 KO mice also significantly reduced 50% at week 3 (p<0.0001). Interestingly, in C3/C5 double KO mice, there were significantly more vitreous cell clusters and higher disease scores on day 28 compared to wild type mice (p<0.05). In animals that received anti-mC5 Ab (50 mg/kg), inflammation incidence and vitreous cell clusters were significantly lower compared to either no treatment or isotype control group on day 21 (p<0.01). At weeks 3 and 4, OCT scores in anti-C5 antibody-treated group were significantly lower compared to no treatment or isotype control (p<0.0001). (FIG. 7) Hemolysis assays with/without human C3 confirmed the inhibition effect of anti-C5 antibody at week 4 (FIG. 8).

Conclusion

Ocular inflammation due to EAU was mitigated by inhibiting C5 activity, either by genetic deletion or pharmacologic inhibition with a specific anti-C5 antibody. C5 depletion delayed EAU occurrence and reduced OCT disease score. These results indicate that C5 is a potential therapeutic target for autoimmune uveitis. Anti-C5 antibody has protective effect on EAU disease in wild type mice. Our findings also suggest that C3 might be beneficial for EAU disease in mice.

Example 15: Effect of Anti-Human C5 Antibodies on Experimental Autoimmune Uveitis This Example describes the effects of anti-C5 antibodies against human C5 in a mouse model of experimental autoimmune uveitis (EAU). The mice used for this study were humanized to express human C5 protein using Velocigene® technology (Valenzuela et al 2003, Nat. Biotechnol. 21: 652-659). Humanized mice were engineered to replace exon 2 through exon 41 of murine C5 gene with exons 2-42 of human C5 gene (disclosed in US Patent Application Publication 2015/0313194, herein incorporated in its entirety).

Methods

Adult, male mice were immunized subcutaneously in each thigh with 150 μg of human interphotoreceptor retinoid-binding protein (IRBP) peptide 1-20 (GPTH-LFQPSLVLDMAKVLLD) (SEQ ID NO: 364) (Avichezer et al 2000, Invest. Ophthalmol. Vis. Sci. 41:127-131) in 0.2 ml emulsion of CFA, supplemented with *Mycobacterium tuberculosis* strain H37RA to 2.5 mg/ml.

Mice were then inoculated intraperitoneally with 1.0 μg of pertussis toxin (PTX) to facilitate induction of cell-mediated antoimmunity by promoting a Th1 polarization of the immune response (Thurau et al 1997, Clin. Exp. Immunol. 109: 370-376; Silver et al 1999, Invest. Ophthalmol. Vis. Sci. 40: 2898-2905). The animal body weights were monitored twice a week.

Ophthalmic examinations were carried out on day −1, before EAU induction and on days 7, 14, 21 and 28. Mice were anesthetized with ketamine (120 mg/kg, IP) and xylazine (5 mg/kg, IP). Pupils were dilated using a 0.5% ophthalmic solution of Tropicamide, and the fundus of the eye was examined using a contact lens with a fundus camera in a Spectralis Heidelberg retinal angiography platform (HRA)+OCT system (Heidelberg Engineering, Carlsbad, Calif., USA).

A series of 61 lateral optical sections were obtained for each eye using the OCT function on the Spectralis HRA+ OCT system (Heidelberg Engineering, Carlsbad, Calif., USA)). The OCT imaging area was centered on the optic disc allowing for equal imaging above and below the optic nerve head. The retinal thickness was measured as the distance between the bottom of the RPE layer to the inner limiting membrane of the eye. Measurements were taken 1500 μm from the optic disc, and the values from 4 different retinal quadrants (e.g., superior, inferior, temporal and nasal) were averaged for a mean retinal thickness of the eye.

The severity of inflammatory cell infiltration into the vitreous also was graded in OCT images, by assessing the average number of inflammatory cell clusters in the vitreous, in four lateral OCT scans that transected the optic nerve, per eye.

An 4-point scale was developed for assessment of disease severity in OCT images (OCT Scores) (Table 33).

TABLE 33

Scoring EAU in vivo using Optical Coherence Tomography (OCT)

| Grade | Criteria |
|---|---|
| 0 | No Change |
| 0.5 (Trace) | Minor inflammatory cell infiltration in the vitreous, primarily near the optic nerve head (<15 clusters) |
| 1 | Minor inflammatory cell infiltration in the vitreous, primarily near the optic nerve head (<25 clusters); minor focal subretinal lesions (grey spots) in the periphery; minor retinal folds in the periphery; retinal vascular dilation; perivasculitis and vasculitis |
| 2 | Moderate inflammatory cell infiltration in the vitreous more diffuse but not in the far periphery (<50 clusters); retinal layer disruptions; small- to medium-sized granuloma formations with retinal folds primarily in the periphery; vessel dilation; minor focal choroidal neovascularization; perivasculitis and vasculitis; minor retinal edema (<10 μm) |
| 3 | Moderate to severe diffuse inflammatory cell infiltration in the vitreous (>50 clusters); diffuse retinal layer disruptions and dilated vessels in the inner nuclear layer; medium- to large- granuloma formations with retinal folds throughout the retina; severe retinal vascular dilation; perivasculitis and vasculitis; moderate diffuse choroidal neovascularization; moderate- to severe-retinal edema (10-40 μm); minor retinal detachments |
| 4 | Severe diffuse inflammatory cell infiltration in the vitreous (>70 clusters); diffuse layer disruptions and dilated vessels in the inner nuclear layer; severe diffuse granuloma formation with retinal folds; severe diffuse choroidal neovascularization; perivasculitis and vasculitis; retinal degeneration or severe retinal edema (>20 μm loss or >40 μm gain respectively); large retinal detachments |

Statistical Analysis

Statistical analyses for parametric data (body weight, inflammatory cell clusters in the vitreous, and retinal thickness) were performed by one-way ANOVA test and Tukey's multiple comparison test. For nonparametric data (OCT scores and histology scores) analyses were performed by the Kruskal-Wallis test and Dunn's test with the GRAPHPAD™ PRISM™ version 5.0d software relative to isotype control or no-treatment groups. Data show mean values±SEM. A p-value of less than 0.05 was considered as statistically significant.

Results

Figure 9:
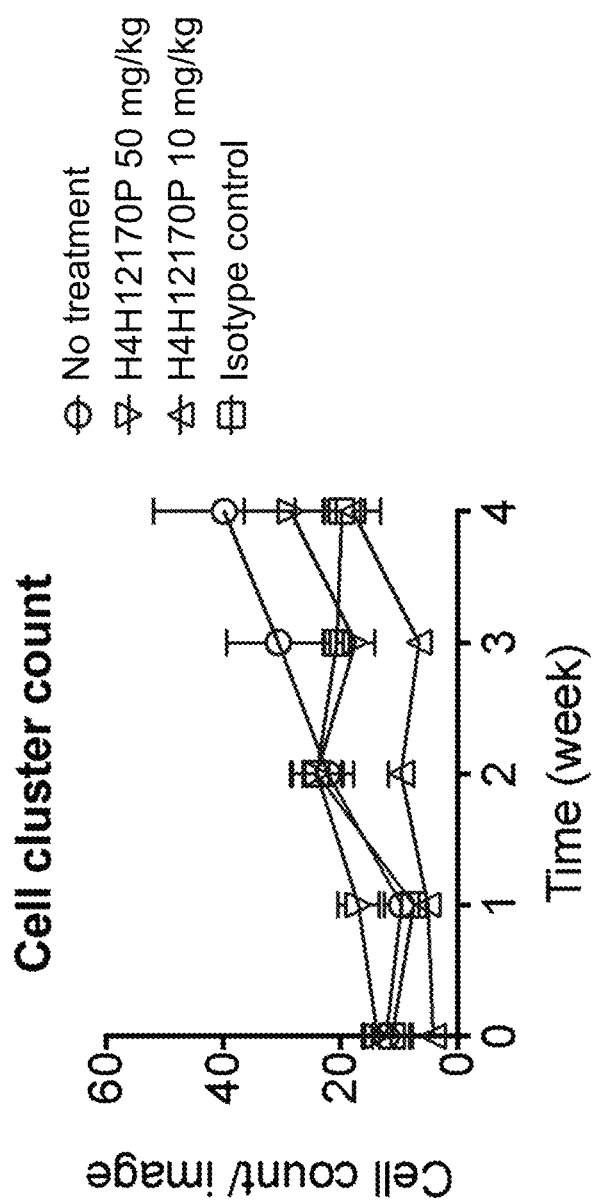
FIG. 9 shows cell cluster count in C5 humanized mice treated with isotype control or with anti-human C5 antibody H4H12170P at 10 mg/kg or 50 mg/kg (described in Example 15 herein). n=8-12 eyes for each group
Figure 10:
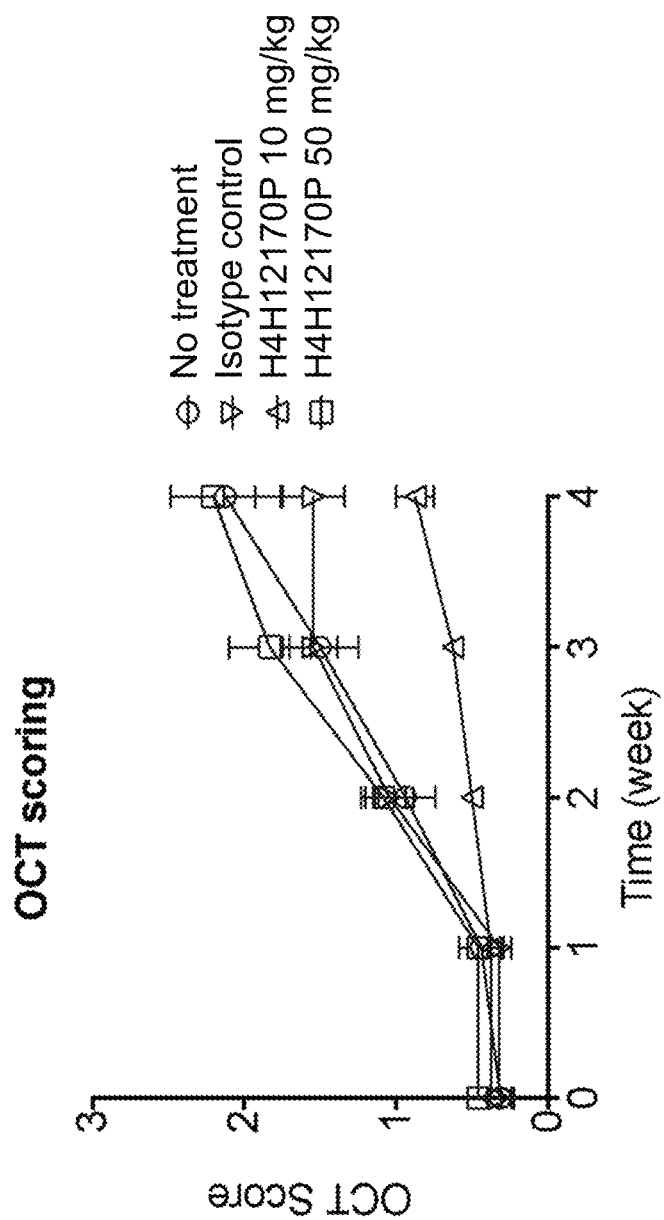
FIG. 10 is a graph showing OCT scores in C5 humanized mice treated with isotype control or with anti-human C5 antibody H4H12170P at 10 mg/kg or 50 mg/kg (described in Example 15 herein). n=8-12 eyes for each group

In a first study (Study A), mice were treated subcutaneously every 3 days from day 5 with isotype control antibody (50 mg/kg), or 10 mg/kg or 50 mg/kg of H4H12170P. Treatment with 10 mg/kg H4H12170P resulted in a reduction in inflammation and retinal damage (FIG. 9). Mice treated with 10 mg/kg H4H12170P also showed a statistically significant reduction in OCT scores on day 21 and day 28 (FIG. 10).

Figure 11:
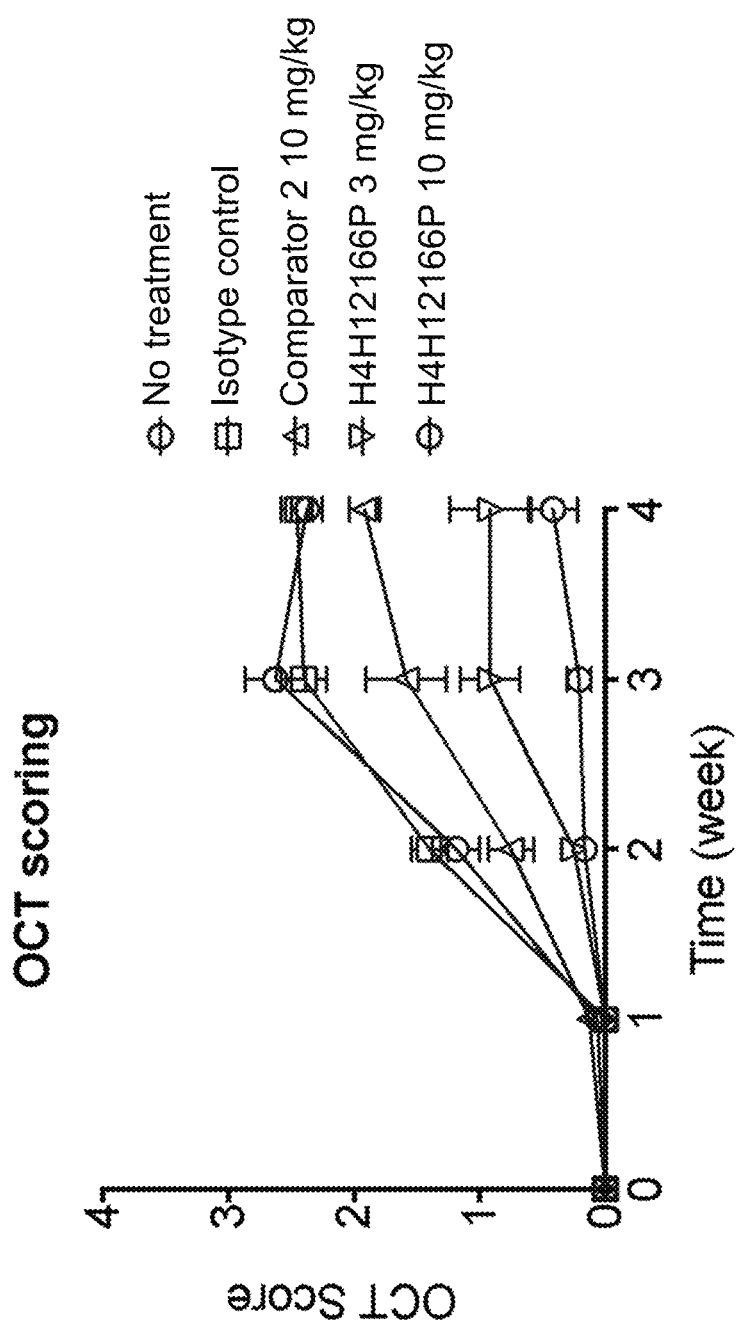
FIG. 11 is a graph showing OCT scores in C5 humanized mice treated with isotype control, anti-human C5 antibody H4H12166P at 3 mg/kg or 10 mg/kg, or Comparator 2 at 10 mg/kg. n=6-12 eyes for each group (described in Example 15 herein).
Figure 12:
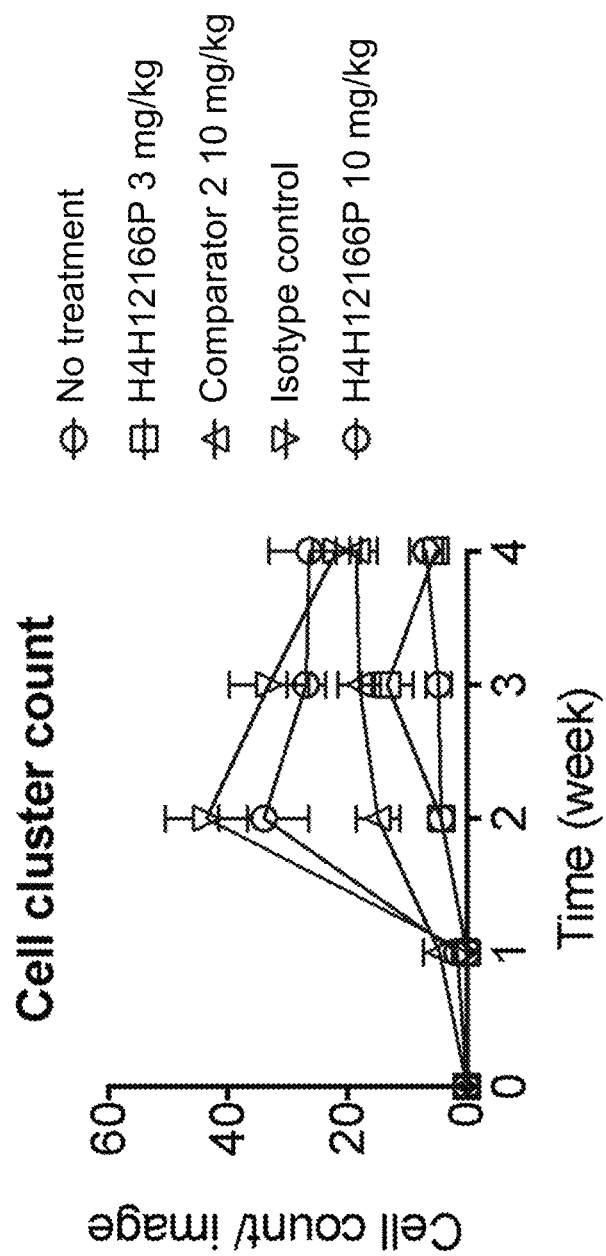
FIG. 12 shows cell cluster count in C5 humanized mice treated with isotype control, anti-human C5 antibody H4H12166P at 3 mg/kg or 10 mg/kg, or Comparator 2 at 10 mg/kg. n=6-12 eyes for each group (described in Example 15 herein).

In a second study (study B), mice were treated subcutaneously every 3 days from day 6 with either isotype control (10 mg/kg), 3 mg/kg or 10 mg/kg of H4H12166P, or with Comparator 2 (see Example 2 herein; "Control Constructs used in the following Examples"). Treatment with H4H12166P either at 3 mg/kg or 10 mg/kg produced a dose-related reduction in OCT scores that was statistically significant on days 14 to 28 (FIG. 11). Treatment with 10 mg/kg H4H12166P in C5 humanized mice starting 6 days following EAU induction resulted in a dose-related reduction in inflammation and retinal damage as determined by OCT obtained on day 14 to 28 (FIG. 12).

For both studies, non-invasive, in-life evaluation by OCT showed a progressive development of inflammation, increased retinal thickness and morphological abnormalities in control animals following immunization with IRBP.

Conclusion

These experiments provide further pharmacological evidence that C5 plays a role in the pathogenesis of autoimmune uveitis. Pharmacologic depletion of human C5 by fully human anti-human C5 antibodies postponed EAU incidence and reduced disease severity, establishing the efficacy of these antibodies in autoimmune uveitis.

Example 16: Effect of Anti-C5 Antibodies on Renal Ischemia-Reperfusion Injury

The present study was carried out to evaluate the role of C5 in renal ischemia-reperfusion injury. Both genetic (using C3 knockout and C5 knockout mice) and pharmacological approaches (using anti-C5 antibodies) were used. Ischemia-reperfusion model was induced by bilateral renal pedicle clamping for 45 min followed by 48 h of reperfusion. Sham laparotomy served as controls. Anti-C5 antibody was administered at 50 mg/kg intravenously as a single dose immediately after ischemia (curative); or subcutaneously as two doses, day −1 and day 1 surgery (preventive). The anti-C5 antibody used for this study was M1M17628N comprising HCVR/LCVR of SEQ ID NO: 362/363. Blood urea nitrogen (BUN) and serum creatinine markers were used to assess levels of disease and protection in the mice.

TABLE 34

Percent change in blood urea nitrogen levels in mice treated with anti-C5 antibody (M1M17628N) in preventive and therapeutic modes

| BUN, % Change Vs. | RIRI + Veh Day 2 | RIRI + Iso. Ctl Day 2 |
|---|---|---|
| RIRI + M1M17628N (Prev) | −37.19 | −34.68 |
| RIRI + M1M17628N (Cur) | −53.70 | −51.85 |

TABLE 35

Percent change in serum creatinine levels in mice treated with anti-C5 antibody (M1M17628N) in preventive and therapeutic modes

| SCr, % Change Vs. | RIRI + Veh Day 2 | RIRI + Iso. Ctl Day 2 |
|---|---|---|
| RIRI + M1M17628N (Prev) | −53.09 | −49.34 |
| RIRI + M1M17628N (Cur) | −59.40 | −56.16 |

Compared to wild type mice, C3 and C5 knockout mice showed significant functional protection in the RIRI model of acute kidney injury, as evidenced by reduction in the blood urea nitrogen and serum creatinine levels. The anti-C5 antibody showed functional protection in RIRI model in both preventive and therapeutic modes (Tables 34-35).

Example 17: Effect of Anti-C5 Antibodies on Lupus Nephritis

This Example describes the efficacy of anti-C5 antibodies in treating lupus nephritis in a mouse model.

Systemic lupus erythematosus (SLE) is an autoimmune disorder caused by loss of tolerance to self-antigens, the production of autoantibodies and deposition of complement-fixing immune complexes (ICs) in injured tissues. SLE is characterized by a wide range of clinical manifestations and targeted organs, with lupus nephritis being one of the most serious complications. Complement activation in the kidneys of lupus nephritis patients contributes to inflammation and tissue damage. The efficacy of anti-C5 antibodies in treating lupus nephritis was studied in NZBWF1 mice, a spontaneous mouse model of lupus nephritis (Yang et al 1996, PNAS). The mice develop autoimmune disease resembling human SLE, autoantibodies to nuclear antigens and cell membrane proteins, hypergammaglobulinemia, albuminuria, proteinuria, initiate immune complex glomerulonephritis and die of kidney failure and end-stage renal disease at 35 to 50 weeks of age.

For this study, 25-week old NZBWF1 mice were subcutaneously treated with 30 mg/kg of isotype control, or anti-C5 antibodies twice a week for 8 weeks followed by thrice a week for 10 weeks. The anti-mouse C5 antibodies used for this study were M1M17628N and M1M17627N, comprising HCVR/LCVR of SEQ ID NOs: 362/363 and 365/366, respectively.

Figure 13:
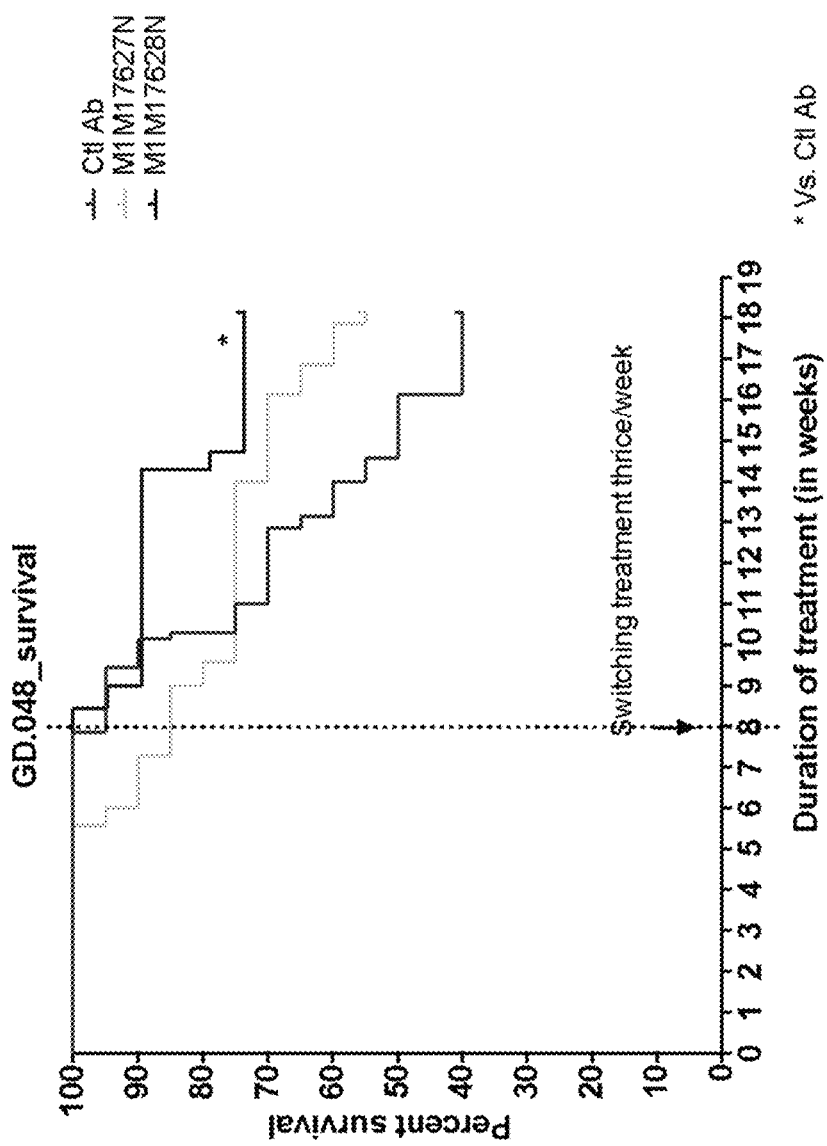
FIG. 13 is a survival curve of NZBWF1 mice treated with isotype control or with anti-C5 antibodies M1M17628N or M1M17627N (described in Example 17 herein).
Figure 14A:
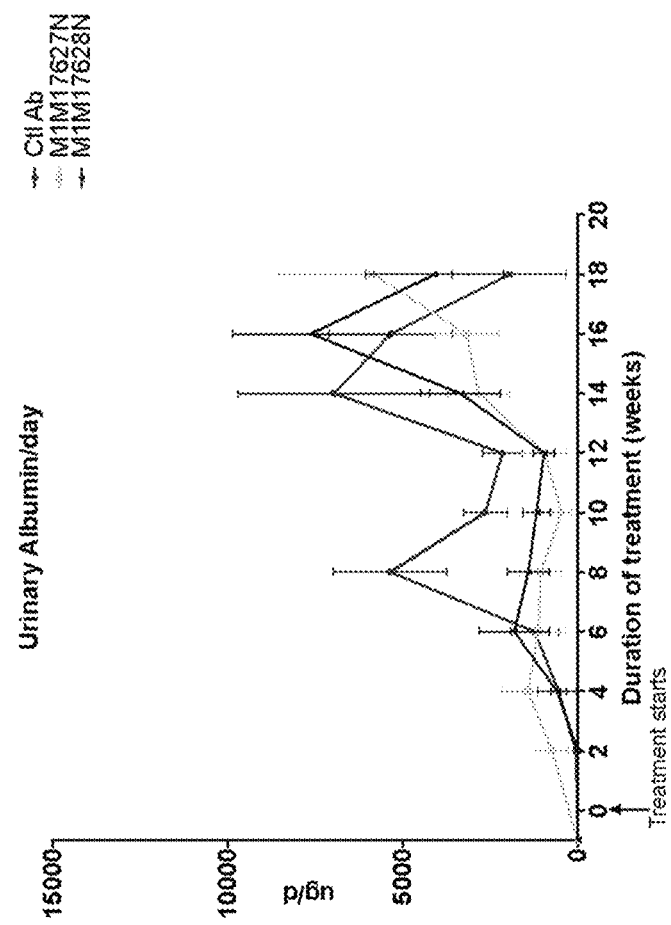
FIG. 14A and FIG. 14B show levels of (A) urinary albumin and (B) urinary albumin normalized to urinary creatinine in NZBWF1 mice treated with isotype control or with anti-C5 antibodies M1M17628N or M1M17627N (described in Example 17 herein).
Figure 14B:
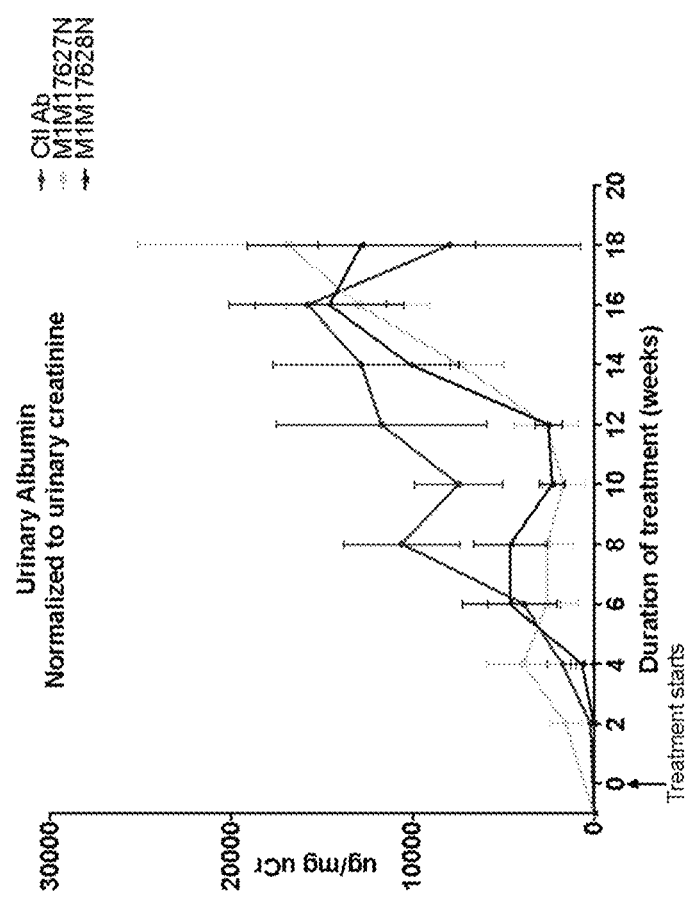
Figure 15:
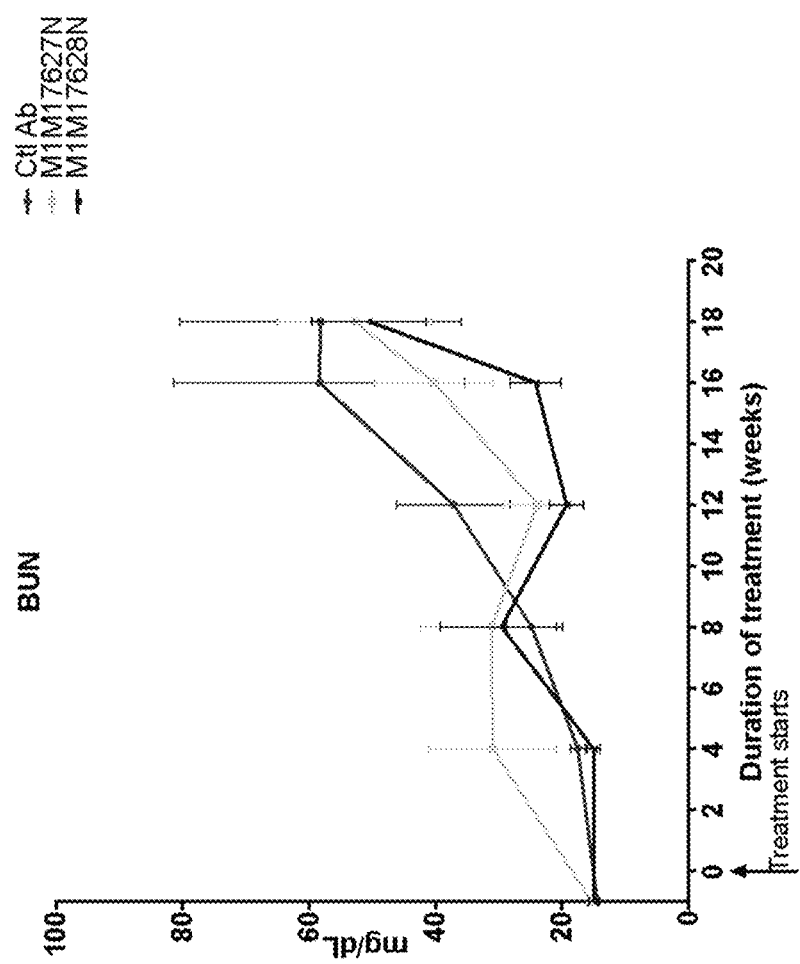
FIG. 15 shows levels of blood urea nitrogen in NZBWF1 mice treated with isotype control or with anti-C5 antibodies M1M17628N or M1M17627N (described in Example 17 herein).

Treatment with anti-C5 antibodies significantly improved survival rate in mice (FIG. 13). Both antibodies improved albuminuria at 8-14 weeks of treatment (FIG. 14), and blood urea nitrogen levels at 12-16 weeks of treatment (FIG. 15).

Example 18: Effect of Anti-C5 Antibodies Against Astrocyte Cell Death

Neuromyelitis optica (NMO) is an autoimmune disease of the central nervous system (CNS) that mainly affects the optic nerve and spinal cord. In NMO, anti-aquaporin-4 autoantibodies (AQP4-Ab) cause damage to astrocytes by activating complement-dependent cytotoxicity (CDC). The goals of this study were to evaluate the role of the complement system in NMO progression and the use of an antibody against a complement protein as a potential therapeutic treatment for NMO.

Primary rat cortical astrocytes were obtained from cerebral brain cortex of post-natal rat pups and were cultured with AQP4-Ab (antibody "rAb-53" from US Patent Application Publication 2014/0170140; Bennett et al 2009, Ann. Neurol. 66: 617-629) and complement proteins to demonstrate cell-mediated cytotoxicity. Then the experiments were repeated with addition of an anti-C5 antibody to demonstrate blocking of the astrocyte cell destruction.

To quantify cell death, a CYTOTOX-GLO™ luminescence cytotoxicity assay was performed. The assay used various concentrations of anti-C5 antibody (0.001m/ml, 0.01m/ml, 0.1m/ml, 1m/ml, 10m/ml, 100m/ml, or 1000m/ml) or an isotype control antibody.

Figure 16:
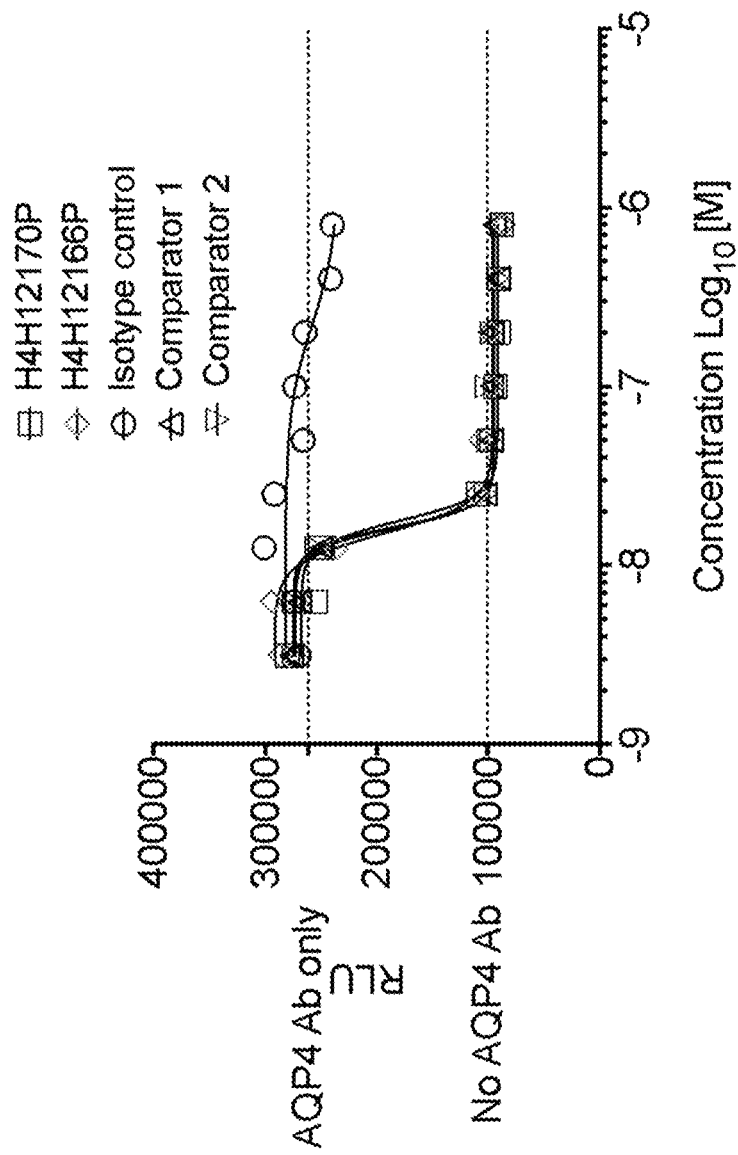
FIG. 16 is a graph showing inhibition of antibody-dependent cytotoxicity of astrocytes by anti-C5 antibodies H4H12166P, H4H12170P, Comparator 1 and Comparator 2, as described in Example 18.

In order to determine whether anti-C5 antibody could block the AQP4-Ab induced CDC, astrocytes were plated and the CYTOTOX-GLO™ Cytotoxicity Assay was repeated to find an optimal dose of AQP4-Ab for that plating. The optimal concentration of AQP4-Ab was found to be 50m/mL, and in a following experiment a constant dose of AQP4-Ab (50m/mL) was used, while the dose of anti-C5 antibody was varied. As shown in FIG. 16, a decrease in RLU was seen (on average 300 k to on average 100 k) with increasing amounts of anti-C5 antibody demonstrating that the anti-C5 antibody blocked astrocyte cell death. For both experiments, the RLU did not vary with the isotype control antibody. As shown in FIG. 16, anti-C5 antibodies inhibited AQP4 Ab induced cytotoxicity on primary cortical astrocyte with IC50 of 15-17 nM.

In a subsequent study, anti-AQP4 antibody and anti-C5 antibody will be injected into rat brains to assess the therapeutic efficacy against complement-mediated cytotoxicity of astrocytes in CNS.

Example 19: Endothelial Assay

This Example describes an in vitro glomerular endothelial assay to examine if anti-C5 antibodies block C5b-9 and C3 deposition.

Reproducible methods for evaluating inhibitory effects of drug candidates on complement activation are essential for preclinical development. Due to the complexity of complement activation pathways, an assay should use relevant cells and endpoints to the given therapeutic indication. Here, using an immortalized human glomerular endothelial cell line (HGECs), a complement C3 & C5 deposition model was validated for use evaluating the blocking activity of anti-C3 or C5 mAbs.

Methods

Human primary kidney glomerular endothelial cells (HGEC; Cell Biologics) were plated overnight in complete media into collagen I—coated black clear bottom 96-well plates. The cells were treated with either PBS (control) or activated for 10 mins with 10 uM ADP. After PBS washing, 50% human serum (complement-preserved, C3-depleted, or C5-depleted) was added for 4 hours. Anti-C5 antibodies were added at 1 mg/mL to the serum prior to the treatment. The cells were washed and fixed and probed with anti-C3b antibodies (Thermofisher) and/or anti-C5b-9 antibodies (Abcam), secondary antibodies and counterstained with DAPI. Images were captured on ImagExpress and high content image analysis was used to quantify fluorescent staining for each image and averaged per condition.

Results

C3 and C5b-9 deposition was observed on ADP-activated HGECs exposed to normal human serum but not on non-activated HGECs (C3: $1.5 \times 10^7 \pm 1.0 \times 10^7$; C5: $7.9 \times 10^6 \pm 6.6 \times 10^6$, $P<0.05$ vs non-ADP-activated HGEC). The deposition of C3 and C5b-9 were significantly reduced on ADP-activated HGEC exposed to C3 or C5 depleted serum (C3:

$3.3 \times 10^5 \pm 4.8 \times 10^4$; C5: $1.5 \times 10^6 \pm 6.0 \times 10^5$, P<0.05). Addition of a blocking anti-C5 mAb significantly reduced normal human serum derived C5b-9 deposition onto ADP-activated HGEC, deposition was comparable to C5 depleted sera (C5 mAb: $1.02 \times 10^6 + 6.0 \times 10^5$, Control mAb $3.7 \times 10^6 \pm 1.6 \times 10^6$, P<0.05 vs. control mAb).

CONCLUSION

These data demonstrate the utility of an in vitro human glomerular endothelial assay to model complement C3 & C5 deposition. In addition to in-vitro screening, this assay offers potential as a translational model to evaluate anti-complement strategies in renal disease using patient derived serum samples.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. An antibody or antigen-binding fragment thereof that binds specifically to C5 comprising HCDR1-HCDR2-HCDR3-LCDR1-LCDR2-LCDR3 comprising amino acid sequences of SEQ ID NOs: 100-102-104-108-110-112.

2. An antibody or antigen-binding fragment thereof that binds specifically to C5, wherein the antibody or antigen-binding fragment thereof comprises a HCVR/LCVR amino acid sequence pair of SEQ ID NOs: 98/106.

3. The antibody or antigen-binding fragment thereof of claim 2 comprising a heavy chain and a light chain, wherein the heavy chain comprises an amino acid sequence of SEQ ID NO: 353.

4. The antibody or antigen-binding fragment thereof of claim 2 comprising a heavy chain and a light chain, wherein the light chain comprises an amino acid sequence of SEQ ID NO: 354.

5. An antibody or antigen-binding fragment thereof that binds specifically to C5 comprising a heavy chain/light chain amino acid sequence pair of SEQ ID NOs: 353/354.

6. A pharmaceutical composition comprising an antibody or antigen-binding fragment thereof that binds specifically to C5 according to claim 1 and a pharmaceutically acceptable carrier or diluent.

7. The antibody or antigen-binding fragment thereof of claim 1 which is an antibody.

8. The antibody or antigen-binding fragment thereof of claim 2 which is an antibody.

9. The antibody or antigen-binding fragment thereof of claim 5 which is an antibody.

10. A pharmaceutical composition comprising the antibody of claim 7 and a pharmaceutically acceptable carrier or diluent.

11. A pharmaceutical composition comprising the antibody of claim 8 and a pharmaceutically acceptable carrier or diluent.

12. A pharmaceutical composition comprising the antibody of claim 9 and a pharmaceutically acceptable carrier or diluent.

13. A reusable pen delivery device comprising the pharmaceutical composition of claim 10.

14. A reusable pen delivery device comprising the pharmaceutical composition of claim 11.

15. A reusable pen delivery device comprising the pharmaceutical composition of claim 12.

16. An autoinjector delivery device comprising the pharmaceutical composition of claim 10.

17. An autoinjector delivery device comprising the pharmaceutical composition of claim 11.

18. An autoinjector delivery device comprising the pharmaceutical composition of claim 12.

* * * * *